US011878998B2

(12) United States Patent
Kwong et al.

(10) Patent No.: US 11,878,998 B2
(45) Date of Patent: Jan. 23, 2024

(54) PREFUSION RSV F PROTEINS AND THEIR USE

(71) Applicant: The United States of America, as represented by the Secretary, Department of Health and Human Services, Bethesda, MD (US)

(72) Inventors: Peter Kwong, Washington, DC (US); Barney Graham, Rockville, MD (US); John Mascola, Rockville, MD (US); Li Ou, Potomac, MD (US); Aliaksandr Druz, Germantown, MD (US); Man Chen, Bethesda, MD (US); Wing-Pui Kong, Germantown, MD (US); Ivelin Stefanov Georgiev, Nashville, TN (US); Emily Rundlet, New York, NY (US); Michael Gordon Joyce, Washington, DC (US); Yaroslav Tsybovsky, Frederick, MD (US); Paul Thomas, Washington, DC (US); Marie Pancera, Seattle, WA (US); Mallika Sastry, Rockville, MD (US); Cinque Soto, Nashville, TN (US); Joseph Van Galen, North Wales, PA (US); Guillaume Stewart-Jones, Cambridge, MA (US); Yongping Yang, Potomac, MD (US); Baoshan Zhang, Bethesda, MD (US); Ulrich Baxa, Frederick, MD (US)

(73) Assignee: The United States of America, as represented by the Secretary Department of Health and Human Services, Bethesda, MD (US)

( * ) Notice: Subject to any disclaimer, the term of this patent is extended or adjusted under 35 U.S.C. 154(b) by 63 days.

(21) Appl. No.: 17/524,380

(22) Filed: Nov. 11, 2021

(65) Prior Publication Data

US 2022/0064222 A1 Mar. 3, 2022

Related U.S. Application Data

(63) Continuation of application No. 16/089,993, filed as application No. PCT/US2017/024714 on Mar. 29, 2017, now Pat. No. 11,174,292.

(60) Provisional application No. 62/314,946, filed on Mar. 29, 2016.

(51) Int. Cl.

| | |
|---|---|
| ***C07K 14/005*** | (2006.01) |
| ***A61K 39/12*** | (2006.01) |
| ***A61P 37/04*** | (2006.01) |
| ***A61P 31/14*** | (2006.01) |
| *A61K 39/00* | (2006.01) |

(52) U.S. Cl.

CPC ............ *C07K 14/005* (2013.01); *A61K 39/12* (2013.01); *A61P 31/14* (2018.01); *A61P 37/04* (2018.01); *A61K 39/00* (2013.01); *A61K 2039/5252* (2013.01); *A61K 2039/5254* (2013.01); *A61K 2039/53* (2013.01); *A61K 2039/543* (2013.01); *A61K 2039/55505* (2013.01); *A61K 2039/55561* (2013.01); *A61K 2039/55566* (2013.01); *C07K 2319/21* (2013.01); *C07K 2319/22* (2013.01); *C07K 2319/50* (2013.01); *C07K 2319/70* (2013.01); *C07K 2319/735* (2013.01); *C12N 2710/10343* (2013.01); *C12N 2760/18522* (2013.01); *C12N 2760/18523* (2013.01); *C12N 2760/18534* (2013.01)

(58) Field of Classification Search

None

See application file for complete search history.

(56) References Cited

U.S. PATENT DOCUMENTS

| | | | | |
|---|---|---|---|---|
| 10,017,543 | B2 | 7/2018 | Kwong et al. | |
| 2010/0239593 | A1 | 9/2010 | Spits et al. | |
| 2012/0070446 | A1 | 3/2012 | Beaumont et al. | |
| 2016/0046675 | A1 * | 2/2016 | Kwong .................. | A61P 43/00 424/186.1 |

FOREIGN PATENT DOCUMENTS

| | | | |
|---|---|---|---|
| CN | 101952321 | A | 1/2011 |
| CN | 102639147 | A | 8/2012 |
| CN | 103842374 | A | 6/2014 |
| WO | WO 2009/079796 | A1 | 7/2009 |

(Continued)

OTHER PUBLICATIONS

Barouch, et al. "A human T-cell leukemia virus type 1 regulatory element enhances the immunogenicity of human immunodeficiency virus type 1 DNA vaccines in mice and nonhuman primates." *Journal of Virology* 79, No. 14 (2005): 8828-8834.

(Continued)

*Primary Examiner* — Shanon A. Foley
*Assistant Examiner* — Myron G Hill
(74) *Attorney, Agent, or Firm* — Klarquist Sparkman, LLP

(57) ABSTRACT

Embodiments of a recombinant Respiratory Syncytial Virus (RSV) F ectodomain trimer stabilized in a prefusion conformation are provided. Also disclosed are nucleic acids encoding the RSV F ectodomain trimer and methods of producing the RSV F ectodomain trimer. Methods for inducing an immune response in a subject are also disclosed. In some embodiments, the method can be a method for treating or preventing a RSV infection in a subject by administering a therapeutically effective amount of the recombinant RSV F ectodomain trimer to the subject.

27 Claims, 33 Drawing Sheets

Specification includes a Sequence Listing.

(56) References Cited

FOREIGN PATENT DOCUMENTS

| | | | | |
|---|---|---|---|---|
| WO | WO 2011/008974 A2 | | 1/2011 | |
| WO | WO 2012/158613 A1 | | 11/2012 | |
| WO | WO 2014/160463 | | 10/2014 | |
| WO | WO 2014/174018 | | 10/2014 | |
| WO | WO-2014160463 A1 | * | 10/2014 | ............. A61K 39/12 |

OTHER PUBLICATIONS

Cohen, et al. American Association for the Advancement of Science. "In vaccine design, looks do matter." (2013): 1442-1443.

Corti, et al. "Cross-neutralization of four paramyxoviruses by a human monoclonal antibody." *Nature* 501, No. 7467 (2013): 439-443.

Gilman, et al. "Characterization of a Prefusion-Specific Antibody That Recognizes a Quaternary, Cleavage-Dependent Epitope on the RSV Fusion Glycoprotein," *PLoS Pathog*, 11(7): e1005035, 2015 (17 pages).

International Search Report and Written Opinion from International Application No. PCT/US2017/024714 filed Mar. 29, 2017, ISA European Patent Office, dated Jul. 13, 2017 (18 pages).

Johnson, et al. "The histopathology of fatal untreated human respiratory syncytial virus infection." *Modern Pathology* 20, No. 1 (2007): 108-119.

Joyce, et al. "Iterative structure-based improvement of a fusion-glycoprotein vaccine against RSV." *Nature Structural & Molecular Biology* 23, No. 9 (2016): 811-820.

Kanekiyo, et al. "Self-assembling influenza nanoparticle vaccines elicit broadly neutralizing H1N1 antibodies." *Nature* 499, No. 7456: 102-106 (2013).

Krarup, et al. "A highly stable prefusion RSV F vaccine derived from structural analysis of the fusion mechanism." *Nature Communications* 6 (2015): 8143 (12 pages).

Kwakkenbos, et al. "Generation of stable monoclonal antibody-producing B cell receptor-positive human memory B cells by genetic programming." *Nature Medicine* 16.1 (2010): 123-128.

Langley, et al. "A dose-ranging study of a subunit Respiratory Syncytial Virus subtype A vaccine with and without aluminum phosphate adjuvantation in adults ≥65 years of age." *Vaccine* 27, No. 42 (2009): 5913-5919.

Leuridan, et al. "Early waning of maternal measles antibodies in era of measles elimination: longitudinal study." *BMJ* 340 (2010): c1626 (7 pages).

Liljeroos, et al. "Architecture of respiratory syncytial virus revealed by electron cryotomography." *Proceedings of the National Academy of Sciences* 110, No. 27 (2013): 11133-11138.

Magro, et al. "Neutralizing antibodies against the preactive form of respiratory syncytial virus fusion protein offer unique possibilities for clinical intervention." *Proceedings of the National Academy of Sciences* 109.8 (2012): 3089-3094.

McLellan, et al. "Structure of respiratory syncytial virus fusion glycoprotein in the postfusion conformation reveals preservation of neutralizing epitopes." *Journal of Virology* 85.15 (2011): 7788-7796.

McLellan, et al. "Structure of RSV fusion glycoprotein trimer bound to a prefusion-specific neutralizing antibody." *Science* 340, No. 6136 (2013); 1113-1117.

McLellan, et al. "Structure-based design of a fusion glycoprotein vaccine for respiratory syncytial virus." *Science* 342, No. 6158 (2013): 592-598.

Ngwuta, et al. "Prefusion F-specific antibodies determine the magnitude of RSV neutralizing activity in human sera." *Science Translational Medicine* 7, No. 309 (2015): 309ra162-309ra162 (19 pages).

Pancera, et al. "N332-Directed broadly neutralizing antibodies use diverse modes of HIV-1 recognition: inferences from heavy-light chain complementation of function." *Plos One*, 8.2 (2013): e55701 (10 pages).

Paradiso, et al. "Safety and immunogenicity of a subunit respiratory syncytial virus vaccine in children 24 to 48 months old." *The Pediatric Infectious Disease Journal 13*, No. 9 (1994): 792-798.

Stewart-Jones, et al. "A cysteine zipper stabilizes a pre-fusion F glycoprotein vaccine for respiratory syncytial virus." *Plos one* 10, No. 6 (2015): e0128779 (16 pages).

Swanson, et al. "Structural basis for immunization with postfusion respiratory syncytial virus fusion F glycoprotein (RSV F) to elicit high neutralizing antibody titers." *Proceedings of the National Academy of Sciences* 108.23 (2011): 9619-9624.

Tristram, et al. "Second-year surveillance of recipients of a respiratory syncytial virus (RSV) F protein subunit vaccine, PFP-1: evaluation of antibody persistence and possible disease enhancement." *Vaccine* 12, No. 6 (1994): 551-556.

Weisshaar, et al. "Blocking Respiratory Syncytial Virus Entry: A Story with Twists." *DNA Cell Biol.* 34.8 (Aug. 2015): 505-510.

Zhang, et al. "Protection of calves by a prefusion-stabilized bovine RSV F vaccine." *NPJ Vaccines* 2, No. 1 (2017): 7 (11 pages).

Zhang, et al. "Self-assembly in the ferritin nano-cage protein superfamily." *International Journal of Molecular Sciences* 12.8 (2011): 5406-5421.

* cited by examiner

FIG. 1C

Antigenic characteristics of single chain RSV F glycoproteins stabilized in the pre-fusion state

| Construct | Linker sequence | C-terminus | Oligomeric state | Yield (mg/L) | Antibody $K_D$ value (nM) D25 | Site Ø AM22 | 5C4 | Site II Mota[$] | Quaternary epitope MPE8 | AM14 |
|---|---|---|---|---|---|---|---|---|---|---|
| DS-Cav1 | N.A. | Foldon | Trimer | 3.5 | 0.15 | <0.01 | 13 | 0.04 | 0.5 | 3.3 |
| sc4 DS-Cav1 | $M_{97}$ **GSGGNGIGLG** $G_{151}$ | Foldon | Trimer | 3.4 | N. B. | N. B. | N. B. | 7.6 | N. B. | N. B. |
| sc8 DS-Cav1 | $M_{97}$ **GSGNVGLGG** $G_{151}$ | L512C,L513C | Monomer and Trimer | 1.0 | 7.4 | 3.9 | N. B | <0.01 | 0.5 | 1330 |
| sc9 DS-Cav1 | $M_{97}$QSTPATNN**GS**GSAIASG$_{151}$ | Foldon | Trimer | 18.5 | 0.8 | <0.01 | 31.3 | 13.7 | 0.8 | 33.1 |
| sc10 DS-Cav1 | $M_{97}$QSTPATNN**GS**GSAIASG$_{151}$ | S491 | Monomer and Trimer | 0.5 | 0.3 | 0.3 | 38.1 | 22.4 | 0.8 | N. B. |
| sc11 DS-Cav1 | $M_{97}$QSTPATNN**GS**GSAIASG$_{151}$ | A514 | Monomer | 1.0 | 0.7 | 1.6 | 58.8 | 29.3 | 1.6 | N. B. |

N.B.: No binding observed at 1000 nM Fab. N.T.: Not tested. $Motavizumab (Mota).

Physical stability of single chain RSV F glycoproteins stabilized in the pre-fusion state

| | Physical stability (fractional D25 reactivity) | | | | | | |
|---|---|---|---|---|---|---|---|
| | Temp (°C) | | pH | | Free zeTh aw | Osmolality (mM) | |
| Construct | 50 | 70 | 3.5 | 10.0 | | 10 | 3000 |
| DS-Cav1 | 0.9 | 0.0 | 0.8 | 0.5 | 0.1 | 0.9 | 1.0 |
| sc8 DS-Cav1 | 1.1 | 0.1 | 0.4 | 0.5 | 0.1 | 0.2 | 0.1 |
| sc9 DS-Cav1 | 0.4 | 0.4 | 0.2 | 0.1 | 0.2 | 0.1 | 0.1 |
| sc10 DS-Cav1 | 0.3 | 0.3 | 0.2 | 0.2 | 0.1 | 0.1 | 0.1 |
| sc11 DS-Cav1 | 0.2 | 0.1 | 0.5 | 0.2 | 0.0 | 0.1 | 0.1 |

RSV F sc9 DS-Cav1 — Trimer

RSV F sc9 DS-Cav1 — Protomer

DS-Cav1

DS-Cav1 residues with rmsd > 5 Å or not present in single-chain construct

RSV F sc9 DS-Cav1

RSV F sc9 DS-Cav1

DS-Cav1

Antigenic and physical characteristics of single chain RSV F glycoproteins stabilized in the pre-fusion state

| | | | | | | Antibody $K_D$ value (nM) | | | | |
|---|---|---|---|---|---|---|---|---|---|---|
| | | | | | | Site Ø | | Site II | Quaternary epitope | |
| Construct | Linker sequence | Oligomeric state | Elution volume (mL)† | Yield (mg/L) | D25 | AM22 | 5C4 | Mota | MPE8 | AM14 |
| sc9 DS-Cav1 | $M_{97}$QSTPATNNGS $G_{145}$ | Trimer* | 55.77 | 18.5 | 0.8 | <0.01 | 31.3 | 13.7 | 0.8 | 33.1 |
| sc9-9 DS-Cav1 | $M_{97}$QSTPAT $G_{145}$ | Trimer | 62.87 | 17.1 | 0.2 | 2.8 | 17.9 | 1.0 | <0.01 | 3.3 |
| sc9-10 DS-Cav1 | $M_{97}$QSTPAT GS $G_{145}$ | Trimer | 61.59 | 17.8 | 0.8 | <0.01 | 26.2 | 9.7 | 0.8 | 6.6 |
| sc9-19 DS-Cav1 | $M_{97}$QSTPAT GGSGGSG$G_{145}$ | Trimer* | 58.87 | 16.1 | 0.8 | 0.06 | 22.6 | 16.7 | 1.0 | 25.6 |
| sc9-24 DS-Cav1 | $N_{97}$SALSAT GS $G_{145}$ | Trimer* | 60.75 | 14.5 | 0.8 | 0.3 | 20.8 | 15.1 | 0.8 | 25.1 |
| sc9-41 DS-Cav1 | $M_{97}$QST G $G_{145}$ | Trimer* | 59.60 | 12.3 | N. B. | N. B. | N. B. | 0.04 | N. B. | N. B. |
| sc9-42 DS-Cav1 | $A_{97}$QST G $G_{145}$ | Trimer* | 62.19 | 11.2 | N. B. | N. B. | N. B. | 5.9 | N. B. | N. B. |
| sc9 DS-Cav1-105Q | $M_{97}$QSTPATNQGS $G_{145}$ | Trimer* | 56.65 | 13.5 | 0.7 | <0.01 | 28.8 | 16.3 | 0.8 | 46.2 |

* Elution volume by gel filtration was slightly lower than DS-Cav1. †Elution volume was determined using size-exclusion column HiLoad 16/60 Superdex 200, GE. N.B.: No binding observed at 1000 nM Fab. $Motavizumab (Mota).

FIG. 3D

Physical stability of single chain RSV F glycoproteins stabilized in the pre-fusion state

| | Physical stability (fractional D25 reactivity) | | | | | | |
|---|---|---|---|---|---|---|---|
| | Temp (°C) | | pH | | Freeze Thaw | Osmolality (mM) | |
| Construct | 50 | 70 | 3.5 | 10.0 | | 10 | 3000 |
| DS-Cav1 | 0.9 | 0.0 | 0.8 | 0.5 | 0.1 | 0.9 | 1.0 |
| sc9-10 DS-Cav1 | 0.9 | 0.9 | 1.5 | 0.7 | 0.2 | 1.4 | 0.7 |
| sc9-19 DS-Cav1 | 0.9 | 0.9 | 0.7 | 0.8 | 0.04 | 0.6 | 0.5 |
| sc9-24 DS-Cav1 | 0.9 | 0.9 | 0.7 | 0.7 | 0.0 | 0.5 | 0.5 |

sc9-24 sc9-19 sc9-10

Design of covalent trimer constructs

FIG. 5C

Antigenic and physical characteristics of single chain RSV F glycoproteins stabilized in the pre-fusion state

| | | | | Antibody $K_D$ value (nM) | | | | | | Physical stability | | | | | | |
|---|---|---|---|---|---|---|---|---|---|---|---|---|---|---|---|---|
| | | | | | Site Ø | | Site II | Quaternary epitope | | Temp (°C) | | pH | | Freeze/ Thaw | Osmolality (mM) | |
| Construct | Oligomeric state | Elution Vol (mL)† | Yield (mg/L) | D25 | AM22 | 5C4 | Mota | MPE8 | AM14 | 50 | 70 | 3.5 | 10.0 | | 10 | 3000 |
| DS-Cav1 | Trimer | 16.05 | 3.5 | 0.15 | <0.01 | 13 | 0.04 | 0.5 | 3.3 | 0.9 | 0.0 | 0.8 | 0.5 | 0.1 | 0.9 | 1.0 |
| sc9-10 A DS-Cav1 A149C, Y458C | Trimer | 16.21 | 0.8 | 0.2 | 0.1 | 32.1 | 0.4 | 0.1 | 6.3 | 1.0 | 0.8 | 2.3 | 0.7 | 0.3 | 0.7 | 0.6 |
| sc9-10 DS-Cav1 N183GC,N428C | Trimer | 16.02 | 0.1 | 0.2 | 0.2 | 14.0 | 0.3 | 0.1 | 787# | 1.0 | 0.5 | 2.6 | 0.7 | 0.3 | 0.9 | 0.4 |

†Elution volume was determined using size-exclusion column Superose 6 Increase 5/150GL, GE. #N183 is a contact residue of antibody AM14.

FIG. 5D

Half-life (h) for RSV F glycoprotein immunogens

| | $T_{1/2}^{AM14}$ | $T_{1/2}^{D25}$ | $T_{1/2}^{MPE8}$ | $T_{1/2}^{Average}$ | Fold increase |
|---|---|---|---|---|---|
| DS-Cav1 | 1.4 | 3.2 | 2.0 | 2.2±0.9 | n/a |
| sc9-10 A DS-Cav1 A149C, Y458C | 7.8 | 16.5 | 14.4 | 12.9±4.5 | 5.8 |
| sc9-10 DS-Cav1 N183GC N428C | 33.8 | 42.4 | 48.3 | 41.5±7.3 | 19 |

FIG. 7C

Antigenic and physical properties of single chain RSV F glycoproteins stabilized in the pre-fusion state.

| | | | | | Antibody $K_D$ value (nM) | | | | | | Physical stability (fractional D25 reactivity) | | | | | | |
|---|---|---|---|---|---|---|---|---|---|---|---|---|---|---|---|---|---|
| | | | | | Site Ø | | | Site II | Quaternary epitope | | Temp (°C) | | pH | | Freeze/Thaw | Osmolality (mM) | |
| Construct | mutations | Strain | Oligomeric state | Yield (mg/L) | D25 | AM22 | 5C4 | Mota | MPE8 | AM14 | 50 | 70 | 3.5 | 10.0 | | 10 | 3000 |
| DS-Cav1 | N.A. | | Trimer | 3.5 | 0.15 | <0.01 | 13 | 0.04 | 0.5 | 3.3 | 0.9 | 0.0 | 0.8 | 0.5 | 0.1 | 0.9 | 1.0 |
| sc9-10 DS-Cav1 A149C, Y458C | S46G-E92D-S215P-K465Q | A2 | Trimer | 10.8 | 0.2 | 0.3 | 314.6 | 0.6 | 0.2 | 15.9 | 0.9 | 0.8 | 3.8 | 0.6 | 0.2 | 0.5 | 0.6 |
| | S46G-N67I-E92D-S215P-K465Q | A2 | Trimer | 14.0 | 0.6 | 0.2 | 126.9 | 0.1 | 0.2 | 1.0 | 1.0 | 0.9 | 2.7 | 0.7 | 0.1 | 0.8 | 0.7 |
| | S46G-S215P-K465Q | A2 | Trimer | 10.4 | 0.1 | 0.5 | 92.2 | 0.4 | 0.4 | 35.1 | 1.0 | 0.9 | 2.7 | 0.4 | 0.1 | 0.7 | 0.8 |
| sc9-10 DS-Cav1 N183GC, N428C | S46G-N67I-E92D-S215P-K465Q | A2 | Trimer | 5.1 | 0.2 | 0.4 | 79.7 | 0.6 | 0.2 | 2210 | 1.0 | 0.9 | 2.7 | 0.5 | 0.2 | 0.8 | 0.7 |
| sc9-10 DS-Cav1 Q98C, Q361C | L95M-I221M-R429K | B18537 | Trimer | 1.0 | 0.1 | 0.1 | 100.9 | 0.2 | 0.2 | 18.5 | 1.0 | 0.1 | 1.0 | 0.2 | 0.0 | 0.3 | 0.2 |
| | S46G-E92D-L95M-S215P-I217P-I221M-R429K-K465Q | Long (VR26) | Trimer | 1.0 | 0.1 | 0.1 | 35.8 | 11.1 | 0.2 | 33.9 | 1.0 | 0.8 | 1.7 | 0.3 | 0.1 | 0.3 | 0.3 |

FIG. 7D

RSV F glycoprotein immunogen half-life (h) assessed by prefusion-specific antibodies AM14, MPE8 and D25 at 60°C

| | | $T_{1/2}^{AM14}$ | $T_{1/2}^{D25}$ | $T_{1/2}^{MPE8}$ | $T_{1/2}^{Average}$ | Average fold increase |
|---|---|---|---|---|---|---|
| DS-Cav1 | | 1.4 | 3.2 | 2.0 | 2.2±0.9 | n/a |
| sc-9-10 DS Cav1-A149C, Y458C | S46G-N67I-E92D-S215P-K465Q | 7.5 | 26.4 | 12.7 | 15.5±9.7 | 7.06 |
| | S46G-E92D-S215P-K465Q | 8.3 | 26.7 | 12.6 | 15.9±9.7 | 7.21 |
| | S46G-S215P-K465Q | 6.0 | 23.4 | 11.2 | 13.6±8.9 | 6.15 |
| sc-9-10 DS Cav1 N183GC, N428C | S46G-N67I-E92D-S215P-K465Q | 27.1 | 23.3 | 35.1 | 28.5±6.0 | 12.95 |

FIG. 9C

| Construct | Physical stability (higher salt cond.) | | | | | | |
|---|---|---|---|---|---|---|---|
| | Temp (°C) | | pH | | Freeze/Thaw | Osmolality (mM) | |
| | 50 | 70 | 3.5 | 10.0 | | 10 | 3000 |
| sc9-10 A DS-Cav1 A149C, Y458C | 1.0 | 0.9 | 2.7 | 0.8 | 0.2 | 1.0 | 0.5 |
| sc9-10 A DS-Cav1 A149C, Y458C S46G-E92D-S215P-K465Q | 1.0 | 0.9 | 2.0 | 0.5 | 0.2 | 0.9 | 0.5 |
| sc9-10 DS-Cav1 N183GC N428C | 0.9 | 0.8 | 2.1 | 0.6 | 0.1 | 0.8 | 0.4 |
| sc9-10 DS-Cav1 N183GC N428C S46G-N67I-E92D-S215P-K465Q | 0.9 | 0.8 | 2.0 | 0.4 | 0.1 | 0.6 | 0.4 |
| DS-Cav1 | 1.0 | 0.0 | 2.0 | 0.5 | 0.8 | 1.0 | 1.1 |

FIG. 9D

| Construct | Freeze/Thaw (Glycerol Conc.) | |
|---|---|---|
| | 5% | 10% |
| sc9-10 A DS-Cav1 A149C, Y458C | 0.6 | 0.9 |
| sc9-10 DS-Cav1 N183GC N428C | 0.6 | 0.7 |

D25 or AM14 epitope-specific response

FIG. 11

| Protein | sc9 DS-Cav1 | sc9-10 DS-Cav1 | sc9-19 DS-Cav1 | sc9-24 DS-Cav1 | sc9-10 DS-Cav1 A149C, Y458C | sc9-10 DS-Cav1 A149C, Y458C, S46G- N67I-E92D- S215P-K465Q |
|---|---|---|---|---|---|---|
| **Crystal growth conditions** | 0.1 M NaOAc-Acetic Acid pH 5.5, 1.09 M $Li_2SO_4$, 0.12 M $MgSO_4$, 3.33 % (w/v) PEG 400 | 0.1 M HEPES pH 7.5, 0.19 M $(NH4)_2SO4$, 11 % iso-propanol, 17 % PEG 8,000 | 0.1 M Na citrate pH 5.6, 15 % iso-propanol, 17 % PEG 4,000 | 0.1 M NaOAc-Acetic Acid pH 5.5, 1.82 M $Li_2SO_4$, 0.1 M $MgSO_4$, 5 % (w/v) PEG 400 | 0.1 M phosphate-citrate, pH4.2, 0.12 M NaCl, 9.5% (w/v) PEG 8,000 | 0.1M Na Cacodylate, pH 6.5, 0.2M ZnAC, 17% (w/v) PEG 8,000 |
| **Cryoprotectant** | Mother liquor + 1.0 M $Li_2SO_4$ | Mother liquor + 30 % glycerol | Mother liquor + 15 % 2R-3R-butanediol | Mother liquor | Mother liquor + 15 % 2R-3R-butanediol | Mother liquor + 22% ethylene glycol |
| **Data collection** | | | | | | |
| Space group | $P4_132$ | $P4_132$ | $P4_132$ | $P4_132$ | $P4_132$ | $P4_132$ |
| Cell constants | | | | | | |
| *a, b, c* (Å) | 171.3, 171.3, 171.3 | 171.2, 171.2, 171.2 | 168.9, 168.9, 168.9 | 168.2, 168.2, 168.2 | 169.1, 169.1, 169.1 | 170.7, 170.7, 170.7 |
| α, β, γ (°) | 90, 90, 90 | 90, 90, 90 | 90, 90, 90 | 90, 90, 90 | 90, 90, 90 | 90, 90, 90 |
| Wavelength (Å) | 1.0 | 1.0 | 1.0 | 1.0 | 1.0 | 1.0 |
| Resolution (Å) | 50-2.98 (3.21-3.09; 3.09-2.98) | 50-3.58 (3.86-3.71, 3.71-3.58) | 50-2.55 (2.75-2.64, 2.64-2.55) | 50-2.90 (3.12-3.00, 3.00-2.90) | 50.0-2.65 (2.74-2.65) | 50-2.92 (3.02-2.92) |
| $R_{merge}$ | 10.9 | 8.2 | 15.0 | 14.9 | 11.8 | 14.0 |
| $I / \sigma I$ | 11.5 (1.8, 1.0) | 11.3 (1.67, 1.0) | 16.2 (2.5, 1.3) | 13.8 (1.9, 1.0) | 8.2 (1.87) | 11.57 (2.25) |
| Completeness (%) | 97.3 (99.7, 89.2) | 91.5 (94.1, 91.2) | 100.0 (100.0, 49.6) | 100.0 (100.0, 99.9) | 79.4 (66.3) | 98.0 (94.2) |
| Redundancy | 4.3 (4.0, 2.7) | 5.9 (5.5, 3.6) | 19.9 (14.7, 7.3) | 11.6 (10.7, 8.8) | 3.2 (1.9) | 5.4 (3.2) |
| Unique reflections | 17691(1757, 1578) | 9782 (979, 928) | 26218 (2690, 1337) | 18674 (1805, 1826) | 19610 (1601) | 18371 (1707) |
| **Refinement** | | | | | | |
| Resolution (Å) | 50-2.98 | 50-3.58 | 50-2.55 | 50-2.90 | 50.0-2.65 | 50.0-2.92 |
| No. reflections | 17652 | 9773 | 12401 | 18563 | 19565 | 18357 |
| $R_{work}$ / $R_{free}$ (%) | 19.4/23.7 | 25.3/28.9 | 19.1/25.3 | 27.2/31.1 | 22.7/27.1 | 22.3/25.9 |
| No. atoms | | | | | | |
| Protein | 3522 | 3488 | 3461 | 3435 | 3433 | 3462 |
| Ligand/ion | 19 | - | - | - | - | 54 |
| Water | - | - | - | - | - | - |
| *B*-factors | | | | | | |
| Protein | 111.3 | 108.3 | 100.8 | 92.9 | 72.5 | 82.3 |
| Ligand/ion | 181 | - | - | - | - | 131 |
| Water | - | - | - | - | - | - |
| R.m.s. deviation | | | | | | |
| Bond lengths (Å) | 0.009 | 0.002 | 0.010 | 0.010 | 0.004 | 0.002 |
| Bond angles (°) | 1.26 | 0.63 | 1.42 | 1.31 | 0.815 | 0.514 |
| Ramachandran | | | | | | |
| Most favored regions (%) | 93.4 | 94.5 | 93.4 | 93.3 | 93.7 | 96.4 |
| Disallowed regions (%) | 1.2 | 1.1 | 1.8 | 1.3 | 1.4 | 0.7 |

M MW Marker
1 DS-Cav1-Glf7
2 sc9-10 DS-Cav1, A149C, Y458C
3 sc9-10 DS-Cav1, N183GC, N428C
4 sc9-10 DS-Cav1, A149C, Y458C-Long
5 sc9-10 DS-Cav1, N183GC, N428C-Long
6 sc9-10 Cav1, A149C, Y458C-Long
7 sc9-10 Cav1, N183GC, N428C-Long

FIG. 14

| Immunogen | Antigenicity following 1 week incubation at 4C Antibodies D25 | AM14 | MPE8 | Mota |
|---|---|---|---|---|
| RSVF Cav1only | 3.3333 | 2.8114 | 3.0754 | 3.3547 |
| sc9-10 Cav1only | 3.5987 | 3.3142 | 3.5449 | 3.5936 |
| sc9-10 Cav1only 98-360 | 1.1414 | 0.1986 | 0.7336 | 1.0446 |
| sc9-10 Cav1only 99-360 | 1.3951 | 0.0553 | 0.6253 | 1.1131 |
| sc9-10 Cav1only 100-360 | 1.7571 | 0.3436 | 1.285 | 1.6116 |
| sc9-10 Cav1only 98-361 | 1.8362 | 0.356 | 1.3981 | 2.2396 |
| sc9-10 Cav1only 99-361 | 2.8939 | 2.6425 | 2.6571 | 2.7124 |
| sc9-10 Cav1only 100-361 | 0.9199 | 0.0969 | 0.7865 | 2.7983 |
| sc9-10 Cav1only 98-362 | 0.9572 | 0.516 | 0.845 | 0.8278 |
| sc9-10 Cav1only 99-362 | 1.3874 | 0.8055 | 1.2817 | 1.376 |
| sc9-10 Cav1only 100-362 | 0.4158 | 0.0541 | 0.298 | 1.5278 |
| sc9-10 Cav1only 146-458 | 2.3424 | 0.1015 | 1.8463 | 1.9459 |
| sc9-10 Cav1only 369-455 | 2.9446 | 0.0785 | 2.3195 | 2.4987 |
| sc9-10 A149C Y458C Long CAV1only | 2.8819 | 0.211 | 2.5002 | 2.5484 |
| sc9-10 N183GC N428C Long CAV1only | 0.5024 | 0.0514 | 0.2282 | 2.0691 |
| RSVF DS-Cav1 | 2.1255 | 1.7062 | 2.1632 | 1.723 |
| RSVF dFP | 0.902 | 0.05 | 2.7677 | 3.4194 |
| No DNA | 0.053 | 0.055 | 0.058 | 0.0788 |
| No DNA | 0.0529 | 0.0593 | 0.0745 | 0.0274 |
| No DNA | 0.0339 | 0.0496 | 0.0285 | 0.0988 |
| No DNA | 0.0361 | 0.0873 | 0.0942 | 0.0331 |

PREFUSION RSV F PROTEINS AND THEIR USE

CROSS REFERENCE TO RELATED APPLICATIONS

This application is a continuation of U.S. patent application Ser. No. 16/089,993, filed Sep. 28, 2018, which is the U.S. National Stage of International Application No. PCT/US2017/024714, filed Mar. 29, 2017, which was published in English under PCT Article 21(2), which in turn claims the benefit of U.S. Provisional Application No. 62/314,946, filed Mar. 29, 2016. Each of the above-listed applications is incorporated by reference herein in its entirety.

FIELD

This disclosure relates to polypeptides, polynucleotides, compositions, and methods of their use for elicitation and detection of an immune response to respiratory syncytial virus (RSV).

BACKGROUND

Respiratory syncytial virus (RSV) is an enveloped non-segmented negative-strand RNA virus in the family Paramyxoviridae, genus *Pneumovirus*. It is the most common cause of bronchiolitis and pneumonia among children in their first year of life. RSV also causes repeated infections including severe lower respiratory tract disease, which may occur at any age, especially among the elderly or those with compromised cardiac, pulmonary, or immune systems. Passive immunization currently is used to prevent severe illness caused by RSV infection, especially in infants with prematurity, bronchopulmonary dysplasia, or congenital heart disease.

The envelope protein of RSV, RSV F, is initially expressed as a single polypeptide precursor, designated $F_0$. $F_0$ trimerizes in the endoplasmic reticulum and is processed by a cellular furin-like protease at two conserved sites, generating, $F_1$, $F_2$, and Pep27 polypeptides. The Pep27 polypeptide is excised and does not form part of the mature F protein. The $F_2$ polypeptide originates from the N-terminal portion of the $F_0$ precursor and links to the $F_1$ polypeptide via two disulfide bonds. The $F_1$ polypeptide anchors the mature F protein in the membrane via a transmembrane domain, which is linked to a ~24 amino acid cytoplasmic tail. Three protomers of the $F_2$-$F_1$ heterodimer assemble to form a mature F protein, which adopts a metastable "prefusion" conformation that is triggered to undergo a conformational change that fuses the viral and target-cell membranes.

RSV F proteins stabilized in the prefusion conformation have been identified that produce a greater neutralizing immune response in animal models than that observed with RSV F proteins in the post-fusion conformation. For example, a recombinant RSV F ectodomain including the "DS-Cav1" substitutions (155C, 290C, 190F, and 207L) was previously shown to elicit a neutralizing immune response in animal models that is multi-fold greater than the immune response observed for post-fusion based RSV F immunogens. Although the DS-Cav1 immunogens are effective for eliciting an immune response to RSV, new RSV immunogens that can elicit an even greater immune response are of interest, particularly for preventing or reducing the most severe disease caused by RSV and for maternal immunization protocols.

SUMMARY

Disclosed herein are embodiments of immunogens including recombinant RSV F proteins developed using iterative cycles of structure-based design that surprisingly increase RSV-protective titers a further ~4-fold above that provided by prior RSV F-based immunogens, such as "DS-Cav1." In addition to enhanced immunogenicity, the novel RSV F immunogens disclosed herein provide superior attributes, such as the absence of a requirement for furin cleavage and increased antigenic stability to heat inactivation, with several embodiments over 10-fold more stable than DS-Cav1 at 60° C.

In some embodiments, a recombinant RSV F ectodomain trimer is provided that comprises three recombinant $F_2$-$F_1$ ectodomain protomers. The protomers each comprise a deletion of RSV F positions 104-144 and a glycine-serine peptide linker between RSV F positions 103 and 145. Additionally, the protomers comprise 190F and 207L cavity filling substitutions, and optionally a non-native disulfide bond between cysteines introduced by 155C and 290C substitutions, to stabilize the recombinant RSV F ectodomain trimer in a prefusion conformation. Further the protomers comprise one or more of (a) a non-native inter-protomer disulfide bond between cysteines introduced by 149C and 458C substitutions, (b) a non-native inter-protomer disulfide bond between cysteines introduced by 183GC and 428C substitutions, (c) a non-native inter-protomer disulfide bond between cysteines introduced by 369C and 455C substitutions, and/or (d) a non-native inter-protomer disulfide bond between cysteines introduced by substitutions at one of RSV F positions 98-100 and one of RSV F positions 360-362. The recombinant RSV F ectodomain trimers are stabilized in a prefusion conformation and therefore comprise an antigenic site Ø that can specifically bind to prefusion specific antibodies, such as D25, AM22, and/or 5C4.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, and a non-native disulfide bond between cysteines introduced by A149C and Y458C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, and a non-native disulfide bond between cysteines introduced by N183GC and N428C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, a non-native disulfide bond between cysteines introduced by N183GC and N428C substitutions, and a non-native disulfide bond between cysteines introduced by A149C and Y458C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, and a non-native disulfide bond between cysteines introduced by T369C and T455C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, and a non-native disulfide bond between cysteines introduced by L98C and Q361C substitutions, for stabilization in the prefusion conformation.

In some embodiments, the recombinant $F_2$-$F_1$ ectodomain protomers in the recombinant RSV F ectodomain trimer comprise, S190F and V207L substitutions, a non-native disulfide bond between cysteines introduced by S155C and S290C substitutions, and a non-native disulfide bond between cysteines introduced by L99C and Q361C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by S155C and S290C substitutions, and a non-native disulfide bond between cysteines introduced by L100C and Q362C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by A149C and Y458C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by N183GC and N428C substitutions, for stabilization in the prefusion conformation.

In some embodiments, the recombinant $F_2$-$F_1$ ectodomain protomers in the recombinant RSV F ectodomain trimer comprise S190F and V207L substitutions, a non-native disulfide bond between cysteines introduced by N183GC and N428C substitutions, and a non-native disulfide bond between cysteines introduced by A149C and Y458C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by T369C and T455C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by L98C and Q361C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by L99C and Q361C substitutions, for stabilization in the prefusion conformation.

In some embodiments, the recombinant $F_2$-$F_1$ ectodomain protomers in the recombinant RSV F ectodomain trimer comprise S190F and V207L substitutions, and a non-native disulfide bond between cysteines introduced by L100C and Q362C substitutions, for stabilization in the prefusion conformation.

In some embodiments, the recombinant $F_2$-$F_1$ ectodomain protomers of any of the RSV F ectodomain trimers disclosed herein can comprise a C-terminal linkage to a trimerization domain, such as a T4 Fibritin trimerization domain. The trimerization domain promotes trimerization and stabilization of the membrane proximal aspect of the recombinant RSV F ectodomain trimer. In some such embodiments, the recombinant $F_2$-$F_1$ ectodomain protomers in the recombinant RSV F ectodomain trimer comprise RSV F positions 26-103 and 145-513, and are linked to the C-terminal trimerization domain.

In additional embodiments, the recombinant $F_2$-$F_1$ ectodomain protomers of any of the RSV F ectodomain trimers disclosed herein can comprise a C-terminal linkage to a transmembrane domain, such as a RSV F transmembrane domain. In some such embodiments, the recombinant $F_2$-$F_1$ ectodomain protomers in the recombinant RSV F ectodomain trimer comprise RSV F positions 26-103 and 145-574.

In additional embodiments, the recombinant RSV F ectodomain trimer can be included on a protein nanoparticle, such as a ferritin protein nanoparticle. Nucleic acid molecules encoding the disclosed recombinant RSV F ectodomain trimer are also provided, as are vectors including the nucleic acid molecules, and methods of producing the disclosed RSV F ectodomains.

Immunogenic compositions including the recombinant RSV F ectodomain trimer that are suitable for administration to a subject are also provided, and may also be contained in a unit dosage form. The compositions can further include an adjuvant. The recombinant RSV F ectodomains may also be conjugated to a carrier to facilitate presentation to the immune system.

Methods of inducing an immune response in a subject are disclosed, as are methods of treating, inhibiting or preventing a RSV infection in a subject, by administering to the subject an effective amount of a disclosed recombinant RSV F ectodomain trimer, nucleic acid molecule, or vector. In some embodiments, a method for inhibiting or preventing an RSV infection in an infant is provided. In some such embodiments, the method can comprise administering a therapeutically effective amount of a recombinant RSV F ectodomain trimer as disclosed herein to a pregnant subject to induce an immune response to RSV that provides passive immunity to RSV infection to an infant born from the pregnant subject.

The foregoing and other features and advantages of this disclosure will become more apparent from the following detailed description of several embodiments which proceeds with reference to the accompanying figures.

BRIEF DESCRIPTION OF THE FIGURES

FIGS. 1A-1E show a set of diagraphs and a table illustrating the design and properties of single chain RSV F glycoproteins stabilized in the pre-fusion form. (A) RSV F DS-Cav1 structure is shown in ribbon format with F2 domain colored in dark gray and F1 domain colored in light gray. A close-up view of the cleavage site of a single protomer is shown with the fusion peptide indicated. (B) Single-chain RSV F (sc) constructs were designed by replacing both of the furin cleavage sites (R109/E110 and R136/F137) and the fusion peptide with a variable-length linker from either residue 97 to 151 or from residue 105 to 145. The DS-Cav1 mutations (DS: a disulfide between residues 155 and 290; Cav1: Ser to Phe mutation at residue 190 and Val to Leu at residue 207) are incorporated in all designs with other mutations labeled and indicted by a vertical black line. (C) Antigenic characteristics of single chain RSV F glycoprotein variants stabilized in the pre-fusion state. The observed oligomeric state of the variants is indicated based on size-exclusion chromatography. The protein yield from 1 L of Expi cells is shown and the antibody affinity for six antibodies with epitopes on antigenic site Ø, site II as well as the prefusion specific antibodies MPE8 and AM14 are shown. The sequences shown include MGSGGNGIGLGG (SEQ ID NO: 85), MGSGNVGLGG (SEQ ID NO: 86), and MQSTPATNNGSGSAIASG (SEQ ID NO: 87, shown for sc9, sc10, and sc11)). (D) Size-exclusion chromatography profiles of sc variants analyzed using a Superose 6 Increase 5/150GL gel filtration column. (E) Physical stability of sc variants as assessed by D25 reactivity after exposure to various physical extremes.

FIG. 3A-3D show a set of graphs and tables illustrating the design and properties of single chain RSV F with altered F2-F1 linkers. (A) Round 2 design of altered F2-F1 linkers. The sequences shown include MQSTPATNNGSG (residues 1-12 of SEQ ID NO: 87) and NSALSATGSG (SEQ ID NO: 88), TGG, and TGSG (SEQ ID NO: 89). (B) Representative dynamic light scattering profile and gel filtration chromatograms of single chain RSV F glycoprotein variants with altered linkers. sc9-10 DS-Cav1 exhibit similar elution profiles characteristic of DS-Cav1. (C) Antigenic and physical characteristics of single chain RSV F glycoprotein variants stabilized in the pre-fusion state. The amino acid sequence of sc variants is shown. The observed oligomeric state of the variants is indicated based on size-exclusion chromatography. The protein yield from 1 L of Expi cells is given and the antibody affinity for six antibodies is shown. The sequences shown include MQSTPATNNGSG (residues 1-12 of SEQ ID NO: 87), MQSTPATG (SEQ ID NO: 90), MQSTPATGSG (SEQ ID NO: 91), MQSTPATGGSGGSGG (SEQ ID NO: 92), NSALSATGSG (SEQ ID NO: 88), MQSTGG (SEQ ID NO: 93), AQSTGG (SEQ ID NO: 94), and MQSTPATNQGSG (SEQ ID NO: 95). (D) Physical stability of sc variants as assessed by D25 reactivity after exposure to various physical extremes.

FIG. 5A-5D illustrate the design and properties of single chain RSV F glycoproteins with inter-protomer disulfides. (A) Crystal structure of RSV sc9-10 DS-Cav1 trimer is shown in cartoon representation. Inset shows close-up view of the round 3 designs for which residues were mutated to Cys to form inter-protomer disulfides; mutations are labeled and shown in stick representation. (B) Engineered single-chain RSV F glycoproteins with inter-protomer disulfides were characterized by negative-stain EM and SDS-PAGE. (C) Antigenic and physical characteristics of single chain RSV F glycoprotein variants with inter-protomer disulfides. The observed oligomeric state of the variants is indicated based on size-exclusion chromatography. The protein yield from 1 L of Expi cells is given and the antibody affinity for five antibodies is shown. Physical stability of sc variants as assessed by D25 reactivity after exposure to various physical extremes is shown. (D) Antigenic stability of pre-fusion RSV F glycoprotein immunogens assessed at 60° C. against pre-fusion specific antibodies AM14, D25 and MPE8 (decay curve shown in FIG. 9).

FIG. 7A-7D show results concerning the combination of inter-protomer disulfides with other mutations. (A) Design for round 4 involving interprotomer disulfides combined with other variants. (B) Phylogenetic tree of strains tested. (C) RSV F single chain variant molecule antigenicity and physical stabilities. (D) Antigenic stability of pre-fusion RSV F glycoprotein immunogens assessed at 60° C. against pre-fusion specific antibodies AM14, D25 and MPE8 (decay curve shown in FIG. 9).

FIGS. 9A-9D are a set of graphs and tables showing the stability of prefusion RSV F glycoprotein immunogens. Decay curves at 60° C. for RSV F glycoprotein immunogens of (A) design cycle3 and (B) design cycle4 were assessed by Octet BLI using prefusion-specific antibodies AM14, D25 and MPEG. (C) Physical stability RSV F immunogens in high salt buffer. (D) Assessment of RSV F variant D25 reactivity following 10 cycles of freeze-thaw in the presence of glycerol.

Figure 10A:
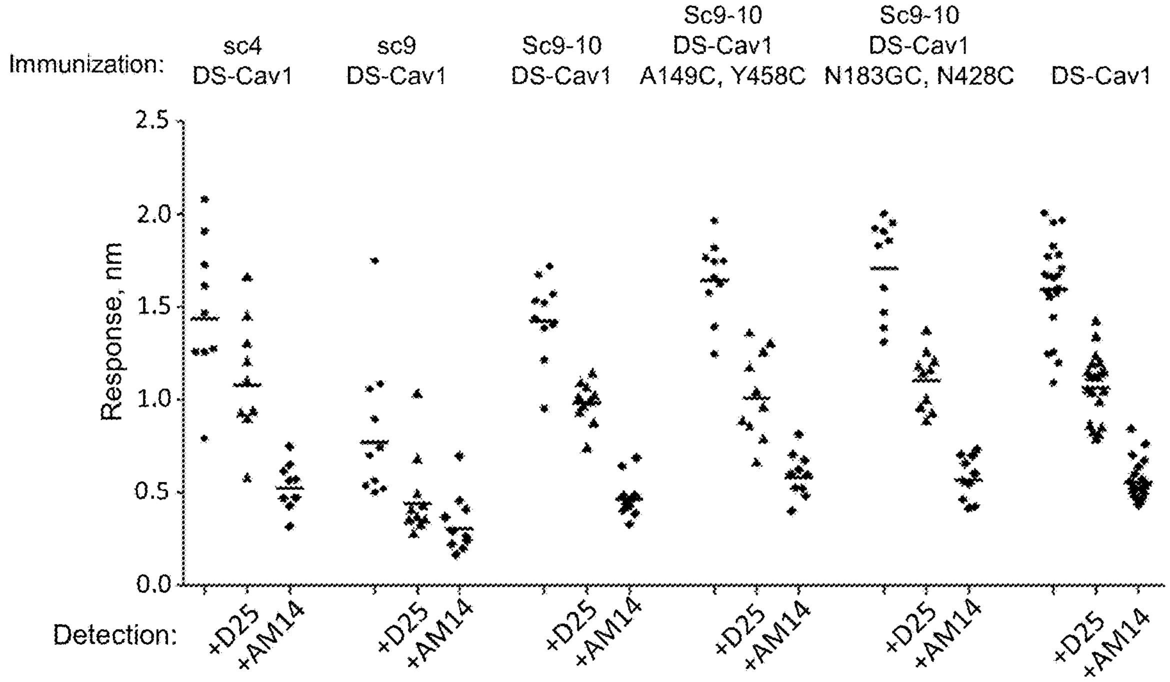
Figure 10B:
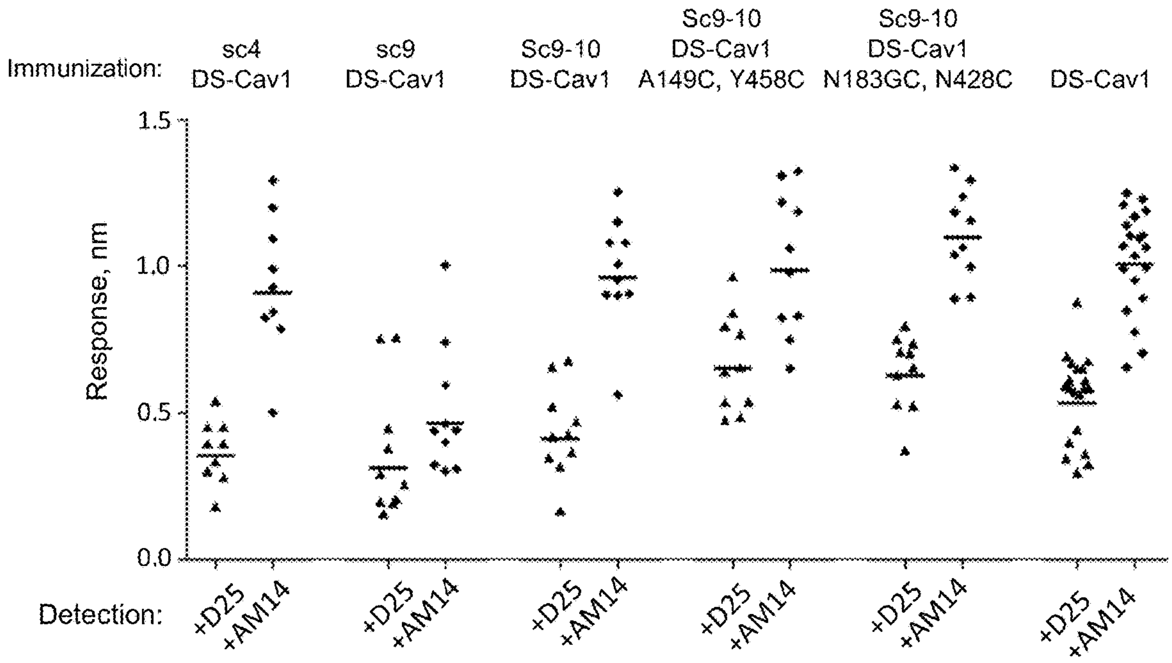

FIGS. 10A-10B are a set of graphs showing immunized mice sera reactivity to D25 and AM14 epitopes. Sera from mice immunized with single chain variants of RSV F were assessed for binding to immobilized DS-CAV1 or immobilized DS-CAV1 bound by prefusion-specific antibodies D25 or AM14 to assess site specific responses. (A) RSV F DS-Cav1-loaded sensor tips were blocked with D25 and AM14 respectively. Responses were measured by BLI. (B) D25 and AM14 epitope specific response was calculated by subtracting DS-Cav1 bound by D25 or AM14 responses from the overall DS-Cav1 response.

FIG. 11 is a table showing Crystallographic data collection and refinement statistics. Values in parentheses are for highest-resolution shells.

Figure 12:
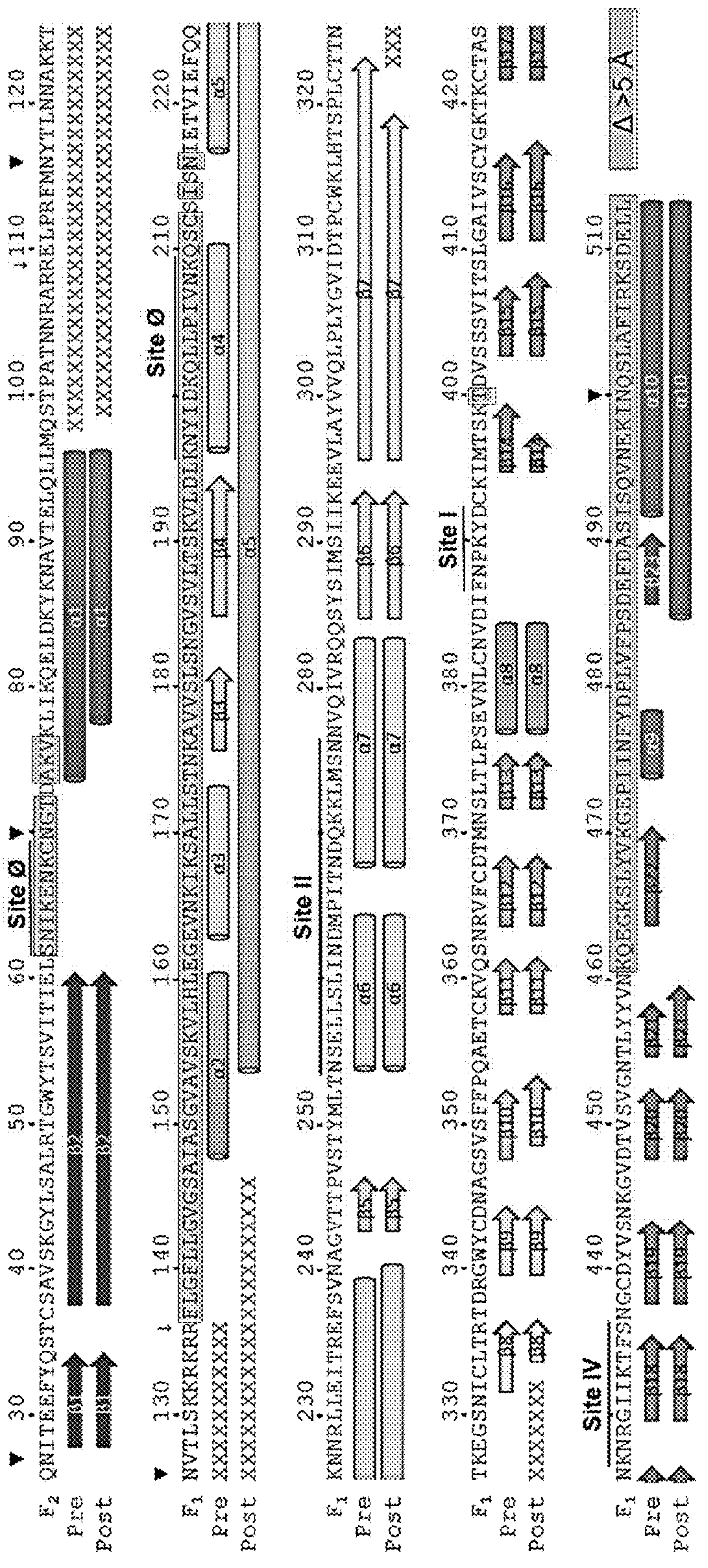

FIG. 12 is a schematic diagram illustrating RSV F sequence and secondary structure. Sites of N-linked glycosylation are highlighted by black triangles, antigenic sites are labeled, and downward arrows indicate the position of furin cleavage sites. Secondary structures are shown below the sequence, with cylinders representing α-helices and arrows representing β-strands. Disordered or missing residues are indicated by an "X"; residues that move over 5 Å between prefusion and postfusion conformations shown with grey shadow and are boxed. SEQ ID NO: 57 is shown.

Figure 13:
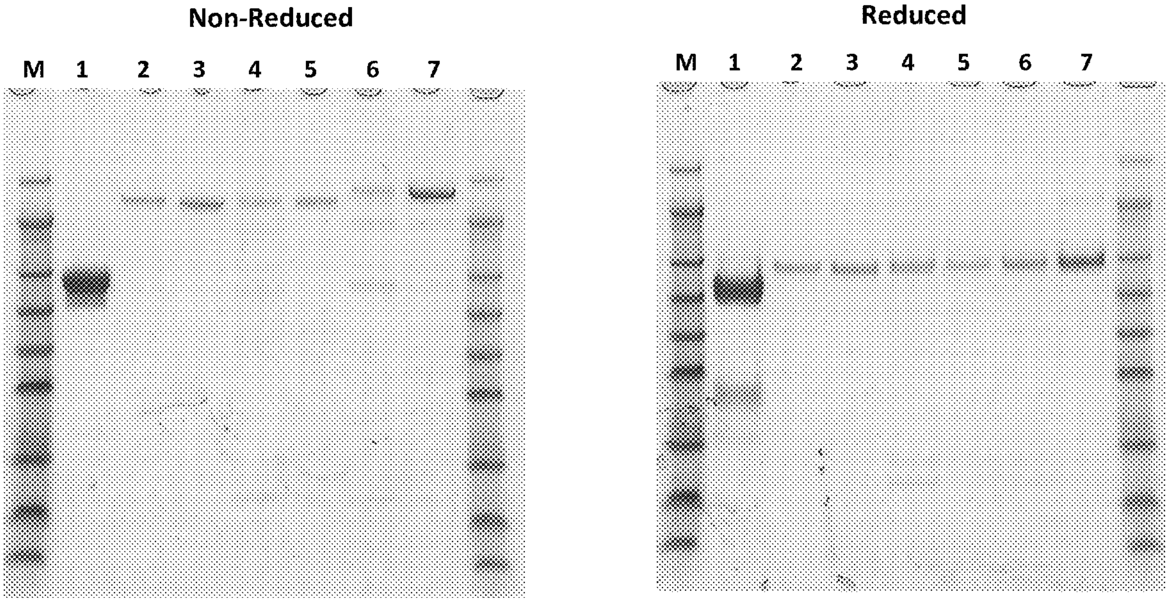

FIG. 13 shows two PAGE gels illustrating the purification yields of the indicated recombinant RSV F ectodomain constructs. All of the constructs have a C-terminal Foldon trimerization domain. The C-terminal residue of the RSV F ectodomain for constructs 2-3 is position 513. Reference to "long" for constructs 4-7 indicates that the C-terminal residue of the RSV F ectodomain included in the construct is position 532.

FIG. 14 is a table providing ELISA antigenic data for a series of single chain variants of RSV F binding to prefusion specific antibodies D25, AM14, and MPE8, as well as Motavizumab antibody.

Figure 15A:
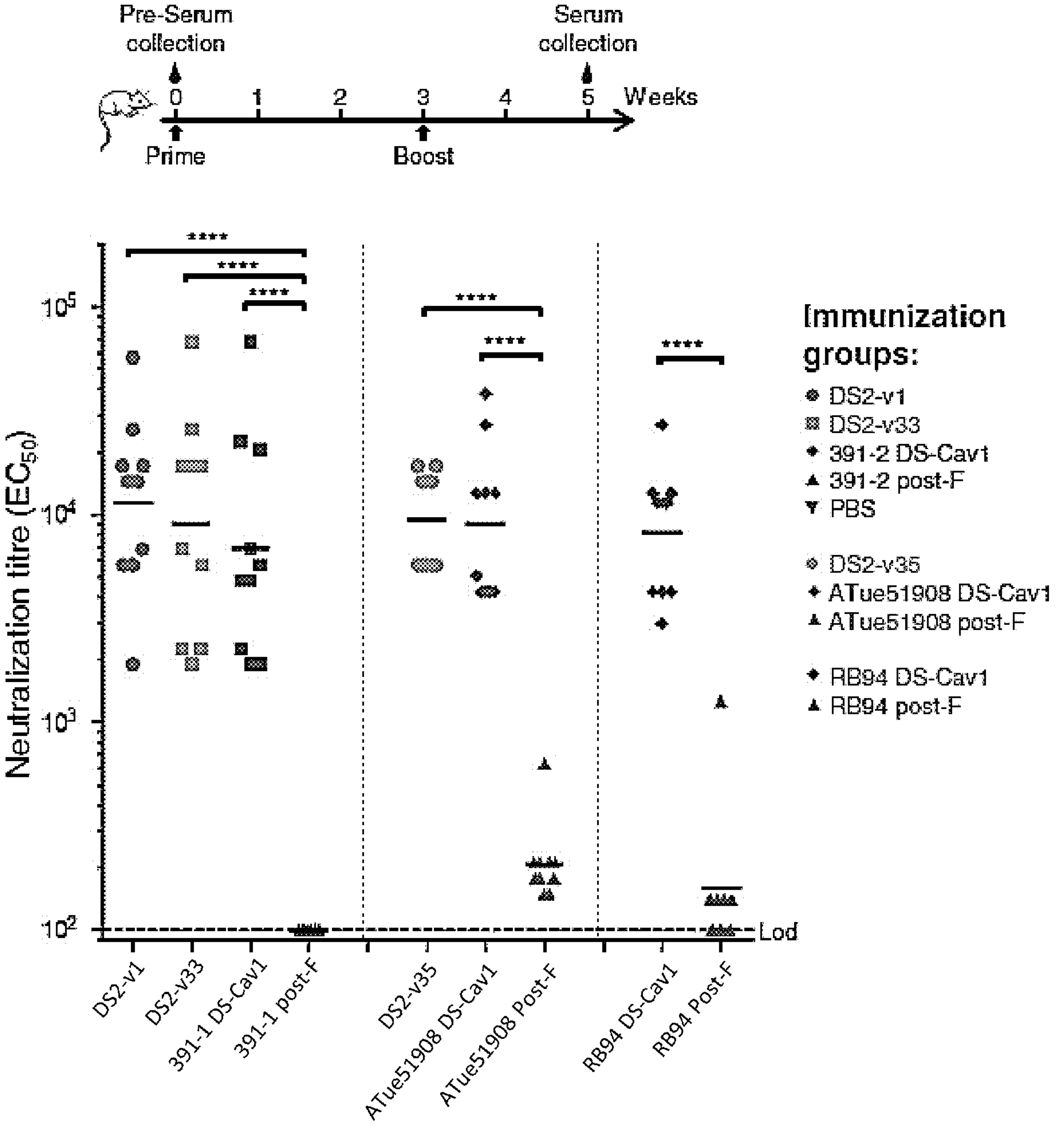
Figure 15B:
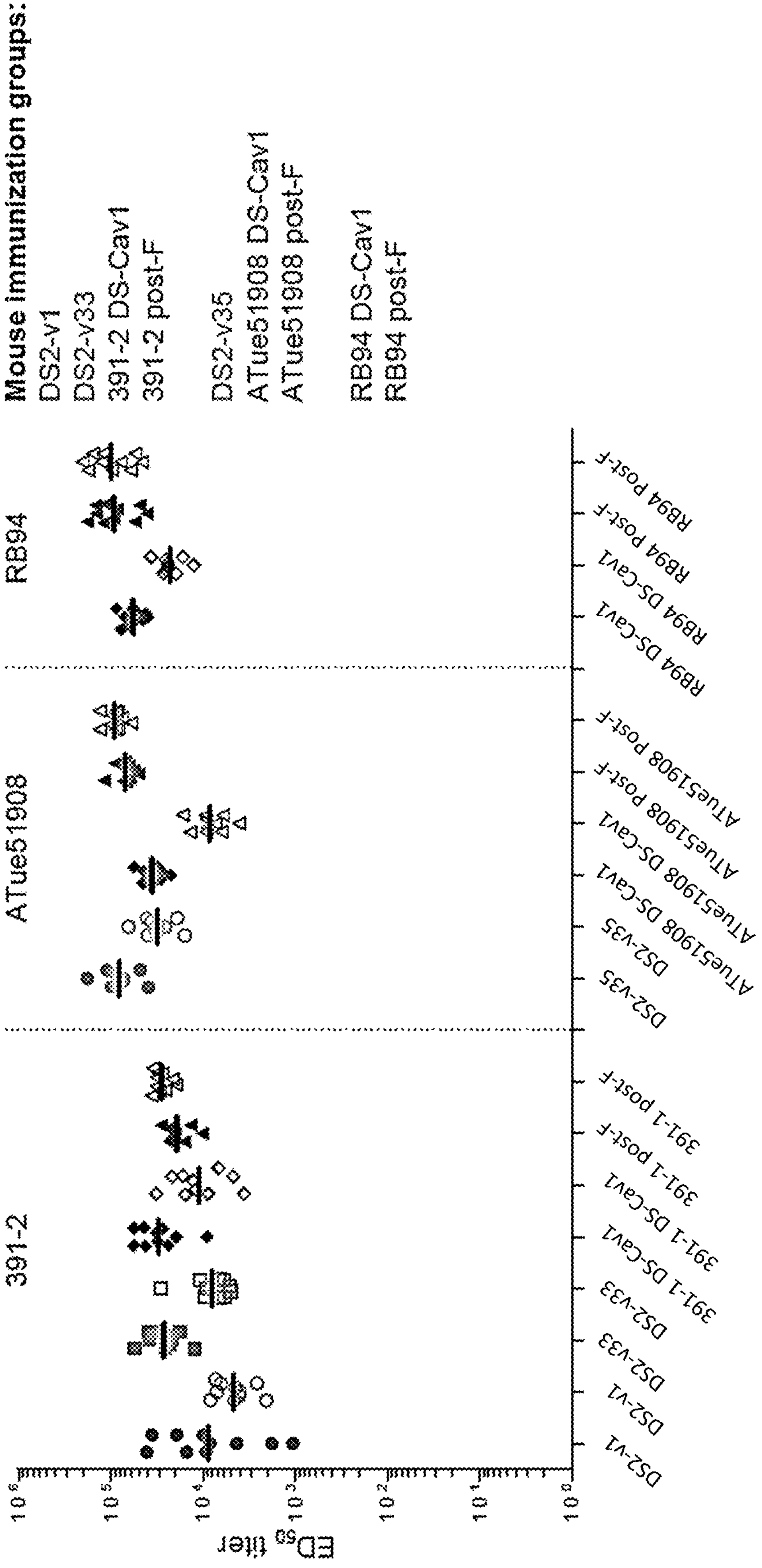

FIGS. 15A and 15B are a set of tables showing serum neutralizing antibody titers elicited by engineered bRSV F pre-F trimers in mice. (FIG. 15A) Pre-F-stabilized bRSV F glycoproteins elicited geometric mean EC50 neutralization titers between 43-344-fold higher than post-F in mice. The immunization protocol is shown. There are 10 mice per group for the mouse immunizations. Neutralization titer from each animal is shown as an individual dot, and geometric means are indicated by black horizontal lines. Lod, limit of detection (titer=100) is indicated with a horizontal dashed line. Vertical dotted lines separate immunogen strains. P values were determined by two-tailed Mann-Whitney tests. *Indicates P≤0.05, indicates P≤0.01, *indicates P≤0.001 and **indicates P≤0.0001. (FIG. 15**B) ELISA binding titers of week five sera from mice immunized with the bRSV F variants. Titers from each animal are represented by color-coded symbols. Solid symbols indicate sera recognition of immobilized D52-v1 RSV F trimers and open symbols indicate recognition of immobilized 391-2 post-F RSV F trimers. Vertical dotted lines separate immunogen strains. Geometric mean titers are indicated by black horizontal lines.

SEQUENCES

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~424 kb), which was created on Nov. 5, 2021, which is incorporated by reference herein. In the accompanying sequence listing:

SEQ ID NOs: 1-56 are exemplary amino acid sequences of recombinant $F_2$-$F_1$ ectodomain protomers linked to a T4 Fibritin trimerization domain as disclosed herein. These sequences include N-terminal signal peptides and C-terminal protein tags that can be proteolytically removed during production to generate a soluble recombinant RSV F ectodomain trimer.

SEQ ID NOs: 57-64 are the amino acid sequence of exemplary native RSV F proteins.

SEQ ID NO: 65 is the amino acid sequence of a peptide linker.

SEQ ID NO: 66 is the amino acid sequence of an exemplary T4 Fibritin trimerization domain SEQ ID NOs: 67-72 are the amino acid sequences of exemplary cysteine zipper trimerization domains.

SEQ ID NOs: 73-74 are the amino acid sequences of exemplary transmembrane domains.

SEQ ID NOs: 76-78 are the amino acid sequences of exemplary protein nanoparticle subunits. SEQ ID NOs: 79-80 are the amino acid sequences of exemplary signal peptides.

SEQ ID NOs: 81-84 are exemplary amino acid sequences encoding recombinant $F_2$-$F_1$ ectodomain protomers linked to a T4 Fibritin trimerization domain as disclosed herein.

SEQ ID NOs: 85-95 are single chain RSV F proteins sequences.

SEQ ID NOs: 96-99 are exemplary nucleic acid sequences encoding recombinant $F_2$-$F_1$ ectodomain protomers linked to a T4 Fibritin trimerization domain as disclosed herein.

SEQ ID NOs: 10-113 are exemplary amino acid sequences of recombinant $F_2$-$F_1$ ectodomain protomers linked to a T4 Fibritin trimerization domain as disclosed herein. These sequences include N-terminal signal peptides and C-terminal protein tags that can be proteolytically removed during production to generate a soluble recombinant RSV F ectodomain trimer.

SEQ ID NOs: 114-116 are the amino acid sequence of exemplary native RSV F proteins.

SEQ ID NOs: 117-162 are the amino acid sequences of peptide linkers.

SEQ ID NO: 163 is the amino acid sequence of a signal peptide.

DETAILED DESCRIPTION

RSV F proteins stabilized in the prefusion conformation produce a greater neutralizing immune response in animal models than that observed with RSV F proteins stabilized in the post-fusion conformation (see, McLellan et al., *Science,* 342:592-598, 2013). Thus, prefusion-stabilized RSV F proteins are leading candidates for inclusion in a RSV vaccine. Soluble RSV F ectodomains stabilized in the prefusion conformation have previously been generated by introducing modifications (e.g., introduction of disulfide bonds) that "lock" the membrane distal apex of the trimeric protein in the prefusion conformation including antigenic site Ø, and replacing the transmembrane domain and cytosolic tail with a T4 Fibritin trimerization domain to maintain the F ectodomain in a trimeric configuration. One example is a recombinant RSV F ectodomain including the "DS-Cav1" substitutions (155C, 290C, 190F, 207L) and a C-terminal T4 Fibritin trimerization domain, which can elicit a neutralizing immune response in animal models. However, such immunogens may not induce an immune response sufficient for preventing the most severe disease caused by RSV or for maternal immunization to provide passive immunization to newborn infants.

Severe disease from RSV occurs most frequently during the first six months of life, when infant lungs are still developing. Maternal antibodies—transferred during the last weeks of pregnancy—provide protective immunity, but this protection wanes ~2-fold each month and should be ~$2^6$-fold (64-fold) the protective threshold at birth to safeguard infants during their most vulnerable period.

Disclosed herein are embodiments of RSV F-based immunogens developed using iterative cycles of structure-based design to increase RSV-protective titers a further ~4-fold above that provided by prior RSV F-based immunogens, including DS-Cav1. The novel RSV F immunogens provided herein include genetically linked $F_1$ and $F_2$ subunits with the fusion peptide deleted, the DS-Cav1 substitutions, and additional stabilizing substitutions to restrict the RSV F ectodomain to its prefusion conformation. In addition to enhanced immunogenicity, the novel RSV F immunogens disclosed herein provide superior attributes, such as the absence of a requirement for furin cleavage and increased antigenic stability to heat inactivation, with several embodiments over 10-fold more stable than DS-Cav1 at 60° C. Thus, the disclosed recombinant RSV F proteins provide an unexpectedly superior combination of immunogenicity and stability. In some embodiments, the recombinant RSV F ectodomain trimers provided herein can be used to induce an immune response in a pregnant subject that provides sufficient passively acquired neutralizing activity to protect and/or reduce RSV F infection the first six months of life in the infant born to the subject.

I. Summary of Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references. As used herein, the singular forms "a," "an," and "the," refer to both the singular as well as plural, unless the context indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

5C4: A neutralizing monoclonal antibody that specifically binds to the antigenic site Ø present on the prefusion conformation of RSV F protein. 5C4 protein and nucleic acid sequences are known, for example, the heavy and light chain amino acid sequences of the 5C4 antibody are set forth in McLellan et al., *Science,* 340(6136):1113-7, 2013, which is incorporated herein in its entirety.

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages) Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed recombinant.

Administration: The introduction of a composition into a subject by a chosen route. Administration can be local or systemic. For example, if the chosen route is intranasal, the composition (such as a composition including a disclosed recombinant RSV F ectodomain) is administered by introducing the composition into the nasal passages of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

AM22: A neutralizing monoclonal antibody that specifically binds to the antigenic site Ø present on the prefusion conformation of RSV F protein. AM22 protein and nucleic acid sequences are known, for example, the heavy and light chain amino acid sequences of the AM22 antibody are set forth in U.S. Pat. App. Pub. No. 2012/0070446, which is incorporated herein in its entirety.

Amino acid substitution: The replacement of an amino acid in a polypeptide with one or more different amino acids. In some examples, an amino acid in a polypeptide is substituted with an amino acid from a homologous polypeptide, for example, an amino acid in a recombinant group A RSV F polypeptide can be substituted with the corresponding amino acid from a group B RSV F polypeptide. Reference to a "155C" substitution in an RSV F protein refers to an RSV F protein comprising a cysteine residue at position 155 that has been substituted for a the corresponding native residue at position 155. Reference to a "S155C" substitution in an RSV F protein refers to an RSV F protein comprising a cysteine residue at position 155 that has been substituted for a serine residue in a reference (e.g., native) sequence.

Antibody: An immunoglobulin, antigen-binding fragment, or derivative thereof, that specifically binds and recognizes an analyte (antigen) such as RSV F protein, an antigenic fragment thereof, or a dimer or multimer of the antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010).

Cavity-filling amino acid substitution: An amino acid substitution that fills a cavity within the protein core of a protein, such as a RSV F ectodomain. Cavities are essentially voids within a folded protein where amino acids or amino acid side chains are not present. In several embodiments, a cavity filling amino acid substitution is introduced to fill a cavity present in the prefusion conformation of the RSV F ectodomain core that collapses (e.g., has reduced volume) after transition to the postfusion conformation.

Conservative variants: "Conservative" amino acid substitutions are those substitutions that do not substantially affect or decrease a function of a protein, such as the ability of the protein to induce an immune response when administered to a subject. The term conservative variation also includes the use of a substituted amino acid in place of an unsubstituted parent amino acid. Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant RSV F ectodomain trimer, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Control: A reference standard. In some embodiments, the control is a negative control sample obtained from a healthy patient. In other embodiments, the control is a positive control sample obtained from a patient diagnosed with RSV infection. In still other embodiments, the control is a historical control or standard reference value or range of values (such as a previously tested control sample, such as a group of RSV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Cysteine zipper domain: A trimeric coiled-coil domain with inter-helix disulfide bonds between cysteine residues in rings of di-cysteine motifs include on the helices of the coiled-coil domain. The cysteine zipper domain is similar in structure to a leucine zipper domain, and includes a coiled-coil domain with cysteine residues in place of the corresponding leucine residues of a leucine zipper coiled-coil domain Similar to a leucine zipper, the di-cysteine motifs are included at heptad positions a and g.

D25: A neutralizing monoclonal antibody that specifically binds to the antigenic site Ø present on the prefusion conformation of RSV F protein. D25 protein and nucleic acid sequences are known, for example, the heavy and light chain amino acid sequences of the D25 antibody are set forth in U.S. Pat. App. Pub. No. 2010/0239593, which is incorporated herein in its entirety; see also, Kwakkenbos et al., *Nat. Med.,* 16:123-128, 2009).

Degenerate variant: In the context of the present disclosure, a "degenerate variant" refers to a polynucleotide encoding a polypeptide that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on the antigenic site Ø of RSV F protein. Epitopes can be formed both from contiguous amino acids or noncontiguous amino acids juxtaposed by tertiary folding of a protein.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term “expression” is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term “control sequences” is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Glycosylation site: An amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a recombinant RSV F polypeptide is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Host cells: Cells in which a vector can be propagated and its nucleic acid expressed. The cell may be prokaryotic or eukaryotic. The term also includes any progeny of the subject host cell. It is understood that all progeny may not be identical to the parental cell since there may be mutations that occur during replication. However, such progeny are included when the term “host cell” is used.

Immune response: A response of a cell of the immune system, such as a B cell, T cell, or monocyte, to a stimulus. In one embodiment, the response is specific for a particular antigen (an “antigen-specific response”). In one embodiment, an immune response is a T cell response, such as a CD4+ response or a CD8+ response. In another embodiment, the response is a B cell response, and results in the production of specific antibodies.

Immunogen: A compound, composition, or substance (for example, a recombinant RSV F ectodomain trimer) that can elicit an immune response in an animal, including compositions that are injected or absorbed into an animal Administration of an immunogen to a subject can lead to protective immunity against a pathogen of interest.

Immunogenic composition: A composition comprising a disclosed recombinant RSV F ectodomain trimer that induces a measurable CTL response against the RSV, or induces a measurable B cell response (such as production of antibodies) against the RSV, when administered to a subject. It further refers to isolated nucleic acid molecules and vectors encoding a protomer of a disclosed recombinant RSV F ectodomain trimer that can be used to express the protomer (and thus be used to elicit an immune response against recombinant RSV F ectodomain trimer). For in vivo use, the immunogenic composition will typically include the recombinant RSV F ectodomain trimer or a nucleic acid molecule encoding a protomer of the recombinant RSV F ectodomain trimer in a pharmaceutically acceptable carrier and may also include other agents, such as an adjuvant.

Isolated: An “isolated” biological component has been substantially separated or purified away from other biological components, such as other biological components in which the component naturally occurs, such as other chromosomal and extrachromosomal DNA, RNA, and proteins. Proteins, peptides, nucleic acids, and viruses that have been “isolated” include those purified by standard purification methods. Isolated does not require absolute purity, and can include protein, peptide, nucleic acid, or virus molecules that are at least 50% isolated, such as at least 75%, 80%, 90%, 95%, 98%, 99%, or even 99.9% isolated.

Linker and Linked: A bi-functional molecule that can be used to link two molecules into one contiguous molecule. Non-limiting examples of peptide linkers include glycine-serine peptide linkers. Unless context indicates otherwise, reference to "linking" a first polypeptide and a second polypeptide, or to two polypeptides "linked" together, or to a first polypeptide having a "linkage" to a second polypeptide, refers to covalent linkage by peptide bond (for example via a peptide linker) such that the first and second polypeptides form a contiguous polypeptide chain. If a peptide linker is involved, the covalent linkage of the first and second polypeptides can be to the N- and C-termini of the peptide linker. Typically, such linkage is accomplished using molecular biology techniques to genetically manipulate DNA encoding the first polypeptide linked to the second polypeptide by the peptide linker.

Native protein, sequence, or disulfide bond: A polypeptide, sequence or disulfide bond that has not been modified, for example, by selective mutation. For example, selective mutation to focus the antigenicity of the antigen to a target epitope, or to introduce a disulfide bond into a protein that does not occur in the native protein. Native protein or native sequence are also referred to as wild-type protein or wild-type sequence. A non-native disulfide bond is a disulfide bond that is not present in a native protein, for example, a disulfide bond that forms in a protein due to introduction of one or more cysteine residues into the protein by genetic engineering.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form. "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

Prefusion specific antibody: An antibody that specifically binds to the RSV F protein in a prefusion conformation, but does not specifically bind to the RSV F protein in a post-fusion conformation. Exemplary prefusion specific antibodies include the D25, AM22, and 5C4 antibodies Pharmaceutically acceptable carriers: The pharmaceutically acceptable carriers of use are conventional. *Remington's Pharmaceutical Sciences*, by E. W. Martin, Mack Publishing Co., Easton, PA, 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions (such as immunogenic compositions) to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example, an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

Polypeptide modifications: Polypeptides and peptides, such as the recombinant RSV F proteins disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, *Y. Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a recombinant RSV F ectodomain and self-assemble into a protein nanoparticle presenting the recombinant RSV F ectodomain on its surface, which can be administered to a subject to stimulate an immune response to the antigen.

Recombinant: A recombinant nucleic acid molecule is one that has a sequence that is not naturally occurring, for example, includes one or more nucleic acid substitutions, deletions or insertions, and/or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

A recombinant virus is one that includes a genome that includes a recombinant nucleic acid molecule.

A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell, or into the genome of a recombinant virus.

Respiratory Syncytial Virus (RSV): An enveloped non-segmented negative-sense single-stranded RNA virus of the family Paramyxoviridae. The RSV genome is ~15,000 nucleotides in length and includes 10 genes encoding 11 proteins, including the glycoproteins SH, G, and F. The F protein mediates fusion, allowing entry of the virus into the cell cytoplasm and also promoting the formation of syncytia. Two antigenic subgroups of human RSV strains have been described, the A and B subgroups, based primarily on differences in the antigenicity of the G glycoprotein. RSV strains for other species are also known, including bovine RSV. Exemplary RSV strain sequences are known to the person of ordinary skill in the art. Further, several models of human RSV infection are available, including model organisms infected with hRSV, as well as model organisms infected with species specific RSV, such as use of bRSV infection in cattle (see, e.g., Bern et al., *Am J, Physiol. Lung Cell Mol. Physiol.,* 301: L148-L156, 2011; and Nam and Kun (Eds.). Respiratory Syncytial Virus: Prevention, Diagnosis and Treatment. Nova Biomedical Nova Science Publisher, 2011; and Cane (Ed.) Respiratory Syncytial Virus. Elsevier Science, 2007.)

RSV Fusion (F) protein: An RSV envelope glycoprotein that facilitates fusion of viral and cellular membranes. In nature, the RSV F protein is initially synthesized as a single polypeptide precursor approximately 574 amino acids in length, designated $F_0$. $F_0$ includes an N-terminal signal peptide that directs localization to the endoplasmic reticulum, where the signal peptide (approximately the first 25 residues of $F_0$) is proteolytically cleaved. The remaining $F_0$ residues oligomerize to form a trimer and are proteolytically processed by a cellular protease at two conserved consensus furin cleavage sequences (approximately $F_0$ positions 109 and 136; for example, $RARR_{109}$ (SEQ ID NO: 57, residues 106-109) and $RKRR_{136}$ (SEQ ID NO: 57, residues 133-136) to generate two disulfide-linked fragments, $F_1$ and $F_2$. The smaller of these fragments, $F_2$, originates from the N-terminal portion of the $F_0$ precursor and includes approximately residues 26-109 of $F_0$. The larger of these fragments, $F_1$, includes the C-terminal portion of the $F_0$ precursor (approximately residues 137-574) including an extracellular/lumenal region (residues 137-529), a transmembrane domain (~residues 530-550), and a cytoplasmic tail (~residues 551-574) at the C-terminus. The extracellular portion of the RSV F protein is the RSV F ectodomain, which includes the $F_2$ protein and the $F_1$ ectodomain.

The RSV F protein exhibits remarkable sequence conservation across RSV subtypes. For example, RSV subtypes A and B share 90% sequence identity, and RSV subtypes A and B each share 81% sequence identify with bRSV F protein, across the $F_0$ precursor molecule. Within RSV subtypes the $F_0$ sequence identity is even greater; for example within each of RSV A, B, and bovine subtypes, the RSV $F_0$ precursor protein has ~98% sequence identity. Nearly all identified RSV $F_0$ precursor proteins are approximately 574 amino acids in length, with minor differences in length typically due to the length of the C-terminal cytoplasmic tail. In view of the conservation of RSV F sequences, the person of ordinary skill in the art can easily compare amino acid positions between different native RSV F sequences, to identify corresponding RSV F amino acid positions between different RSV strains and subtypes. Thus, the conservation of RSV F protein sequences across strains and subtypes allows use of a reference RSV F sequence for comparison of amino acids at particular positions in the RSV F protein. The numbering of amino acid substitutions disclosed herein is made with reference to the RSV $F_0$ subtype A protein precursor polypeptide sequence set forth as SEQ ID NO: 57, unless context indicates otherwise.

Three $F_2$-$F_1$ protomers oligomerize in the mature F protein, which adopts a metastable prefusion conformation that is triggered to undergo a conformational change to a postfusion conformation upon contact with a target cell membrane. This conformational change exposes a hydrophobic sequence, known as the fusion peptide, which is located at the N-terminus of the $F_1$ ectodomain, and which associates with the host cell membrane and promotes fusion of the membrane of the virus, or an infected cell, with the target cell membrane. The three-dimensional structure of an exemplary RSV F protein in a prefusion conformation is known, and disclosed for example in WO2014160463, McLellan et al., *Science,* 340(6136): p. 1113-7, 2013, McLellan et al., *Science,* 342:592-598, 2013, and structural coordinates provided in PDB Accession No. 4JHW, each of which is incorporated by reference herein in its entirety.

In the prefusion conformation, the RSV F protein includes an antigenic site at its membrane distal apex termed "antigenic site Ø," that includes RSV F residues 62-69 and 196-209, and also includes the epitopes of the 5C4, D25, and AM22 monoclonal antibodies (see, McLellan et al., *Science,* 340(6136): p. 1113-7, 2013, McLellan et al., *Science,* 342: 592-598, 2013, and structural coordinates provided in PDB Accession No. 4JHW, each of which is incorporated by reference herein in its entirety). Further, the RSV F ectodomain undergoes a structural rearrangement between its pre- and post-fusion conformations (see FIG. 12). The N-terminal region of the $F_1$ ectodomain in the prefusion conformation includes the indicated α2, α3, β3, β4, and α4 helical and beta sheet structures, whereas the corresponding region of the N-terminus of the $F_1$ ectodomain in the postfusion structure includes an extended α5 helical structure—the α2, α3, β3, β4, and α4 helical and beta sheet structures are absent (see FIG. 12). The C-terminal region of the $F_1$ ectodomain in the prefusion conformation includes the indicated (β22, α9, and β23 beta sheet and α10 helical structures, whereas the corresponding C-terminal region of the $F_1$ ectodomain in the postfusion conformation structure includes an extended α10 helical structure and extended coil—the β22, α9, and β23 beta sheet and helical structures are absent. Thus, the membrane distal and membrane proximal lobes of the RSV F protein in its prefusion conformation include several distinct structural elements that are absent from the corresponding regions of the RSV F protein in its postfusion conformation.

A recombinant RSV F protein in a prefusion conformation can be specifically bound by an antibody that binds the pre- but not post-fusion conformation of the RSV F protein, such as an antibody that specifically binds to an epitope within antigenic site Ø, for example, the 5C4, D25, or AM22 antibody.

A RSV F ectodomain trimer "stabilized in a prefusion conformation" comprises one or more amino acid substitutions, deletions, or insertions compared to a native RSV F sequence that provide for increased retention of the prefusion conformation compared to RSV F ectodomain trimers formed from a corresponding native RSV F sequence. The "stabilization" of the prefusion conformation by the one or more amino acid substitutions, deletions, or insertions can be, for example, energetic stabilization (for example, reducing the energy of the prefusion conformation relative to the post-fusion open conformation) and/or kinetic stabilization (for example, reducing the rate of transition from the prefusion conformation to the postfusion conformation). Additionally, stabilization of the RSV F ectodomain trimer in the prefusion conformation can include an increase in resistance to denaturation compared to a corresponding native RSV F sequence. Methods of determining if a RSV F ectodomain trimer is in the prefusion conformation are provided herein, and include (but are not limited to) negative stain electron microscopy and antibody binding assays using a prefusion conformation specific antibody, such as the 5C4, D25, or AM22 antibody.

Sequence identity/similarity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Homologs and variants of a polypeptide (such as a RSV F ectodomain) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). Exemplary signal peptide sequences are set forth as residues 1-25 of SEQ ID NOs: 57-64 (RSV F protein signal peptides from A, B, and bovine RSV).

Single chain RSV F ectodomain: A recombinant RSV F ectodomain including the RSV $F_2$ polypeptide and the RSV $F_1$ ectodomain in a single contiguous polypeptide chain. Single chain RSV F ectodomains can trimerize to form a RSV F ectodomain trimer. A single chain RSV F ectodomain does not include the furin cleavage sites flanking the pep27 polypeptide of RSV F protein; therefore, when produced in cells, the $F_0$ polypeptide is not cleaved into separate $F_1$ and $F_2$ polypeptide chains. In one embodiment, position 103 of the F2 polypeptide is linked to position 145 of the $F_1$ polypeptide by a glycine-serine linker to generate the single chain RSV F ectodomain.

Specifically bind: When referring to the formation of an antibody:antigen protein complex, or a protein:protein complex, refers to a binding reaction which determines the presence of a target protein, peptide, or polysaccharide (for example, a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example, Antigenic site zero on an RSV F ectodomain trimer) and does not bind in a significant amount to other proteins or polysaccharides present in the sample or subject. Specific binding can be determined by methods known in the art. A first protein or antibody specifically binds to a target protein when the interaction has a $K_D$ of less than $10^{-6}$ Molar, such as less than $10^{-7}$ Molar, less than $10^{-8}$ Molar, less than $10^{-9}$, or even less than $10^{-10}$ Molar.

Soluble protein: A protein capable of dissolving in aqueous liquid at room temperature and remaining dissolved. The solubility of a protein may change depending on the concentration of the protein in the water-based liquid, the buffering condition of the liquid, the concentration of other solutes in the liquid, for example salt and protein concentrations, and the heat of the liquid. In several embodiments, a soluble protein is one that dissolves to a concentration of at least 0.5 mg/ml in phosphate buffered saline (pH 7.4) at room temperature and remains dissolved for at least 48 hours.

Subject: Living multi-cellular vertebrate organisms, a category that includes human and non-human mammals. In an example, a subject is a human. In a particular example, the subject is a newborn infant. In an additional example, a subject is selected that is in need of inhibiting of an RSV infection. For example, the subject is either uninfected and at risk of RSV infection or is infected in need of treatment.

T4 Fibritin trimerization domain: Also referred to as a "foldon" domain, the T4 Fibritin trimerization domain comprises an amino acid sequence that naturally forms a trimeric structure. In some examples, a T4 Fibritin trimerization domain can be included in the amino acid sequence of a disclosed recombinant protein so that the antigen will form a trimer. In one example, a T4 Fibritin trimerization domain comprises the amino acid sequence set forth as (GYIPEAPRDGQAYVRKDGEWVLLSTF (SEQ ID NO: 66). Several embodiments include a T4 Fibritin trimerization domain that can be cleaved from a purified protein, for example by incorporation of a thrombin cleave site adjacent to the T4 Fibritin trimerization domain that can be used for cleavage purposes.

Therapeutically effective amount: The amount of agent, such as a disclosed recombinant RSV F ectodomain, that is sufficient to prevent, treat (including prophylaxis), reduce and/or ameliorate the symptoms and/or underlying causes of a disorder or disease, for example to prevent, inhibit, and/or treat RSV infection. In some embodiments, a therapeutically effective amount is sufficient to reduce or eliminate a symptom of a disease, such as RSV infection. For instance, this can be the amount necessary to inhibit or prevent viral replication or to measurably alter outward symptoms of the viral infection.

In one example, a desired response is to inhibit or reduce or prevent RSV infection. The RSV infection does not need to be completely eliminated or reduced or prevented for the method to be effective. For example, administration of a therapeutically effective amount of the agent can decrease the RSV infection (for example, as measured by infection of cells, or by number or percentage of subjects infected by RSV) by a desired amount, for example by at least 50%, at least 60%, at least 70%, at least 80%, at least 90%, at least 95%, at least 98%, or even at least 100% (elimination or prevention of detectable RSV infection), as compared to a suitable control.

It is understood that to obtain a protective immune response against a pathogen can require multiple administrations of the immunogenic composition. Thus, a therapeutically effective amount encompasses a fractional dose that contributes in combination with previous or subsequent administrations to attaining a protective immune response. For example, a therapeutically effective amount of an agent can be administered in a single dose, or in several doses, for example daily, during a course of treatment (such as a prime-boost vaccination treatment). However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a RSV F transmembrane domain.

Treating or preventing a disease: Inhibiting the full development of a disease or condition, for example, in a subject who is at risk for a disease such as RSV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

The term "reduces" is a relative term, such that an agent reduces a response or condition if the response or condition is quantitatively diminished following administration of the agent, or if it is diminished following administration of the agent, as compared to a reference agent. Similarly, the term "prevents" does not necessarily mean that an agent completely eliminates the response or condition, so long as at least one characteristic of the response or condition is eliminated. Thus, an immunogenic composition that reduces or prevents an infection, can, but does not necessarily completely, eliminate such an infection, so long as the infection or response is measurably diminished, for example, by at least about 50%, such as by at least about 70%, or about 80%, or even by about 90% of (that is to 10% or less than) the infection in the absence of the agent, or in comparison to a reference agent.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides, or DNA derived from them. A vaccine may include a disclosed immunogen (such as a recombinant RSV F ectodomain trimer or nucleic acid molecule encoding same), a virus, a cell or one or more cellular constituents. Vaccines may elicit both prophylactic (preventative or protective) and therapeutic responses. Methods of administration vary according to the vaccine, but may include inoculation, ingestion, inhalation or other forms of administration. Vaccines may be administered with an adjuvant to boost the immune response. In one specific, non-limiting example, a vaccine prevents and/or reduces the severity of the symptoms associated with RSV infection and/or decreases the viral load compared to a control.

Vector: An entity containing a DNA or RNA molecule bearing a promoter(s) that is operationally linked to the coding sequence of an antigen(s) of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

II. Recombinant RSV F Ectodomain Trimers

Recombinant RSV F ectodomain trimers are disclosed herein that are modified from a native form (e.g., by introduction of one or more amino acid substitutions) to be stabilized in a RSV F prefusion conformation that comprises antigenic site Ø and specifically binds to antibodies targeting the pre-fusion but not-post-fusion RSV F conformation, such as the D25, AM22, 5C4, or MPE8 antibody. As described in Example 1, the disclosed RSV F ectodomain trimers have been selected through multiple rounds of structure based design for optimized solubility, stability, expression, and immunogenicity. The recombinant RSV F ectodomain trimers are useful to induce an immune response in a vertebrate animal (such as mammals, for example, humans and cattle) to RSV (for example RSV A, RSV B, or bovine RSV).

The recombinant RSV F ectodomain trimers comprise three recombinant protomers comprising modified forms of the RSV $F_2$ protein and the RSV $F_1$ ectodomain ("recombinant $F_2$-$F_1$ ectodomain protomers"). Unlike native RSV F protomers, the recombinant $F_2$-$F_1$ ectodomain protomers in the disclosed recombinant RSV F ectodomain trimers are "single chain" proteins comprising a single polypeptide chain comprising the $F_2$ polypeptide and the $F_1$ ectodomain. In particular, the recombinant $F_2$—$F_1$ ectodomain protomers in the disclosed recombinant RSV F ectodomain trimers comprise a deletion of RSV F positions 104-144 to remove the native protease cleavage sites and the pep27 peptide, and a glycine-serine peptide linker between RSV F positions 103 and 145.

In some embodiments, the recombinant RSV F ectodomain trimer can be a soluble protein complex, for example, for use as a recombinant subunit vaccine. In several such embodiments, the recombinant $F_2$-$F_1$ ectodomain protomers can comprise a C-terminal linkage to a trimerization domain, such as a T4 fibritin trimerization domain. The trimerization domain promotes trimerization and stabilization of the membrane proximal aspect of the recombinant RSV F ectodomain trimer.

In other embodiments, the recombinant RSV F ectodomain trimer can be a membrane anchored protein complex, for example, for use in an attenuated virus or virus like particle vaccine. Membrane anchoring can be accomplished, for example, by C-terminal linkage of the recombinant $F_2$-$F_1$ ectodomain protomers to a transmembrane domain and optionally a cytoplasmic tail, such as an RSV F transmembrane domain and cytoplasmic tail.

The recombinant $F_2$-$F_1$ ectodomain protomers comprise amino acid substitutions compared to native RSV F sequences for stabilization of the recombinant RSV F ectodomain trimer in the RSV F prefusion conformation. In several embodiments, the recombinant $F_2$-$F_1$ ectodomain protomers comprise the "DS" substitutions, which include a non-native disulfide bond between cysteines introduced by 155C and 290C substitutions (such as S155C and S290C substitutions) and/or the "Cav1" substitutions, which include 190F and 207L cavity filling amino acid substitutions (such as S190F and V207L substitutions). Together, these are referred to as the "DS-Cav1" substitutions. In some instances, the recombinant $F_2$-$F_1$ ectodomain protomers comprise the Cav1 substitutions, but not the DS substitutions. It is believe that the absence of the DS substitutions can, in some circumstances, improve the expression of the recombinant $F_2$-$F_1$ ectodomain protomers in cellular systems.

In several embodiments, in addition to the DS, Cav1, or DS-Cav1 substitutions, the recombinant $F_2$-$F_1$ ectodomain protomers in the disclosed RSV F ectodomain trimers comprise one or more additional non-native inter-protomer disulfide bonds between cysteines introduced by at least one (such as 2, 3, or all 4) of the following pairs of substitutions: 149C and 458C substitutions (such as A149C and Y458C substitutions), 183GC and 428C substitutions (such as N183GC and N428C substitutions), 369C and 455C substitutions (such as T369C and T455C substitutions), and a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions).

In some embodiments, the recombinant $F_2$-$F_1$ ectodomain protomers in the RSV F ectodomain trimer can comprise the DS-Cav1 substitutions, and also a non-native disulfide bond between cysteines introduced by 149C and 458C substitutions (such as A149C and Y458C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 183GC and 428C substitutions (such as N183GC and N428C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 149C and 458C substitutions (such as A149C and Y458C substitutions), and a non-native disulfide bond between cysteines introduced by 183GC and 428C substitutions (such as N183GC and N428C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 149C and 458C substitutions (such as A149C and Y458C substitutions), and a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 149C and 458C substitutions (such as A149C and Y458C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 183GC and 428C substitutions (such as N183GC and N428C substitutions), and a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 183GC and 428C substitutions (such as N183GC and N428C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the DS-Cav1 substitutions, and also a non-native disulfide bond between cysteines introduced by 183GC and 428C substitutions (such as N183GC and N428C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 149C and 458C substitutions (such as A149C and Y458C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 183GC and 428C substitutions (such as N183GC and N428C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 149C and 458C substitutions (such as A149C and Y458C substitutions), and a non-native disulfide bond between cysteines introduced by 183GC and 428C substitutions (such as N183GC and N428C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 149C and 458C substitutions (such as A149C and Y458C substitutions), and a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 149C and 458C substitutions (such as A149C and Y458C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 183GC and 428C substitutions (such as N183GC and N428C substitutions), and a pair of cysteines introduced by substitutions at one of RSV F positions 98-100 and one of RSV F positions 360-362 (such as 100C and 362C substitutions, 99C and 362C substitutions, 98C and S362C substitution, 100C and 361C substitutions, 99C and 361C substitutions, or 98C and S361C substitutions, for example, T100C and S362C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 183GC and 428C substitutions (such as N183GC and N428C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in the RSV F ectodomain trimer can comprise the Cav1 substitutions, and also a non-native disulfide bond between cysteines introduced by 183GC and 428C substitutions (such as N183GC and N428C substitutions), and a non-native disulfide bond between cysteines introduced by 369C and 455C substitutions (such as T369C and T455C substitutions), for stabilization of the RSV F ectodomain trimer in the RSV F prefusion conformation.

In some embodiments, the recombinant $F_2$-$F_1$ ectodomain protomers in any of the RSV F ectodomain trimers disclosed herein can further comprise a non-native inter-protomer disulfide bond between cysteines introduced by 74C and 218C substitutions (such as A74C and E218C substitutions).

In some embodiments, the recombinant $F_2$-$F_1$ ectodomain protomers in any of the RSV F ectodomain trimers disclosed herein can further comprise a non-native inter-protomer disulfide bond between cysteines introduced by 485C and 494C substitutions (such as S485C and Q4948C substitutions).

In some embodiments, the recombinant $F_2$-$F_1$ ectodomain protomers in any of the RSV F ectodomain trimers disclosed herein can further comprise a non-native inter-protomer disulfide bond between cysteines introduced by 485C and 494C substitutions (such as S485C and Q4948C substitutions).

In some embodiments, the recombinant $F_2$-$F_1$ ectodomain protomers in any of the RSV F ectodomain trimers disclosed herein can further comprise an L373R substitution. In the single-chain RSV F context, the fusion peptide is deleted. The fusion peptide (L141, L142) would normally interact with the L373 residue and it would not be solvent exposed. In the absence of the fusion peptide, the L373R mutation can be introduced as a compatible solvent exposed residue to increase protein yield.

In some embodiments, the recombinant $F_2$-$F_1$ ectodomain protomers in any of the RSV F ectodomain trimers disclosed herein can comprise additional amino acid substitutions that are known to increase the stability or expression of the RSV F ectodomain trimer. For example, in some embodiments, the recombinant $F_2$-$F_1$ ectodomain protomers in any of the RSV F ectodomain trimers disclosed herein can comprise at least one of the following amino acid substitutions: S46G, N67I, E92D, L95M, I221M, R429K, K465Q, S215P, or I217P.

In some embodiments, the recombinant $F_2$-$F_1$ ectodomain protomers in any of the RSV F ectodomain trimers disclosed herein can further comprise L95M, I221M, and R429K substitutions to increase the stability and/or expression of the RSV F ectodomain trimer.

In some embodiments, the recombinant $F_2$-$F_1$ ectodomain protomers in any of the RSV F ectodomain trimers disclosed herein can further comprise L95M, I221M, R429K, and I217P substitutions to increase the stability and/or expression of the RSV F ectodomain trimer.

In some embodiments, the recombinant $F_2$-$F_1$ ectodomain protomers in any of the RSV F ectodomain trimers disclosed herein can further comprise S46G, K465Q, S215P, and E92D substitutions to increase the stability and/or expression of the RSV F ectodomain trimer.

In some embodiments, the recombinant $F_2$-$F_1$ ectodomain protomers in any of the RSV F ectodomain trimers disclosed herein can further comprise S46G, K465Q, S215P, E92D, and N67I substitutions to increase the stability and/or expression of the RSV F ectodomain trimer.

Stabilization of the recombinant RSV F ectodomain trimer in the prefusion conformation preserves the presence of antigenic site Ø. Thus, the disclosed recombinant RSV F ectodomain can specifically bind to a pre-fusion specific antibody that targets antigenic site Ø, such as AM22, D25, or 5C4. Additionally, other antibodies that are pre-fusion specific, but do not bind antigenic site Ø (such as MPE8) can also be used to identify a RSV F protein stabilized in a prefusion conformation. Typically, the recombinant RSV F ectodomain specifically binds to the prefusion specific antibody with a dissociation constant of less than about $10^{-6}$ Molar, such as less than about $10^{-7}$ Molar, $10^{-8}$ Molar, or less than $10^{-9}$ Molar. Specific binding can be determined by methods known in the art. The determination of specific binding may readily be made by using or adapting routine procedures, such as ELISA, immunocompetition, surface plasmon resonance, or other immunosorbant assays (described in many standard texts, including Harlow and Lane, *Using Antibodies: A Laboratory Manual*, CSHL, New York, 1999).

In the purified trimer, recombinant $F_2$-$F_1$ ectodomain protomers typically do not include a signal peptide (for example, the recombinant $F_2$-$F_1$ ectodomain protomers typically do not include RSV F positions 1-25), as the signal peptide is proteolytically cleaved during cellular processing. In embodiments including a soluble recombinant RSV F ectodomain trimer, the recombinant $F_2$-$F_1$ ectodomain protomers are not linked to a transmembrane domain or other membrane anchor. However, in embodiments including a membrane anchored recombinant RSV F ectodomain trimer, the F2 ectodomain portion of the recombinant $F_2$-$F_1$ ectodomain protomer can be linked to a transmembrane domain (such as, but not limited to, an RSV F transmembrane domain) In several embodiments, the N-terminal position of the recombinant F2 polypeptide in the recombinant $F_2$-$F_1$ ectodomain protomer can be one of RSV F positions 20-30 (such as position 26), and the C-terminal position of the $F_1$ ectodomain in the recombinant $F_2$-$F_1$ ectodomain protomer can be one of RSV F positions 510-525 (such as position 511, position 513, or position 523. In some embodiments, the C-terminal position of the F1 ectodomain in the recombinant $F_2$-$F_1$ ectodomain protomer can be one of RSV F positions 520-525.

Native RSV F proteins from different RSV groups, as well as nucleic acid sequences encoding such proteins and methods, are known. The disclosed recombinant RSV F ectodomain trimers can be derived from any type of RSV, such as subtype A (e.g., A1 or A2), subtype B (e.g., B1 or B2), or bovine RSV. RSV F proteins from the different RSV subtypes, as well as nucleic acid sequences encoding such proteins and methods for the manipulation and insertion of such nucleic acid sequences into vectors, are known (see, e.g., PCT Pub. No. WO2014160463, incorporated by reference herein; Sambrook et al. (Molecular Cloning: A Laboratory Manual, 4$^{th}$ ed, Cold Spring Harbor, New York, 2012) and Ausubel et al. (In Current Protocols in Molecular Biology, John Wiley & Sons, New York, through supplement 104, 2013).

In some embodiments, any of the RSV F ectodomain trimers including a recombinant $F_2$-$F_1$ ectodomain protomer disclosed herein can include an amino acid sequence (such as positions 26-103 and 145-513) of a native RSV F, for example, from subtype A (e.g., A1 or A2), subtype B (e.g., B1 or B2), or bovine RSV as available as SEQ ID NOs: 1-184 in PCT Pub. No. WO2014160463, or as set forth in Table 1 below, or an amino acid sequence at least 90% (such as at least 95%, at least 96%, at least 97%, at least 98% or at least 99%) identical thereto that has been modified by one or more amino acid substitutions and/or insertions as discussed herein for optimization of immunogenicity, expression, and stabilization in the prefusion conformation (for example, that include the sc9-10 single chain modification, Cav1 or DS-Cav1 substitutions, and at least one of A149C and Y458C substitutions, N183GC and N428C substitutions, T100C and S362C substitutions, or T369C and T455C substitutions).

TABLE 1

Exemplary Native RSV F protein sequences

RSV F subtype A (Accession No. P03420.1)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPPTNNRARRELPRFMNYTLNNAKKTNVTLSKKRKRRFLGFLLGVGSAIASGV
AVSKVLHLEGEVNKIKSALLSTNKAVVSLSNGVSVLTSKVLDLKNYIDKQLLPIVNKQSCSISNIETVIEFQQKNN
RLLEITREFSVNAGVTTPVSTYMLTNSELLSLINDMPITNDQKKLMSNNVQIVRQQSYSIMSIIKEEVLAYVVQLP
LYGVIDTPCWKLHTSPLCTTNTKEGSNICLTRTDRGWYCDNAGSVSFFPQAETCKVQSNRVFCDTMNSLTLPSEIN
LCNVDIFNPKYDCKIMTSKTDVSSSVITSLGAIVSCYGKTKCTASNKNRGIIKTFSNGCDYVSNKGMDTVSVGNTL
YYVNKQEGKSLYVKGEPIINFYDPLVFPSDEFDASISQVNEKINQSLAFIRKSDELLHNVNAGKSTTNIMITTIII
VIIVILLSLIAVGLLLYCKARSTPVTLSKDQLSGINNIAFSN (SEQ ID NO: 57)

RSV F subtype A (Accession No. P03420.1 with P102A substitution)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATNNRARRELPRFMNYTLNNAKKTNVTLSKKRKRRFLGFLLGVGSAIASGV
AVSKVLHLEGEVNKIKSALLSTNKAVVSLSNGVSVLTSKVLDLKNYIDKQLLPIVNKQSCSISNIETVIEFQQKNN
RLLEITREFSVNAGVTTPVSTYMLTNSELLSLINDMPITNDQKKLMSNNVQIVRQQSYSIMSIIKEEVLAYVVQLP
LYGVIDTPCWKLHTSPLCTTNTKEGSNICLTRTDRGWYCDNAGSVSFFPQAETCKVQSNRVFCDTMNSLTLPSEVN
LCNVDIFNPKYDCKIMTSKTDVSSSVITSLGAIVSCYGKTKCTASNKNRGIIKTFSNGCDYVSNKGVDTVSVGNTL
YYVNKQEGKSLYVKGEPIINFYDPLVFPSDEFDASISQVNEKINQSLAFIRKSDELLHNVNAGKSTTNIMITTIII
VIIVILLSLIAVGLLLYCKARSTPVTLSKDQLSGINNIAFSN (SEQ ID NO: 58)

RSV F subtype A (Accession No. CAA26143.1)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATNNRARRELPRFMNYTLNNAKKTNVTLSKKRKRRFLGFLLGVGSAIASGV
AVSKVLHLEGEVNKIKSALLSINKAVVSLSNGVSVLTSKVLDLKNYIDKQLLPIVNKQSCSISNIETVIEFQQKNN
RLLEITREFSVNAGVTTPVSTYMLINSELLSLINDMPITNDQKKLMSNNVQIVRQQSYSIMSIIKEEVLAYVVQLP
LYGVIDTPCWKLHTSPLCTTNTKEGSNICLTRTDRGWFCDNAGSVSFFPQAETCKVQSNRVFCDTMNSLTLPSEVN
LCNVDIFNPKYDCKIMTSKTDVSSSVITSLGAIVSCYGKTKCTASNKNRGIIKTFSNGCDYVSNKGVDTVSVGNTL
YYVNKQEGKSLYVKGEPIINFYDPLVFPSDEFDASISQVNEKINQSLAFIRKSDELLHNVNAGKSTTNIMITTIII
VIIVILLSLIAVGLLLYCKARSTPVTLSKDQLSGINNIAFSN (SEQ ID NO: 59)

RSV F subtype B (Accession No. O36634.1)
MELLIHRLSAIFLTLAINALYLTSSQNITEEFYQSTCSAVSRGYFSALRTGWYTSVITIELSNIKETKCNGTDTKV
KLIKQELDKYKNAVTELQLLMQNTPAANNRARREAPQYMNYTINTTKNLNVSISKKRKRRFLGFLLGVGSAIASGI
AVSKVLHLEGEVNKIKNALLSTNKAVVSLSNGVSVLTSKVLDLKNYINNQLLPIVNQQSCRISNIETVIEFQQKNS
RLLEINREFSVNAGVTTPLSTYMLTNSELLSLINDMPITNDQKKLMSSNVQIVRQQSYSIMSIIKEEVLAYVVQLP
IYGVIDTPCWKLHTSPLCTTNIKEGSNICLTRTDRGWYCDNAGSVSFFPQADTCKVQSNRVFCDTMNSLTLPSEVS
LCNTDIFNSKYDCKIMTSKTDISSSVITSLGAIVSCYGKTKCTASNKNRGIIKTFSNGCDYVSNKGVDTVSVGNTL
YYVNKLEGKNLYVKGEPIINYYDPLVFPSDEFDASISQVNEKINQSLAFIRRSDELLHNVNTGKSTTNIMITTIII
VIIVVLLSLIAIGLLLYCKAKNTPVTLSKDQLSGINNIAFSK (SEQ ID NO: 60)

hRSV F subtype B (Accession No. NP_056863.1)
MELLIHRLSAIFLTLAINALYLTSSQNITEEFYQSTCSAVSRGYFSALRTGWYTSVITIELSNIKETKCNGTDTKV
KLIKQELDKYKNAVTELQLLMQNTPAANNRARREAPQYMNYTINTTKNLNVSISKKRKRRFLGFLLGVGSAIASGI
AVSKVLHLEGEVNKIKNALLSTNKAVVSLSNGVSVLTSKVLDLKNYINNQLLPIVNQQSCRISNIETVIEFQQKNS
RLLEINREFSVNAGVTTPLSTYMLTNSELLSLINDMPITNDQKKLMSSNVQIVRQQSYSIMSIIKEEVLAYVVQLP
IYGVIDTPCWKLHTSPLCTTNIKEGSNICLTRTDRGWYCDNAGSVSFFPQADTCKVQSNRVFCDTMNSLTLPSEVS
LCNTDIFNSKYDCKIMTSKTDISSSVITSLGAIVSCYGKTKCTASNKNRGIIKTFSNGCDYVSNKGVDTVSVGNTL
YYVNKLEGKNLYVKGEPIINYYDPLVFPSDEFDASISQVNEKINQSLAFIRRSDELLHNVNTGKSTTNIMITTIII
VIIVVLLSLIAIGLLLYCKAKNTPVTLSKDQLSGINNIAFSK (SEQ ID NO: 61)

RSV F subtype B (Accession No. AAB82436)
MELLIHRLSAIFLTLAINALYLTSSQNITEEFYQSTCSAVSRGYFSALRTGWYTSVITIELSNIKETKCNGTDTKV
KLIKQELDKYKNAVTELQLLMQNTPAANNRARREAPQYMNYTINTTKNLNVSISKKRKRRFLGFLLGVGSAIASGI
AVSKVLHLEGEVNKIKNALLSTNKAVVSLSNGVSVLTSKVLDLKNYINNQLLPIVNQQSCRISNIETVIEFQQKNS
RLLEINREFSVNAGVTTPLSTYMLTNSELLSLINDMPITNDQKKLMSSNVQIVRQQSYSIMSIIKEEVLAYVVQLP
IYGVIDTPCWKLHTSPLCTTNIKEGSNICLTRTDRGWYCDNAGSVSFFPQADTCKVQSNRVFCDTMNSLTLPSEVS
LCNTDIFNSKYDCKIMTSKTDISSSVITSLGAIVSCYGKTKCTASNKNRGIIKTFSNGCDYVSNKGVDTVSVGNTL
YYVNKLEGKNLYVKGEPIINYYDPLVFPSDEFDASISQVNEKINQSLAFIRRSDELLHNVNTGKSTTNIMITTIII
VIIVVLLSLIAIGLLLYCKAKNTPVTLSKDQLSGINNIAFSK (SEQ ID NO: 62)

TABLE 1-continued

| Exemplary Native RSV F protein sequences |
| --- |
| Bovine RSV F (Accession No. P29791.1)<br>MATTTMRMIISIILISTYVPHITLCQNITEEFYQSTCSAVSRGYLSALRTGWYTSVVTIELSKIQKNVCNGTDSKV<br>KLIKQELERYNNAVAELQSLMQNEPTSSSRAKRGIPESIHYTRNSTKKFYGLMGKKRKRRFLGFLLGIGSAIASGV<br>AVSKVLHLEGEVNKIKNALLSTNKAVVSLSNGVSVLTSKVLDLKNYIDKELLPKVNNHDCRISNIATVIEFQQKNN<br>RLLEIAREFSVNAGITTPLSTYMLINSELLSIINDMPITNDQKKLMSVCQIVRQQSYSIMSVLREVIAYVVQLPLY<br>GVIDTPCWKLHTSPLCTTDNKEGSNICLTRTDRGWYCDNAGSVSFFPQAETCKVQSNRVFCDTMNSLTLPTDVNLC<br>NTDIFNSKYDCKIMTSKTDISSSVITSIGAIVSCYGKTKCTASNKNRGIIKTFSNGCDYVSNKGVDTVSVGNTLYY<br>VNKLEGKALYIKGEPIINYYNPLVFPSDEFDASIAQVNAKINQSLAFIRRSDELLHSVDVGKSTTNVVITTIIIVI<br>VVVILMLITVGLLFYCKTRSTPIMLGKDQLSSINNLSFSK (SEQ ID NO: 63) |
| Bovine RSV F (Accession No. P22167.1)<br>MAATAMRMIISIIFISTYMTHITLCQNITEEFYQSTCSAVSRGYLSALRTGWYTSVVTIELSKIQKNVCKSTDSKV<br>KLIKQELERYNNAVIELQSLMQNEPASFSRAKRGIPELIHYTRNSTKRFYGLMGKKRKRRFLGFLLGIGSAIASGV<br>AVSKVLHLEGEVNKIKNALLSTNKAVVSLSNGVSVLTSKVLDLKNYIDKELLPKVNNHDCRISNIETVIEFQQKNN<br>RLLEIAREFSVNAGITTPLSTYMLTNSELLSLINDMPITNDQKKLMSSNVQIVRQQSYSIMSVVKEEVIAYVVQLP<br>IYGVIDTPCWKLHTSPLCTTDNKEGSNICLTRTDRGWYCDNAGSVSFFPQAETCKVQSNRVFCDTMNSLTLPTDVN<br>LCNTDIFNTKYDCKIMTSKTDISSSVITSIGAIVSCYGKTKCTASNKNRGIIKTFSNGCDYVSNKGVDTVSVGNTL<br>YYVNKLEGKALYIKGEPIINYYDPLVFPSDEFDASIAQVNAKINQSLAFIRRSDELLHSVDVGKSTTNVVITTIII<br>VIVVVILMLIAVGLLFYCKTRSTPIMLGKDQLSGINNLSFSK (SEQ ID NO: 64) |
| bRSV F strain ATue51908 (Accession No. NP_048055.1, and also SEQ ID NO: 181 of WO2014160463) (SEQ ID NO: 114)<br>MATTAMRMIISIIFISTYVTHITLCQNITEEFYQSTCSAVSRGYLSALRTGWYTSVVTIELSKIQKNVCKSTDSKV<br>KLIKQELERYNNAVVELQSLMQNEPASFSRAKRGIPELIHYTRNSTKKFYGLMGKKRKRRFLGFLLGIGSAVASGV<br>AVSKVLHLEGEVNKIKNALLSTNKAVVSLSNGVSVLTSKVLDLKNYIDKELLPQVNNHDCRISNIETVIEFQQKNN<br>RLLEIAREFSVNAGITTPLSTYMLTNSELLSLINDMPITNDQKKLMSSNVQIVRQQSYSIMSVVKEEVIAYVVQLP<br>IYGVIDTPCWKLHTSPLCTTDNKEGSNICLTRTDRGWYCDNAGSVSFFPQTETCKVQSNRVFCDTMNSLTLPTDVN<br>LCNTDIFNTKYDCKIMTSKTDISSSVITSIGAIVSCYGKTKCTASNKNRGIIKTFSNGCDYVSNKGVDTVSVGNTL<br>YYVNKLEGKALYIKGEPIINYYDPLVFPSDEFDASIAQVNAKINQSLAFIRRSDELLHSVDVGKSTTNVVITTIII<br>VIVVVILMLIAVGLLFYCKTKSTPIMLGKDQLSGINNLSFSK |
| bRSV F strain RB94 (Accession No. CAN90052.1) (SEQ ID NO: 115)<br>MATTTMRMIISIIIIFIYVQHITLCQNITEEFYQSTCSAVSRGYLSALRTGWYTSVVTIELSKIQKNVCNSTDSNV<br>KLIKQELERYNNAVVELQSLMQNEPASSSRAKRGIPELIHYKRNSTKKFYGLMGKKRKRRFLGFLLGIGSAIASGV<br>AVSKVLHLEGEVNKIKNALLSTNKAVVSLSNGVSVLTSKVLDLKNYIDKELLPKVNNHDCQISNIATVIEFQQKNN<br>RLLEIAREFSVNAGITTPLSTYMLTNSELLSLINDMPITNDQKKLMSSNVQIVRQQSYSIMSVVKEEVMAYVVQLP<br>IYGVIDTPCWKLHTSPLCTTDNKEGSNICLTRTDRGWYCDNAGSVSFFPQAETCKVQSNRVFCDTMNSLTLPTDVN<br>LCNTDIFNAKYDCKIMTSKTDISSSVITSIGAIVSCYGKTKCTASNKNRGIIKTFSNGCDYVSNRGVDTVSVGNTL<br>YYVNKLEGKALYIKGEPIINYYDPLVFPSDEFDASIAQVNAKINQSLAFIRRSDELLHSVDVGKSTTNVVITTIII<br>VIVVVILMLIAVGLLFYSKTRSTPIMLGKDQLSGINNLSFSK |
| bRSV F strain 391-2 (Accession No. AAA42808.1, and also SEQ ID NO: 178 of WO2014160463)) (SEQ ID NO: 116)<br>MAATAMRMIISIIFISTYMTHITLCQNITEEFYQSTCSAVSRGYLSALRTGWYTSVVTIELSKIQKNVCKSTDSKV<br>KLIKQELERYNNAVIELQSLMQNEPASFSRAKRGIPELIHYTRNSTKRFYGLMGKKRKRRFLGFLLGIGSAIASGV<br>AVSKVLHLEGEVNKIKNALLSTNKAVVSLSNGVSVLTSKVLDLKNYIDKELLPKVNNHDCRISNIETVIEFQQKNN<br>RLLEIAREFSVNAGITTPLSTYMLINSELLSLINDMPITNDQKKLMSSNVQIVRQQSYSIMSVVKEEVIAYVVQLP<br>IYGVIDTPCWKLHTSPLCTTDNKEGSNICLTRTDRGWYCDNAGSVSFFPQAETCKVQSNRVFCDTMNSLTLPTDVN<br>LCNTDIFNTKYDCKIMTSKTDISSSVITSIGAIVSCYGKTKCTASNKNRGIIKTFSNGCDYVSNKGVDTVSVGNTL<br>YYVNKLEGKALYIKEPIINYYDPLVFPSDEFDASIAQVNAKINQSLAFIRRSDELLHSVDVGKSTTNVVITTIIIV<br>IVVVILMLIAVGLLFYCKTRSTPIMLGKDQLSGINNLSFSK |

The recombinant $F_2$-$F_1$ ectodomain protomers in the recombinant RSV F ectodomain trimer can comprise modifications of the native RSV sequence, such as amino acid substitutions, deletions or insertions, glycosylation and/or covalent linkage to unrelated proteins (e.g., a protein tag), as long as the recombinant RSV F ectodomain remains stabilized in the prefusion conformation. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, $4^{th}$ ed., Cold Spring Harbor, New York, 2012) and Ausubel et al. (In Current Protocols in Molecular Biology, John Wiley & Sons, New York, through supplement 104, 2013, both of which are incorporated herein by reference in their entirety.

In some embodiments, the recombinant $F_2$-$F_1$ ectodomain protomers in the recombinant RSV F ectodomain trimer can comprise one or more amino acid substitutions compared to a corresponding native RSV F sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions (such as conservative amino acid substitutions) compared to a native RSV F ectodomain sequence (e.g., a native $F_2$ or $F_1$ ectodomain protein sequence from a subgroup A, B, or bovine RSV F protein), such the sequence of a RSV F protein set forth as one of SEQ ID NOs: 57-64, in addition to the sc9-10 modification, the DS-Cav2 substitutions, and the additional amino acid substitutions as described above. The simplest modifications involve the substitution of one or more amino acids for amino acids having similar biochemical properties, such as conservative amino acid substitutions. Such substitutions are likely to have minimal impact on the activity of the resultant protein.

In some embodiments, recombinant $F_2$-$F_1$ ectodomain protomers in the recombinant RSV F ectodomain trimer can be joined at either end to other unrelated sequences (for example non-RSV F protein sequences, non-viral envelope, or non-viral protein sequences)

In several embodiments, the recombinant RSV F ectodomain trimers disclosed herein are soluble in aqueous solution. In some embodiments, the recombinant RSV F ectodomain dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remain dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM). The person of skill in the art is familiar with methods of determining if a protein remains in solution over time. For example, the concentration of the protein dissolved in an aqueous solution can be tested over time using standard methods.

In some embodiments, the recombinant RSV F ectodomain trimer can be provided as a homogenous population that does not include detectable RSV F ectodomain trimer in a post-fusion conformation. The conformation of the RSV F ectodomain trimer can be detected, for example, by negative stain electron microscopy and/or specific binding by appropriate pre- or post-fusion specific antibody. In some embodiments, at least about 95% of the recombinant RSV F ectodomain trimer (such as at least about 95%, 96%, 97%, 98%, 99% or 99.9% of the RSV F proteins) in the homogeneous population are stabilized in the prefusion conformation.

In some embodiments, the recombinant RSV F ectodomain trimer retains specific binding for a prefusion specific antibody following incubation at 70° C. for one hour in phosphate buffered saline. For example, a solution of the recombinant RSV F ectodomain trimer in phosphate buffered saline can retain at least 50% (such at least 70%) binding activity for a prefusion specific antibody (such as D25, AM22, 5C4, or MPE8) following incubation at 70° C.

In some embodiments, the recombinant RSV F ectodomain trimer retains specific binding for a prefusion specific antibody following incubation at 70° C. for one hour in phosphate buffered saline. For example, a solution of the recombinant RSV F ectodomain trimer in phosphate buffered saline can retain at least 50% (such at least 70%) binding activity for a prefusion specific antibody (such as D25, AM22, 5C4, or MPE8) following incubation at 70° C.

In some embodiments, the recombinant RSV F ectodomain trimer retains specific binding for a prefusion specific antibody following incubation at 4° C. for six months in phosphate buffered saline. For example, a solution of the recombinant RSV F ectodomain trimer in phosphate buffered saline can retain at least 50% (such at least 70%, at least 80%, or at least 90%) binding activity for a prefusion specific antibody (such as D25, AM22, 5C4, or MPE8) following incubation at 4° C. for six months.

In certain embodiments, an immunogen provided herein may be further modified to contain additional nonproteinaceous moieties that are known in the art and readily available. The moieties suitable for derivatization of the immungen include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

The recombinant RSV F ectodomain can be derivatized or linked to another molecule (such as another peptide or protein). In general, the recombinant RSV F ectodomain is derivatized such that the binding to broadly neutralizing antibodies to a trimer of the recombinant RSV F protein, such as D25 or AM22, is not affected adversely by the derivatization or labeling. For example, the recombinant RSV F ectodomain can be functionally linked (by chemical coupling, genetic fusion, non-covalent association or otherwise) to one or more other molecular entities, such as an antibody or protein or detection tag.

Some of the sequences of recombinant RSV F ectodomain provided herein include the sequence of protease cleavage sites (such as thrombin sites), protein tags (such as a His tag, a Strep Tag II, a Avi tag, etc.), signal peptides, that the person of ordinary skill in the art will understand would not be included in an isolated immunogen including a recombinant RSV F ectodomain trimer for therapeutic use.

Linkage to a Trimerization Domain

In several embodiments, the recombinant $F_2$-$F_1$ ectodomain protomers in the disclosed recombinant RSV F ectodomain trimers can be linked at their C-terminus (C-terminal linkage) to a trimerization domain to promote trimerization of the recombinant $F_2$-$F_1$ ectodomain protomers, and to stabilize the membrane proximal aspect of the recombinant RSV F ectodomain trimer in a trimeric configuration.

For example, the C-terminus of each of the recombinant $F_2$-$F_1$ ectodomain protomers in a disclosed recombinant RSV F ectodomain trimer can be directly linked to the trimerization domain, or indirectly linked to the trimerization domain via a peptide linker. Exemplary linkers include glycine and glycine-serine linkers. In some embodiments, the peptide linker can comprise the amino acid sequence set forth as SAIG (SEQ ID NO: 65).

Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344:191-195), collagen (McAlinden et al. 2003 *J Biol Chem* 278:42200-42207), and the phage T4 fibritin Foldon (Miroshnikov et al. 1998 *Protein Eng* 11:329-414), any of which can be linked to the C-terminus of the recombinant $F_2$-$F_1$ ectodomain protomers to promote trimerization, as long as the recombinant RSV F ectodomain trimer retains the antigenic site Ø and specific binding activity for a prefusion specific antibodies (e.g., D25).

In some examples, the recombinant $F_2$-$F_1$ ectodomain protomers in a disclosed recombinant RSV F ectodomain trimer can be linked to a T4 fibritin trimerization domain, for example, each recombinant $F_2$-$F_1$ ectodomain protomer in a trimer can include a C-terminal linkage to the T4 fibritin trimerization domain, such as a linkage to any one of RSV F positions 490-515, such as RSV F position 513. In specific examples, the T4 fibritin trimerization domain can comprise the amino acid sequence GYIPEAPRDGQAY-VRKDGEWVLLSTF (SEQ ID NO: 66), which adopts a β-propeller conformation, and can fold and trimerize in an autonomous way (Tao et al. 1997 *Structure* 5:789-798).

The recombinant RSV F ectodomain linked to the trimerization domain can include any of the stabilizing mutations provided herein (or combinations thereof) as long as the recombinant RSV F ectodomain linked to the trimerization domain retains the desired properties (e.g., the RSV F prefusion conformation including antigenic site Ø).

In additional embodiments, the recombinant $F_2$-$F_1$ ectodomain protomers in the disclosed recombinant RSV F ectodomain trimers can be linked to a "cysteine-zipper" trimerization domain. The cysteine zipper trimerization domain is similar in structure to a leucine zipper domain, and includes a coiled-coil domain with cysteine residues in place of the corresponding leucine residues of the coiled-coil domain of a leucine zipper (see, e.g., Stewart-Jones et al, PLoS One, 10(6):e0128779, 2015, which is incorporated by reference herein in its entirety). The cysteine residues form inter-protomer disulfide bonds to stabilize the three protomers in a trimeric configuration.

In such embodiments, the cysteine zipper domain comprises a coiled-coil domain with three parallel α-helices, each based on a portion of the α10 helix of the native RSV F protein beginning at approximately position 512. The α10 helix of the native RSV F protein in its prefusion conformation begins at approximately position 492 of the F protein and extends in the C-terminal direct to the transmembrane domain (which begins approximately at residue 529). Adjacent to the cell membrane, the three α10 helices of the native RSV F ectodomain form a coiled-coil domain Cysteine residues are introduced into the sequence of the coiled-coil to allow for formation of inter-protomer disulfide bonds between the α-helices of the coiled-coil, thereby "locking" the three α-helices in the trimeric configuration. The length of the native coiled-coil domain is sufficient for introduction of three rings of di-cysteine motifs (at heptad positions g and a, beginning at RSV F position 512). In several embodiments, the cysteine substitutions are present at RSV F positions 512, 513, 519, 520, 526, and 527. Interprotomer disulfide bonds can form between the cysteine residues of each ring of di-cysteine motifs, thereby stabilizing the recombinant RSV F protein in the trimeric configuration. For example, position 511 of each recombinant $F_2$-$F_1$ ectodomain protomer in the Recombinant RSV F ectodomain trimer can be linked to one of the following cysteine zipper domain sequences (depending on RSV subtype):

hRSV F subtype A DS-Cav1, ABC ring: ${}_{512}$CCHNVN-ACCSTTNICCTT (SEQ ID NO: 67)

hRSV F subtype B DS-Cav1, ABC ring: ${}_{512}$CCHNVNT-CCSTTNICCTT (SEQ ID NO: 68)

Bovine RSV F DS-Cav1, ABC ring: ${}_{512}$CCHSVDVCC-STTNVCCTT (SEQ ID NO: 69)

In some embodiments, the three parallel a-helices in the cysteine zipper trimerization domain can be elongated compared to the corresponding a-helical structures in a native RSV F protein. Typically, the α-helices in the elongated coiled-coil domain include about 23-25 residues extending C-terminal from position 512 of the $F_1$ ectodomain In contrast, the α-helices in the corresponding native coiled-coil domain include about 18 residues extending C-terminal from position 512 of the $F_1$ ectodomain. Any sequences that adequately form a trimeric coiled-coil domain can be used in the elongated coiled-coil domain, as long as the resulting elongated coiled-coil domain includes cysteine residues and appropriate g and a heptad positions that can form interprotomer disulfide bonds. In several embodiments, the cysteine substitutions are present at RSV F positions 512, 513, 519, 520, 526, and 527, and also "RSV F positions" 533 and 534 of the elongated portion of the cysteine zipper. Interprotomer disulfide bonds can form between the cysteine residues of each ring of di-cysteine motifs, thereby stabilizing the recombinant RSV F protein in the trimeric configuration. For example, position 511 of each recombinant $F_2$-$F_1$ ectodomain protomer in the Recombinant RSV F ectodomain trimer can be linked to one of the following cysteine zipper domain sequences (depending on RSV subtype):

hRSV F subtype A DS-Cav1, ABCD ring: ${}_{512}$CCHN-VNACCSTTNICCTTTNICCTT (SEQ ID NO: 70)

hRSV F subtype B DS-Cav1, ABCD ring: ${}_{512}$CCHNVNT-CCSTTNICCTTTNICCTT (SEQ ID NO: 71)

Bovine RSV F DS-Cav1, ABCD ring: ${}_{512}$CCHSVDVCC-STTNVCCTTTNVCCTT (SEQ ID NO: 72)

Membrane Anchored Embodiments

In some embodiments, the RSV F ectodomain trimer can be membrane anchored, for example, for embodiments where the RSV F ectodomain trimer is expressed on an attenuated viral vaccine, or a virus like particle. In such embodiments, the recombinant $F_2$-$F_1$ ectodomain protomers in the trimer typically each comprise a C-terminal linkage to a transmembrane domain. In some embodiments, one or more peptide linkers (such as a gly-ser linker, for example, a 10 amino acid glycine-serine peptide linker can be used to link the recombinant $F_2$-$F_1$ ectodomain protomer to the transmembrane domain.

Non-limiting examples of transmembrane domains for use with the disclosed embodiments include a RSV F transmembrane domain, such as IIIVIIVILLSLIAVGLL-LYC (SEQ ID NO: 57, residues 530-550), the Influenza A Hemagglutinin™ domain (ILAIYSTVASSLVLLVSL-GAISF, SEQ ID NO: 73), and the Influenza A Neuraminidase™ domain (IITIGSICMVVGIISLILQIGNIISIWVS, SEQ ID NO: 74).

The recombinant $F_2$-$F_1$ ectodomain protomers linked to the transmembrane domain can include any of the stabilizing mutations provided herein (or combinations thereof) as long as the recombinant RSV F ectodomain trimer formed from the recombinant $F_2$-$F_1$ ectodomain protomers linked to the transmembrane domain retains the desired properties (e.g., the RSV F prefusion conformation including antigenic site Ø). In some embodiments, the recombinant RSV F ectodomain trimer can be linked to the $F_1$ transmembrane domain and cytosolic tail, for example, the protomers can comprise RSV F positions 26-103 linked (via a GS linker) to RSV F positions 145 to the F1 C-terminus (approximately position 574).

Exemplary Sequences

The following table provides sequences of recombinant $F_2$-$F_1$ ectodomain protomers including the sc9-10 single chain mutation and the DS-Cav1 mutations, and additional mutations identified herein for optimized stabilization, expression, and/or immunogenicity of the RSV F ectodomain trimer (for example, the D113C/X429GCG substitutions or D113C/G431GCG substitutions). The provided sequences include RSV F positions 1-103 linked to positions 145-513 by a glycine-serine peptide linker, and also include a T4 Fibritin trimerization domain linked to RSV F position 513 or 523 by a short peptide linker (SAIG). The signal peptide (RSV F positions 1-25) is removed during production in mammalian cells, leaving the recombinant $F_2$-$F_1$ ectodomain protomer (as a single polypeptide chain) linked to the T4 Fibritin trimerization domain. This protomer trimerizes to form the corresponding recombinant RSV F ectodomain trimer with a C-terminal T4 Fibritin trimerization domain at the membrane proximal lobe of the ectodomain.

TABLE 2

| Exemplary recombinant $F_2$-$F_1$ ectodomain protomer sequences |
|---|
| RSV A2 strain sc9-10, DS-Cav1, A149C-Y458C (SEQ ID NO: 1) |
| MELLILKANAITTILTAVTFCFASGQNITEEFYQSTCSAVSKGYLSALRTGWYTSVITIELSNIKENKCNGTDAKV |
| KLIKQELDKYKNAVTELQLLMQSTPATGSGSAICSGVAVCKVLHLEGEVNKIKSALLSTNKAVVSLSNGVSVLTFK |
| VLDLKNYIDKQLLPILNKQSCSISNIETVIEFQQKNNRLLEITREFSVNAGVTTPVSTYMLINSELLSLINDMPIT |
| NDQKKLMSNNVQIVRQQSYSIMCIIKEEVLAYVVQLPLYGVIDTPCWKLHTSPLCTTNTKEGSNICLTRTDRGWYC |
| DNAGSVSFFPQAETCKVQSNRVFCDTMNSRTLPSEVNLCNVDIFNPKYDCKIMTSKTDVSSSVITSLGAIVSCYGK |
| TKCTASNKNRGIIKTFSNGCDYVSNKGVDTVSVGNTLYCVNKQEGKSLYVKGEPIINFYDPLVFPSDEFDASISQV |
| NEKINQSLAFIRKSDELLSAIGGYIPEAPRDGQAYVRKDGEWVLLSTFLGGLVPRGSHHHHHHSAWSHPQFEK |
| |
| RSV A2 strain sc9-10, DS-Cav1, N183GC-N428C (SEQ ID NO: 2) |
| MELLILKANAITTILTAVTFCFASGQNITEEFYQSTCSAVSKGYLSALRTGWYTSVITIELSNIKENKCNGTDAKV |
| KLIKQELDKYKNAVTELQLLMQSTPATGSGSAIASGVAVCKVLHLEGEVNKIKSALLSTNKAVVSLSGCGVSVLTF |
| KVLDLKNYIDKQLLPILNKQSCSISNIETVIEFQQKNNRLLEITREFSVNAGVTTPVSTYMLINSELLSLINDMPI |
| TNDQKKLMSNNVQIVRQQSYSIMCIIKEEVLAYVVQLPLYGVIDTPCWKLHTSPLCTTNTKEGSNICLTRTDRGWY |
| CDNAGSVSFFPQAETCKVQSNRVFCDTMNSRTLPSEVNLCNVDIFNPKYDCKIMTSKTDVSSSVITSLGAIVSCYG |
| KTKCTASNKCRGIIKTFSNGCDYVSNKGVDTVSVGNTLYYVNKQEGKSLYVKGEPIINFYDPLVFPSDEFDASISQ |
| VNEKINQSLAFIRKSDELLSAIGGYIPEAPRDGQAYVRKDGEWVLLSTFLGGLVPRGSHHHHHHSAWSHPQFEK |
| |
| RSV A2 strain sc9-10, DS-Cav1, T100C-S362C (SEQ ID NO: 3) |
| MELLILKANAITTILTAVTFCFASGQNITEEFYQSTCSAVSKGYLSALRTGWYTSVITIELSNIKENKCNGTDAKV |
| KLIKQELDKYKNAVTELQLLMQSCPATGSGSAIASGVAVCKVLHLEGEVNKIKSALLSTNKAVVSLSNGVSVLTFK |
| VLDLKNYIDKQLLPILNKQSCSISNIETVIEFQQKNNRLLEITREFSVNAGVTTPVSTYMLINSELLSLINDMPIT |
| NDQKKLMSNNVQIVRQQSYSIMCIIKEEVLAYVVQLPLYGVIDTPCWKLHTSPLCTTNTKEGSNICLTRTDRGWYC |
| DNAGSVSFFPQAETCKVQCNRVFCDTMNSRTLPSEVNLCNVDIFNPKYDCKIMTSKTDVSSSVITSLGAIVSCYGK |
| TKCTASNKNRGIIKTFSNGCDYVSNKGVDTVSVGNTLYYVNKQEGKSLYVKGEPIINFYDPLVFPSDEFDASISQV |
| NEKINQSLAFIRKSDELLSAIGGYIPEAPRDGQAYVRKDGEWVLLSTFLGGLVPRGSHHHHHHSAWSHPQFEK |
| |
| RSV A2 strain sc9-10, DS-Cav1, T369C-T455C (SEQ ID NO: 4) |
| MELLILKANAITTILTAVTFCFASGQNITEEFYQSTCSAVSKGYLSALRTGWYTSVITIELSNIKENKCNGTDAKV |
| KLIKQELDKYKNAVTELQLLMQSTPATGSGSAIASGVAVCKVLHLEGEVNKIKSALLSTNKAVVSLSNGVSVLTFK |
| VLDLKNYIDKQLLPILNKQSCSISNIETVIEFQQKNNRLLEITREFSVNAGVTTPVSTYMLINSELLSLINDMPIT |
| NDQKKLMSNNVQIVRQQSYSIMCIIKEEVLAYVVQLPLYGVIDTPCWKLHTSPLCTTNTKEGSNICLTRTDRGWYC |
| DNAGSVSFFPQAETCKVQSNRVFCDCMNSRTLPSEVNLCNVDIFNPKYDCKIMTSKTDVSSSVITSLGAIVSCYGK |
| TKCTASNKNRGIIKTFSNGCDYVSNKGVDTVSVGNCLYYVNKQEGKSLYVKGEPIINFYDPLVFPSDEFDASISQV |
| NEKINQSLAFIRKSDELLSAIGGYIPEAPRDGQAYVRKDGEWVLLSTFLGGLVPRGSHHHHHHSAWSHPQFEK |
| |
| RSV B18537 strain sc9-10, DS-Cav1, A149C-Y458C (SEQ ID NO: 5) |
| MELLIHRSSAIFLTLAVNALYLTSSQNITEEFYQSTCSAVSRGYFSALRTGWYTSVITIELSNIKETKCNGTDTKV |
| KLIKQELDKYKNAVTELQLLMQNTPAAGSGSAICSGIAVCKVLHLEGEVNKIKNALLSTNKAVVSLSNGVSVLTFK |
| VLDLKNYINNRLLPILNQQSCRISNIETVIEFQQMNSRLLEITREFSVNAGVTTPLSTYMLTNSELLSLINDMPIT |
| NDQKKLMSSNVQIVRQQSYSIMCIIKEEVLAYVVQLPIYGVIDTPCWKLHTSPLCTTNIKEGSNICLTRTDRGWYC |
| DNAGSVSFFPQADTCKVQSNRVFCDTMNSRTLPSEVSLCNTDIFNSKYDCKIMTSKTDISSSVITSLGAIVSCYGK |
| TKCTASNKNRGIIKTFSNGCDYVSNKGVDTVSVGNTLYCVNKLEGKNLYVKGEPIINYYDPLVFPSDEFDASISQV |
| NEKINQSLAFIRRSDELLSAIGGYIPEAPRDGQAYVRKDGEWVLLSTFLGGLVPRGSHHHHHHSAWSHPQFEKS |
| |
| RSV B18537 strain sc9-10, DS-Cav1, N183GC-N428C (SEQ ID NO: 6) |
| MELLIHRSSAIFLTLAVNALYLTSSQNITEEFYQSTCSAVSRGYFSALRTGWYTSVITIELSNIKETKCNGTDTKV |
| KLIKQELDKYKNAVTELQLLMQNTPAAGSGSAIASGIAVCKVLHLEGEVNKIKNALLSTNKAVVSLSGCGVSVLTF |
| KVLDLKNYINNRLLPILNQQSCRISNIETVIEFQQMNSRLLEITREFSVNAGVTTPLSTYMLTNSELLSLINDMPI |
| TNDQKKLMSSNVQIVRQQSYSIMCIIKEEVLAYVVQLPIYGVIDTPCWKLHTSPLCTTNIKEGSNICLTRTDRGWY |
| CDNAGSVSFFPQADTCKVQSNRVFCDTMNSRTLPSEVSLCNTDIFNSKYDCKIMTSKTDISSSVITSLGAIVSCYG |
| KTKCTASNKCRGIIKTFSNGCDYVSNKGVDTVSVGNTLYYVNKLEGKNLYVKGEPIINYYDPLVFPSDEFDASISQ |
| VNEKINQSLAFIRRSDELLSAIGGYIPEAPRDGQAYVRKDGEWVLLSTFLGGLVPRGSHHHHHHSAWSHPQFEKS |
| |
| RSV B18537 strain sc9-10, DS-Cav1, T100C-S362C (SEQ ID NO: 7) |
| MELLIHRSSAIFLTLAVNALYLTSSQNITEEFYQSTCSAVSRGYFSALRTGWYTSVITIELSNIKETKCNGTDTKV |
| KLIKQELDKYKNAVTELQLLMQNCPAAGSGSAIASGIAVCKVLHLEGEVNKIKNALLSTNKAVVSLSNGVSVLTFK |
| VLDLKNYINNRLLPILNQQSCRISNIETVIEFQQMNSRLLEITREFSVNAGVTTPLSTYMLTNSELLSLINDMPIT |
| NDQKKLMSSNVQIVRQQSYSIMCIIKEEVLAYVVQLPIYGVIDTPCWKLHTSPLCTTNIKEGSNICLTRTDRGWYC |
| DNAGSVSFFPQADTCKVQCNRVFCDTMNSRTLPSEVSLCNTDIFNSKYDCKIMTSKTDISSSVITSLGAIVSCYGK |
| TKCTASNKNRGIIKTFSNGCDYVSNKGVDTVSVGNTLYYVNKLEGKNLYVKGEPIINYYDPLVFPSDEFDASISQV |
| NEKINQSLAFIRRSDELLSAIGGYIPEAPRDGQAYVRKDGEWVLLSTFLGGLVPRGSHHHHHHSAWSHPQFEKS |
| |
| RSV B18537 strain sc9-10, DS-Cav1, T369C-T455C (SEQ ID NO: 8) |
| MELLIHRSSAIFLTLAVNALYLTSSQNITEEFYQSTCSAVSRGYFSALRTGWYTSVITIELSNIKETKCNGTDTKV |
| KLIKQELDKYKNAVTELQLLMQNTPAAGSGSAIASGIAVCKVLHLEGEVNKIKNALLSTNKAVVSLSNGVSVLTFK |
| VLDLKNYINNRLLPILNQQSCRISNIETVIEFQQMNSRLLEITREFSVNAGVTTPLSTYMLINSELLSLINDMPIT |
| NDQKKLMSSNVQIVRQQSYSIMCIIKEEVLAYVVQLPIYGVIDTPCWKLHTSPLCTTNIKEGSNICLTRTDRGWYC |
| DNAGSVSFFPQADTCKVQSNRVFCDCMNSRTLPSEVSLCNTDIFNSKYDCKIMTSKTDISSSVITSLGAIVSCYGK |

TABLE 2-continued

| Exemplary recombinant $F_2$-$F_1$ ectodomain protomer sequences |
|---|

TKCTASNKNRGIIKTFSNGCDYVSNKGVDTVSVGNCLYYVNKLEGKNLYVKGEPIINYYDPLVFPSDEFDASISQV
NEKINQSLAFIRRSDELLSAIGGYIPEAPRDGQAYVRKDGEWVLLSTFLGGLVPRGSHHHHHHSAWSHPQFEKS bRSV F strain 376 sc9-10, DS-Cav1 (SEQ ID NO: 9)
MAATAMRMIISIIFISTYMTHITLCQNITEEFYQSTCSAVSRGYLSALRTGWYTSVVTIELSKIQKNVCKSTDSKV
KLIKQELERYNNAVIELQSLMQNEPASGSGSAIASGVAVCKVLHLEGEVNKIKNALLSTNKAVVSLSNGVSVLTFK
VLDLKNYIDKELLPKLNNHDCRISNIETVIEFQQKNNRLLEIAREFSVNAGITTPLSTYMLTNSELLSLINDMPIT
NDQKKLMSSNVQIVRQQSYSIMCVVKEEVIAYVVQLPIYGVIDTPCWKLHTSPLCTTDNKEGSNICLTRTDRGWYC
DNAGSVSFFPQAETCKVQSNRVFCDTMNSRTLPTDVNLCNTDIFNTKYDCKIMTSKTDISSSVITSIGAIVSCYGK
TKCTASNKNRGIIKTFSNGCDYVSNKGVDTVSVGNTLYYVNKLEGKALYIKGEPIINYYDPLVFPSDEFDASIAQV
NAKINQSLAFIRRSDELLSAIGGYIPEAPRDGQAYVRKDGEWVLLSTFLGGLVPRGSHHHHHHSAWSHPQFEK bRSV F strain 376 sc9-10, DS-Cav1, A149C-Y458C (SEQ ID NO: 10)
MAATAMRMIISIIFISTYMTHITLCQNITEEFYQSTCSAVSRGYLSALRTGWYTSVVTIELSKIQKNVCKSTDSKV
KLIKQELERYNNAVIELQSLMQNEPASGSGSAIASGVAVCKVLHLEGEVNKIKNALLSTNKAVVSLSNGVSVLTFK
VLDLKNYIDKELLPKLNNHDCRISNIETVIEFQQKNNRLLEIAREFSVNAGITTPLSTYMLTNSELLSLINDMPIT
NDQKKLMSSNVQIVRQQSYSIMCVVKEEVIAYVVQLPIYGVIDTPCWKLHTSPLCTTDNKEGSNICLTRTDRGWYC
DNAGSVSFFPQAETCKVQSNRVFCDTMNSRTLPTDVNLCNTDIFNTKYDCKIMTSKTDISSSVITSIGAIVSCYGK
TKCTASNKNRGIIKTFSNGCDYVSNKGVDTVSVGNTLYCVNKLEGKALYIKGEPIINYYDPLVFPSDEFDASIAQV
NAKINQSLAFIRRSDELLSAIGGYIPEAPRDGQAYVRKDGEWVLLSTFLGGLVPRGSHHHHHHSAWSHPQFEK bRSV F strain 376 sc9-10, DS-Cav1, N183GC-N428C (SEQ ID NO: 11)
MAATAMRMIISIIFISTYMTHITLCQNITEEFYQSTCSAVSRGYLSALRTGWYTSVVTIELSKIQKNVCKSTDSKV
KLIKQELERYNNAVIELQSLMQNEPASGSGSAIASGVAVCKVLHLEGEVNKIKNALLSTNKAVVSLSGCGVSVLTF
KVLDLKNYIDKELLPKLNNHDCRISNIETVIEFQQKNNRLLEIAREFSVNAGITTPLSTYMLTNSELLSLINDMPI
TNDQKKLMSSNVQIVRQQSYSIMCVVKEEVIAYVVQLPIYGVIDTPCWKLHTSPLCTTDNKEGSNICLTRTDRGWY
CDNAGSVSFFPQAETCKVQSNRVFCDTMNSRTLPTDVNLCNTDIFNTKYDCKIMTSKTDISSSVITSIGAIVSCYG
KTKCTASNKCRGIIKTFSNGCDYVSNKGVDTVSVGNTLYYVNKLEGKALYIKGEPIINYYDPLVFPSDEFDASIAQ
VNAKINQSLAFIRRSDELLSAIGGYIPEAPRDGQAYVRKDGEWVLLSTFLGGLVPRGSHHHHHHSAWSHPQFEK bRSV F strain 376 sc9-10, DS-Cav1, E100C-S362C (SEQ ID NO: 12)
MAATAMRMIISIIFISTYMTHITLCQNITEEFYQSTCSAVSRGYLSALRTGWYTSVVTIELSKIQKNVCKSTDSKV
KLIKQELERYNNAVIELQSLMQNCPASGSGSAIASGVAVCKVLHLEGEVNKIKNALLSTNKAVVSLSNGVSVLTFK
VLDLKNYIDKELLPKLNNHDCRISNIETVIEFQQKNNRLLEIAREFSVNAGITTPLSTYMLTNSELLSLINDMPIT
NDQKKLMSSNVQIVRQQSYSIMCVVKEEVIAYVVQLPIYGVIDTPCWKLHTSPLCTTDNKEGSNICLTRTDRGWYC
DNAGSVSFFPQAETCKVQCNRVFCDTMNSRTLPTDVNLCNTDIFNTKYDCKIMTSKTDISSSVITSIGAIVSCYGK
TKCTASNKNRGIIKTFSNGCDYVSNKGVDTVSVGNTLYYVNKLEGKALYIKGEPIINYYDPLVFPSDEFDASIAQV
NAKINQSLAFIRRSDELLSAIGGYIPEAPRDGQAYVRKDGEWVLLSTFLGGLVPRGSHHHHHHSAWSHPQFEK bRSV F strain 376 sc9-10, DS-Cav1, T369C-T455C (SEQ ID NO: 13)
MAATAMRMIISIIFISTYMTHITLCQNITEEFYQSTCSAVSRGYLSALRTGWYTSVVTIELSKIQKNVCKSTDSKV
KLIKQELERYNNAVIELQSLMQNEPASGSGSAIASGVAVCKVLHLEGEVNKIKNALLSTNKAVVSLSNGVSVLTFK
VLDLKNYIDKELLPKLNNHDCRISNIETVIEFQQKNNRLLEIAREFSVNAGITTPLSTYMLTNSELLSLINDMPIT
NDQKKLMSSNVQIVRQQSYSIMCVVKEEVIAYVVQLPIYGVIDTPCWKLHTSPLCTTDNKEGSNICLTRTDRGWYC
DNAGSVSFFPQAETCKVQSNRVFCDCMNSRTLPTDVNLCNTDIFNTKYDCKIMTSKTDISSSVITSIGAIVSCYGK
TKCTASNKNRGIIKTFSNGCDYVSNKGVDTVSVGNCLYYVNKLEGKALYIKGEPIINYYDPLVFPSDEFDASIAQV
NAKINQSLAFIRRSDELLSAIGGYIPEAPRDGQAYVRKDGEWVLLSTFLGGLVPRGSHHHHHHSAWSHPQFEK bRSV F strain NP048055 sc9-10, DS-Cav1 (SEQ ID NO: 14)
MDSKGSSQKGSRLLLLLVVSNLLLPQGVVGQNITEEFYQSTCSAVSRGYLSALRTGWYTSVVTIELSKIQKNVCKS
TDSKVKLIKQELERYNNAVVELQSLMQNEPASGSGSAVASGVAVCKVLHLEGEVNKIKNALLSTNKAVVSLSNGVS
VLTFKVLDLKNYIDKELLPQLNNHDCRISNIETVIEFQQKNNRLLEIAREFSVNAGITTPLSTYMLTNSELLSLIN
DMPITNDQKKLMSSNVQIVRQQSYSIMCVVKEEVIAYVVQLPIYGVIDTPCWKLHTSPLCTTDNKEGSNICLTRTD
RGWYCDNAGSVSFFPQTETCKVQSNRVFCDTMNSRTLPTDVNLCNTDIFNTKYDCKIMTSKTDISSSVITSIGAIV
SCYGKTKCTASNKNRGIIKTFSNGCDYVSNKGVDTVSVGNTLYYVNKLEGKALYIKGEPIINYYDPLVFPSDEFDA
SIAQVNAKINQSLAFIRRSDELLSAIGGYIPEAPRDGQAYVRKDGEWVLLSTFLGGLVPRGSHHHHHHSAWSHPQF
EK bRSV F strain NP048055 sc9-10, DS-Cav1, A149C-Y458C (SEQ ID NO: 15)
MDSKGSSQKGSRLLLLLVVSNLLLPQGVVGQNITEEFYQSTCSAVSRGYLSALRTGWYTSVVTIELSKIQKNVCKS
TDSKVKLIKQELERYNNAVVELQSLMQNEPASGSGSAVCSGVAVCKVLHLEGEVNKIKNALLSTNKAVVSLSNGVS
VLTFKVLDLKNYIDKELLPQLNNHDCRISNIETVIEFQQKNNRLLEIAREFSVNAGITTPLSTYMLTNSELLSLIN
DMPITNDQKKLMSSNVQIVRQQSYSIMCVVKEEVIAYVVQLPIYGVIDTPCWKLHTSPLCTTDNKEGSNICLTRTD
RGWYCDNAGSVSFFPQTETCKVQSNRVFCDTMNSRTLPTDVNLCNTDIFNTKYDCKIMTSKTDISSSVITSIGAIV
SCYGKTKCTASNKNRGIIKTFSNGCDYVSNKGVDTVSVGNTLYCVNKLEGKALYIKGEPIINYYDPLVFPSDEFDA
SIAQVNAKINQSLAFIRRSDELLSAIGGYIPEAPRDGQAYVRKDGEWVLLSTFLGGLVPRGSHHHHHHSAWSHPQF
EK bRSV F strain NP048055 sc9-10, DS-Cav1, N183GC-N428C (SEQ ID NO: 16)
MDSKGSSQKGSRLLLLLVVSNLLLPQGVVGQNITEEFYQSTCSAVSRGYLSALRTGWYTSVVTIELSKIQKNVCKS
TDSKVKLIKQELERYNNAVVELQSLMQNEPASGSGSAVCSGVAVCKVLHLEGEVNKIKNALLSTNKAVVSLSNGVS
SVLTFKVLDLKNYIDKELLPQLNNHDCRISNIETVIEFQQKNNRLLEIAREFSVNAGITTPLSTYMLTNSELLSLI
NDMPITNDQKKLMSSNVQIVRQQSYSIMCVVKEEVIAYVVQLPIYGVIDTPCWKLHTSPLCTTDNKEGSNICLTRT
DRGWYCDNAGSVSFFPQTETCKVQSNRVFCDTMNSRTLPTDVNLCNTDIFNTKYDCKIMTSKTDISSSVITSIGAI
VSCYGKTKCTASNKCRGIIKTFSNGCDYVSNKGVDTVSVGNTLYYVNKLEGKALYIKGEPIINYYDPLVFPSDEFD
ASIAQVNAKINQSLAFIRRSDELLSAIGGYIPEAPRDGQAYVRKDGEWVLLSTFLGGLVPRGSHHHHHHSAWSHPQ
FEK TABLE 2-continued

| Exemplary recombinant $F_2$-$F_1$ ectodomain protomer sequences |
| --- |
| bRSV F strain NP048055 sc9-10, DS-Cav1, E100C-S362C (SEQ ID NO: 17)<br>MDSKGSSQKGSRLLLLLVVSNLLLPQGVVGQNITEEFYQSTCSAVSRGYLSALRTGWYTSVVTIELSKIQKNVCKS<br>TDSKVKLIKQELERYNNAVVELQSLMQNCPASGSGSAVASGVAVCKVLHLEGEVNKIKNALLSTNKAVVSLSNGVS<br>VLTFKVLDLKNYIDKELLPQLNNHDCRISNIETVIEFQQKNNRLLEIAREFSVNAGITTPLSTYMLTNSELLSLIN<br>DMPITNDQKKLMSSNVQIVRQQSYSIMCVVKEEVIAYVVQLPIYGVIDTPCWKLHTSPLCTTDNKEGSNICLTRTD<br>RGWYCDNAGSVSFFPQTETCKVQCNRVFCDTMNSRTLPTDVNLCNTDIFNTKYDCKIMTSKTDISSSVITSIGAIV<br>SCYGKTKCTASNKNRGIIKTFSNGCDYVSNKGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain NP048055 sc9-10, DS-Cav1, T369C-T455C (SEQ ID NO: 18)<br>MDSKGSSQKGSRLLLLLVVSNLLLPQGVVGQNITEEFYQSTCSAVSRGYLSALRTGWYTSVVTIELSKIQKNVCKS<br>TDSKVKLIKQELERYNNAVVELQSLMQNEPASGSGSAVASGVAVCKVLHLEGEVNKIKNALLSTNKAVVSLSNGVS<br>VLTFKVLDLKNYIDKELLPQLNNHDCRISNIETVIEFQQKNNRLLEIAREFSVNAGITTPLSTYMLTNSELLSLIN<br>DMPITNDQKKLMSSNVQIVRQQSYSIMCVVKEEVIAYVVQLPIYGVIDTPCWKLHTSPLCTTDNKEGSNICLTRTD<br>RGWYCDNAGSVSFFPQTETCKVQSNRVFCDCMNSRTLPTDVNLCNTDIFNTKYDCKIMTSKTDISSSVITSIGAIV<br>SCYGKTKCTASNKNRGIIKTFSNGCDYVSNKGVDTVSVGNCLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, DS-Cav1 (SEQ ID NO: 19)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMQNEPASGSGSAIASGVAVCKVLHLEGEVNKIKNALLSTNKAVVSLSNGVS<br>VLTFKVLDLKNYIDKELLPKLNNHDCQISNIATVIEFQQKNNRLLEIAREFSVNAGITTPLSTYMLTNSELLSLIN<br>DMPITNDQKKLMSSNVQIVRQQSYSIMCVVKEEVMAYVVQLPIYGVIDTPCWKLHTSPLCTTDNKEGSNICLTRTD<br>RGWYCDNAGSVSFFPQAETCKVQSNRVFCDTMNSRTLPTDVNLCNTDIFNAKYDCKIMTSKTDISSSVITSIGAIV<br>SCYGKTKCTASNKNRGIIKTFSNGCDYVSNRGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, DS-Cav1, A149C-Y458C (SEQ ID NO: 20)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMQNEPASGSGSAICSGVAVCKVLHLEGEVNKIKNALLSTNKAVVSLSNGVS<br>VLTFKVLDLKNYIDKELLPKLNNHDCQISNIATVIEFQQKNNRLLEIAREFSVNAGITTPLSTYMLTNSELLSLIN<br>DMPITNDQKKLMSSNVQIVRQQSYSIMCVVKEEVMAYVVQLPIYGVIDTPCWKLHTSPLCTTDNKEGSNICLTRTD<br>RGWYCDNAGSVSFFPQAETCKVQSNRVFCDTMNSRTLPTDVNLCNTDIFNAKYDCKIMTSKTDISSSVITSIGAIV<br>SCYGKTKCTASNKNRGIIKTFSNGCDYVSNRGVDTVSVGNTLYCVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, DS-Cav1, N183GC-N428C (SEQ ID NO: 21)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMQNEPASGSGSAIASGVAVCKVLHLEGEVNKIKNALLSTNKAVVSLSNGVS<br>SVLTFKVLDLKNYIDKELLPKLNNHDCQISNIATVIEFQQKNNRLLEIAREFSVNAGITTPLSTYMLTNSELLSLI<br>NDMPITNDQKKLMSSNVQIVRQQSYSIMCVVKEEVMAYVVQLPIYGVIDTPCWKLHTSPLCTTDNKEGSNICLTRT<br>DRGWYCDNAGSVSFFPQAETCKVQSNRVFCDTMNSRTLPTDVNLCNTDIFNAKYDCKIMTSKTDISSSVITSIGAI<br>VSCYGKTKCTASNKCRGIIKTFSNGCDYVSNRGVDTVSVGNTLYYVNKLEGKALYIKGEPIINYYDPLVFPSDEFD<br>ASIAQVNAKINQSLAFIRRSDELLSAIGGYIPEAPRDGQAYVRKDGEWVLLSTFLGGLVPRGSHHHHHHSAWSHPQ<br>FEK |
| bRSV F strain RB94 sc9-10, DS-Cav1, E100C-S362C (SEQ ID NO: 22)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMQNCPASGSGSAIASGVAVCKVLHLEGEVNKIKNALLSTNKAVVSLSNGVS<br>VLTFKVLDLKNYIDKELLPKLNNHDCQISNIATVIEFQQKNNRLLEIAREFSVNAGITTPLSTYMLTNSELLSLIN<br>DMPITNDQKKLMSSNVQIVRQQSYSIMCVVKEEVMAYVVQLPIYGVIDTPCWKLHTSPLCTTDNKEGSNICLTRTD<br>RGWYCDNAGSVSFFPQAETCKVQCNRVFCDTMNSRTLPTDVNLCNTDIFNAKYDCKIMTSKTDISSSVITSIGAIV<br>SCYGKTKCTASNKNRGIIKTFSNGCDYVSNRGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, DS-Cav1, T369C-T455C (SEQ ID NO: 23)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMQNEPASGSGSAIASGVAVCKVLHLEGEVNKIKNALLSTNKAVVSLSNGVS<br>VLTFKVLDLKNYIDKELLPKLNNHDCQISNIATVIEFQQKNNRLLEIAREFSVNAGITTPLSTYMLTNSELLSLIN<br>DMPITNDQKKLMSSNVQIVRQQSYSIMCVVKEEVMAYVVQLPIYGVIDTPCWKLHTSPLCTTDNKEGSNICLTRTD<br>RGWYCDNAGSVSFFPQAETCKVQSNRVFCDCMNSRTLPTDVNLCNTDIFNAKYDCKIMTSKTDISSSVITSIGAIV<br>SCYGKTKCTASNKNRGIIKTFSNGCDYVSNRGVDTVSVGNCLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| RSV A2 strain sc9-10, DS-Cav1, A149C-Y458C, S46G (SEQ ID NO: 24)<br>MELLILKANAITTILTAVTFCFASGQNITEEFYQSTCSAVSKGYLGALRTGWYTSVITIELSNIKENKCNGTDAKV<br>KLIKQELDKYKNAVTELQLLMQSTPATGSGSAICSGVAVCKVLHLEGEVNKIKSALLSTNKAVVSLSNGVSVLTFK<br>VLDLKNYIDKQLLPILNKQSCSISNIETVIEFQQKNNRLLEITREFSVNAGVTTPVSTYMLTNSELLSLINDMPIT<br>NDQKKLMSNNVQIVRQQSYSIMCIIKEEVLAYVVQLPLYGVIDTPCWKLHTSPLCTTNTKEGSNICLTRTDRGWYC<br>DNAGSVSFFPQAETCKVQSNRVFCDTMNSRTLPSEVNLCNVDIFNPKYDCKIMTSKTDVSSSVITSLGAIVSCYGK<br>TKCTASNKNRGIIKTFSNGCDYVSNKGVDTVSVGNTLYCVNKQEGKSLYVKGEPIINFYDPLVFPSDEFDASISQV<br>NEKINQSLAFIRKSDELLSAIGGYIPEAPRDGQAYVRKDGEWVLLSTFLGGLVPRGSHHHHHHSAWSHPQFEK |

TABLE 2-continued

Exemplary recombinant F₂-F₁ ectodomain protomer sequences

RSV A2 strain sc9-10, DS-Cav1, A149C-Y458C, S46G-K465Q (SEQ ID NO: 25)
MELLILKANAITTILTAVTFCFASGQNITEEFYQSTCSAVSKGYLGALRTGWYTSVITIELSNIKENKCNGTDAKV
KLIKQELDKYKNAVTELQLLMQSTPATGSGSAICSGVAVCKVLHLEGEVNKIKSALLSTNKAVVSLSNGVSVLTFK
VLDLKNYIDKQLLPILNKQSCSISNIETVIEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, S46G-K465Q-S215P (SEQ ID NO: 26)
MELLILKANAITTILTAVTFCFASGQNITEEFYQSTCSAVSKGYLGALRTGWYTSVITIELSNIKENKCNGTDAKV
KLIKQELDKYKNAVTELQLLMQSTPATGSGSAICSGVAVCKVLHLEGEVNKIKSALLSTNKAVVSLSNGVSVLTFK
VLDLKNYIDKQLLPILNKQSCSIPNIETVIEFQQKNNRLLEITREFSVNAGVTTPVSTYMLTNSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, S46G-K465Q-S215P-E92D (SEQ ID NO: 27)
MELLILKANAITTILTAVTFCFASGQNITEEFYQSTCSAVSKGYLGALRTGWYTSVITIELSNIKENKCNGTDAKV
KLIKQELDKYKNAVTDLQLLMQSTPATGSGSAICSGVAVCKVLHLEGEVNKIKSALLSTNKAVVSLSNGVSVLTFK
VLDLKNYIDKQLLPILNKQSCSIPNIETVIEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, S46G-K465Q-S215P-E92D-N67I (SEQ ID NO: 28)
MELLILKANAITTILTAVTFCFASGQNITEEFYQSTCSAVSKGYLGALRTGWYTSVITIELSNIKEIKCNGTDAKV
KLIKQELDKYKNAVTDLQLLMQSTPATGSGSAICSGVAVCKVLHLEGEVNKIKSALLSTNKAVVSLSNGVSVLTFK
VLDLKNYIDKQLLPILNKQSCSIPNIETVIEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, S46G-K465Q-S215P-N67I (SEQ ID NO: 29)
MELLILKANAITTILTAVTFCFASGQNITEEFYQSTCSAVSKGYLGALRTGWYTSVITIELSNIKEIKCNGTDAKV
KLIKQELDKYKNAVTELQLLMQSTPATGSGSAICSGVAVCKVLHLEGEVNKIKSALLSTNKAVVSLSNGVSVLTFK
VLDLKNYIDKQLLPILNKQSCSIPNIETVIEFQQKNNRLLEITREFSVNAGVTTPVSTYMLTNSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, S46G (SEQ ID NO: 30)
MELLILKANAITTILTAVTFCFASGQNITEEFYQSTCSAVSKGYLGALRTGWYTSVITIELSNIKENKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLINSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, S46G-K465Q (SEQ ID NO: 31)
MELLILKANAITTILTAVTFCFASGQNITEEFYQSTCSAVSKGYLGALRTGWYTSVITIELSNIKENKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKQLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, S46G-K465Q-S215P (SEQ ID NO: 32)
MELLILKANAITTILTAVTFCFASGQNITEEFYQSTCSAVSKGYLGALRTGWYTSVITIELSNIKENKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSIPNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKQLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK TABLE 2-continued Exemplary recombinant $F_2$-$F_1$ ectodomain protomer sequences RSV A2 strain sc9-10, DS-Cav1, N183GC-N428C, S46G-K465Q-S215P-E92D (SEQ ID NO: 33)
MELLILKANAITTILTAVTFCFASGQNITEEFYQSTCSAVSKGYLGALRTGWYTSVITIELSNIKENKCNGTDAKV
KLIKQELDKYKNAVTDLQLLMQSTPATGSGSAIASGVAVCKVLHLEGEVNKIKSALLSTNKAVVSLSGCGVSVLTF
KVLDLKNYIDKQLLPILNKQSCSIPNIETVIEFQQKNNRLLEITREFSVNAGVTTPVSTYMLINSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKQLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, S46G-K465Q-S215P-E92D-N67I (SEQ ID NO: 34)
MELLILKANAITTILTAVTFCFASGQNITEEFYQSTCSAVSKGYLGALRTGWYTSVITIELSNIKEIKCNGTDAKV
KLIKQELDKYKNAVTDLQLLMQSTPATGSGSAIASGVAVCKVLHLEGEVNKIKSALLSTNKAVVSLSGCGVSVLTF
KVLDLKNYIDKQLLPILNKQSCSIPNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKQLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, S46G-K465Q-S215P-N67I (SEQ ID NO: 35)
MELLILKANAITTILTAVTFCFASGQNITEEFYQSTCSAVSKGYLGALRTGWYTSVITIELSNIKEIKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSIPNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKQLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV strain B18537-sc9-10, DS-Cav1, Q98C-361C-L95M-I221M-R429K (SEQ ID NO: 36)
MELLIHRSSAIFLTLAVNALYLTSSQNITEEFYQSTCSAVSRGYFSALRTGWYTSVITIELSNIKETKCNGTDTKV
KLIKQELDKYKNAVTELQMLMCNTPAAGSGSAIASGIAVCKVLHLEGEVNKIKNALLSTNKAVVSLSNGVSVLTFK
VLDLKNYINNRLLPILNQQSCRISNPETVMEFQQMNSRLLEITREFSVNAGVTTPLSTYMLINSELLSLINDMPIT
NDQKKLMSSNVQIVRQQSYSIMCIIKEEVLAYVVQLPIYGVIDTPCWKLHTSPLCTTNIKEGSNICLTRTDRGWYC
DNAGSVSFFPQADTCKVCSNRVFCDTMNSRTLPSEVSLCNTDIFNSKYDCKIMTSKTDISSSVITSLGAIVSCYGK
TKCTASNKNKGIIKTFSNGCDYVSNKGVDTVSVGNTLYYVNKLEGKNLYVKGEPIINYYDPLVFPSDEFDASISQV
NEKINQSLAFIRRSDELLSAIGGYIPEAPRDGQAYVRKDGEWVLLSTFLGGLVPRGSHHHHHHSAWSHPQFEK RSV LongVR26 strain sc9-10, DS-Cav1, Q98C-361C-L95M-I221M-R429K-I217P-S46G-K465Q-S215P-E92D (SEQ ID NO: 37)
MELPILKANAITTILAAVTFCFASSQNITEEFYQSTCSAVSKGYLSALRTGWYTSVITIELSNIKENKCNGTDAKV
KLINQELDKYKNAVTELQMLMCSTTATGSGSAIASGIAVCKVLHLEGEVNKIKSALLSTNKAVVSLSNGVSVLFSK
VLDLKNYIDKQLLPILNKQSCRISNIETVMEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVCSNRVFCDTMNSRTLPSEVNLCNVDIFNPKYDCKIMTSKTDVSSSVITSLGAIVSCYGK
TKCTASNKNKGIIKTFSNGCDYVSNKGVDTVSVGNTLYYVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, N183GC-N428C (SEQ ID NO: 38)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAICSGVAVCKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYCVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, T369C-T455C (SEQ ID NO: 39)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDCMNSRTLPSEVNLCNVDIFNPKYDCKIMTSKTDVSSSVITSLGAIVSCYG
KTKCTASNKCRGIIKTFSNGCDYVSNKGVDTVSVGNCLYYVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, T369C-T455C (SEQ ID NO: 40)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAICSGVAVCKVLHLEGEVNKIKSALLSTNKAVVSLSNGVSVLTFK
VLDLKNYIDKQLLPILNKQSCSISNIETVIEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDCMNSRTLPSEVNLCNVDIFNPKYDCKIMTSKTDVSSSVITSLGAIVSCYGK
TKCTASNKNRGIIKTFSNGCDYVSNKGVDTVSVGNCLYCVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK TABLE 2-continued

| Exemplary recombinant $F_2$-$F_1$ ectodomain protomer sequences |
| --- |
| RSV A2 strain sc9-10, DS-Cav1, T369C-T455C, S46G-K465Q-S215P-E92D-N67I (SEQ ID NO: 41)<br>MELLILKANAITTILTAVTFCFASGQNITEEFYQSTCSAVSKGYLGALRTGWYTSVITIELSNIKEIKCNGTDAKV<br>KLIKQELDKYKNAVTDLQLLMQSTPATGSGSAIASGVAVCKVLHLEGEVNKIKSALLSTNKAVVSLSNGVSVLTFK<br>VLDLKNYIDKQLLPILNKQSCSIPNIETVIEFQQKNNRLLEITREFSVNAGVTTPVSTYMLTNSELLSLINDMPIT<br>NDQKKLMSNNVQIVRQQSYSIMCIIKEEVLAYVVQLPLYGVIDTPCWKLHTSPLCTTNTKEGSNICLTRTDRGWYC<br>DNAGSVSFFPQAETCKVQSNRVFCDCMNSRTLPSEVNLCNVDIFNPKYDCKIMTSKTDVSSSVITSLGAIVSCYGK<br>TKCTASNKNRGIIKTFSNGCDYVSNKGVDTVSVGNCLYYVNKQEGQSLYVKGEPIINFYDPLVFPSDEFDASISQV<br>NEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, A149C-Y458C, N183GC-N428C, S46G-K465Q-S215P-E92D-N67I (SEQ ID NO: 42)<br>MELLILKANAITTILTAVTFCFASGQNITEEFYQSTCSAVSKGYLGALRTGWYTSVITIELSNIKEIKCNGTDAKV<br>KLIKQELDKYKNAVTDLQLLMQSTPATGSGSAICSGVAVCKVLHLEGEVNKIKSALLSTNKAVVSLSGCGVSVLTF<br>KVLDLKNYIDKQLLPILNKQSCSIPNIETVIEFQQKNNRLLEITREFSVNAGVTTPVSTYMLTNSELLSLINDMPI<br>TNDQKKLMSNNVQIVRQQSYSIMCIIKEEVLAYVVQLPLYGVIDTPCWKLHTSPLCTTNTKEGSNICLTRTDRGWY<br>CDNAGSVSFFPQAETCKVQSNRVFCDTMNSRTLPSEVNLCNVDIFNPKYDCKIMTSKTDVSSSVITSLGAIVSCYG<br>KTKCTASNKCRGIIKTFSNGCDYVSNKGVDTVSVGNTLYCVNKQEGQSLYVKGEPIINFYDPLVFPSDEFDASISQ<br>VNEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, N183GC-N428C, T369C-T455C, S46G-K465Q-S215P-E92D-N67I (SEQ ID NO: 43)<br>MELLILKANAITTILTAVTFCFASGQNITEEFYQSTCSAVSKGYLGALRTGWYTSVITIELSNIKEIKCNGTDAKV<br>KLIKQELDKYKNAVTDLQLLMQSTPATGSGSAIASGVAVCKVLHLEGEVNKIKSALLSTNKAVVSLSGCGVSVLTF<br>KVLDLKNYIDKQLLPILNKQSCSIPNIETVIEFQQKNNRLLEITREFSVNAGVTTPVSTYMLTNSELLSLINDMPI<br>TNDQKKLMSNNVQIVRQQSYSIMCIIKEEVLAYVVQLPLYGVIDTPCWKLHTSPLCTTNTKEGSNICLTRTDRGWY<br>CDNAGSVSFFPQAETCKVQSNRVFCDCMNSRTLPSEVNLCNVDIFNPKYDCKIMTSKTDVSSSVITSLGAIVSCYG<br>KTKCTASNKCRGIIKTFSNGCDYVSNKGVDTVSVGNCLYYVNKQEGQSLYVKGEPIINFYDPLVFPSDEFDASISQ<br>VNEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, A149C-Y458C, T369C-T455C, S46G-K465Q-S215P-E92D-N67I (SEQ ID NO: 44)<br>MELLILKANAITTILTAVTFCFASGQNITEEFYQSTCSAVSKGYLGALRTGWYTSVITIELSNIKEIKCNGTDAKV<br>KLIKQELDKYKNAVTDLQLLMQSTPATGSGSAICSGVAVCKVLHLEGEVNKIKSALLSTNKAVVSLSNGVSVLTFK<br>VLDLKNYIDKQLLPILNKQSCSIPNIETVIEFQQKNNRLLEITREFSVNAGVTTPVSTYMLTNSELLSLINDMPIT<br>NDQKKLMSNNVQIVRQQSYSIMCIIKEEVLAYVVQLPLYGVIDTPCWKLHTSPLCTTNTKEGSNICLTRTDRGWYC<br>DNAGSVSFFPQAETCKVQSNRVFCDCMNSRTLPSEVNLCNVDIFNPKYDCKIMTSKTDVSSSVITSLGAIVSCYGK<br>TKCTASNKNRGIIKTFSNGCDYVSNKGVDTVSVGNCLYCVNKQEGQSLYVKGEPIINFYDPLVFPSDEFDASISQV<br>NEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, T369C-T455C, S46G-K465Q-S215P-E92D (SEQ ID NO: 45)<br>MELLILKANAITTILTAVTFCFASGQNITEEFYQSTCSAVSKGYLGALRTGWYTSVITIELSNIKENKCNGTDAKV<br>KLIKQELDKYKNAVTDLQLLMQSTPATGSGSAIASGVAVCKVLHLEGEVNKIKSALLSTNKAVVSLSNGVSVLTFK<br>VLDLKNYIDKQLLPILNKQSCSIPNIETVIEFQQKNNRLLEITREFSVNAGVTTPVSTYMLTNSELLSLINDMPIT<br>NDQKKLMSNNVQIVRQQSYSIMCIIKEEVLAYVVQLPLYGVIDTPCWKLHTSPLCTTNTKEGSNICLTRTDRGWYC<br>DNAGSVSFFPQAETCKVQSNRVFCDCMNSRTLPSEVNLCNVDIFNPKYDCKIMTSKTDVSSSVITSLGAIVSCYGK<br>TKCTASNKNRGIIKTFSNGCDYVSNKGVDTVSVGNCLYYVNKQEGQSLYVKGEPIINFYDPLVFPSDEFDASISQV<br>NEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, A149C-Y458C, N183GC-N428C, S46G-K465Q-S215P-E92D (SEQ ID NO: 46)<br>MELLILKANAITTILTAVTFCFASGQNITEEFYQSTCSAVSKGYLGALRTGWYTSVITIELSNIKENKCNGTDAKV<br>KLIKQELDKYKNAVTDLQLLMQSTPATGSGSAICSGVAVCKVLHLEGEVNKIKSALLSTNKAVVSLSGCGVSVLTF<br>KVLDLKNYIDKQLLPILNKQSCSIPNIETVIEFQQKNNRLLEITREFSVNAGVTTPVSTYMLTNSELLSLINDMPI<br>TNDQKKLMSNNVQIVRQQSYSIMCIIKEEVLAYVVQLPLYGVIDTPCWKLHTSPLCTTNTKEGSNICLTRTDRGWY<br>CDNAGSVSFFPQAETCKVQSNRVFCDTMNSRTLPSEVNLCNVDIFNPKYDCKIMTSKTDVSSSVITSLGAIVSCYG<br>KTKCTASNKCRGIIKTFSNGCDYVSNKGVDTVSVGNTLYCVNKQEGQSLYVKGEPIINFYDPLVFPSDEFDASISQ<br>VNEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, N183GC-N428C, T369C-T455C, S46G-K465Q-S215P-E92D (SEQ ID NO: 47)<br>MELLILKANAITTILTAVTFCFASGQNITEEFYQSTCSAVSKGYLGALRTGWYTSVITIELSNIKENKCNGTDAKV<br>KLIKQELDKYKNAVTDLQLLMQSTPATGSGSAIASGVAVCKVLHLEGEVNKIKSALLSTNKAVVSLSGCGVSVLTF<br>KVLDLKNYIDKQLLPILNKQSCSIPNIETVIEFQQKNNRLLEITREFSVNAGVTTPVSTYMLINSELLSLINDMPI<br>TNDQKKLMSNNVQIVRQQSYSIMCIIKEEVLAYVVQLPLYGVIDTPCWKLHTSPLCTTNTKEGSNICLTRTDRGWY<br>CDNAGSVSFFPQAETCKVQSNRVFCDCMNSRTLPSEVNLCNVDIFNPKYDCKIMTSKTDVSSSVITSLGAIVSCYG<br>KTKCTASNKCRGIIKTFSNGCDYVSNKGVDTVSVGNCLYYVNKQEGQSLYVKGEPIINFYDPLVFPSDEFDASISQ<br>VNEKINQSLAFIRKSDELLSAIGGYIPEAPRDGQAYVRKDGEWVLLSTFLGGLVPRGSHHHHHHSAWSHPQFEK |
| RSV A2 strain sc9-10, DS-Cav1, A149C-Y458C, T369C-T455C, S46G-K465Q-S215P-E92D (SEQ ID NO: 48)<br>MELLILKANAITTILTAVTFCFASGQNITEEFYQSTCSAVSKGYLGALRTGWYTSVITIELSNIKENKCNGTDAKV<br>KLIKQELDKYKNAVTDLQLLMQSTPATGSGSAICSGVAVCKVLHLEGEVNKIKSALLSTNKAVVSLSNGVSVLTFK<br>VLDLKNYIDKQLLPILNKQSCSIPNIETVIEFQQKNNRLLEITREFSVNAGVTTPVSTYMLTNSELLSLINDMPIT<br>NDQKKLMSNNVQIVRQQSYSIMCIIKEEVLAYVVQLPLYGVIDTPCWKLHTSPLCTTNTKEGSNICLTRTDRGWYC<br>DNAGSVSFFPQAETCKVQSNRVFCDCMNSRTLPSEVNLCNVDIFNPKYDCKIMTSKTDVSSSVITSLGAIVSCYGK |

TABLE 2-continued

| Exemplary recombinant $F_2$-$F_1$ ectodomain protomer sequences |
|---|

TKCTASNKNRGIIKTFSNGCDYVSNKGVDTVSVGNCLYCVNKQEGQSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK

RSV A2 strain sc9-10, DS-Cav1, T369C-T455C, L95M-I221M-R429K (SEQ ID NO: 49)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAIASGVAVCKVLHLEGEVNKIKSALLSTNKAVVSLSNGVSVLTFK
VLDLKNYIDKQLLPILNKQSCSISNIETVMEFQQKNNRLLEITREFSVNAGVTTPVSTYMLTNSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDCMNSRTLPSEVNLCNVDIFNPKYDCKIMTSKTDVSSSVITSLGAIVSCYGK
TKCTASNKNKGIIKTFSNGCDYVSNKGVDTVSVGNCLYYVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, N183GC-N428C, L95M-I221M-R429K
(SEQ ID NO: 50)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAICSGVAVCKVLHLEGEVNKIKSALLSTNKAVVSLSGCGVSVLTF
KVLDLKNYIDKQLLPILNKQSCSISNIETVMEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCKGIIKTFSNGCDYVSNKGVDTVSVGNTLYCVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, T369C-T455C, L95M-I221M-R429K
(SEQ ID NO: 51)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAIASGVAVCKVLHLEGEVNKIKSALLSTNKAVVSLSGCGVSVLTF
KVLDLKNYIDKQLLPILNKQSCSISNIETVMEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDCMNSRTLPSEVNLCNVDIFNPKYDCKIMTSKTDVSSSVITSLGAIVSCYG
KTKCTASNKCKGIIKTFSNGCDYVSNKGVDTVSVGNCLYYVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, T369C-T455C, L95M-I221M-R429K
(SEQ ID NO: 52)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAICSGVAVCKVLHLEGEVNKIKSALLSTNKAVVSLSNGVSVLTFK
VLDLKNYIDKQLLPILNKQSCSISNIETVMEFQQKNNRLLEITREFSVNAGVTTPVSTYMLTNSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDCMNSRTLPSEVNLCNVDIFNPKYDCKIMTSKTDVSSSVITSLGAIVSCYGK
TKCTASNKNKGIIKTFSNGCDYVSNKGVDTVSVGNCLYCVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, T369C-T455C, L95M-I221M-R429K-I217P (SEQ ID
NO: 53)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAIASGVAVCKVLHLEGEVNKIKSALLSTNKAVVSLSNGVSVLTFK
VLDLKNYIDKQLLPILNKQSCSISNPETVMEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDCMNSRTLPSEVNLCNVDIFNPKYDCKIMTSKTDVSSSVITSLGAIVSCYGK
TKCTASNKNKGIIKTFSNGCDYVSNKGVDTVSVGNCLYYVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, N183GC-N428C, L95M-I221M-R429K-
I217P (SEQ ID NO: 54)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAICSGVAVCKVLHLEGEVNKIKSALLSTNKAVVSLSGCGVSVLTF
KVLDLKNYIDKQLLPILNKQSCSISNPETVMEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCKGIIKTFSNGCDYVSNKGVDTVSVGNTLYCVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, N183GC-N428C, T369C-T455C, L95M-I221M-R429K-
I217P (SEQ ID NO: 55)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAIASGVAVCKVLHLEGEVNKIKSALLSTNKAVVSLSGCGVSVLTF
KVLDLKNYIDKQLLPILNKQSCSISNPETVMEFQQKNNRLLEITREFSVNAGVTTPVSTYMLINSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDCMNSRTLPSEVNLCNVDIFNPKYDCKIMTSKTDVSSSVITSLGAIVSCYG
KTKCTASNKCKGIIKTFSNGCDYVSNKGVDTVSVGNCLYYVNKQEGKSLYVKGEPIINFYDPLVFPSDEFDASISQ
VNEKINQSLAFIRKSDELLSAIGGYIPEAPRDGQAYVRKDGEWVLLSTFLGGLVPRGSHHHHHHSAWSHPQFEK RSV A2 strain sc9-10, DS-Cav1, A149C-Y458C, T369C-T455C, L95M-I221M-R429K-
I217P (SEQ ID NO: 56)
MELLILKANAITTILTAVTFCFASGQNITEEFYQSTCSAVSKGYLSALRTGWYTSVITIELSNIKENKCNGTDAKV
KLIKQELDKYKNAVTELQMLMQSTPATGSGSAICSGVAVCKVLHLEGEVNKIKSALLSTNKAVVSLSNGVSVLTFK
VLDLKNYIDKQLLPILNKQSCSISNPETVMEFQQKNNRLLEITREFSVNAGVTTPVSTYMLTNSELLSLINDMPIT
NDQKKLMSNNVQIVRQQSYSIMCIIKEEVLAYVVQLPLYGVIDTPCWKLHTSPLCTTNTKEGSNICLTRTDRGWYC TABLE 2-continued

| Exemplary recombinant $F_2$-$F_1$ ectodomain protomer sequences |
|---|

DNAGSVSFFPQAETCKVQSNRVFCDCMNSRTLPSEVNLCNVDIFNPKYDCKIMTSKTDVSSSVITSLGAIVSCYGK
TKCTASNKNKGIIKTFSNGCDYVSNKGVDTVSVGNCLYCVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK

RSV A2 STRAIN SC9-10, A149C-Y458C_Long (SEQ ID NO: 81)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAICSGVAVCKVLHLEGEVNKIKSALLSTNKAVVSLSNGVSVLTFK
VLDLKNYIDKQLLPILNKQSCSISNIETVIEFQQKNNRLLEITREFSVNAGVTTPVSTYMLINSELLSLINDMPIT
NDQKKLMSNNVQIVRQQSYSIMCIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGKSLYVKGEPIINFYDPLVFPSDEFDASISQV
NEKINQSLAFIRKSDELLhnvnagksttSAIGGYIPEAPRDGQAYVRKDGEWVLLSTFLGGLVPRGSHHHHHHSAW
SHPQFEK RSV A2 STRAIN SC9-10, N183GC-N428C_Long (SEQ ID NO: 82)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAIASGVAVCKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKSLYVKGEPIINFYDPLVFPSDEFDASISQ
VNEKINQSLAFIRKSDELLhnvnagksttSAIGGYIPEAPRDGQAYVRKDGEWVLLSTFLGGLVPRGSHHHHHHSA
WSHPQFEK RSV A2 STRAIN SC9-10, A149C-Y458C_Long_Cav1only (SEQ ID NO: 83)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAICSGVAVSKVLHLEGEVNKIKSALLSTNKAVVSLSNGVSVLTFK
VLDLKNYIDKQLLPILNKQSCSISNIETVIEFQQKNNRLLEITREFSVNAGVTTPVSTYMLTNSELLSLINDMPIT
NDQKKLMSNNVQIVRQQSYSIMSIIKEEVLAYVVQLPLYGVIDTPCWKLHTSPLCTTNTKEGSNICLTRTDRGWYC
DNAGSVSFFPQAETCKVQSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGKSLYVKGEPIINFYDPLVFPSDEFDASISQV
NEKINQSLAFIRKSDELLhnvnagksttSAIGGYIPEAPRDGQAYVRKDGEWVLLSTFLGGLVPRGSHHHHHHSAW
SHPQFEK RSV A2 STRAIN SC9-10, N183GC-N428C_Long_Cav1only (SEQ ID NO: 84)
MELLILKANAITTILTAVTFCFASGQNITEEFYQSTCSAVSKGYLSALRTGWYTSVITIELSNIKENKCNGTDAKV
KLIKQELDKYKNAVTELQLLMQSTPATGSGSAIASGVAVSKVLHLEGEVNKIKSALLSTNKAVVSLSGCGVSVLTF
KVLDLKNYIDKQLLPILNKQSCSISNIETVIEFQQKNNRLLEITREFSVNAGVTTPVSTYMLTNSELLSLINDMPI
TNDQKKLMSNNVQIVRQQSYSIMCIIKEEVLAYVVQLPLYGVIDTPCWKLHTSPLCTTNTKEGSNICLTRTDRGWY
CDNAGSVSFFPQAETCKVQSNRVFCDTMNSRTLPSEVNLCNVDIFNPKYDCKIMTSKTDVSSSVITSLGAIVSCYG
KTKCTASNKCRGIIKTFSNGCDYVSNKGVDTVSVGNTLYYVNKQEGKSLYVKGEPIINFYDPLVFPSDEFDASISQ
VNEKINQSLAFIRKSDELLhnvnagksttSAIGGYIPEAPRDGQAYVRKDGEWVLLSTFLGGLVPRGSHHHHHHSA
WSHPQFEK RSV A2 strain sc9-10, Cav1, 99C-Q361C (SEQ ID NO: 100)
MELLILKANAITTILTAVTFCFASGQNITEEFYQSTCSAVSKGYLSALRTGWYTSVITIELSNIKENKCNGTDAKV
KLIKQELDKYKNAVTELQLLMQCTPATGSGSAICSGVAVSKVLHLEGEVNKIKSALLSTNKAVVSLSNGVSVLTFK
VLDLKNYIDKQLLPILNKQSCSISNIETVIEFQQKNNRLLEITREFSVNAGVTTPVSTYMLTNSELLSLINDMPIT
NDQKKLMSNNVQIVRQQSYSIMSIIKEEVLAYVVQLPLYGVIDTPCWKLHTSPLCTTNTKEGSNICLTRTDRGWYC
DNAGSVSFFPQAETCKVCSNRVFCDTMNSRTLPSEVNLCNVDIFNPKYDCKIMTSKTDVSSSVITSLGAIVSCYGK
TKCTASNKNRGIIKTFSNGCDYVSNKGVDTVSVGNTLYCVNKQEGKSLYVKGEPIINFYDPLVFPSDEFDASISQV
NEKINQSLAFIRKSDELLSAIGGYIPEAPRDGQAYVRKDGEWVLLSTFLGGLVPRGSHHHHHHSAWSHPQFEK RSV B18537 strain sc9-10, Cav1, 99C-Q361C (SEQ ID NO: 101)
MELLIHRSSAIFLTLAVNALYLTSSQNITEEFYQSTCSAVSRGYFSALRTGWYTSVITIELSNIKETKCNGTDTKV
KLIKQELDKYKNAVTELQLLMQCTPAAGSGSAICSGIAVSKVLHLEGEVNKIKNALLSTNKAVVSLSNGVSVLTFK
VLDLKNYINNRLLPILNQQSCRISNIETVIEFQQMNSRLLEITREFSVNAGVTTPLSTYMLTNSELLSLINDMPIT
NDQKKLMSSNVQIVRQQSYSIMSIIKEEVLAYVVQLPIYGVIDTPCWKLHTSPLCTTNIKEGSNICLTRTDRGWYC
DNAGSVSFFPQADTCKVCSNRVFCDTMNSRTLPSEVSLCNTDIFNSKYDCKIMTSKTDISSSVITSLGAIVSCYGK
TKCTASNKNRGIIKTFSNGCDYVSNKGVDTVSVGNTLYCVNKLEGKNLYVKGEPIINYYDPLVFPSDEFDASISQV
NEKINQSLAFIRRSDELLSAIGGYIPEAPRDGQAYVRKDGEWVLLSTFLGGLVPRGSHHHHHHSAWSHPQFEKS bRSV F strain 376 sc9-10, Cav1, 99C-Q361C (SEQ ID NO: 102)
MAATAMRMIISIIFISTYMTHITLCQNITEEFYQSTCSAVSRGYLSALRTGWYTSVVTIELSKIQKNVCKSTDSKV
KLIKQELDKYKNAVTELQLLMQCTPAAGSGSAICSGIAVSKVLHLEGEVNKIKNALLSTNKAVVSLSNGVSVLTFK
VLDLKNYIDKELLPKLNNHDCRISNIETVIEFQQKNNRLLEIAREFSVNAGITTPLSTYMLINSELLSLINDMPIT
NDQKKLMSSNVQIVRQQSYSIMSVVKEEVLAYVVQLPIYGVIDTPCWKLHTSPLCTTDNKEGSNICLTRTDRGWYC
DNAGSVSFFPQAETCKVCSNRVFCDTMNSRTLPTDVNLCNTDIFNTKYDCKIMTSKTDISSSVITSIGAIVSCYGK
TKCTASNKNRGIIKTFSNGCDYVSNKGVDTVSVGNTLYYVNKLEGKALYIKGEPIINYYDPLVFPSDEFDASIAQV
NAKINQSLAFIRRSDELLSAIGGYIPEAPRDGQAYVRKDGEWVLLSTFLGGLVPRGSHHHHHHSAWSHPQFEK bRSV F strain NP048055 sc9-10, Cav1, 99C-Q361C (SEQ ID NO: 103)
MDSKGSSQKGSRLLLLLVVSNLLLPQGVVGQNITEEFYQSTCSAVSRGYLSALRTGWYTSVVTIELSKIQKNVCKS
TDSKVKLIKQELERYNNAVVELQSLMQCEPASGSGSAVASGVAVSKVLHLEGEVNKIKNALLSTNKAVVSLSNGVS
VLTFKVLDLKNYIDKELLPQLNNHDCRISNIETVIEFQQKNNRLLEIAREFSVNAGITTPLSTYMLTNSELLSLIN
DMPITNDQKKLMSSNVQIVRQQSYSIMSVVKEEVIAYVVQLPIYGVIDTPCWKLHTSPLCTTDNKEGSNICLTRTD
RGWYCDNAGSVSFFPQTETCKVCSNRVFCDTMNSRTLPTDVNLCNTDIFNTKYDCKIMTSKTDISSSVITSIGAIV TABLE 2-continued

| Exemplary recombinant $F_2$-$F_1$ ectodomain protomer sequences |
| --- |
| SCYGKTKCTASNKNRGIIKTFSNGCDYVSNKGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, Cav1, 99C-Q361C (SEQ ID NO: 104)<br>MDSKGSSQKGSRLLLLLVVSNLLLPQGVVGQNITEEFYQSTCSAVSRGYLSALRTGWYTSVVTIELSKIQKNVCNS<br>TDSKVKLIKQELERYNNAVVELQSLMQCEPASGSGSAIASGVAVSKVLHLEGEVNKIKNALLSTNKAVVSLSNGVS<br>VLT**F**KVLDLKNYIDKELLPK**L**NNHDCQISNIATVIEFQQKNNRLLEIAREFSVNAGITTPLSTYMLTNSELLSLIN<br>DMPITNDQKKLMSSNVQIVRQQSYSIMSVVKEEVIAYVVQLPIYGVIDTPCWKLHTSPLCTTDNKEGSNICLTRTD<br>RGWYCDNAGSVSFFPQAETCKVCSNRVFCDTMNSRTLPTDVNLCNTDIFNAKYDCKIMTSKTDISSSVITSIGAIV<br>SCYGKTKCTASNKNRGIIKTFSNGCDYVSNRGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| RSV A2 strain sc9-10, DS-Cav1, Q98C-Q361C (SEQ ID NO: 105)<br>MELLILKANAITTILTAVTFCFASGQNITEEFYQSTCSAVSKGYLSALRTGWYTSVITIELSNIKENKCNGTDAKV<br>KLIKQELDKYKNAVTELQLLMCSTPATGSGSAICSGVAVSKVLHLEGEVNKIKSALLSTNKAVVSLSNGVSVLTFK<br>VLDLKNYIDKQLLPILNKQSCSISNIETVIEFQQKNNRLLEITREFSVNAGVTTPVSTYMLTNSELLSLINDMPIT<br>NDQKKLMSSNVQIVRQQSYSIMSIIKEEVLAYVVQLPLYGVIDTPCWKLHTSPLCTTDNKEGSNICLTRTDRGWYC<br>DNAGSVSFFPQAETCKVCSNRVFCDTMNSRTLPSEVNLCNVDIFNPKYDCKIMTSKTDVSSSVITSLGAIVSCYGK<br>TKCTASNKNRGIIKTFSNGCDYVSNKGVDTVSVGNTLYCVNKQEGKSLYVKGEPIINFYDPLVFPSDEFDASISQV<br>NEKINQSLAFIRKSDELLSAIGGYIPEAPRDGQAYVRKDGEWVLLSTFLGGLVPRGSHHHHHHSAWSHPQFEK |
| RSV B18537 strain sc9-10, DS-Cav1, Q98C-Q361C (SEQ ID NO: 106)<br>MELLIHRSSAIFLTLAVNALYLTSSQNITEEFYQSTCSAVSRGYFSALRTGWYTSVITIELSNIKETKCNGTDTKV<br>KLIKQELDKYKNAVTELQLLMCNTPAAGSGSAICSGIAVSKVLHLEGEVNKIKNALLSTNKAVVSLSNGVSVLTFK<br>VLDLKNYINNRLLPILNQQSCRISNIETVIEFQQMNSRLLEITREFSVNAGVTTPLSTYMLINSELLSLINDMPIT<br>NDQKKLMSSNVQIVRQQSYSIMSIIKEEVLAYVVQLPIYGVIDTPCWKLHTSPLCTTDNKEGSNICLTRTDRGWYC<br>DNAGSVSFFPQADTCKVCSNRVFCDTMNSRTLPSEVSLCNTDIFNSKYDCKIMTSKTDISSSVITSLGAIVSCYGK<br>TKCTASNKNRGIIKTFSNGCDYVSNKGVDTVSVGNTLYCVNKLEGKNLYVKGEPIINYYDPLVFPSDEFDASISQV<br>NEKINQSLAFIRRSDELLSAIGGYIPEAPRDGQAYVRKDGEWVLLSTFLGGLVPRGSHHHHHHSAWSHPQFEKS |
| bRSV F strain 376 sc9-10, DS-Cav1, Q98C-Q361C (SEQ ID NO: 107)<br>MAATAMRMIISIIFISTYMTHITLCQNITEEFYQSTCSAVSRGYLSALRTGWYTSVVTIELSKIQKNVCKSTDSKV<br>KLIKQELERYNNAVIELQSLMCNEPASGSGSAIASGVAVSKVLHLEGEVNKIKNALLSTNKAVVSLSNGVSVLTFK<br>VLDLKNYIDKELLPKLNNHDCRISNIETVIEFQQKNNRLLEIAREFSVNAGITTPLSTYMLTNSELLSLINDMPIT<br>NDQKKLMSSNVQIVRQQSYSIMSVVKEEVIAYVVQLPIYGVIDTPCWKLHTSPLCTTDNKEGSNICLTRTDRGWYC<br>DNAGSVSFFPQAETCKVCSNRVFCDTMNSRTLPTDVNLCNTDIFNTKYDCKIMTSKTDISSSVITSIGAIVSCYGK<br>TKCTASNKNRGIIKTFSNGCDYVSNKGVDTVSVGNTLYYVNKLEGKALYIKGEPIINYYDPLVFPSDEFDASIAQV<br>NAKINQSLAFIRRSDELLSAIGGYIPEAPRDGQAYVRKDGEWVLLSTFLGGLVPRGSHHHHHHSAWSHPQFEK |
| bRSV F strain NP048055 sc9-10, DS-Cav1, Q98C-Q361C (SEQ ID NO: 108)<br>MDSKGSSQKGSRLLLLLVVSNLLLPQGVVGQNITEEFYQSTCSAVSRGYLSALRTGWYTSVVTIELSKIQKNVCKS<br>TDSKVKLIKQELERYNNAVVELQSLMCNEPASGSGSAVASGVAVSKVLHLEGEVNKIKNALLSTNKAVVSLSNGVS<br>VLTFKVLDLKNYIDKELLPQLNNHDCRISNIETVIEFQQKNNRLLEIAREFSVNAGITTPLSTYMLTNSELLSLIN<br>DMPITNDQKKLMSSNVQIVRQQSYSIMSVVKEEVIAYVVQLPIYGVIDTPCWKLHTSPLCTTDNKEGSNICLTRTD<br>RGWYCDNAGSVSFFPQTETCKVCSNRVFCDTMNSRTLPTDVNLCNTDIFNTKYDCKIMTSKTDISSSVITSIGAIV<br>SCYGKTKCTASNKNRGIIKTFSNGCDYVSNKGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain RB94 sc9-10, DS-Cav1, Q98C-Q361C (SEQ ID NO: 109)<br>MDSKGSSQKGSRLLLLLVVSNLLLPQGVVGQNITEEFYQSTCSAVSRGYLSALRTGWYTSVVTIELSKIQKNVCNS<br>TDSNVKLIKQELERYNNAVVELQSLMCNEPASGSGSAIASGVAVSKVLHLEGEVNKIKNALLSTNKAVVSLSNGVS<br>VLTFKVLDLKNYIDKELLPKLNNHDCQISNIATVIEFQQKNNRLLEIAREFSVNAGITTPLSTYMLTNSELLSLIN<br>DMPITNDQKKLMSSNVQIVRQQSYSIMSVVKEEVMAYVVQLPIYGVIDTPCWKLHTSPLCTTDNKEGSNICLTRTD<br>RGWYCDNAGSVSFFPQAETCKVCSNRVFCDTMNSRTLPTDVNLCNTDIFNAKYDCKIMTSKTDISSSVITSIGAIV<br>SCYGKTKCTASNKNRGIIKTFSNGCDYVSNRGVDTVSVGNTLYYVNKLEGKALYIKGEPIINYYDPLVFPSDEFDA<br>SIAQVNAKINQSLAFIRRSDELLSAIGGYIPEAPRDGQAYVRKDGEWVLLSTFLGGLVPRGSHHHHHHSAWSHPQF<br>EK |
| bRSV F strain ATue51908 sc9-10, Cav1, 99C-Q361C (SEQ ID NO: 110)<br>MATTAMRMIISIIFISTYVTHITLCQNITEEFYQSTCSAVSRGYLSALRTGWYTSVVTIELSKIQKNVCKSTDSKV<br>KLIKQELERYNNAVVELQSLMQCEPASGSGSAVASGVAVSKVLHLEGEVNKIKNALLSTNKAVVSLSNGVSVLTFK<br>VLDLKNYIDKELLPQLNNHDCRISNIETVIEFQQKNNRLLEIAREFSVNAGITTPLSTYMLINSELLSLINDMPIT<br>NDQKKLMSSNVQIVRQQSYSIMSVVKEEVIAYVVQLPIYGVIDTPCWKLHTSPLCTTDNKEGSNICLTRTDRGWYC<br>DNAGSVSFFPQTETCKVCSNRVFCDTMNSLTLPTDVNLCNTDIFNTKYDCKIMTSKTDISSSVITSIGAIVSCYGK<br>TKCTASNKNRGIIKTFSNGCDYVSNKGVDTVSVGNTLYYVNKLEGKALYIKGEPIINYYDPLVFPSDEFDASIAQV<br>NAKINQSLAFIRRSDELLSAIGGYIPEAPRDGQAYVRKDGEWVLLSTFLGGLVPRGSHHHHHHSAWSHPQFEK |
| bRSV F strain 391-2 sc9-10, Cav1, 99C-Q361C (SEQ ID NO: 111)<br>MAATAMRMIISIIFISTYMTHITLCQNITEEFYQSTCSAVSRGYLSALRTGWYTSVVTIELSKIQKNVCKSTDSKV<br>KLIKQELERYNNAVIELQSLMQCEPASGSGSAIASGVAVSKVLHLEGEVNKIKNALLSTNKAVVSLSNGVSVLTFK<br>VLDLKNYIDKELLPKLNNHDCRISNIETVIEFQQKNNRLLEIAREFSVNAGITTPLSTYMLTNSELLSLINDMPIT<br>NDQKKLMSSNVQIVRQQSYSIMSVVKEEVIAYVVQLPIYGVIDTPCWKLHTSPLCTTDNKEGSNICLTRTDRGWYC<br>DNAGSVSFFPQAETCKVCSNRVFCDTMNSLTLPTDVNLCNTDIFNTKYDCKIMTSKTDISSSVITSIGAIVSCYGK<br>TKCTASNKNRGIIKTFSNGCDYVSNKGVDTVSVGNTLYYVNKLEGKALYIKEPIINYYDPLVFPSDEFDASIAQVN<br>AKINQSLAFIRRSDELLSAIGGYIPEAPRDGQAYVRKDGEWVLLSTFLGGLVPRGSHHHHHHSAWSHPQFEK |

TABLE 2-continued

| Exemplary recombinant $F_2$-$F_1$ ectodomain protomer sequences |
|---|
| bRSV F strain ATue51908 sc9-10, DS-Cav1, Q98C-Q361C (SEQ ID NO: 112)<br>MATTAMRMIISIIFISTYVTHITLCQNITEEFYQSTCSAVSRGYLSALRTGWYTSVVTIELSKIQKNVCKSTDSKV<br>KLIKQELERYNNAVVELQSLMCNEPASGSGSAVASGVAVCKVLHLEGEVNKIKNALLSTNKAVVSLSNGVSVLTFK<br>VLDLKNYIDKELLPQLNNHDCRISNIETVIEFQQKNNRLLEIAREFSVNAGITTPLSTYMLINSELLSLINDMPIT<br>NDQKKLMSSNVQIVRQQSYSIMCVVKEEVIAYVVQLPIYGVIDTPCWKLHTSPLCTTDNKEGSNICLTRTDRGWYC<br>DNAGSVSFFPQTETCKVCSNRVFCDTMNSLTLPTDVNLCNTDIFNTKYDCKIMTSKTDISSSVITSIGAIVSCYGK<br>TKCTASNKNRGIIKTFSNGCDYVSNKGVDTVSVGNTLYYVNKLEGKALYIKGEPIINYYDPLVFPSDEFDASIAQV<br>NAKINQSLAFIRRSDELLSAIGGYIPEAPRDGQAYVRKDGEWVLLSTFLGGLVPRGSHHHHHHSAWSHPQFEK |
| bRSV F strain 391-2 sc9-10, DS-Cav1, Q98C-Q361C (SEQ ID NO: 113)<br>MAATAMRMIISIIFISTYMTHITLCQNITEEFYQSTCSAVSRGYLSALRTGWYTSVVTIELSKIQKNVCKSTDSKV<br>KLIKQELERYNNAVIELQSLMCNEPASGSGSAIASGVAVCKVLHLEGEVNKIKNALLSTNKAVVSLSNGVSVLTFK<br>VLDLKNYIDKELLPKLNNHDCRISNIETVIEFQQKNNRLLEIAREFSVNAGITTPLSTYMLINSELLSLINDMPIT<br>NDQKKLMSSNVQIVRQQSYSIMCVVKEEVIAYVVQLPIYGVIDTPCWKLHTSPLCTTDNKEGSNICLTRTDRGWYC<br>DNAGSVSFFPQAETCKVCSNRVFCDTMNSLTLPTDVNLCNTDIFNTKYDCKIMTSKTDISSSVITSIGAIVSCYGK<br>TKCTASNKNRGIIKTFSNGCDYVSNKGVDTVSVGNTLYYVNKLEGKALYIKEPIINYYDPLVFPSDEFDASIAQVN<br>AKINQSLAFIRRSDELLSAIGGYIPEAPRDGQAYVRKDGEWVLLSTFLGGLVPRGSHHHHHHSAWSHPQFEK |

In some embodiments, the recombinant $F_2$-$F_1$ ectodomain protomers in the recombinant RSV F ectodomain trimer each comprise or consist of an amino acid sequence set forth as one of:

- residues 26-474 of any one of SEQ ID NOs: 1, 3-5, 7-10, 12-13, 24-29, 36-37, 40-41, 44-45, 48-49, 52-53, 56, 100-102, 105-107, or 110-113;
- residues 26-475 of any one of SEQ ID NOs: 2, 6, 11, 30-35, 38-39, 42-43, 46-47, 50-51, 54-55.
- residues 31-479 of any one of SEQ ID NOs: 14-15, 17-20, 22-23, 103-104, or 108-109;
- residues 31-480 of any one of SEQ ID NOs: 16 or 21;
- residues 26-484 of any one of SEQ ID NOs: 81-84;
- residues 26-504 of any one of SEQ ID NOs: 1, 3-5, 7-10, 12-13, 24-29, 36-37, 40-41, 44-45, 48-49, 52-5356, 100-102, 105-107, or 110-113;
- residues 26-505 of any one of SEQ ID NOs: 2, 6, 11, 30-35, 38-39, 42-43, 46-47, 50-51, 54-55.
- residues 31-509 of any one of SEQ ID NOs: 14-15, 17-20, or 22-23, 103-104, or 108-109;
- residues 31-510 of any one of SEQ ID NOs: 16 or 21; or residues 26-514 of any one of SEQ ID NOs: 81-84;
- or an amino acid sequence at least 90% (such as at least 95% or at least 98%) identical thereto.

III. Protein Nanoparticles

In some embodiments a protein nanoparticle is provided that includes one or more of the disclosed recombinant RSV F ectodomains (e.g., a RSV F ectodomain including DS-Cav1 substitutions stabilized in a trimeric configuration by inter-protomer disulfide bonds between cysteine residues in four rings of di-cysteine motifs in the cysteine zipper domain) Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase, respectively. Exemplary sequences of recombinant RSV F ectodomains linked to a nanoparticle subunit are provided below. To construct protein nanoparticles including a recombinant RSV F ectodomain, the RSV F ectodomain can be linked to a subunit of the protein nanoparticle (such as a ferritin protein, an encapsulin protein, a SOR protein, or a lumazine synthase protein). The fusion protein self-assembles into a nanoparticle under appropriate conditions.

In several embodiments, the protein nanoparticle comprises two or more recombinant RSV F ectodomains, wherein the two or more recombinant RSV F ectodomains are from at least two different strains of RSV.

In some embodiments, a recombinant RSV F ectodomain (such as a recombinant RSV F ectodomain including the $F_2$ and $F^1$ ectodomain of any one of SEQ ID NOs: 9-16) can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such monomeric ferritin subunit is represented by:

(SEQ ID NO: 75)
ESQVRQQFSKDIEKLLNEQVNKEMQSSNLYMSMSSWCYTHSLDGAGLFLF

DHAAEEYEHAKKLIIFLNENNVPVQLTSISAPEHKFEGLTQIFQKAYEHE

QHISESINNIVDHAIKSKDHATFNFLQWYVAEQHEEEVLFKDILDKIELI

GNENHGLYLADQYVKGIAKSRKS

Each monomeric subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, *Int. J. Mol. Sci.,* 12:5406-5421, 2011, which is incorporated herein by reference in its entirety).

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant RSV F ectodomain can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Apr. 10, 2015. In some embodiments, a recombinant RSV F ectodomain can be linked to a ferritin subunit including an amino acid sequence at least 80% (such as at least 85%, at least 90%, at least 95%, or at least 97%) identical to amino acid sequence set forth as SEQ ID NO: 75.

In additional embodiments, any of the disclosed recombinant RSV F ectodomain can be linked to a lumazine synthase subunit to construct a lumazine synthase nanoparticle. The globular form of lumazine synthase nanoparticle is made up of monomeric subunits; an example of the sequence of one such lumazine synthase subunit is provides as the amino acid sequence set forth as:

```
                                          (SEQ ID NO: 76)
MQIYEGKLTAEGLRFGIVASRFNHALVDRLVEGAIDAIVRHGGREEDIT

LVRVPGSWEIPVAAGELARKEDIDAVIAIGVLIRGATPHFDYIASEVSK

GLADLSLELRKPITFGVITADTLEQAIERAGTKHGNKGWEAALSAIEMA

NLFKSLR.
```

In some embodiments, a disclosed recombinant RSV F ectodomain thereof can be linked to a lumazine synthase subunit including an amino acid sequence at least 80% (such as at least 85%, at least 90%, at least 95%, or at least 97%) identical to amino acid sequence set forth as SEQ ID NO: 76.

In additional embodiments, the recombinant RSV F ectodomain thereof can be linked to an encapsulin nanoparticle subunit to construct an encapsulin nanoparticle. The globular form of the encapsulin nanoparticle is made up of monomeric subunits; an example of the sequence of one such encapsulin subunit is provides as the amino acid sequence set forth as

```
                                          (SEQ ID NO: 77)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a recombinant RSV F ectodomain can be linked to an encapsulin subunit including an amino acid sequence at least 80% (such as at least 85%, at least 90%, at least 95%, or at least 97%) identical to amino acid sequence set forth as SEQ ID NO: 77.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60, or in some cases, 180 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *Thermotoga maritime* or *Pyrococcus furiosus* or *Rhodococcus erythropolis* or *Myxococcus xanthus* encapsulin.

In additional embodiments, a recombinant RSV F ectodomain can be linked to a Sulfur Oxygenase Reductase (SOR) subunit to construct a recombinant SOR nanoparticle. In some embodiments, the SOR subunit can include the amino acid sequence set forth as

```
                                          (SEQ ID NO: 78)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a recombinant RSV F ectodomain thereof can be linked to a SOR subunit including an amino acid sequence at least 80% (such as at least 85%, at least 90%, at least 95%, or at least 97%) identical to amino acid sequence set forth as SEQ ID NO: 78.

SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

For production purposes, the recombinant $F_2$-$F_1$ ectodomain protomer linked to the nanoparticle subunit can include a signal peptide that is cleaved during cellular processing. For example, the recombinant $F_2$-$F_1$ ectodomain protomer linked to the protein nanoparticle subunit can include a signal peptide at its N-terminus including, for example, a native RSV F signal peptide, or the amino acid sequence set forth as: MDSKGSSQKGSRLLLLLVVSNLLLPQGVLA (bPRL(LA) signal peptide, SEQ ID NO: 79) or MPMGSLQ-PLATLYLLGMLVASVLA (hCD5 signal peptide, SEQ ID NO: 80).

In some examples, the recombinant RSV F ectodomain or immunogenic fragment thereof can be linked to the N- or C-terminus, or placed within an internal loop of a ferritin, encapsulin, SOR, or lumazine synthase subunit, for example with a linker, such as a Ser-Gly linker. When the constructs have been made in HEK 293 Freestyle cells, the fusion proteins are secreted from the cells and self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein Amino acid sequences from monomeric subunits of any known ferritin, encapsulin, SOR, or lumazine synthase protein can be used to produce fusion proteins with the recombinant RSV F ectodomain or immunogenic fragment thereof, so long as the monomeric subunit is capable of self-assembling into a nanoparticle displaying the recombinant RSV F ectodomain or immunogenic fragment thereof on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

Fusion of any of the recombinant RSV F ectodomains (e.g., in trimeric form) or immunogenic fragment thereof to the ferritin, encapsulin, SOR, or lumazine synthase protein is done such that the recombinant RSV F ectodomain or immunogenic fragment thereof does not interfere with self-assembly of the monomeric ferritin, encapsulin, SOR, or lumazine synthase subunits into the globular protein, and that the ferritin, encapsulin, SOR, or lumazine synthase subunits do not interfere with the ability of the disclosed recombinant RSV F ectodomain or immunogenic fragment thereof to elicit an immune response to RSV F. In some embodiments, the ferritin, encapsulin, SOR, or lumazine synthase protein and recombinant RSV F ectodomain or immunogenic fragment thereof can be joined together directly without affecting the activity of either portion. In other embodiments, the ferritin, encapsulin, SOR, or lumazine synthase protein and the recombinant RSV F ectodomain or immunogenic fragment thereof can be joined using a linker (also referred to as a spacer) sequence. The linker sequence is designed to position the ferritin, encapsulin, SOR, or lumazine synthase portion of the fusion protein and the recombinant RSV F ectodomain or immunogenic fragment thereof can be linked to an portion of the fusion protein, with regard to one another, such that the fusion protein maintains the ability to assemble into nanoparticles, and also elicit an immune response to recombinant RSV F ectodomain. In several embodiments, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG Amino acids can be added or subtracted as needed. Those skilled in the art are capable of determining appropriate linker sequences for construction of protein nanoparticles.

IV. Polynucleotides and Expression

Polynucleotides encoding a recombinant $F_2$-$F_1$ ectodomain protomer of any of the disclosed recombinant RSV F ectodomain trimers are also provided. These polynucleotides include DNA, cDNA and RNA sequences which encode the recombinant $F_2$-$F_1$ ectodomain protomer. One of skill in the art can readily use the genetic code to construct a variety of functionally equivalent nucleic acids, such as nucleic acids which differ in sequence but which encode the same antibody sequence, or encode a conjugate or fusion protein including the nucleic acid sequence. Exemplary nucleic acid sequences include:

```
DNA encoding RSV A2 strain sc9-10, DS-Cav1, A149C-Y458C
                                                    (SEQ ID NO: 96)
atggaactgctgatcctgaaggctaacgccattaccactatcctgactgctgtgactttttgctttgcatccggccag

aacattaccgaggaattctaccagtccacatgctctgccgtgagtaaaggatacctgagcgctctgcggaccggctgg

tatacatccgtgatcactattgagctgtctaacattaaggaaaacaaatgtaacggcaccgacgctaaggtgaaactg

atcaagcaggagctggataagtataaaaatgcagtgacagaactgcagctgctgatgcagtccacccctgccacaggg

agtggatcagccatctgttctggagtggcagtctgcaaagtcctgcacctggagggcgaagtgaacaagatcaaatcc

gctctgctgtctactaacaaggcagtggtcagcctgtccaatggcgtgtccgtcctgacctttaaggtgctggacctg

aaaaattacatcgataagcagctgctgccaattctgaacaaacagtcttgtagtatctcaaacatcgagacagtgatt

gaattccagcagaagaacaataggctgctggagatcactcgcgagttcagcgtgaacgccggggtcaccacaccagtg

tccacctacatgctgacaaatagtgagctgctgtcactgatcaacgacatgcccattaccaatgatcagaagaaactg

atgtccaacaatgtgcagattgtcaggcagcagagctattccatcatgtgcatcattaaggaggaagtcctggcttac

gtggtccagctgcctctgtatggcgtgatcgacaccccatgctggaaactgcatacatctcccctgtgtactaccaac

acaaaggaaggaagtaatatctgcctgacacggactgacagaggctggtactgtgataacgcagggtctgtgagtttc

tttccccaggccgagacctgcaaggtccagtctaacagagtgttctgtgacactatgaatagcaggaccctgccttcc
```

-continued gaagtcaacctgtgcaatgtggacatcttcaacccaaagtacgattgtaagatcatgactagcaagaccgatgtcagc tcctctgtgatcacttcactgggagccattgtgagctgctacggcaagacaaaatgtactgctagcaacaaaaatcgg gggatcattaagaccttcagtaacggatgtgactatgtctcaaacaaggggggtggatacagtgagtgtcggaaacact ctgtactgtgtcaataagcaggagggcaaaagcctgtacgtgaaggggggaacctatcattaacttctatgacccactg gtgttcccctccgacgagtttgatgcctcaatcagccaggtgaacgaaaagatcaaccagtctctggcttttatccgc aagtctgatgagctgctgagtgcaatcggcgggtacattcccgaagcacctcgagacggccaggcctatgtccggaaa gatggggagtgggtgctgctgtcaaccttcctgggaggactggtgccacgaggaagccaccatcaccatcaccattca gcctggagccaccctcagtttgagaagtgatga DNA encoding RSV A2 strain sc9-10, DS-Cav1, N183GC-N428C (SEQ ID NO: 97)

atggaactgctgatcctgaaggctaacgccattaccactatcctgactgctgtgacttttttgctttgcatccggccag aacattaccgaggaattctaccagtccacatgctctgccgtgagtaaaggatacctgagcgctctgcggaccggctgg tatacatccgtgatcactattgagctgtctaacattaaggaaaacaaatgtaacggcaccgacgctaaggtgaaactg atcaagcaggagctggataagtataaaaatgcagtgacagaactgcagctgctgatgcagtccacccctgccacaggg agtggatcagccatcgcttctggagtggcagtctgcaaagtcctgcacctggagggcgaagtgaacaagatcaaatcc gctctgctgtctactaacaaggcagtggtcagcctgtccggctgtggcgtgtccgtcctgacctttaaggtgctggac ctgaaaaattacatcgataagcagctgctgccaattctgaacaaacagtcttgtagtatctcaaacatcgagacagtg attgaattccagcagaagaacaataggctgctggagatcactcgcgagttcagcgtgaacgccggggtcaccacacca gtgtccacctacatgctgacaaatagtgagctgctgtcactgatcaacgacatgcccattaccaatgatcagaagaaa ctgatgtccaacaatgtgcagattgtcaggcagcagagctattccatcatgtgcatcattaaggaggaagtcctggct tacgtggtccagctgcctctgtatggcgtgatcgacaccccatgctggaaactgcatacatctcccctgtgtactacc aacacaaaggaaggaagtaatatctgcctgacacggactgacagaggctggtactgtgataacgcagggtctgtgagt ttctttccccaggccgagacctgcaaggtccagtctaacagagtgttctgtgacactatgaatagcaggaccctgcct tccgaagtcaacctgtgcaatgtggacatcttcaacccaaagtacgattgtaagatcatgactagcaagaccgatgtc agctcctctgtgatcacttcactgggagccattgtgagctgctacggcaagacaaaatgtactgctagcaacaaatgt cgggggatcattaagaccttcagtaacggatgtgactatgtctcaaacaaggggggtggatacagtgagtgtcggaaac actctgtactatgtcaataagcaggagggcaaaagcctgtacgtgaaggggggaacctatcattaacttctatgaccca ctggtgttcccctccgacgagtttgatgcctcaatcagccaggtgaacgaaaagatcaaccagtctctggcttttatc cgcaagtctgatgagctgctgagtgcaatcggcgggtacattcccgaagcacctcgagacggccaggcctatgtccgg aaagatggggagtgggtgctgctgtcaaccttcctgggaggactggtgccacgaggaagccaccatcaccatcaccat tcagcctggagccaccctcagtttgagaagtgatga DNA encoding RSV strain B18537-sc9-10, DS-Cav1, Q98C-361C-L95M-I221M-R429K

SEQ ID NO: 98)

tctagaccaccatggagctgctgatccacaggagctccgccatcttcctgacactggccgtgaatgccctgtacctga catctagccagaacatcaccgaggagttctatcagtccacctgctctgccgtgagcaggggctacttttccgccctgc gcaccggctggtatacatccgtgatcaccatcgagctgtctaatatcaaggagaccaagtgtaacggcaccgacacaa aggtgaagctgatcaagcaggagctggataagtacaagaatgccgtgacagagctgcagatgctgatgtgcaacaccc cagcagcaggcagcggctccgccatcgccagcggcatcgccgtgtgcaaggtgctgcacctggagggcgaggtgaaca agatcaagaatgccctgctgtccacaaataaggccgtggtgtctctgagcaacggcgtgtctgtgctgacctttaagg tgctggacctgaagaactatatcaacaatcggctgctgcctatcctgaatcagcagtcttgcagaatcagcaacccag agacagtgatggagttccagcagatgaattcccggctgctggagatcaccagagagttttctgtgaacgccggcgtga ccacaccactgagcacatacatgctgaccaattccgagctgctgtctctgatcaacgacatgcccatcaccaatgatc agaagaagctgatgtcctctaacgtgcagatcgtgcgccagcagtcctattctatcatgtgcatcatcaaggaggagg -continued tgctggcctacgtggtgcagctgcctatctatggcgtgatcgacacaccatgctggaagctgcacaccagccccctgt gcaccacaaacatcaaggagggctccaatatctgcctgaccaggacagaccgcggctggtactgtgataatgccggca gcgtgtccttctttcctcaggccgacacatgcaaggtgtgctccaatagggtgttctgcgatacaatgaactctcgca ccctgccatccgaggtgtctctgtgcaacacagacatctttaattctaagtacgattgtaagatcatgaccagcaaga cagatatcagctcctctgtgatcacctctctgggcgccatcgtgagctgctacggcaagaccaagtgtacagcctcca acaagaataagggcatcatcaagaccttcagcaatggctgtgactacgtgagcaacaagggcgtggatacagtgagcg tgggcaacaccctgtactatgtgaataagctggagggcaagaacctgtacgtgaagggcgagcctatcatcaactact atgacccactggtgttcccctccgacgagtttgatgcctctatcagccaggtgaacgagaagatcaatcagagcctgg cctttatccggagaagcgatgagctgctgtccgccatcggcggctacatcccagaggcacctagggacggacaggcat atgtgagaaaggatggcgagtgggtgctgctgtctaccttcctgggaggactggtgccaaggggcagccaccaccacc accaccacagcgcctggtcccaccctcagtttgagaagtgatgaggatcc DNA encoding RSV LongVR26 strain sc9-10, DS-Cav1, Q98C-361C-L95M-I221M-R429K-I217P-S46G-K465Q-S215P-E92D (SEQ ID NO: 99)

tctagaccaccatggagctgcccatcctgaaggccaacgccatcaccacaatcctggccgccgtgacattctgctttg ccagctcccagaatatcacagaggagttctaccagagcacctgttccgccgtgtctaagggatacctgagcgccctga ggaccggatggtatacatccgtgatcaccatcgagctgtctaacatcaaggagaacaagtgcaatggcaccgacgcca aggtgaagctgatcaaccaggagctggataagtataagaatgccgtgacagagctgcagatgctgatgtgctctacca cagcaaccggctctggcagcgccatcgcaagcggcatcgccgtgtgcaaggtgctgcacctggagggcgaggtgaaca agatcaagtctgccctgctgagcaccaacaaggccgtggtgtccctgtctaatggcgtgtccgtgctgttttctaagg tgctggacctgaagaattacatcgataagcagctgctgcctatcctgaacaagcagagctgcaggatctccaatatcg agacagtgatggagttccagcagaagaacaataggctgctggagatcacccgcgagttttctgtgaacgccggcgtga ccacacctgtgagcacatacatgctgaccaattctgagctgctgagcctgatcaacgacatgccaatcaccaatgatc agaagaagctgatgagcaacaatgtgcagatcgtgcgccagcagagctattccatcatgtgcatcatcaaggaggagg tgctggcctacgtggtgcagctgcctctgtatggcgtgatcgacacaccatgctggaagctgcacacctccccccctgt gcaccacaaacacaaaggagggctctaatatctgcctgacccggacagacagaggctggtactgtgataacgccggct ctgtgagcttctttccccaggccgagacctgcaaggtgtgctccaacagggtgttctgcgacacaatgaattcccgca ccctgccctctgaggtgaacctgtgcaatgtggacatctttaatcctaagtacgattgtaagatcatgaccagcaaga cagacgtgagcagctccgtgatcacatctctgggcgccatcgtgagctgctacggcaagaccaagtgtacagcctcca acaagaataagggcatcatcaagaccttcagcaacggctgtgactacgtgagcaataagggcgtggatacagtgtccg tgggcaacaccctgtactatgtgaataagcaggagggcaagtctctgtacgtgaagggcgagcctatcatcaacttct atgacccactggtgttccccagcgacgagtttgatgcctccatctctcaggtgaacgagaagatcaatcagtccctgg cctttatccggaagagcgatgagctgctgtccgccatcggcggctacatcccagaggcacctagggacggacaggcat atgtgagaaaggatggcgagtgggtgctgctgagcaccttcctgggaggactggtgccaagaggctcccaccaccacc accaccacagcgcctggtcccacccccagtttgagaagtgatgaggatcc In several embodiments, the nucleic acid molecule encodes a precursor of a disclosed recombinant $F_2$-$F_1$ ectodomain protomer, that, when expressed in an appropriate cell, is processed into a disclosed recombinant $F_2$-$F_1$ ectodomain protomer that can self assemble into the corresponding recombinant RSV F ectodomain trimer. For example, the nucleic acid molecule can encode a recombinant RSV F ectodomain including a N-terminal signal sequence for entry into the cellular secretory system that is proteolytically cleaved in the during processing of the recombinant RSV F ectodomain in the cell. In some embodiments, the signal peptide includes the amino acid sequence set forth as residues 1-25 of SEQ ID NO: 57.

In several embodiments, the nucleic acid molecule encodes a precursor $F_0$ polypeptide that, when expressed in an appropriate cell, is processed into a disclosed recombinant $F_2$-$F_1$ ectodomain protomer including an $F_2$ polypeptide linked to a $F_1$ ectodomain from a human RSV A subtype, a human RSV B subtype, or a bovine RSV, wherein the recombinant $F_2$-$F_1$ ectodomain protomer includes any of the stabilizing modifications described herein, and optionally can be linked to a trimerization domain, such as a T4 Fibritin trimerization domain.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, New York, 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (Carlsbad, CA), and Applied Biosystems (Foster City, CA), as well as many other commercial sources known to one of skill.

Nucleic acids can also be prepared by amplification methods Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a disclosed recombinant $F_2$-$F_1$ ectodomain protomer can include a recombinant DNA which is incorporated into a vector (such as an expression vector) into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding a disclosed recombinant $F_2$-$F_1$ ectodomain protomer can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the disclosed recombinant $F_2$-$F_1$ ectodomain protomer can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human) Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., *J. Virol.,* 79, 8828-8834, 2005, which is incorporated by reference herein).

Modifications can be made to a nucleic acid encoding a disclosed recombinant $F_2$-$F_1$ ectodomain protomer without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In some embodiments, the disclosed recombinant $F_2$-$F_1$ ectodomain protomer can be expressed in cells under conditions where the recombinant $F_2$-$F_1$ ectodomain protomer can self assemble into trimers which are secreted from the cells into the cell media, for example as described for other RSV F proteins (see, e.g., PCT Pub. WO2014160463, McLellan et al., *Science,* 340:1113-1117, 2013; McLellan et al., *Science,* 342:592-598, 2013, each of which is incorporated by reference herein in its entirety). In such embodiments, each recombinant $F_2$-$F_1$ ectodomain protomer contains a leader sequence (signal peptide) that causes the protein to enter the secretory system, where the signal peptide is cleaved and the protomers form a trimer, before being secreted in the cell media. The medium can be centrifuged and recombinant RSV F ectodomain trimer purified from the supernatant.

V. Viral Vectors

A nucleic acid molecule encoding a disclosed recombinant $F_2$-$F_1$ ectodomain protomer can be included in a viral vector, for example for expression of the recombinant $F_2$-$F_1$ ectodomain protomer to produce the corresponding recombinant RSV F ectodomain trimer in a host cell, or for immunization of a subject as disclosed herein. In some embodiments, the viral vectors are administered to a subject as part of a prime-boost vaccination. Typically such viral vectors include a nucleic acid molecule encoding a disclosed recombinant $F_2$-$F_1$ ectodomain protomer that is linked to a C-terminal transmembrane domain, for example the recombinant $F_2$-$F_1$ ectodomain protomer can be linked to an RSV F transmembrane domain and cytosolic tail. In several embodiments, the viral vectors are included in a vaccine, such as a primer vaccine or a booster vaccine for use in a prime-boost vaccination.

In several examples, the viral vector encoding the recombinant $F_2$-$F_1$ ectodomain protomer to produce the recombinant RSV F ectodomain trimer can be replication-competent. For example, the viral vector can have a mutation (e.g., insertion of nucleic acid encoding the recombinant $F_2$-$F_1$ ectodomain protomer) in the viral genome that attenuates, but does not completely block viral replication in host cells.

In several embodiments, the viral vector encoding the recombinant $F_2$-$F_1$ ectodomain protomer to produce the recombinant RSV F ectodomain trimer is a viral vector that can be delivered via the respiratory tract. For example, a paramyxovirus (PIV) vector, such as bovine parainfluenza virus (BPIV) vector (e.g., a BPIV-1, BPIV-2, or BPV-3 vector) or human PIV vector, a metapneumovirus (MPV) vector, a Sendia virus vector, or a measles virus vector, is used to express a disclosed antigen. A BPIV3 viral vector expressing the RSV F and the hPIV F proteins (MEDI-534) is currently in clinical trials as a RSV vaccine. Examples of paramyxovirus (PIV) vector for expressing antigens are known to the person of skill in the art (see, e.g., U.S. Pat. App. Pubs. 2012/0045471, 2011/0212488, 2010/0297730, 2010/0278813, 2010/0167270, 2010/0119547, 2009/0263883, 2009/0017517, 2009/0004722, 2008/0096263, 2006/0216700, 2005/0147623, 2005/0142148, 2005/0019891, 2004/0208895, 2004/0005545, 2003/0232061, 2003/0095987, and 2003/0072773; each of which is incorporated by reference herein in its entirety). In another example, a Newcastle disease viral vector is used to express a disclosed antigen (see, e.g., McGinnes et al., J. Virol., 85: 366-377, 2011, describing RSV F and G proteins expressed on Newcastle disease like particles, incorporated by reference in its entirety). In another example, a Sendai virus vector is used to express a disclosed antigen (see, e.g., Jones et al., *Vaccine,* 30:959-968, 2012, incorporated by reference herein in its entirety, which discloses use of a Sendai virus-based RSV vaccine to induce an immune response in primates).

Additional viral vectors are also available for expression of the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158: 39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, *Curr. Top. Microbiol. Immunol.,* 158:91-123; On et al., 1990, *Gene,* 89:279-282), herpes viruses including HSV and EBV and CMV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158: 1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, CA; Protein Sciences Corp., Meriden, Conn.; Stratagene, La Jolla, CA). Additional viral vectors are familiar to the person of ordinary skill in the art.

VI. Virus-Like Particles

In some embodiments, a virus-like particle (VLP) is provided that includes a disclosed recombinant RSV F ectodomain trimer. Typically such VLPs include a recombinant RSV F ectodomain trimer that is membrane anchored by a C-terminal transmembrane domain, for example the recombinant $F_2$-$F_1$ ectodomain protomers in the trimer each can be linked to an RSV F transmembrane domain and cytosolic tail. VLPs lack the viral components that are required for virus replication and thus represent a highly attenuated, replication-incompetent form of a virus. However, the VLP can display a polypeptide (e.g., a recombinant RSV F ectodomain trimer) that is analogous to that expressed on infectious virus particles and can eliciting an immune response to RSV when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

VII. Immunogenic Compositions

Immunogenic compositions comprising a disclosed immunogen (e.g., recombinant RSV F ectodomain trimer, a nucleic acid molecule or vector encoding a recombinant $F_2$-$F_1$ ectodomain protomer of a disclosed recombinant RSV F ectodomain trimer, or a protein nanoparticle or virus like particle comprising a disclosed recombinant RSV F ectodomain trimer) and a pharmaceutically acceptable carrier are also provided. Such compositions can be administered to subjects by a variety of administration modes known to the person of ordinary skill in the art, for example, intramuscular, subcutaneous, intravenous, intra-arterial, intra-articular, intraperitoneal, or parenteral routes. In several embodiments, a pharmaceutical composition including one or more of the disclosed immunogens are immunogenic compositions. Actual methods for preparing administrable compositions will be known or apparent to those skilled in the art and are described in more detail in such publications as *Remingtons Pharmaceutical Sciences,* $19^{th}$ Ed., Mack Publishing Company, Easton, Pennsylvania, 1995.

Such compositions can be administered to subjects by a variety of administration modes known to the person of ordinary skill in the art, for example, intramuscular, subcutaneous, intravenous, intra-arterial, intra-articular, intraperitoneal, or parenteral routes.

Thus, an immunogen described herein can be formulated with pharmaceutically acceptable carriers to help retain biological activity while also promoting increased stability during storage within an acceptable temperature range. Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations (usually 1% w/v) of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The immunogenic compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The immunogenic composition may optionally include an adjuvant to enhance an immune response of the host. Adjuvants, such as aluminum hydroxide (ALHYDROGEL®, available from Brenntag Biosector, Copenhagen, Denmark and Amphogel®, Wyeth Laboratories, Madison, NJ), Freund's adjuvant, MPL™ (3-O-deacylated monophosphoryl lipid A; Corixa, Hamilton, IN) and IL-12 (Genetics Institute, Cambridge, MA), TLR agonists (such as TLR-9 agonists), among many other suitable adjuvants well known in the art, can be included in the compositions. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, IN) and IL-12 (Genetics Institute, Cambridge, MA), among many other suitable adjuvants well known in the art, may be used as an adjuvant (Newman et al., 1998*, Critical Reviews in Therapeutic Drug Carrier Systems* 15:89-142). These adjuvants have the advantage in that they help to stimulate the immune system in a non-specific way, thus enhancing the immune response to a pharmaceutical product.

In several embodiments, the adjuvant is selected to elicit a Th1 biased immune response in a subject.

In some instances, the adjuvant formulation a mineral salt, such as a calcium or aluminum (alum) salt, for example calcium phosphate, aluminum phosphate or aluminum hydroxide. In some embodiments, the adjuvant includes an oil and water emulsion, e.g., an oil-in-water emulsion (such as MF59 (Novartis) or AS03 (GlaxoSmithKline). One example of an oil-in-water emulsion comprises a metabolisable oil, such as squalene, a tocol such as a tocopherol, e.g., alpha-tocopherol, and a surfactant, such as sorbitan trioleate (Span 85) or polyoxyethylene sorbitan monooleate (Tween 80), in an aqueous carrier.

In some instances it may be desirable to combine a disclosed immunogen with other pharmaceutical products (e.g., vaccines) which induce protective responses to other agents. For example, a composition including a recombinant RSV F ectodomain trimer as described herein can be can be administered simultaneously (typically separately) or sequentially with other vaccines recommended by the Advisory Committee on Immunization Practices (ACIP; cdc.gov/vaccines/acip/index.html) for the targeted age group (e.g., infants from approximately one to six months of age). As such, a disclosed immunogen described herein may be administered simultaneously or sequentially with vaccines against, for example, hepatitis B (HepB), diphtheria, tetanus and pertussis (DTaP), pneumococcal bacteria (PCV), *Haemophilus influenzae* type b (Hib), polio, influenza and rotavirus.

In some embodiments, the composition can be provided as a sterile composition. The immunogenic composition typically contains an effective amount of a disclosed immunogen and can be prepared by conventional techniques. Typically, the amount of immunogen in each dose of the immunogenic composition is selected as an amount which induces an immune response without significant, adverse side effects. In some embodiments, the composition can be provided in unit dosage form for use to induce an immune response in a subject, for example, to prevent RSV infection in the subject. A unit dosage form contains a suitable single preselected dosage for administration to a subject, or suitable marked or measured multiples of two or more preselected unit dosages, and/or a metering mechanism for administering the unit dose or multiples thereof.

In some embodiments, the composition includes a first immunogen including a first recombinant RSV F ectodomain trimer as disclosed herein that is based on a RSV F subtype A protein, and a second recombinant RSV F ectodomain trimer as disclosed herein that is based on a RSV F subtype B protein.

VIII. Therapeutic Methods

The disclosed immunogens (e.g., recombinant RSV F ectodomain trimer, a nucleic acid molecule (such as an RNA molecule) or vector encoding a recombinant $F_2$-$F_1$ ectodomain protomer of a disclosed recombinant RSV F ectodomain trimer, or a protein nanoparticle or virus like particle comprising a disclosed recombinant RSV F ectodomain trimer) can be administered to a subject to induce an immune response to RSV F protein in the subject. In a particular example, the subject is a human. The immune response can be a protective immune response, for example a response that prevents or reduces subsequent infection with RSV. Elicitation of the immune response can also be used to treat or inhibit RSV infection and illnesses associated therewith. In several embodiments, the method includes administration of an immunogenic composition including a disclosed recombinant RSV F ectodomain trimer.

A subject can be selected for treatment that has, or is at risk for developing RSV infection, for example because of exposure or the possibility of exposure to RSV. Following administration of a disclosed immunogen, the subject can be monitored for RSV infection or symptoms associated therewith, or both.

Typical subjects intended for treatment with the therapeutics and methods of the present disclosure include humans, as well as non-human primates and other animals, such as cattle. Because nearly all humans are infected with RSV by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age. The scope of this disclosure is meant to include maternal immunization. In several embodiments, the subject is a human subject that is seronegative for RSV specific antibodies. In additional embodiments, the subject is no more than one year old, such as no more than 6 months old, no more than 3 months, or no more than 1 month old.

Subjects at greatest risk of RSV infection with severe symptoms (e.g. requiring hospitalization) include children with prematurity, bronchopulmonary dysplasia, and congenital heart disease are most susceptible to severe disease. Atopy or a family history of atopy has also been associated with severe disease in infancy. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. (See, e.g., Shay et al., JAMA, 282:1440-6, 1999; Hall et al., N Engl J Med. 2009; 360:588-598; Glezen et al., *Am J Dis Child.,* 1986; 140:543-546; and Graham, Immunol. Rev., 239:149-166, 2011, each of which is incorporated by reference herein). Thus, these subjects can be selected for administration of the disclosed immunogens, or a nucleic acid or a viral vector encoding, expressing or including an immunogen.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize RSV infection. These and other routine methods allow the clinician to select patients in need of therapy using the methods and immunogenic compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting RSV infection, and administering a therapeutically effective amount of a disclosed immunogen to the subject. The immunogen can be provided prior to the anticipated exposure to RSV so as to attenuate the anticipated severity, duration or extent of an infection and/or associated disease symptoms, after exposure or suspected exposure to the virus, or after the actual initiation of an infection. When provided therapeutically, the disclosed immunogens are provided at or after the onset of a symptom of RSV infection, or after diagnosis of RSV infection. Treatment of RSV by inhibiting RSV replication or infection can include delaying and/or reducing signs or symptoms of RSV infection in a subject. In some examples, treatment using the methods disclosed herein prolongs the time of survival of the subject.

In some embodiments, administration of a disclosed immunogen to a subject can elicit the production of an immune response that is protective against serious lower respiratory tract disease, such as pneumonia and bronchiolitis, or croup, when the subject is subsequently infected or re-infected with a wild-type RSV. While the naturally circulating virus may still be capable of causing infection, particularly in the upper respiratory tract, there can be a reduced possibility of rhinitis as a result of the vaccination and a possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup. To achieve higher levels of cross-protection, for example, against heterologous strains of another subgroup, subjects can be vaccinated with a composition including recombinant viral vectors including RSV F proteins from at least one predominant strain of both RSV groups A and B.

The immunogens described herein, and immunogenic compositions thereof, are provided to a subject in an amount effective to induce or enhance an immune response against RSV F protein in the subject, preferably a human. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-viral immune response, such as an immune response to RSV proteins. Separate immunogenic compositions that elicit the anti-viral immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be a different disclosed immunogen. In some examples that the boost may be the same immunogen as another boost, or the prime. The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential immunizations. For example a relatively large dose in a primary immunization and then a boost with relatively smaller doses.

In some embodiments, the boost can be administered about two, about three to eight, or about four, weeks following the prime, or about several months after the prime. In some embodiments, the boost can be administered about 5, about 6, about 7, about 8, about 10, about 12, about 18, about 24, months after the prime, or more or less time after the prime. Periodic additional boosts can also be used at appropriate time points to enhance the subject's "immune memory." The adequacy of the vaccination parameters chosen, e.g., formulation, dose, regimen and the like, can be determined by taking aliquots of serum from the subject and assaying antibody titers during the course of the immunization program. In addition, the clinical condition of the subject can be monitored for the desired effect, e.g., prevention of RSV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response.

In some embodiments, the prime administered to the subject includes (or encodes) a disclosed recombinant RSV F ectodomain trimer that is based on a subtype A RSV F protein, and the boost administered to the subject includes (or encodes) a disclosed recombinant RSV F ectodomain trimer that is based on a subtype B RSV F protein. In some embodiments, the prime administered to the subject includes (or encodes) a disclosed recombinant RSV F ectodomain trimer that is based on a subtype B RSV F protein, and the boost administered to the subject includes (or encodes) a disclosed recombinant RSV F ectodomain trimer that is based on a subtype A RSV F protein. In some embodiments, the prime and/or boost compositions administered to the subject each include (or encode) a mixture (such as a 50/50 mixture) of disclosed recombinant RSV F ectodomain trimers that are based on subtype A and subtype B RSV F proteins.

In some embodiments, the prime-boost method can include DNA-primer and protein-boost vaccination protocol to a subject. The method can include two or more administrations of the nucleic acid molecule or the protein.

For protein therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a recombinant RSV F ectodomain or immunogenic fragment thereof, viral vector, or nucleic acid molecule in a immunogenic composition, can include an amount that is ineffective at eliciting an immune response by administration of a single dose, but that is effective upon administration of multiple dosages, for example in a prime-boost administration protocol.

Upon administration of a disclosed immunogen the immune system of the subject typically responds to the immunogenic composition by producing antibodies specific for viral protein. Such a response signifies that an immunologically effective dose was delivered to the subject.

For each particular subject, specific dosage regimens can be evaluated and adjusted over time according to the individual need and professional judgment of the person administering or supervising the administration of the immunogenic composition. The dosage and number of doses will depend on the setting, for example, in an adult or anyone primed by prior RSV infection or immunization, a single dose may be a sufficient booster. In naïve subjects, in some examples, at least two doses would be given, for example, at least three doses. In some embodiments, an annual boost is given, for example, along with an annual influenza vaccination.

In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, an RSV F protein.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes. In one embodiment, a general range of virus administration is about $10^3$ to about $10^7$ plaque forming units (PFU) or more of virus per human subject, including about $10^4$ to about $10^5$ PFU virus per human subject.

Administration of an immunogenic composition that elicits an immune response to reduce or prevent an infection, can, but does not necessarily completely, eliminate such an infection, so long as the infection is measurably diminished. For example, administration of an effective amount of the agent can decrease the RSV infection (for example, as measured by infection of cells, or by number or percentage of subjects infected by RSV) by a desired amount, for example by at least 10%, at least 20%, at least 50%, at least 60%, at least 70%, at least 80%, at least 90%, at least 95%, at least 98%, or even at least 100% (elimination or prevention of detectable RSV infection, as compared to a suitable control.

In some embodiments, administration of a therapeutically effective amount of one or more of the disclosed immunogens to a subject induces a neutralizing immune response in the subject. To assess neutralization activity, following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of RSV pseudoviruses.

One approach to administration of nucleic acids is direct immunization with plasmid DNA, such as with a mammalian expression plasmid Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a recombinant RSV F ectodomain stabilized in a prefusion conformation can be administered to a subject to induce an immune response to RSV F protein. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed recombinant RSV F ectodomain or immunogenic fragment thereof can also be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed recombinant RSV F ectodomain or immunogenic fragment thereof, is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In certain embodiments, the immunogen can be administered sequentially with other anti-RSV therapeutic agents, such as before or after the other agent. One of ordinary skill in the art would know that sequential administration can mean immediately following or after an appropriate period of time, such as hours, days, weeks, months, or even years later.

In several embodiments, it may be advantageous to administer the immunogenic compositions disclosed herein with other agents such as proteins, peptides, antibodies, and other antiviral agents, such as anti-RSV agents. Non-limiting examples of anti-RSV agents include the monoclonal antibody palivizumab (SYNAGIS®; Medimmune, Inc.) and the small molecule anti-viral drug ribavirin (manufactured by many sources, e.g., Warrick Pharmaceuticals, Inc.). In certain embodiments, immunogenic compositions are administered concurrently with other anti-RSV agents. In certain embodiments, the immunogenic compositions are administered sequentially with other anti-RSV therapeutic agents, such as before or after the other agent. One of ordinary skill in the art would know that sequential administration can mean immediately following or after an appropriate period of time, such as hours, days, weeks, months, or even years later.

EXAMPLES

The following examples are provided to illustrate particular features of certain embodiments, but the scope of the claims should not be limited to those features exemplified.

Example 1

Iterative Structure-Based Improvement of a Fusion Glycoprotein Vaccine Against Respiratory Syncytial Virus Abstract Severe disease from respiratory syncytial virus (RSV) occurs most frequently during the first six months of life, when infant lungs are still developing. Maternal antibodies—transferred during the last weeks of pregnancy—provide protective immunity, but this protection wanes ~2-fold each month and should be ~$2^6$-fold (64-fold) the protective threshold at birth to safeguard infants during their most vulnerable period. A $1^{st}$-generation RSV-vaccine antigen called DS-Cav1 was previously developed that comprises a pre-fusion-stabilized form of the fusion (F) glycoprotein. Here iterative cycles of structure-based design were employ to increase RSV-protective titers a further ~4-fold, by engineering $2^{nd}$-generation versions of DS-Cav1 with F subunits genetically linked, fusion peptide deleted, and interprotomer movements stabilized by disulfide bonds. Additionally, these versions showed superior manufacturing attributes, such as the absence of a requirement for furin cleavage and increased antigenic stability to heat inactivation, with several over 10-fold more stable than DS-Cav1 at 60° C. These $2^{nd}$ generation DS-Cav1 antigens are thus promising vaccine candidates to boost maternal antibodies and to extend the protection infants are afforded by passively acquired neutralizing activity. The iterative structure-based design described here may, moreover, have utility in the optimization of other vaccine antigens.

Introduction

Human respiratory syncytial virus (RSV) infects virtually all children by two years of age and accounts for ~50% of hospitalizations due to respiratory infections in this age group. Maternal antibodies—transferred placentally during the last weeks of pregnancy—provide protective immunity to full-term infants (van den Berg et al., *Early Human Development,* 87, 67, 2011; Hobbs and Davis, *Lancet,* 1, 757, 1967), but this protection wanes ~2-fold each month (Leuridan et al., *BMJ,* 340, c1626, 2010; Sarvas et al., *J. Clinical Immunol.,* 13, 145, 1993; Lee et al., *J. Infect. Dis.,* 183, 1281, 2001), with infant hospitalization from RSV peaking in the first five months after birth (Hall et al., *Pediatrics* 132, e341, 2013), as maternal antibodies wane and infant lungs are still developing. For infants born at <28 weeks gestation, monthly injections of palivizumab (Synagis®), a humanized monoclonal antibody, are recommended (Palivizumab: new indication. Moderate reduction in hospitalisation rate. *Prescrire international* 13, 213, 2004), and this reduces the frequency of hospitalization by ~50% (The IMpact-RSV Study Group, *Pediatrics,* 102, 531, 1998). Premature infants born between 28 and 34 weeks gestation also have increased risk for severe RSV disease; and full-term infants without identified risk factors make up 50% of RSV-related hospitalizations (Hall et al., *Pediatrics* 132, e341, 2013). New interventions are thus needed to reduce the disease burden imposed by RSV infection.

One possibility is maternal immunization. However, assuming roughly a one month half-life, titers would have to be $2^6$-fold (64-fold) above the protective threshold at birth to safeguard infants during their most vulnerable period—and it has been unclear how to generate such very high protective responses. Many RSV vaccine candidates are being developed (Glenn et al., *J. Infect. Dis,* 213, 411, 2016; Swanson et al., *PNAS,* 108, 9619, 2011; Modjarrad et al., *Vaccine* 34, 190, 2016; Karron et al., *Curr. Topics Microbiol. Immunol.,* 372, 259, 2013; Graham et al., *Curr. Opin. Immunol.,* 35, 30, 2015). Most include the RSV fusion (F) glycoprotein antigen, the target of palivizumab (Pollack and Groothuis, *J. Infect. Chemother.,* 8, 201, 2002; Young, *Respiratory Medicine,* 96 Suppl B, S31, 2002; Johnson et al., *J infectious dis,* 176, 1215, 1997). The F glycoprotein is a type 1 fusion machine that transitions between pre-fusion and post-fusion states to facilitate RSV entry into target cells (Colman and Lawrence, *Nat. Rev. Mol. Cell. Biol.,* 4, 309, 2003). Initially synthesized as an $F_0$ precursor, RSV $F_0$ folds into a trimer, which is activated by furin cleavage into mature pre-fusion F (pre-F), comprising $F_1$ and $F_2$ subunits (Bolt, Pedersen, and Birkeslund, *Virus Research,* 68, 25, 2000). Pre-F is metastable, and spontaneous rearranges into a stable post-fusion state (Swanson et al., *PNAS,* 108, 9619, 2011; Liljeroos et al., *PNAS,* 110, 11133, 2013; McLellan et al., *J. Virol.,* 85, 7788, 2011). While initial focus had been on post-fusion F (Swanson et al., *PNAS,* 108, 9619, 2011; McLellan et al., *J. Virol.,* 85, 7788, 2011), many neutralization epitopes are not present on post-fusion F (Magro et al., *PNAS,* 109, 3089, 2012; Corti et al., *Nature,* 501, 439, 2013; Gilman et al., *PLoS pathogens,* 11, e1005035, 2015), including those for potent antibodies D25, AM22 and 5C4 (28, 29), directed against the membrane-distal antigenic site Ø (McLellan et al., *Science,* 340, 1113, 2013), and also those for quaternary-specific antibodies MPE8 and AM14 (Corti et al., *Nature,* 501, 439, 2013; Gilman et al., *PLoS pathogens,* 11, e1005035, 2015; Kwakkenbos et al., *Nat. Med.,* 16, 123, 2010). Moreover, the realization that pre-F-specific antibodies determine the magnitude of RSV neutralizing activity in human sera (Ngwuta et al., *Science Transl. Med.,* 7, 309ra162, 2015) has led to a focus on pre-F. Two pre-F antigens, stabilized through structure-based design, appear especially promising. These are "DS-Cav1" (McLellan et al., *Science,* 342, 592, 2013) a pre-F trimer, stabilized by a disulfide between residues 155 and 290 ("DS"), cavity-filling mutations S190F and V207L ("Cav1) and an appended C-terminal fibritin-trimerization domain, and "SC-DM" (Krarup et al., *Nature Commun.,* 6, 8143, 2015) also a pre-F trimer, with F2 linked to F1 ("SC"), stabilizing mutations N67I and S215P ("DM") and an appended fibritin domain. DS-Cav1 induces neutralizing antibody titers 70-80-fold higher than postfusion F (for subtypes A and B, respectively) in rhesus macaques (McLellan et al., *Science,* 342, 592, 2013), whereas SC-DM induces complete protection against viral challenge in cotton rats and remains primarily in the pre-fusion state for over 50 days at 4° C. (Krarup et al., *Nature Commun.,* 6, 8143, 2015). While promising, the duration of infant protection achieved by maternal immunization awaits clinical evaluation, and every 2-fold increase in immunogenicity would potentially extend protection in infants by an additional month. Since RSV-mediated disease may be largely a consequence of obstruction in small airways due to an accumulation of sloughed epithelium, mucus, fibrin and inflammatory debris (Johnson et al., *Modern Pathol.,* 20, 108, 2007), one of the major goals for RSV vaccines is to delay the timing of primary RSV infection until infants are older and airways are larger.

Historically, boosting neutralizing activity in humans with pre-existing immunity has been difficult: decades of RSV-vaccine research had previously achieved an increase of only 2-4-fold in RSV-neutralizing titers in healthy adults (Langley et al., *Vaccine,* 27, 5913, 2009; Paradiso et al., *Pediatric Infect Dis., J* 13, 792, 1994; Tristram et al., *Vaccine* 12, 551, 1994), and the ~70-fold increase in immunogenicity of pre-F DS-Cav1 over postfusion RSV F was considered one of the top scientific breakthroughs of 2013 (Cohen, *Science* 342, 1442, 2013).

As disclosed herein, the immunogenicity of DS-Cav1 through iterative cycles of structure-based design was achieved. In each cycle, atomic-level design was used to engineer variants, expressed and assessed their antigenic and physical properties, determined structures and measured the immunogenicity of select variants, and analyzed results informatically to provide direction for immunogenicity optimization in the next cycle. In total, 4 cycles of structure-based engineering were employed, involving the design, expression and antigenic assessment of hundreds of variants, the crystal structures of 6, and the immunogenicity of 14. The resultant $2^{nd}$-generation DS-Cav1 antigens have increased antigenic stability and induced significantly higher RSV-neutralizing activity—an achievement of importance for improving and extending vaccine-induced immunity against RSV-mediated disease.

Results

Informatics-deduced direction for structure-based design: engineering and properties of design cycle 1. In the structure-based design of DS-Cav1 (McLellan et al., *Science,* 342, 592, 2013), the interplay between design, physical and antigenic properties, atomic-level structure, and immunogenicity was examined to obtain insight into the relationship between antigenic and physical properties of the engineered RSV Fs and the elicitation of RSV-protective responses. Correlation between physical stability of the pre-fusion-specific site Ø and immunogenicity suggested further increases in physical stability might increase immunogenicity (McLellan et al., *Science,* 342, 592, 2013). Ways to increase the physical stability of antigenic site Ø were therefore examined (McLellan et al., *Science,* 340, 1113, 2013).

Figure 1A:
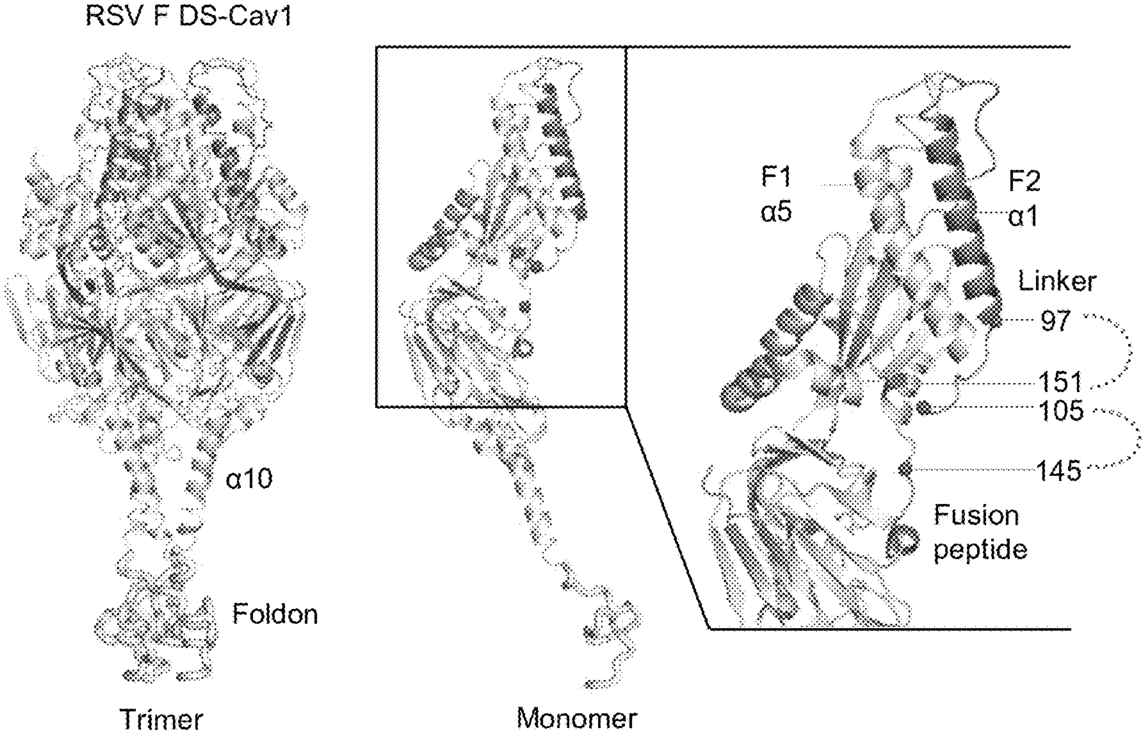
Figure 1B:
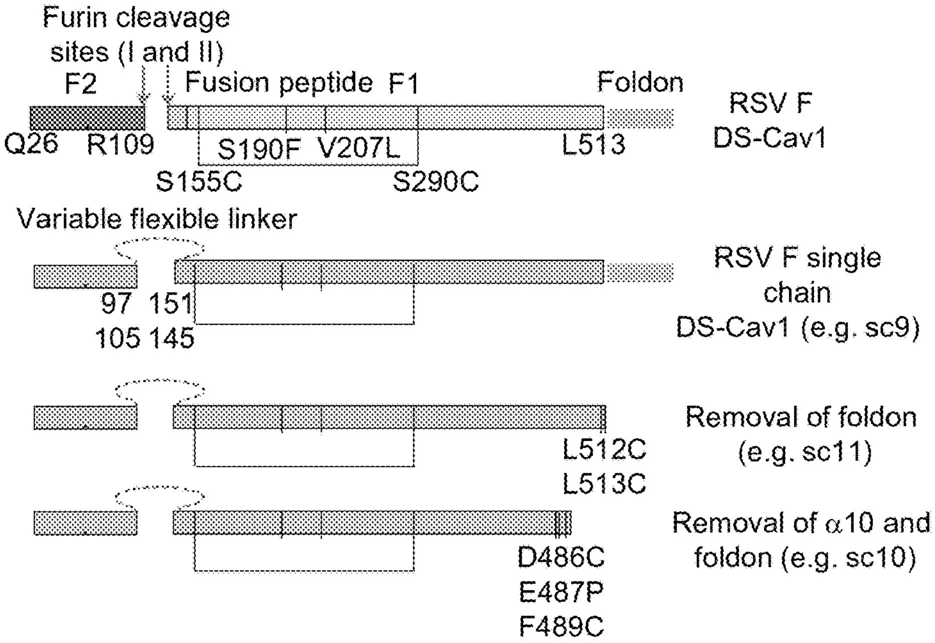

DS-Cav1 variants were engineered with $F_2$ linked genetically to $F_1$ and the fusion peptide deleted (FIG. 1). In particular, for the C terminus of $F_2$ where a genetic linkage was engineered, two positions were selected: residue 97, at the end of the α1-helix, and residue 105, one residue after the last residue of $F_2$ visible in the DS-Cav1 structure (FIG. 1A,B). For the N terminus of $F_1$, either residue 145, just after the fusion peptide, or residue 151, a glycine in α2-helix, which might accommodate flexibility, was selected (FIG. 1A,B).

Figures 1D, 1E:
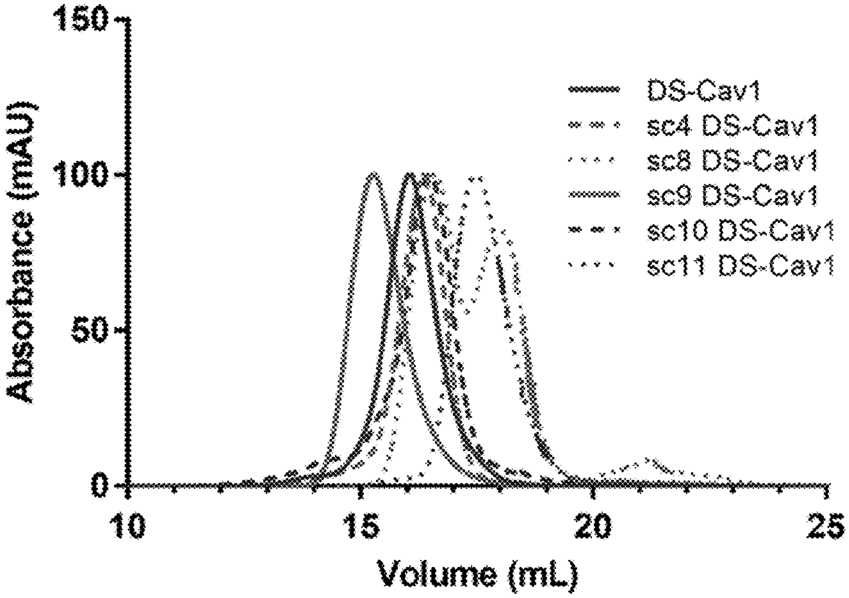

Over a dozen constructs with various linkers were synthesized (Table A) the expression of which was tested in a 96-well microplate-formatted transient transfection format (McLellan et al., *Science,* 342, 592, 2013). Five of these constructs expressed at levels which allowed characterization of their antigenic and physical properties (FIG. 1C). Of these, sc9 DS-Cav1, comprising a GS link between residues 105 and 145, showed 4-fold enhanced expression and recognition by a number of pre-fusion specific antibodies (FIG. 1C). Notably, the single chain variants showed altered mobility in size-exclusion chromatography (SEC) (FIG. 1D) and many displayed reduced tolerance to physical extremes (FIG. 1E). However, sc9 DS-Cav1 did show increased ability to retain antigenic site Ø after incubation at 70° C., as assessed by binding to the site Ø-specific antibody D25. Specifically, 39% of sc9 DS-Cav1 was still active after 1 h of incubation at 70° C., whereas site Ø on the parent DS-Cav1 was completely lost upon 1 h incubation at 70° C. (FIG. 1E).

Figure 2A:
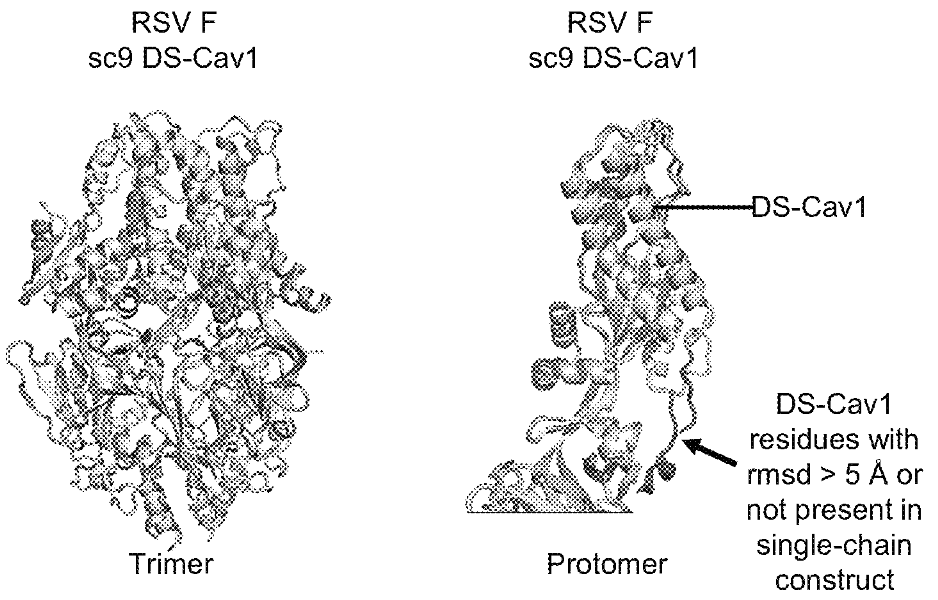
FIGS. 2A-2D show a set of diagrams and graphs illustrating the structure, immunogenicity, and informatics from design cycle 1 of single chain RSV F glycoproteins. (A) RSV F sc9 DS-Cav1 structure is shown in ribbon format. (B) Details of inter-subunit linker between F2 and F1 (electron density ($2F_o$-$F_c$) shown at 1 s). (C) Neutralization titers of sera from mice immunized with 10 μg of RSV F DS-Cav1 single chain variants. Titers from each mouse are shown as individual dots, and geometric means are indicated by horizontal lines. Postfusion F, as well as RSV F DS-Cav1 were administered at 10 μg per mouse (shown in gray dots) as controls. P value <0.0001 and <0.01 indicated by ** and  respectively and non-significant P value indicated by n.s. (D) Left: spearman correlation of each physical property with neutralization titer for design cycle 1 proteins (including DS-Cav1). Right: correlation of elution volume with neutralization titer. Pearson correlation for single chain constructs is denoted.
Figure 2B:
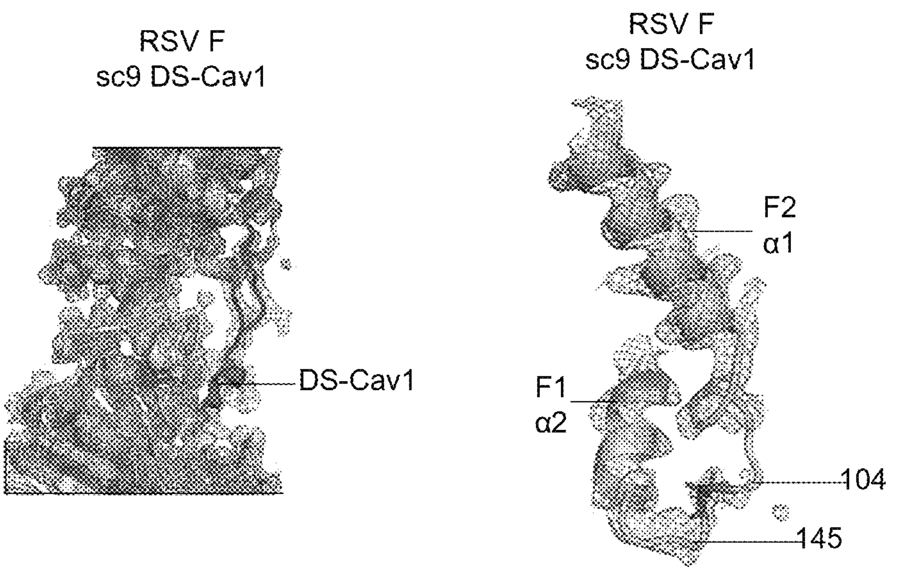
Figure 2C:
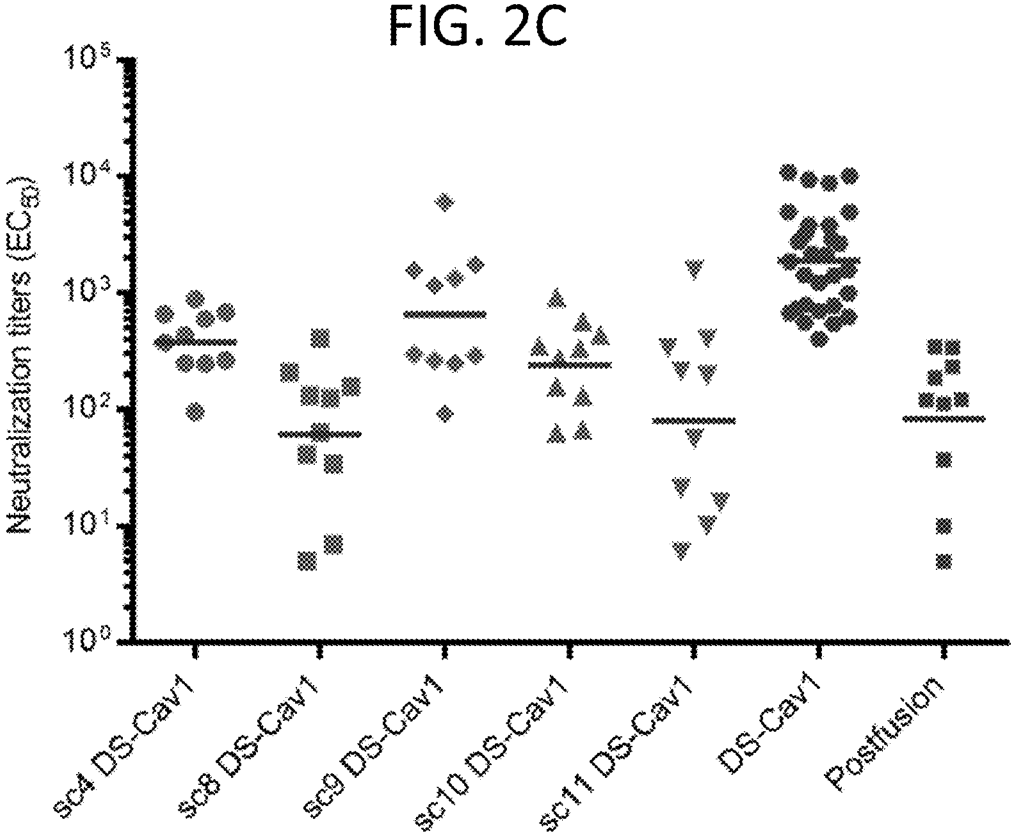

Structures, immunogenicity, and informatics of design cycle 1. To assess the effects of the sc9 alteration on DS-Cav1, sc9 DS-Cav1 was crystallized in a cubic pH5.5 lattice. Diffraction data extended to 2.98 Å resolution, and the sc9 DS-Cav1 structures were refined to $R_{work}/R_{free}$ of 19.4/23.7% (FIG. 11). The structure of sc9 DS-Cav1 was similar to the parent DS-Cav1, with a root-mean-square deviation (rmsd) of 0.6 Å for all residues excluding 105-151 (FIG. 2A). The fusion peptide deletion did not induce any substantial movements in the neighboring region (FIG. 2B, left), where the new connection between 105 and 145 showed partially ordered electron density (FIG. 2B, right). Thus the structural effects of fusing F2 to F1 and removing the fusion peptide on the structure of DS-Cav1 were minimal, localized almost entirely to the linker region.

To measure the immunogenicity of the various single chain DS-Cav1s, CB6F1/J mice were immunized with 10 μg RSV F combined with 50 μg polyinosinic-polycytidylic acid adjuvant at weeks 0 and 3 intra-muscularly, and evaluated the ability of week 5 sera to prevent RSV infection of HEp-2 cells. Notably all titers elicited by these single-chain antigens were lower than those elicited by DS-Cav1. Variants sc8 DS-Cav1 and sc11 DS-Cav1 had especially low immunogenicity, whereas sc9 DS-Cav1, the single chain with highest immunogenicity, had a geometric mean titer one third that of DS-Cav1.

Figure 2D:
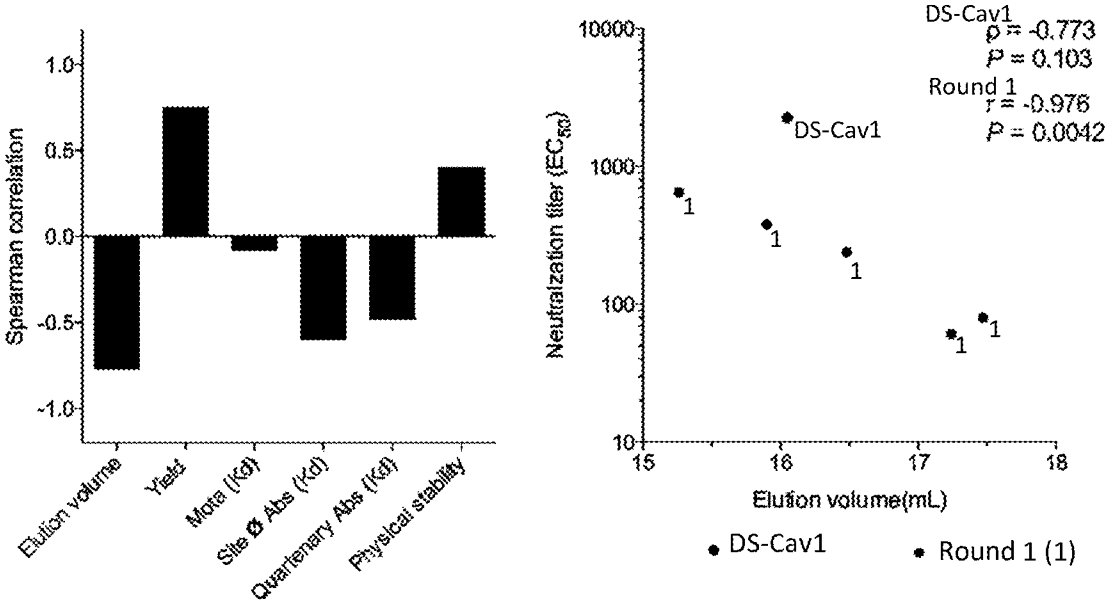

The increased physical stability of sc9 DS-Cav1 at 70° C. did not yield an increase in immunogenicity, likely indicating other factors with more substantial effects of immunogenicity had been altered between DS-Cav1 and sc9 DS-Cav1. The immunogenicity of the five characterized single chain DS-Cav1 constructs, sc4, sc8, sc9, sc10 and sc11, was analyzed in the context of their 1) antigenicity toward site-Ø antibodies (D25, AM22, 5C4), motavizumab, and quaternary antibodies (MPE8 and AM14), and 2) physical properties such as elution volume, expression yield, and physical stability (D25 reactivity retained after exposure to various physical extremes) (FIG. 2*d*). No one single property significantly correlated with the immunogenicity. However, the property that had the largest absolute correlation with the immunogenicity was elution volume (anti-correlates, FIG. 2*d*) (Pearson correlation $r=-0.976$, $P=0.0042$ for single chain constructs), with sc9 DS-Cav1 being most optimal. Therefore, sc9 DS-Cav1 was selected for further optimization based on its high immunogenicity and having similar elution volume as DS-Cav1.

Figure 3A:
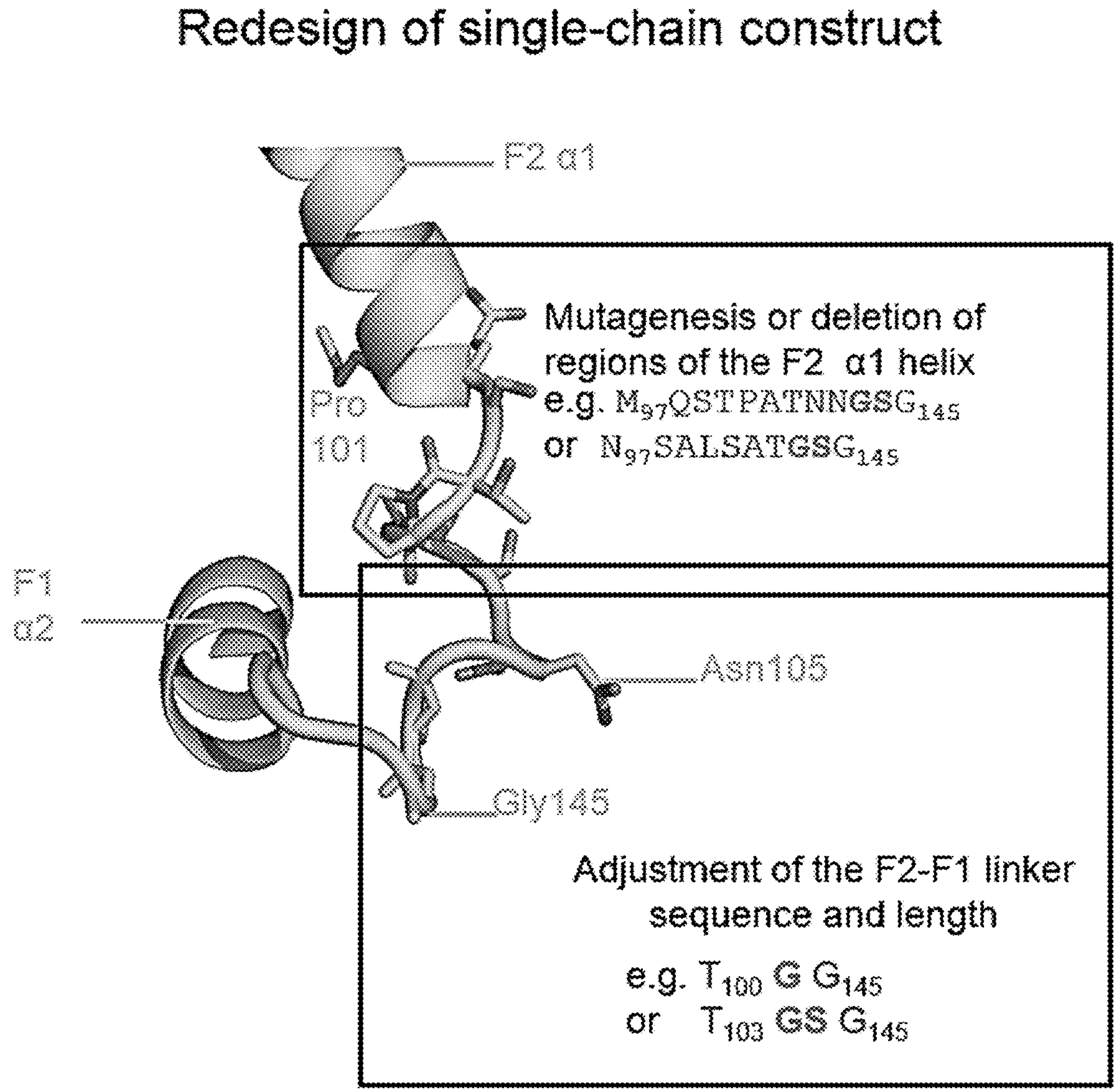
Figure 3B:
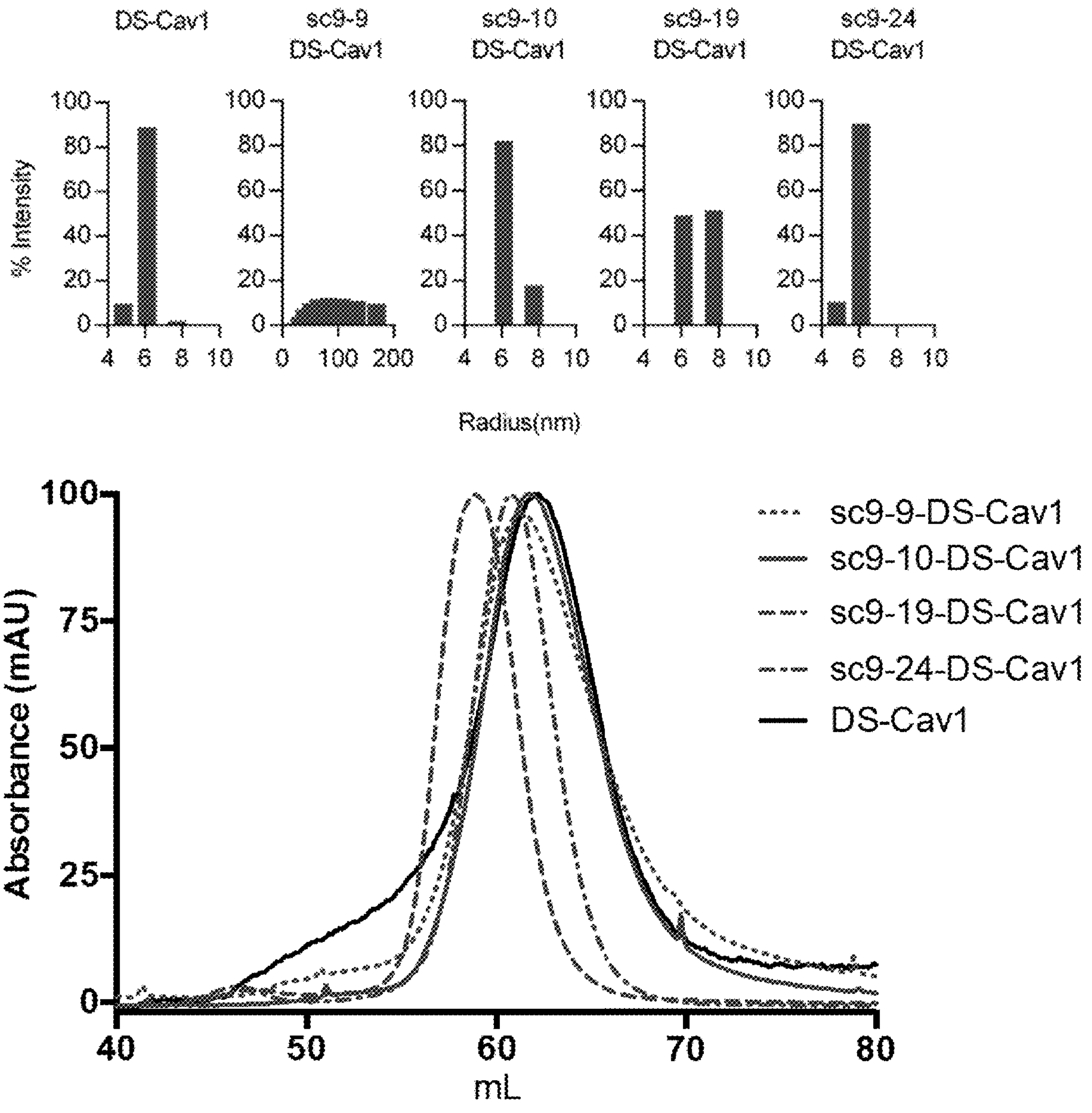

Engineering, properties, structures, immunogenicity, and informatics of design cycle 2. As difference in the linker between F2 and F1 subunits appeared to affect immunogenicity, this linker was further varied, as were the residues in the F2 alpha-1 helix (FIG. 3A) for sc9 DS-Cav1. 45 constructs were synthesized (Table A) and their expression tested in the 96-well microplate transient transfection format (McLellan et al., *Science,* 342, 592, 2013). Most of these constructs expressed at levels which allowed characterization of their antigenic and physical properties (FIG. 3C, D). Of these, sc9-10 DS-Cav1, with residues 104 and 105 deleted compared to sc9 DS-Cav1 had an SEC-elution volume similar to that of DS-Cav1, and displayed improved affinity to the pre-fusion quaternary-specific antibody AM14. Constructs sc9-41 and sc9-42 with shortened F2 linker regions did not bind to the prefusion specific antibodies despite containing DS-Cav1 stabilizing mutations indicating that subtle changes in the F2-F1 linker sequence and length can have substantial impact on antigenicity. sc9-10 had a similar improved affinity over sc9 to antibody AM14 as did sc9-9, however sc9-9 was not chosen for further improvement because it had a suboptimal SEC profile and was poly-disperse by dynamic light scattering (DLS).

Figure 4A:
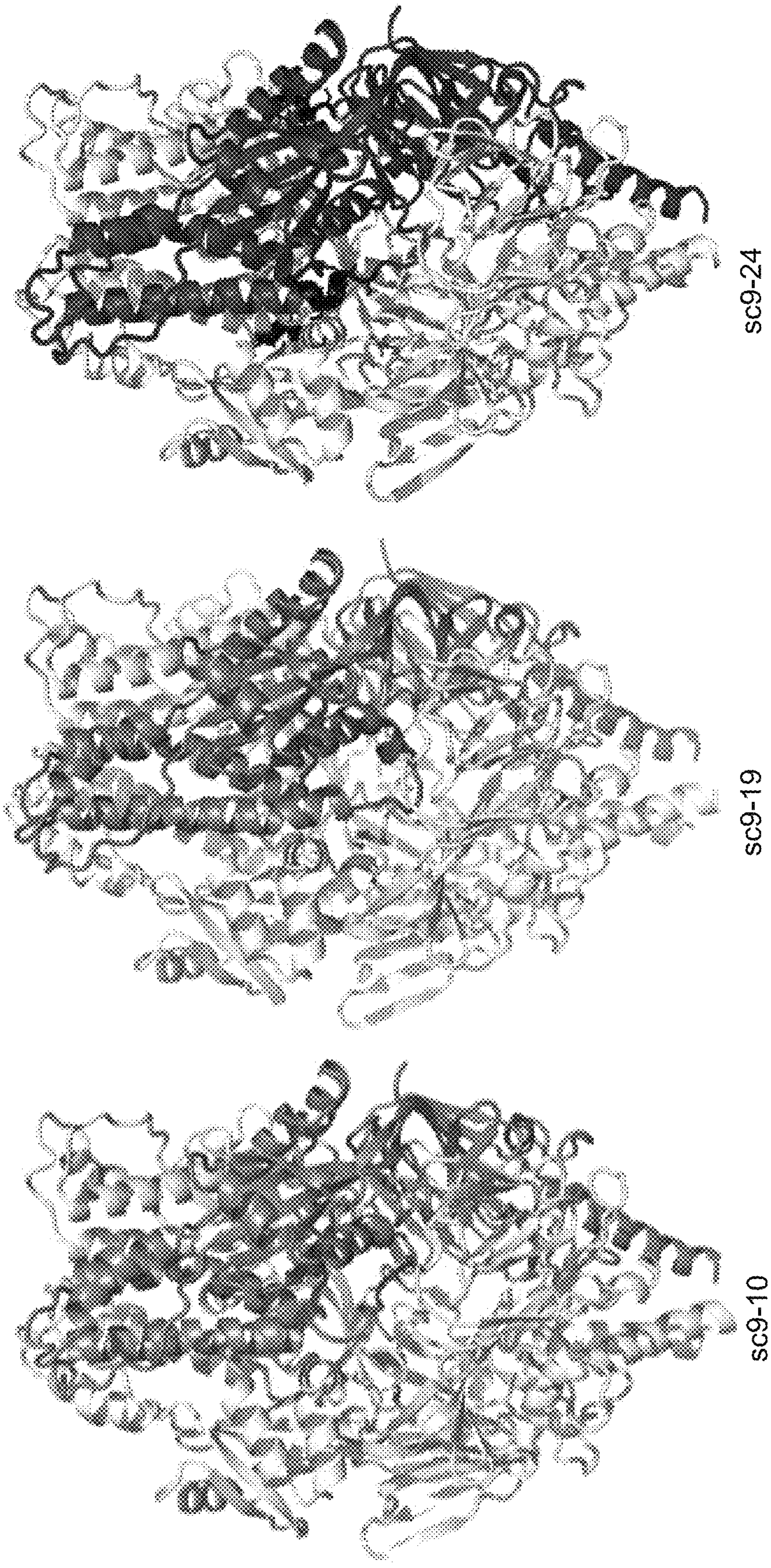
FIGS. 4A-4D show a set of diagrams and graphs illustrating the structure, immunogenicity, and informatics from design cycle 2 of single chain RSV F glycoproteins with an optimized F2-F1 linker. (A) Structures of single chain RSV F glycoproteins with an optimized F2-F1 linker. (B) Structural details of the F2-F1 linker are shown with the linker region shown. The sequences shown include PATGSG (residues 5-10 of SEQ ID NO: 91), PATGGSGGSGG (residues 5-15 of SEQ ID NO: 92), and NSALSATGSG (SEQ ID NO: 88). (C) Neutralization titers of sera from mice immunized with 10 μg of RSV F DS-Cav1 single chain variants with optimized linker. Titers from each mouse are shown as individual dots, and geometric means are indicated by horizontal lines. Postfusion F, as well as RSV F DS-Cav1 were administered at 10 μg per mouse (shown in gray dots) as controls. (D Left: spearman correlation of each physical property with neutralization titer for design cycle 1 and 2 variants (including DS-Cav1). Correlations with adjusted P value (Bonferroni correction) of less than 0.05 were marked with "*". Right: correlation of quaternary antibody antigenicity with neutralization titer. "10,000" was used for antigenicity with "N.B" values.
Figure 4B:
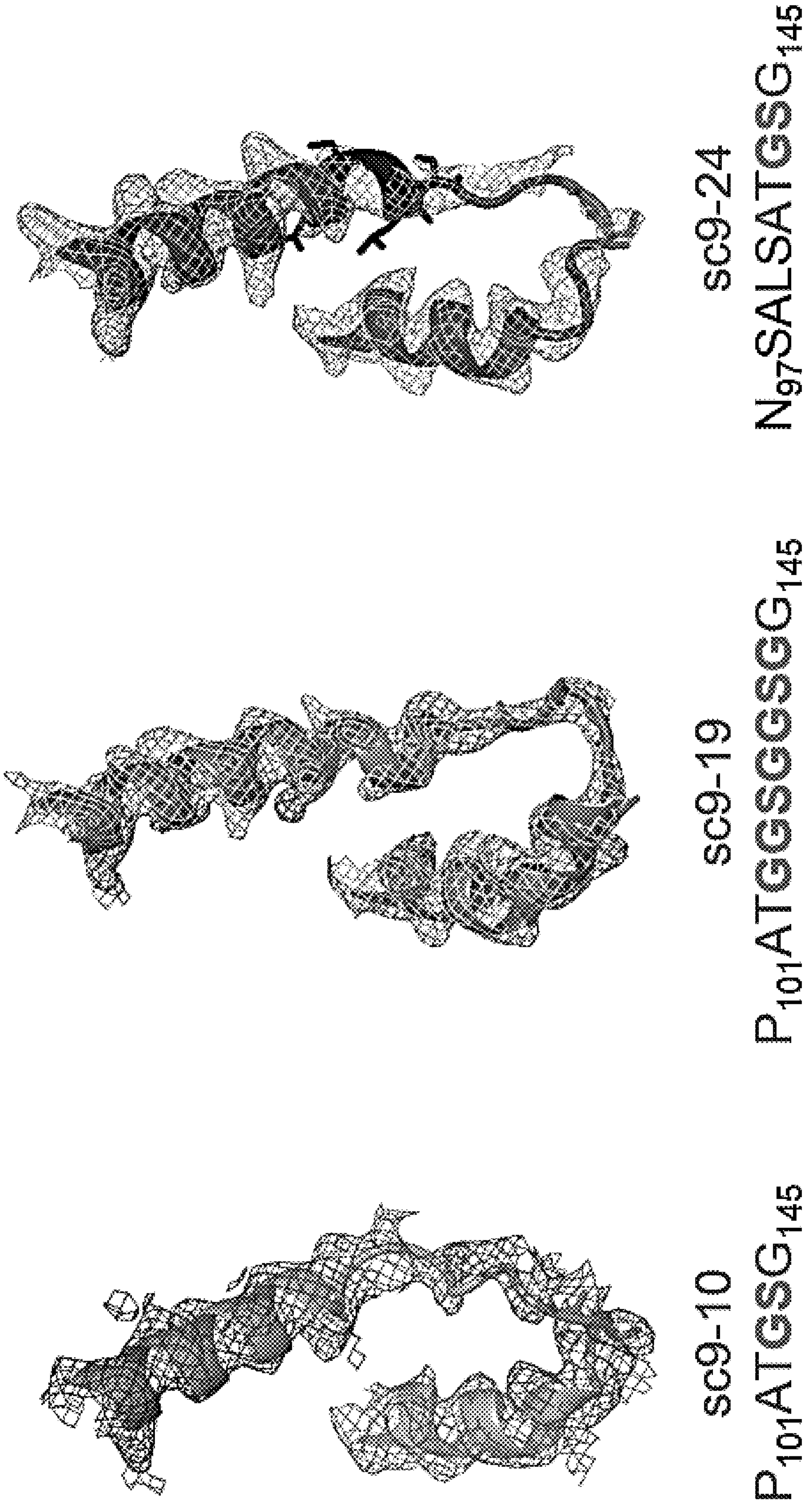

To provide atomic level details, sc9-10, sc9-19, and sc9-24 versions of DS-Cav1 were crystallized. Diffraction data extended to 3.6, 2.6 and 2.9 Å resolution, respectively, and these structures were refined to $R_{work}/R_{free}$ of 25.3/28.9%, 19.1/25.3% and 27.2/31.1%, respectively (FIG. 11). All of these structures were highly similar to the parent sc9 DS-Cav1 (FIG. 4A), though with important differences in their F2-F1 linker as expected from the sequence changes in the linker region (FIG. 4B). The sc9-10 and sc9-19 constructs had improved electron density at the linker region compared to sc9 while sc9-24 electron density was similar to sc9.

Figure 4C:
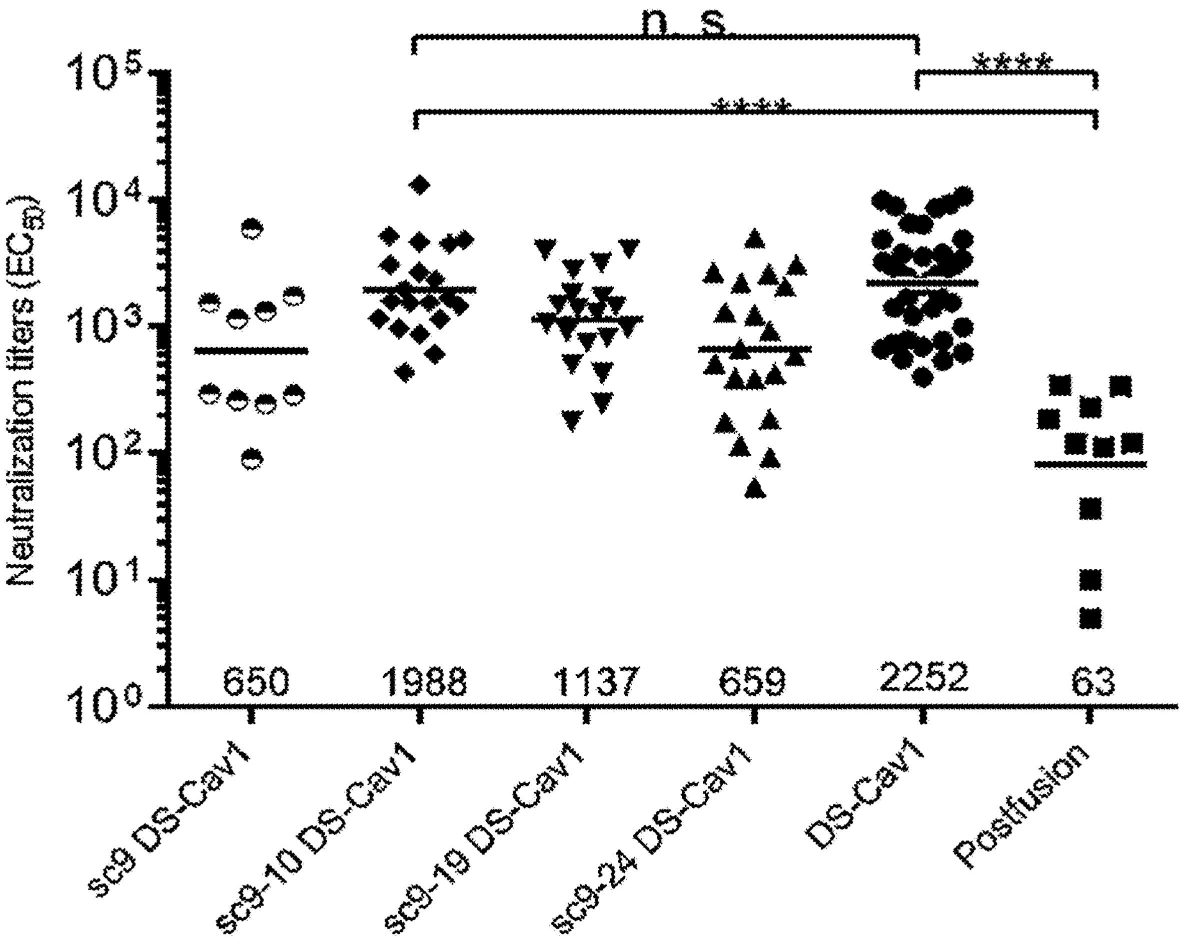
Figure 4D:
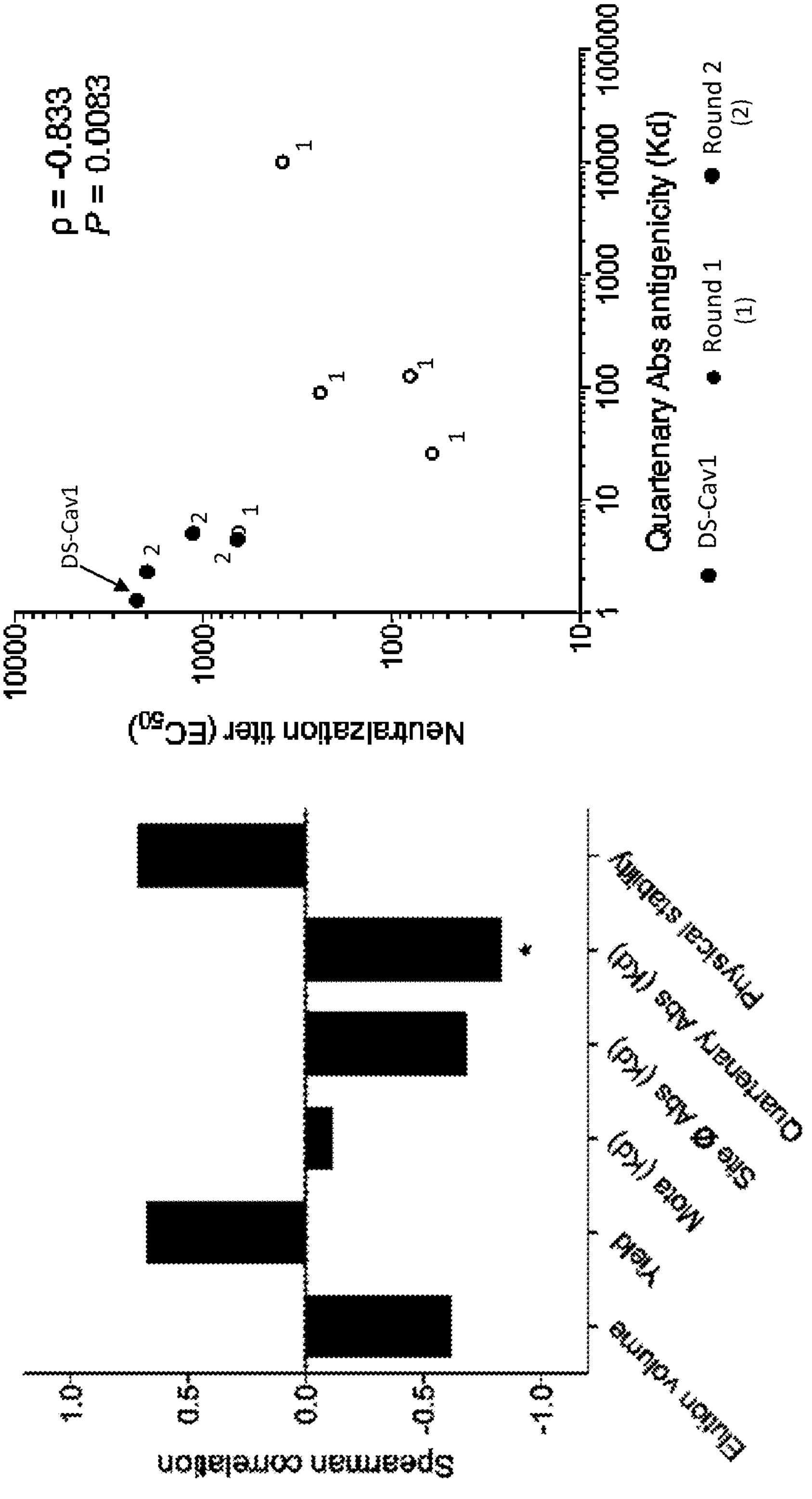

As before, the immunogenicity of the various single chain DS-Cav1 molecules was measured by immunizing CB6F1/J mice at weeks 0 and 3. Importantly, the titers of sc9-10 DS-Cav1 at week 5 (geometric mean of 1988) were statistically indistinguishable from those of DS-Cav1 (FIG. 4C). Notably, informatics analysis indicated quaternary antibody affinity correlated significantly with the improved immunogenicity (P=0.0083, FIG. 4D), suggesting reduced protomer flexibility might lead to improved neutralizing titers. For the 3rd cycle of structure-based design, it was sought to reduce protomer flexibility even further, by introducing inter-protomer disulfide linkages.

Figure 5A:
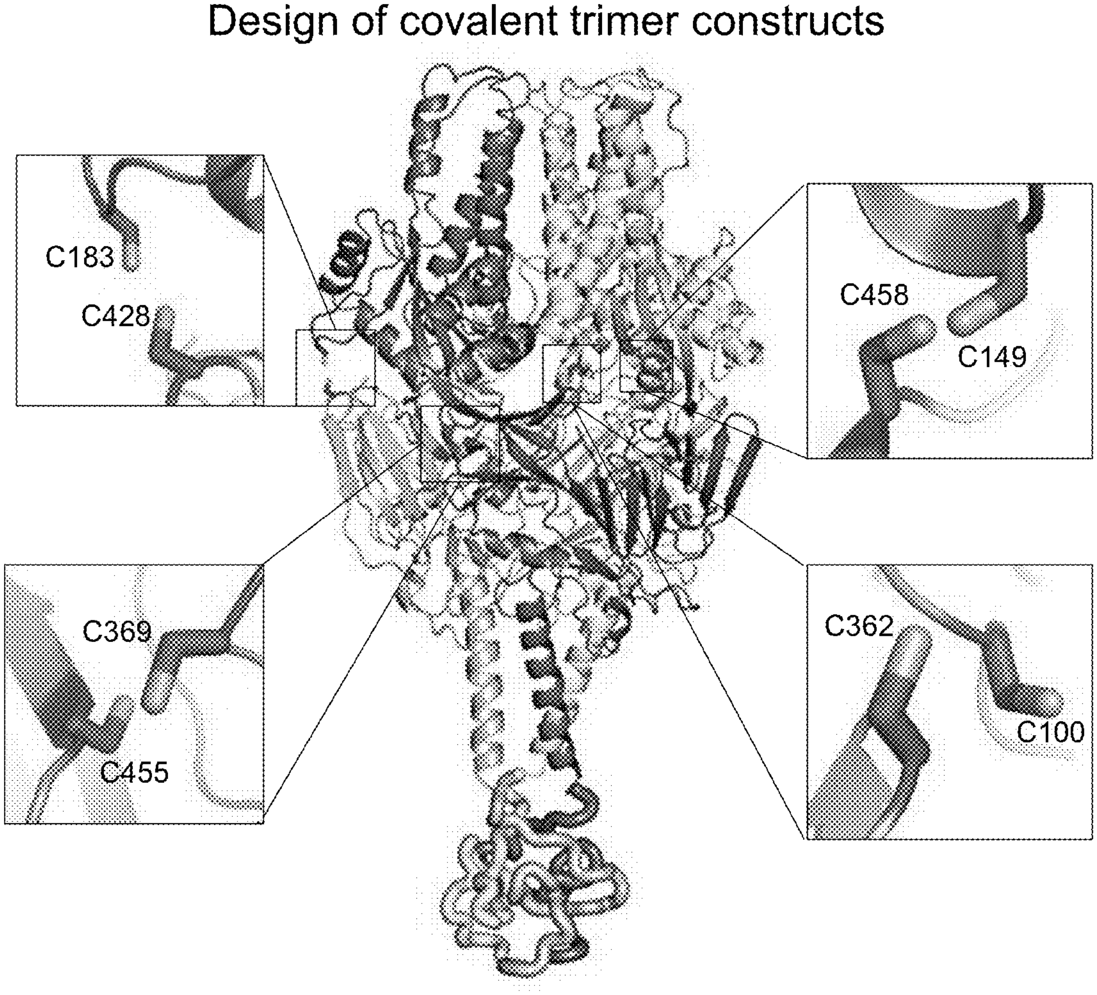
Figure 5B:
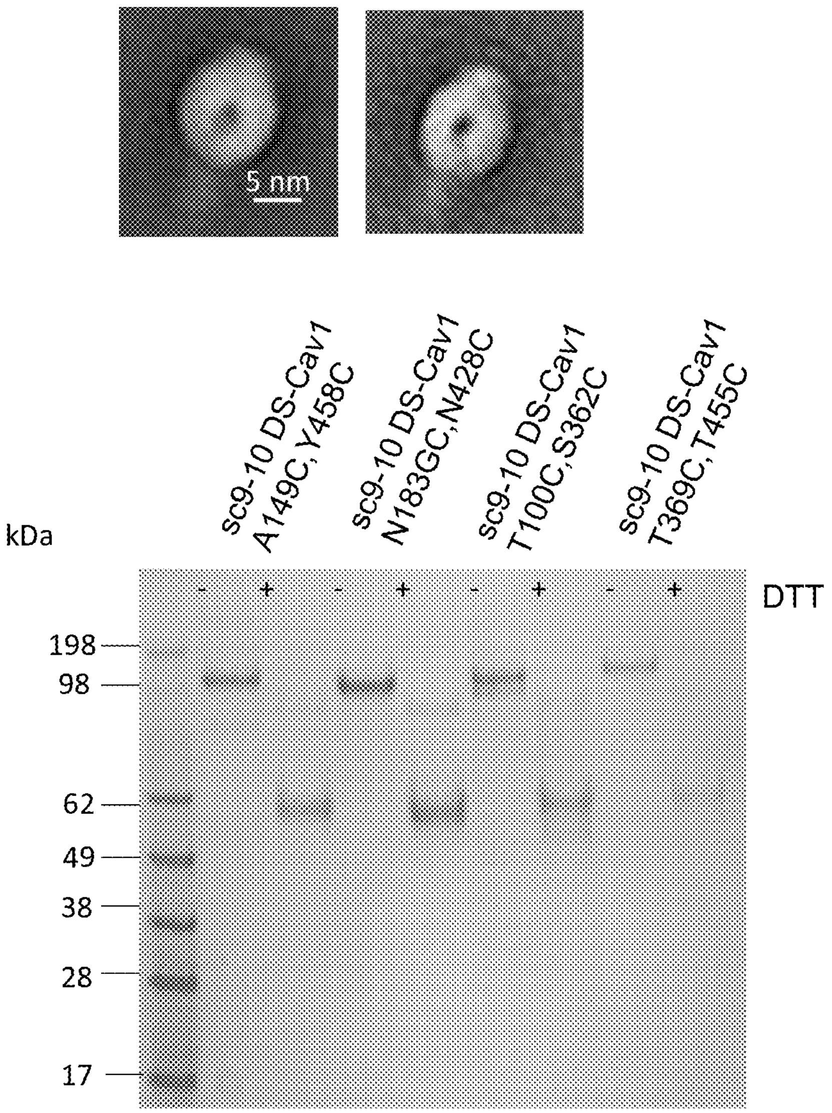

Design, properties, structures, and immunogenicity of interprotomer-stabilized 2' generation RSV F antigens for design cycle 3. The structure of sc9-10 DS-Cav1 was analyzed for interprotomer positions where disulfide linkages might be introduced (FIG. 5A). 17 variants of sc9-10 were synthesized with introduced interprotomer disulfides (Table A) and their expression tested in the 96-well microplate-formatted transient transfection format. Four of these constructs expressed at levels which allowed characterization on a reducing and non-reducing SDS-PAGE (FIG. 5B); in the absence of reducing agent, all of these constructs ran as disulfide-linked oligomers of over 150 kDa without any indication of dimer or monomer populations, and in the presence of reducing agent, all three ran as monomers of ~60 kDa.

Figure 6A:
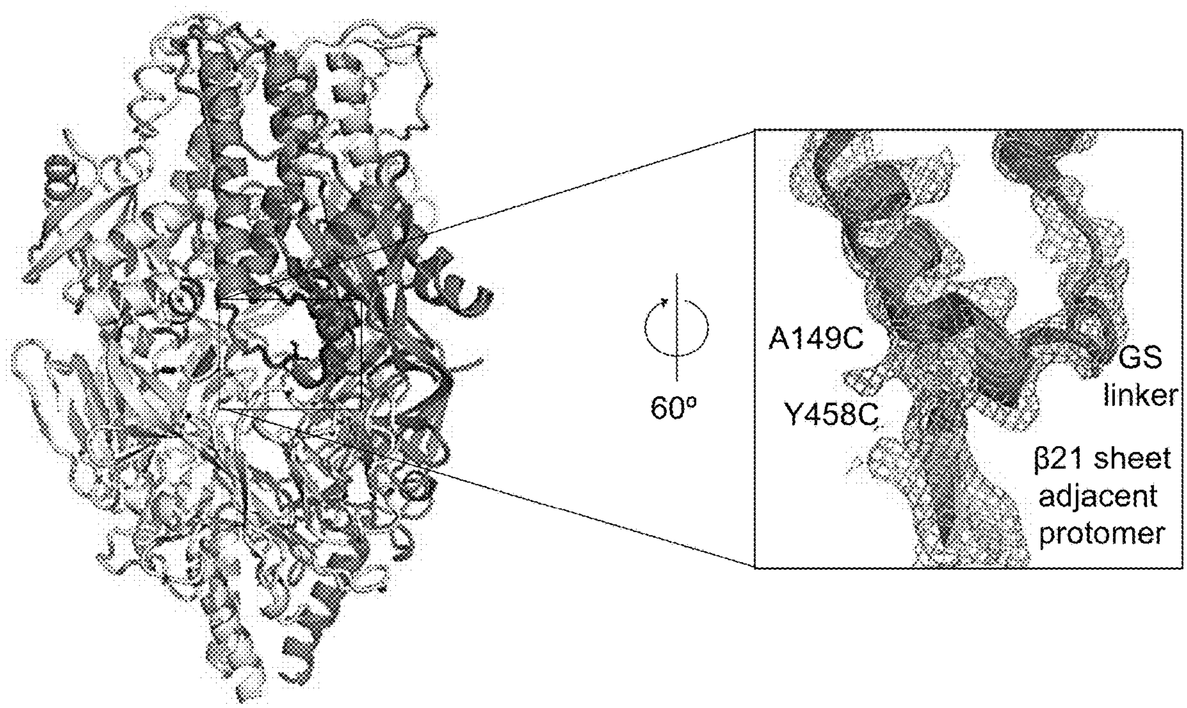
FIG. 6A-6C illustrate the structure, immunogenicity, and informatics from design cycle 3 of single chain RSV F glycoproteins with inter-protomer disulfides. (A) Structure of single chain RSV F glycoproteins sc9-10 with inter-protomer disulfides shown in the close-up view with electron density for this region. (B) Neutralization titers of sera from mice immunized with 10 μg of RSV F DS-Cav1 single chain variants. Titers from each mouse are shown as individual purple dots, and geometric means are indicated by horizontal lines. The sera titers from mice immunized with sc9-10 and RSV F DS-Cav1 (shown in gray dots) are controls. (C) Left: spearman correlation of each physical property with neutralization titers for design cycle 1, 2, and 3 variants (including DS-Cav1). Correlations with adjusted P value (Bonferroni correction) of less than 0.05 were marked with "*". Right: correlation of quaternary antibody antigenicity and physical stability with neutralization titer. Constructs containing a mutation at residue 183 were not included in the correlation for quaternary antibody antigenicity as N183 is part of the AM14 epitope. "10,000" was used for antigenicity with "N.B" values.

The sc9-10 DS-Cav1 A149C-Y458C construct expressed at 1 mg/L, the N183GC-N428C variant at ~0.1 mg/L, and the T100C-S362C and the T369C-T455C variant at quantities too low for characterization (FIG. 5C). Both sc9-10 DS-Cav1 A149C-Y458C and N183GC-N428C variants showed increased physical stability, being 6-fold and 19-fold more stable than DS-Cav1 at 60° C. (FIG. 5D).

sc9-10 DS-Cav1 A149C-Y458C was crystallized in the cubic lattice. Diffraction data extended to 2.65 Å resolution, and the structure was refined to $R_{work}/R_{free}$ of 22.7/27.1% (FIG. 11). The structure of sc9-10 DS-Cav1 A149C-Y458C was similar to the parent sc9-10 DS-Cav1 (FIG. 6A). Notably, strong electron density between residue 149 and 458 was observed, consistent with the formation of a disulfide bond. The overall quaternary structure, moreover, was maintained between sc9-10 and sc9-10 DS-Cav1 A149C-Y458C, with rmsd for protomer (0.9Å) and for entire trimer (1.0 Å).

Figure 6B:
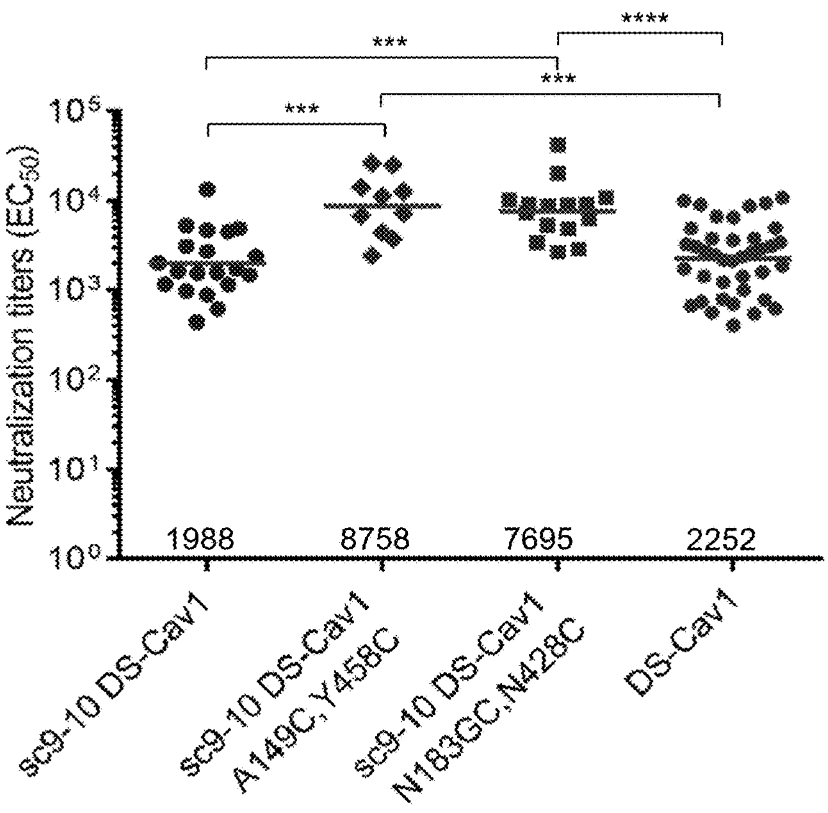
Figure 6C:
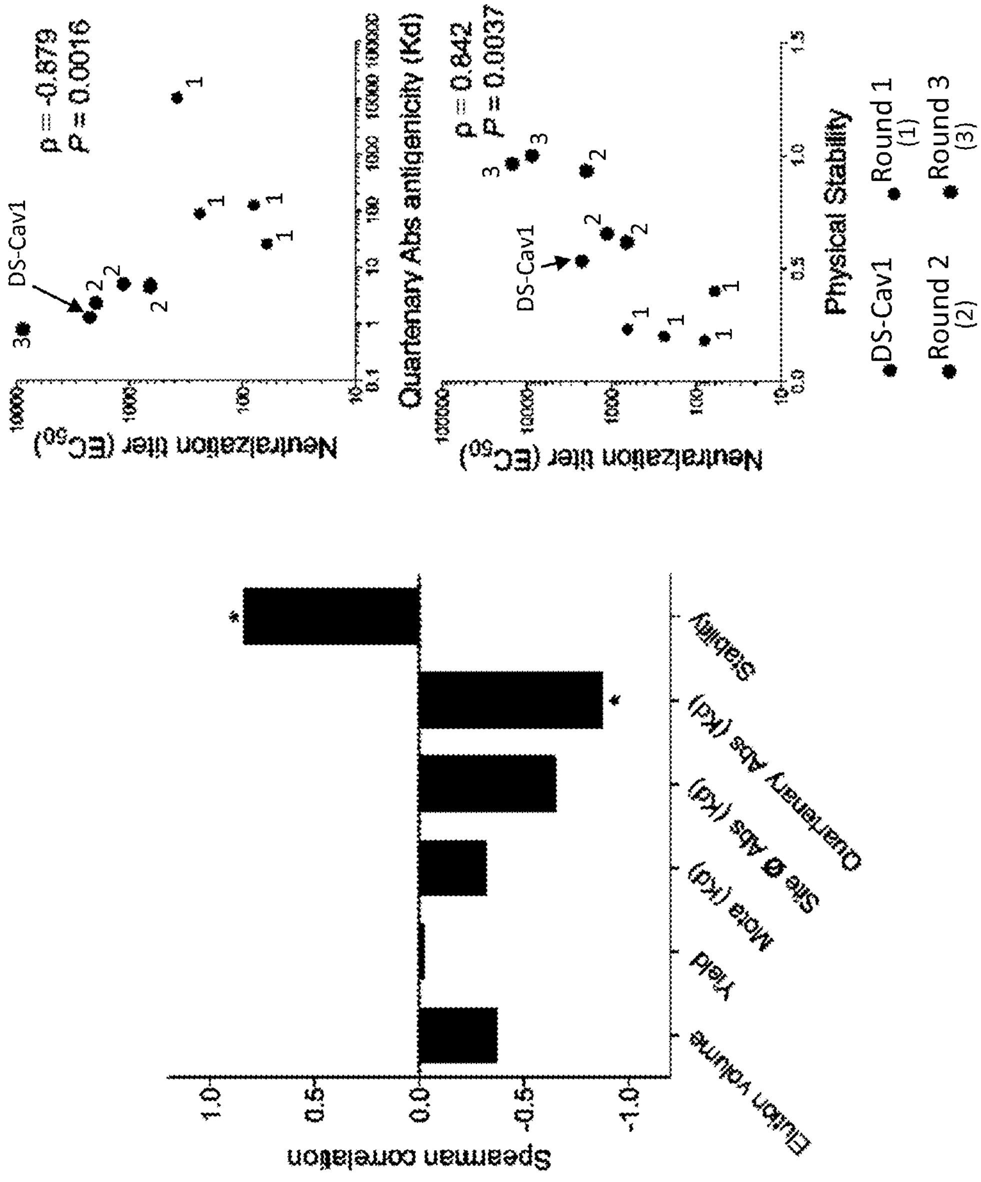

To measure the immunogenicity of the $2^{nd}$-generation DS-Cav1 with interprotomer disulfides, CB6F1/J mice were immunized intra-muscularly as described for earlier variants (FIG. 6B). Notably, both sc9-10 DS-Cav1 A149C-Y458C and N183GC-N428C showed a significant increase in RSV-neutralizing titer, 3-4-fold higher than that of DS-Cav1. When the cumulative data on immunogenicity versus various properties from design cycles 1-3 was analyzed informatically, both quaternary antibody affinity (P=0.0016) and physical stability (P=0.0037) significantly correlated with immunogenicity (FIG. 6C), indicating the importance of appropriate quaternary organization as well as improved physical stability to the elicitation of RSV-neutralizing antibodies.

Figure 7A:
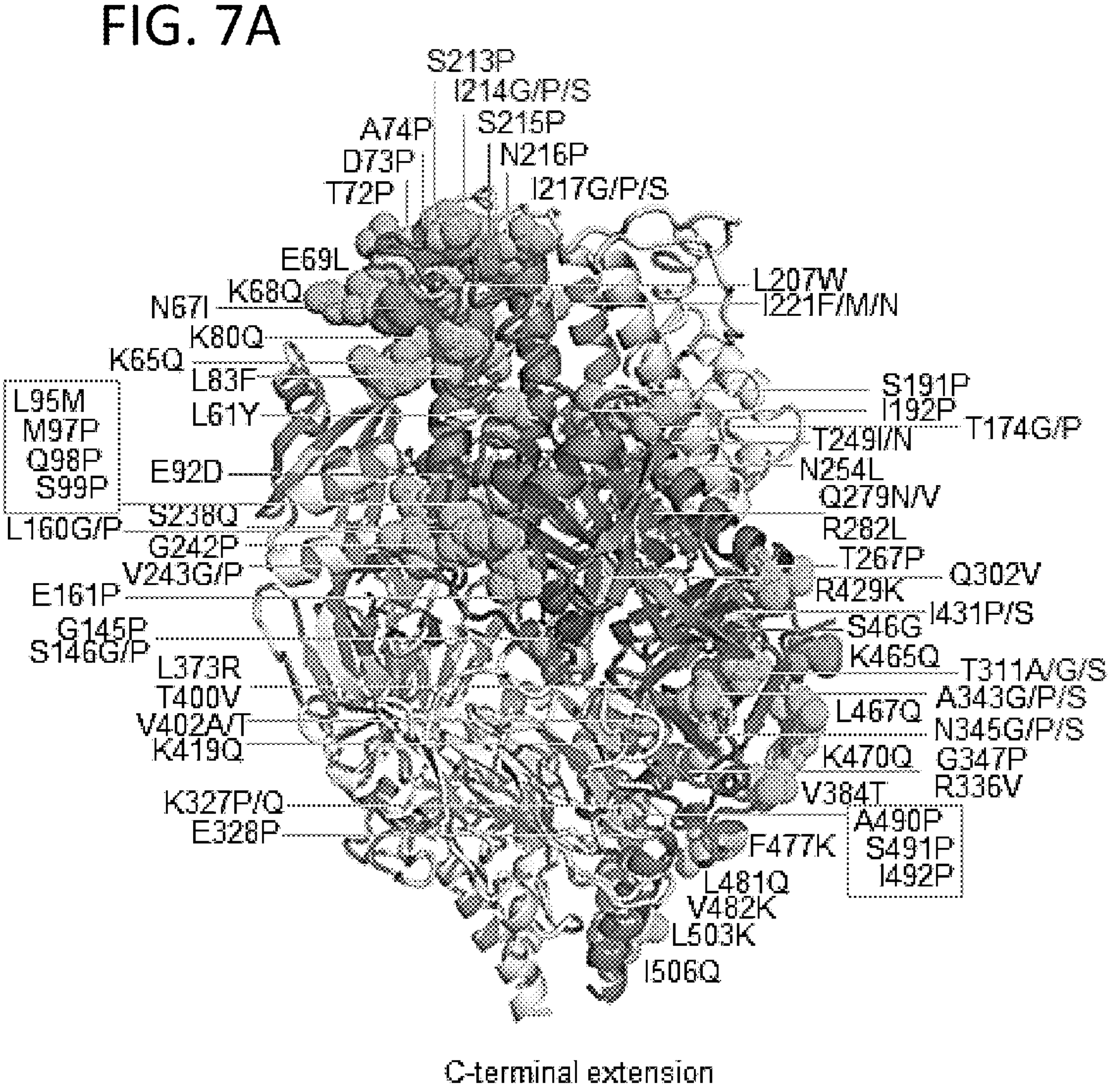
Figure 7B:
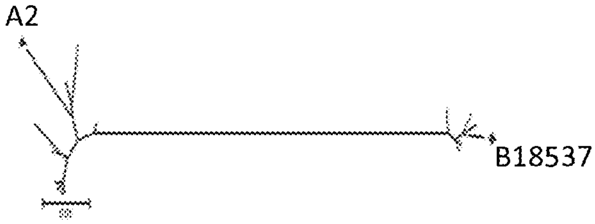

Design, properties, structures, and immunogenicity of additional $2^{nd}$ generation RSV F antigens for design cycle 4. The heightened immunogenicity of DS-Cav1 variants with interprotomer disulfides indicated that interprotomer stabilization might be a general way to increase the elicitation of RSV protective responses. However, the low expression levels for many of the design interprotomer variants revealed expression to be a roadblock. For design cycle 4, interprotomer disulfides A149C-Y458C and N183GC-N428C were combined (FIG. 7A) with other mutations that might additionally stabilize the pre-fusion state or increase expression—including the mutations N67I and S215P, identified by Krarup and colleagues (Krarup et al., *Nature Commun.,* 6, 8143, 2015) as well as variant strains of RSV including B strains such as B18537 (FIG. 7B). 396 constructs were synthesized (Table A) and their antigenicity and level of expression assessed in the 96-well microplate transient transfection format. Six of these constructs expressed at levels which allowed characterization of their antigenic and physical properties (FIG. 7C). Expression levels appeared to be heightened by the presence of the triple mutants, S46G, K465Q and S215P. Importantly, all of these interprotomer-stabilized constructs maintained increased physical stability at 60° C., which ranged from 6-7-fold for the A149C-Y458C-based constructs to 13-19-fold for the N183GC-N428C-based constructs (FIGS. 5C and 7C).

Figure 8A:
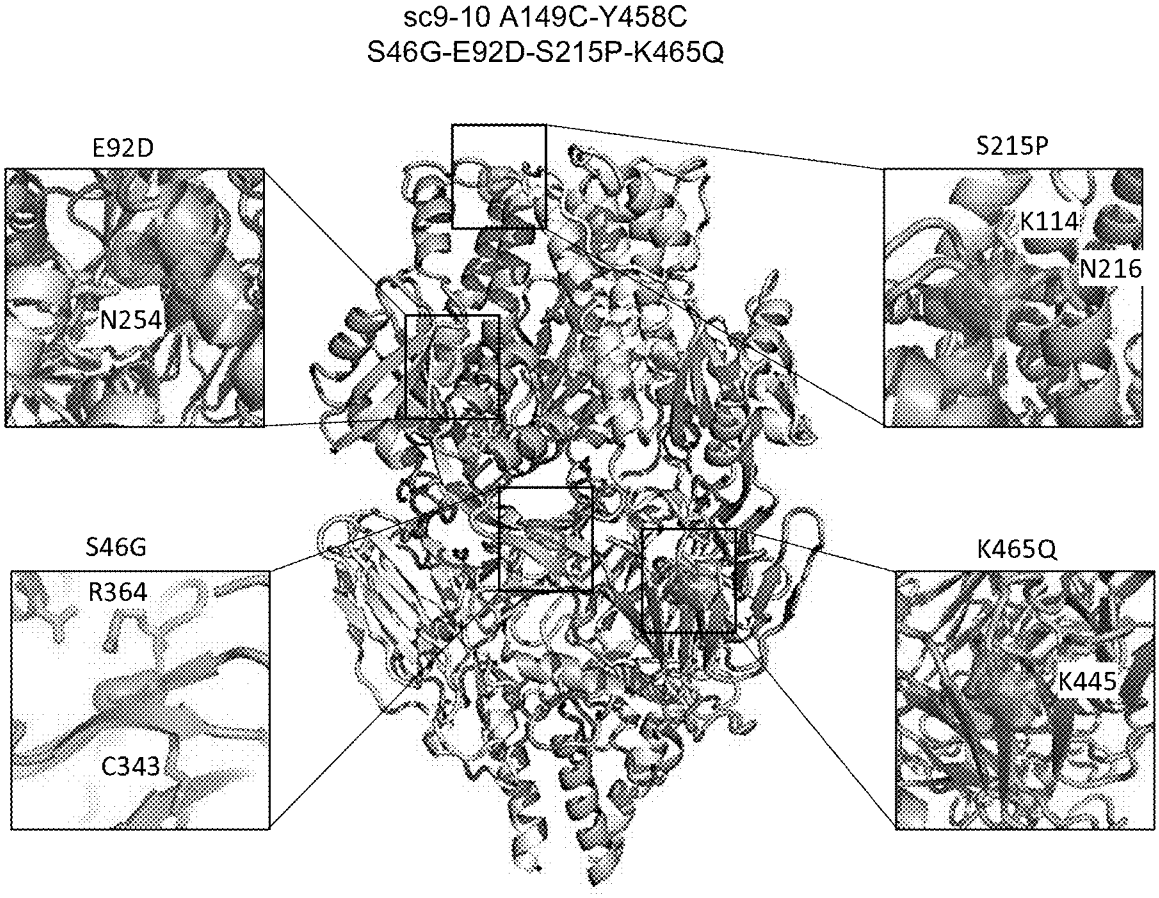
FIGS. 8A-8C illustrate the structure, immunogenicity, and informatics from design cycle 4 comprising combinations of inter-protomer disulfides with other mutations. (A) Structures of single chain RSV F glycoproteins sc9-10 DS-Cav1 A149C, Y458C S46G-E92D-S215P-K465Q with details of surface mutations shown in insets. (B) Neutralization titers of sera from mice immunized with 10 μg of RSV F DS-Cav1 single chain variants. Titers from each mouse are shown as individual dots, and geometric means are indicated by horizontal lines. The titers from mice immunized with design based on sc9-10 DS-Cav1 A149C, Y458C are shown with different format circles, design based on Sc-9-10 DS Cav1 N183GC, N428C is shown with squares and designs based on Sc-9-10 DS Cav1 Q98C, Q361C are shown using variant triangles. RSV F DS-Cav1 (shown in gray dots) are shown for reference. (C) Left: spearman correlation of each physical property with neutralization titers for design cycle 1, 2, 3, and 4 proteins (including DS-Cav1). Correlations with adjusted P value (Bonferroni correction) of less than 0.05 were marked with "*". Right: correlation of quaternary antibody antigenicity and physical stability with neutralization titer. Constructs containing mutations at residue 183 were not included in the correlation for quaternary antibody antigenicity as N183 is part of the AM14 epitope. "10,000" was used for antigenicity with "N.B" values.

To provide insight into the increased expression associated with the S46G, K465Q and S215P mutants, the structure of sc9-10 A149C-Y458C S46G-K465Q-S215P-E92D was determined (FIG. 8A). Diffraction data extended to 2.92 Å resolution, and the structure was refined to $R_{work}/R_{free}$ of 22.3/25.9% (FIG. 11). Notably, none of the crystallographically visualized alterations, S46G, E92D, S215P and K465Q, resulted in changes in backbone movements of over 1 Å (FIG. 8A). The local structure was examined (FIG. 8A) of the mutants S46G, E92D, and K465Q and observed several of these mutations to remove unfavorable interactions with proximal residues: S46 directly points towards another hydroxyl, E92 clashes with N254 (which hydrogen bonds to D92), K465 clashes electrostatically with a neighboring lysine. Meanwhile, as noted previously (Krarup et al., *Nature Commun.,* 6, 8143, 2015), S215P destabilizes the formation of an elongated helix found in the RSV F post-fusion form.

Figure 8B:
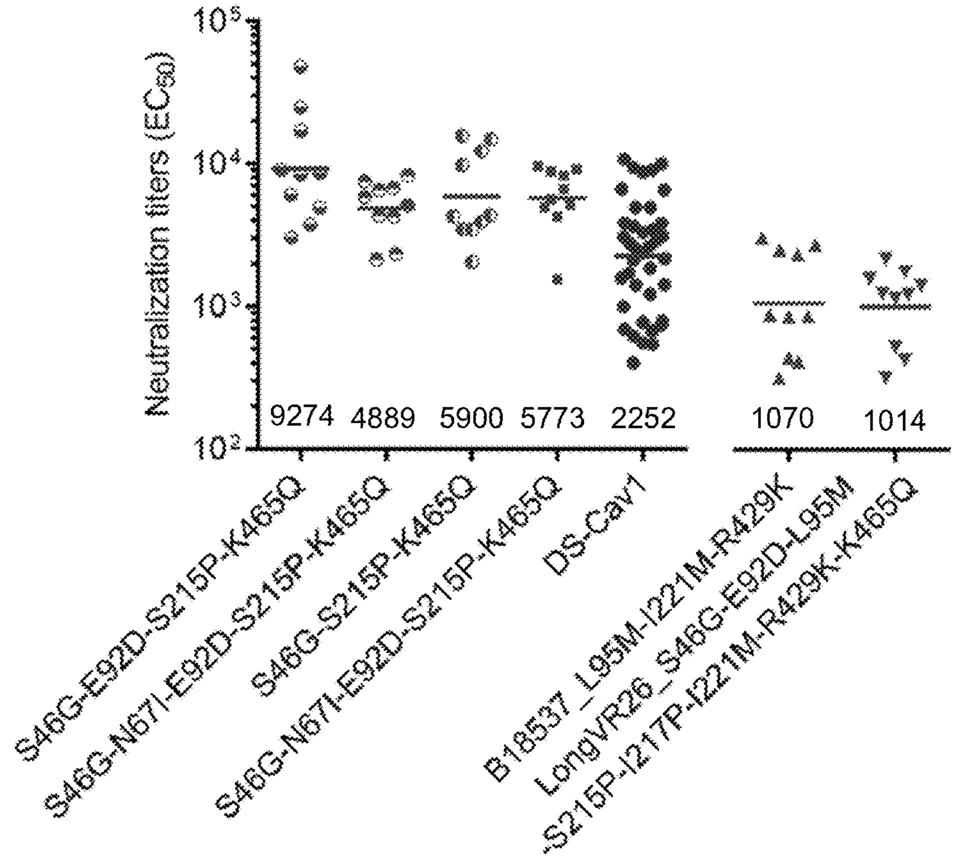
Figure 8C:
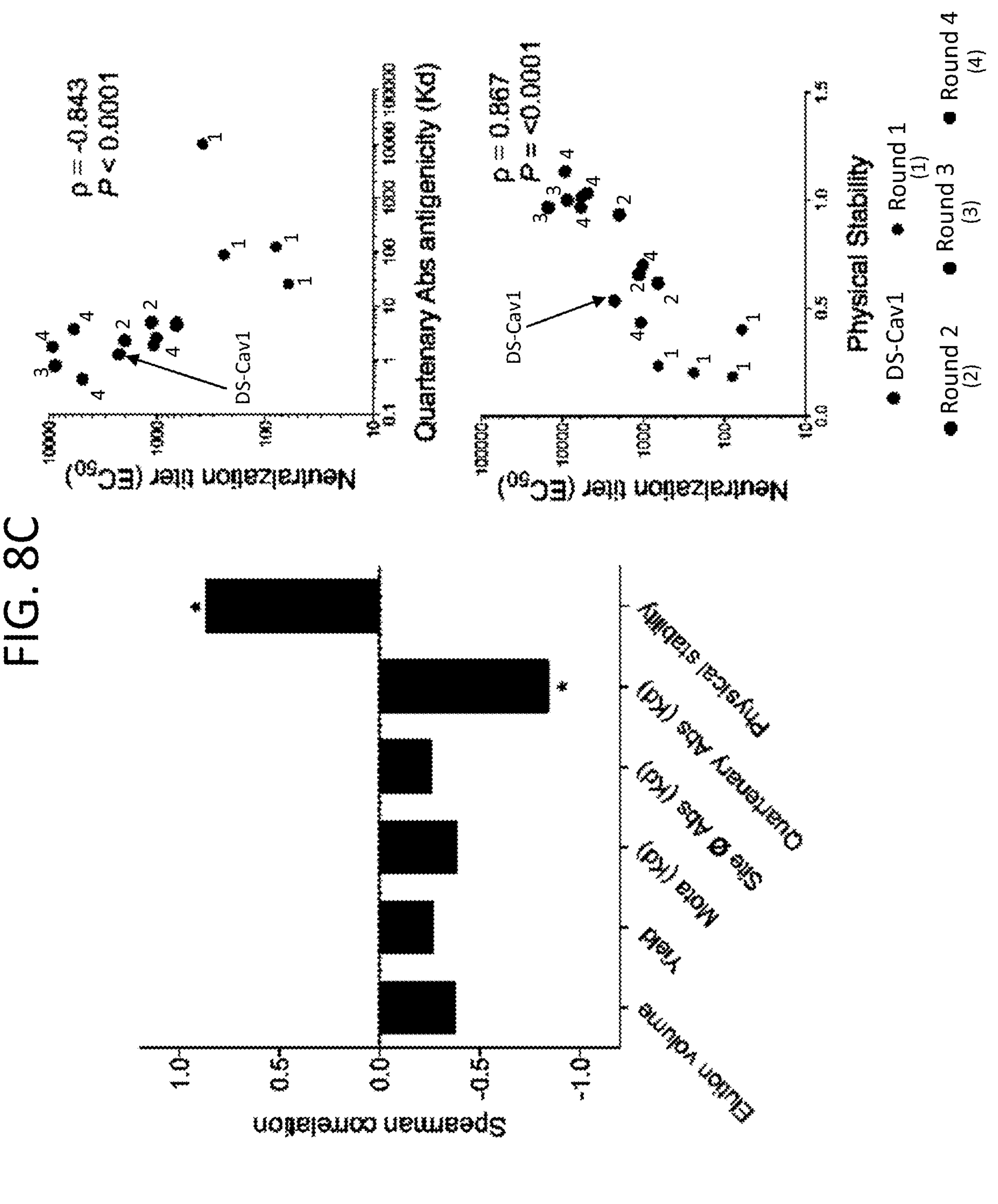
Figure 9A:
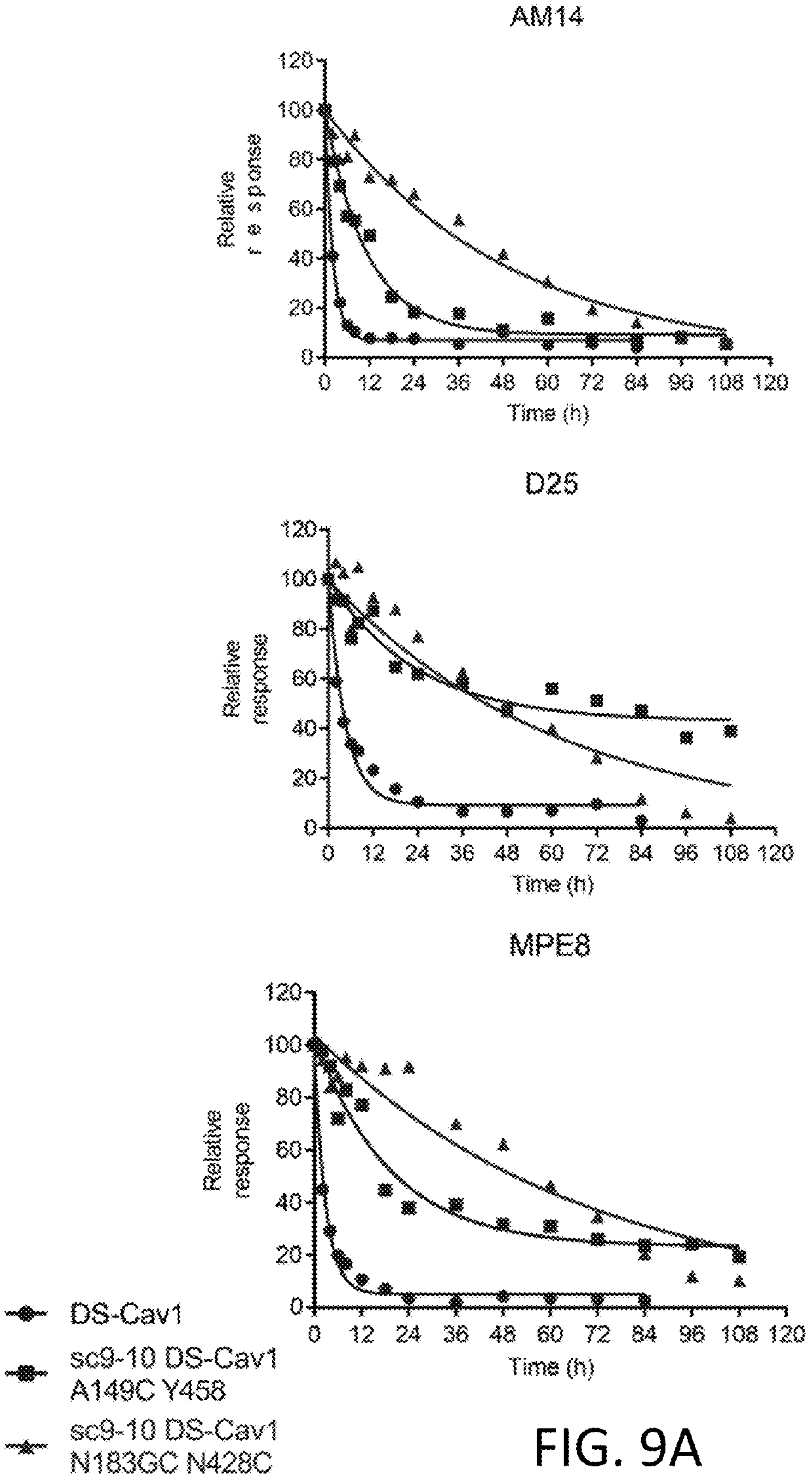
Figure 9B:
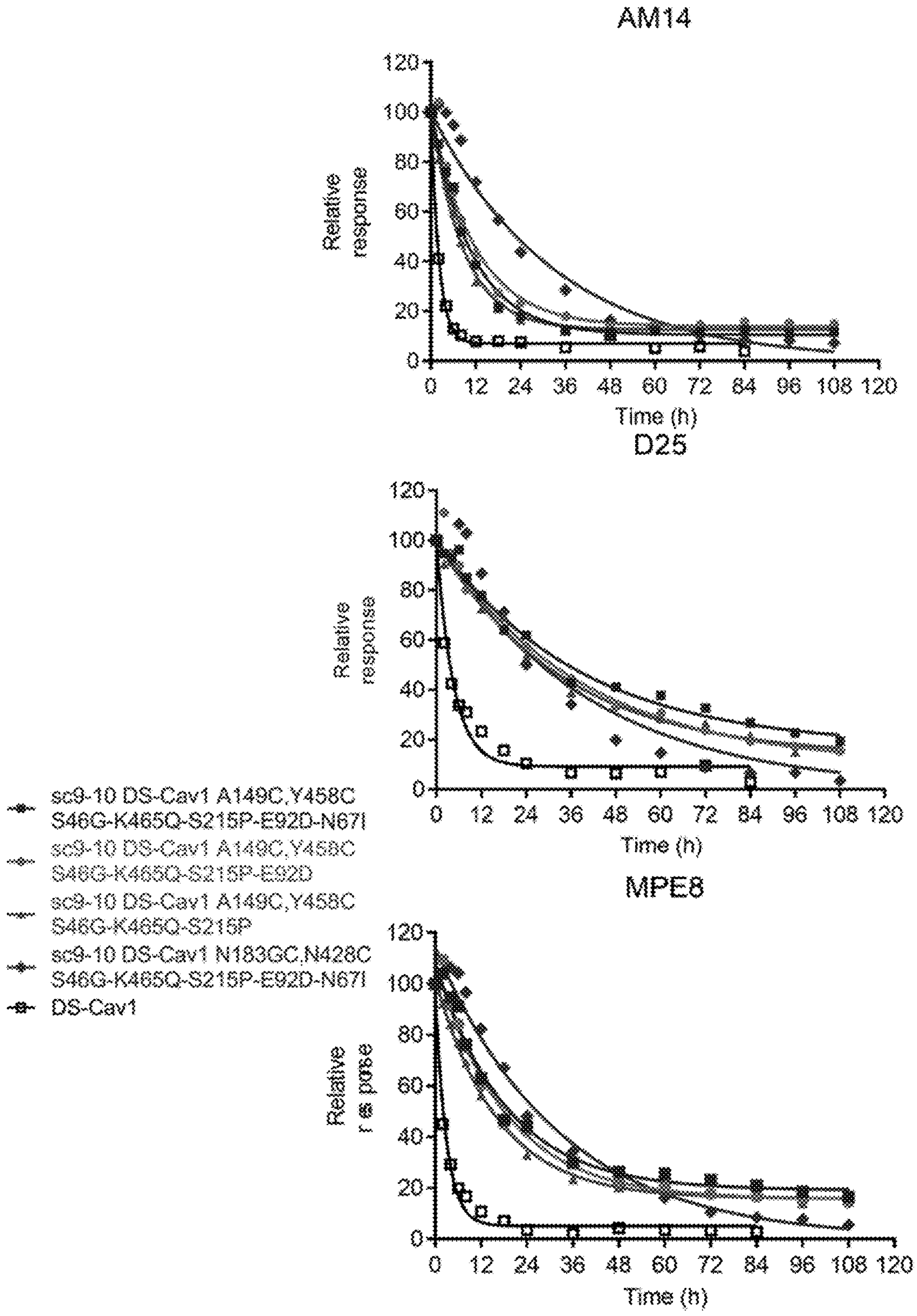

To measure the impact of these mutations on the immunogenicity of these $2^{nd}$ generations DS-Cav1 with interprotomer disulfides, CB6F1/J mice were immunized (FIG. 8B). Notably, four of the interprotomer disulfide linked RSV F trimers showed 2.5-4-fold increased elicitation of RSV-neutralizing responses relative to DS-Cav1. All of the increased titers involved variants with the triple mutant S46G, K465Q and S215P in the A2 strain, whereas the two variants without these mutations showed reduced immunogenicity and were also not of the A2 strain. To understand factors that related to immunogenicity, an informatics approach was used, though this time all information from cycles 1-4 was incorporated (FIG. 8C). Similar to the analyses using cycles 1-3 data, both quaternary antibody affinity (P<0.0001) and physical stability (P<0.0001) significantly correlated with immunogenicity (FIG. 8C), again suggesting the appropriate quaternary organization and improved physical stability can result in higher elicitation of RSV-neutralizing antibodies.

To provide additional insight into factors that might increase immunogenicity, the sera reactivity to DS-Cav1 as well as to D25 and AM14 antigenic sites were assessed from select immunization groups across design cycle 1 to 4 (FIG. 10). Notably, except with sc9, blocking with AM14 reduced the sera reactivity to prefusion stabilized F by at least two-thirds suggesting much of the response to be quaternary specific. Overall, sera reactivity agreed well with the immunogenicity data, with the more stabilized inter-protomer linked immunogens eliciting increased sera reactivity to DS-Cav1 as well as to the D25 and AM14 antigenic sites.

Discussion

By employing iterative cycles of structure-based design, $2^{nd}$ generation F glycoprotein immunogens were identified with interprotomer disulfides that induce up to ~4-fold higher neutralizing activity than DS-Cav1 after two immunizations of RSV-naïve CB6F1/J mice. Titers in these mice and rhesus macaques were previously observed to be correlated (McLellan et al., *Science,* 342, 592, 2013; Elicited levels of RSV protective antibodies in CB6F1/J mice and rhesus macaque correlated (31) (r=0.9975, P=0.0451). Whether the immunogenicity of these $2^{nd}$ generation RSV F antigens is sufficient to induce titers in pregnant women beyond the critical 64-fold protective threshold needed to protect infants during the first 6 months of life, however, will need to be answered through clinical trials. Relevant to this, it is noted that maternal immunization may not require durability, just high magnitude during the last weeks of gestation, and—in the case of neutralizing activity—more is better. These $2^{nd}$ generation constructs are thus likely to extend the duration of protection.

Further optimization of the $2^{nd}$-generation RSV F immunogens is possible. While these RSV F antigens showed clear increases in stability at higher temperature versus DS-Cav1, they were less stable to other physical extremes of pH and osmolality than DS-Cav1. Notably the correlation between physical stability and increased elicitation of RSV protective response was only significant when interprotomer disulfides were considered. This likely relates to the substantial increase in antigenic stability contributed by the interprotomer disulfides.

Materials and Methods

Protein expression and purification. RSV F mutations were made by site-directed mutagenesis using the Stratagene Quik-change procedure. RSV F variants were expressed by transient transfection of Expi293F cells using 293Fectin (Invitrogen). Cell culture supernatants were harvested 5 days post transfection and centrifuged at 10,000 g to remove cell debris. The supernatants were sterile-filtered, and RSV F proteins were purified by nickel and streptactin-affinity chromatography followed by size-exclusion chromatography. The nickel and streptactin purification tags were removed for animal immunization and crystallization studies. To remove the purification tags, proteins were digested with 2 U/mg restriction-grade thrombin (Novagen) overnight at 4° C. and then purified by a second round of size-exclusion chromatography in PBS buffer.

Screening of prefusion-stabilized RSV F constructs. Prefusion RSV F variants were derived from the RSV F (+) Fd construct (Leuridan et al., *BMJ,* 340, c1626, 2010), which consists of RSV F residues 1-513 with a C-terminal T4 fibritin trimerization motif, thrombin site, 6×His-tag, and StreptagII or the modified RSV F DS-Cav1 construct (McLellan et al., *Science,* 342, 592, 2013). A 96-well microplate-formatted transient gene expression approach was used to achieve high-throughput expression of various RSV F proteins as described previously (Pancera et al., *PloS one,* 8, e55701, 2013). Briefly, 24 h prior to transfection HEK 293T cells were seeded in each well of a 96-well microplate at a density of $2.5\times10^5$ cells/ml in expression medium (high glucose DMEM supplemented with 10% ultra-low IgG fetal bovine serum and 1×-non-essential amino acids), and incubated at 37° C., 5% CO2 for 20 h. Plasmid DNA and TrueFect-Max (United BioSystems, MD) were mixed and added to the growing cells, and the 96-well plate incubated at 37° C., 5% CO2. One day post transfection, enriched medium (high glucose DMEM plus 25% ultra-low IgG fetal bovine serum, 2× nonessential amino acids, 1× glutamine) was added to each well, and the 96-well plate was returned to the incubator for continuous culture. On day five, post transfection, supernatants with the expressed RSV F variants were harvested and tested by ELISA for binding to D25, AM22, 5C4, and motavizumab antibodies using Ni2+-NTA microplates. After incubating the harvested supernatants at 4° C. for one week, ELISAs were repeated.

RSV F antigenic characterization. A fortéBio Octet Red384 instrument was used to measure binding kinetics of RSV F T4 Fibritin trimerization-removed variants to antibodies that target the pre-fusion form (van den Berg et al., *Early Human Development,* 87, 67, 2011; Young, *Respiratory Medicine,* 96 Suppl B, S31, 2002; Gilman et al., *PLoS pathogens,* 11, e1005035, 2015; McLellan et al., *Science,* 340, 1113, 2013; McLellan et al., *Nat. Struct. Mol. Biol.,* 17, 248, 2010). All assays were performed with agitation set to 1,000 rpm in phosphate-buffered saline (PBS) supplemented with 1% bovine serum albumin (BSA) to minimize nonspecific interactions. The final volume for all solutions was 50 μl/well. Assays were performed at 30° C. in tilted black 384-well plates (Geiger Bio-One). Ni-NTA sensor tips (ForteBio) were used to load his-tagged proteins for 300 s to capture. Biosensor tips were then equilibrated for 90 s in PBS+1% BSA prior to measuring association with antigen binding fragments (Fabs) in solution (0.007 μM to 0.5 μM) for 300 s; Fabs were then allowed to dissociate for 300 s-1200 s depending on the observed dissociation rate. Parallel correction to subtract systematic baseline drift was carried out by subtracting the measurements recorded for a loaded sensor incubated in PBS+1% BSA. Data analysis and curve fitting were carried out using Octet software, version 8.0. Experimental data were fitted with the binding equations describing a 1:1 interaction. Global and local analyses of the data sets assuming reversible binding (full dissociation) were carried out using nonlinear least-squares fitting allowing a single set of binding parameters to be obtained simultaneously for all of the concentrations used in each experiment.

Physical stability of RSV F variants. To assess the physical stability of the pre-fusion conformation of designed RSV F glycoproteins under various stress conditions, the proteins were treated with a variety of pharmaceutically relevant stresses such as extreme pH, high temperature, low and high osmolarity, and repeated freeze/thaw cycles while at a concentration of 50 μg/ml. The physical stability of treated RSV F variants was evaluated by the preservation of antigenic site Ø after treatment as assessed by the site Ø-specific antibody D25.

In pH treatments, the RSV F glycoprotein solution was adjusted to pH 3.5 and pH 10 with appropriate buffers exchange and incubated at room temperature for 60 minutes and subsequently neutralized to pH 7.4. Temperature treatments were carried out by incubating the RSV F glycoprotein solutions at 50° C. and 70° C. for 60 minutes in a PCR cycler with heated lid. In osmolality treatments, RSV F glycoprotein solutions originally containing 137 mM NaCl in PBS buffer were either diluted with 2.5 mM Tris buffer (pH 7.5) to an osmolality of 10 mM NaCl or adjusted with 4.5 M MgCl2 to a final concentration of 3.0 M MgCl2. Protein solutions were incubated for 60 minutes at room temperature and then returned to PBS buffer through thoroughly buffer, and concentrated to 50 μg/ml. The freeze/thaw treatment was carried out by repeatedly freezing RSV F glycoprotein solutions in liquid nitrogen and thawing at 37° C. ten times. The 10 cycles of freeze/thaw treatment were also used to assess some RSV F variants which were supplemented with 5 or 10% glycerol. All RSV F glycoproteins were diluted to 40 μg/ml with PBS buffer, and their ability to bind D25 Fab was measured with an Octet instrument using the protocol described above. The degree of physical stability is reported as the ratio of steady state D25-binding level before and after stress treatment.

Negative stain electron microscopy. Samples were adsorbed to freshly glow-discharged carbon-film grids, rinsed twice with buffer and stained with freshly made 0.75% uranyl formate. Images were recorded on an FEI T20 microscope with a 2 k×2 k Eagle CCD camera at a pixel size of 1.5 Å. Image analysis and 2D averaging was performed with Bsoft (Heymann and Belnap, *J. Struct Biol.,* 157, 3, 2007) and EMAN (Ludtke, Baldwin, and Chiu, *J. Struct. Biol.,* 128, 82, 1999).

Mouse immunizations. All animal experiments were reviewed and approved by the Animal Care and Use Committee of the Vaccine Research Center, NIAID, NIH, under animal protocol 13-454, and all animals were housed and cared for in accordance with local, state, federal, and institute policies in an American Association for Accreditation of Laboratory Animal Care (AAALAC)-accredited facility at the NIH. Hybrid mice that were the first filial offspring of a cross between BALB/cJ females (C) and C57BL/6J males (B6) (The Jackson Laboratory) known as CB6F1/J at ages 6 weeks to 12 weeks were intramuscularly injected with RSV F immunogens at week 0 and week 3. The frozen RSV F variant immunogen proteins were thawed on ice and mixed with 5-fold w/w poly I:C (Invivogen) adjuvant (i.e. 10 μg RSV F, 50 μg Poly I:C per animal per immunization), with injections taking place within 1 h of immunogen:adjuvant preparation. No adverse effect from immunization was observed. Blood was collected at least three days before immunization, and at week two, week five and week seven post initial immunization.

Viruses and cells. Viral stocks were prepared and maintained as previously described (Graham et al., *J. Med. Virol.,* 26, 153, 1988). Recombinant mKate-RSV expressing prototypic subtype A (strain A2) F genes and the Katushka fluorescent protein were constructed as reported by Hotard et al. (Hotard et al., *Virology* 434, 129, 2012). HEp-2 cells were maintained in Eagle's minimal essential medium containing 10% fetal bovine serum (10% EMEM), supplemented with glutamine, penicillin and streptomycin.

RSV neutralization assays. Sera were distributed as four-fold dilutions from 1:10 to 1:163840, mixed with an equal volume of recombinant mKate-Respiratory syncytial virus expressing prototypic F genes from subtype A (strain A2) and the Katushka fluorescent protein, and incubated at 37° C. for 1 h. Next, 50 μl of each serum dilution/virus mixture was added to HEp-2 cells, which had been seeded at a density of $2.4 \times 10^4$ in 30 μl L1 MEM (minimal essential medium) in each well of 384-well black optical bottom plates, and incubated for 20-22 h before spectrophotometric analysis at 588 nm excitation and 635 nm emission (SpectraMax Paradigm, Molecular Devices, CA). The IC50 for each sample was calculated by curve fitting and non-linear regression using GraphPad Prism (GraphPad Software Inc., CA).

Protective threshold was calculated as follows: clinical administration of Palivizumab (Synagis) at 15 mg/kg, leads to patient sera levels at trough of ~40 μg/ml. This serum concentration provides protection in infants from severe disease and protection in cotton rats from RSV infection. In the neutralization assay described above, 40 μg/ml of Palivizumab yields an EC50 of 100.

Crystallization and X-ray data collection of prefusion-stabilized RSV F proteins. Crystals of RSV F single chain RSV F prefusion variants were grown by the vapor diffusion method in hanging drops at 20° C. by mixing 1 μl of RSV F with 1 μl of reservoir solution. Crystals of RSV F sc9 DS-Cav1 and sc9-24 DS-Cav1 grew in sodium acetate, pH 5.5, lithium sulfate, magnesium sulfate, Peg 400 conditions. Specifically, sc9 DS-Cav1 crystals grew in 0.1 M NaOAc-Acetic Acid pH 5.5, 1.09 M $Li_2SO_4$, 0.12 M $MgSO_4$, 3.33% (w/v) PEG 400 and sc9-24 DS-Cav1 crystals grew in 0.1 M NaOAc-Acetic Acid pH 5.5, 1.82 M Li2SO4, 0.1 M $MgSO_4$, 5% (w/v) PEG 400. sc9 crystals were crystals were transferred to a solution of mother liquor supplemented with 1.0 M $Li_2SO_4$, and flash frozen in liquid nitrogen while sc9-24 crystals could be flash frozen in mother liquor without additional $Li_2SO_4$ addition. sc9-10 DS-Cav1 crystals grew in 0.1 M HEPES pH 7.5, 0.19 M $(NH_4)_2SO_4$, 11% iso-propanol, 17% PEG 8,000 and were transferred to a solution containing mother liquor supplemented with 30% glycerol prior to cryocooling in liquid nitrogen. sc9-19 crystals grew in 0.1 M Na citrate pH 5.6, 15% iso-propanol, 17% PEG 4,000, and were transferred to mother liquor supplemented with 15% 2R-3R-butanediol prior to storage in liquid nitrogen. sc9-10 A149C-Y458C crystals grew in 0.1 M phosphate-citrate, pH4.2, 0.12 M NaCl, 9.5% (w/v) PEG 8,000 and were also transferred to mother liquor supplemented with 15% 2R-3R-butanediol prior to storage in liquid nitrogen. The sc9-10 DS-Cav1 A149C, Y458C, 546G-N67I-E92D-5215P-K465Q crystals grew in 0.1M Na Cacodylate, pH 6.5, 0.2M ZnAC, 17% (w/v) PEG 8,000 and were frozen in mother liquor supplemented with 22% ethylene glycol. All X-ray diffraction data were collected at a wavelength of 1.00 Å at the SER-CAT beamline ID-22.

Structure determination, refinement and analysis of prefusion-stabilized RSV F. X-ray diffraction data were integrated and scaled with the HKL2000 suite (Otwinowski and Minor, in *Methods Enzymol.* (Academic Press, 1997), vol. 276, pp. 307-326), and molecular replacement solutions were obtained by PHASER (McCoy et al., *J. Appl. Crystallogr.,* 40, 658, 2007) using the RSV F DS-Cav1 structure (PDB ID: 4MMU (McLellan et al., *Science,* 342, 592, 2013)) as a search model. Manual model building was carried out using COOT (Emsley et al., *Acta crystall. D, Biol. Crystal.,* 66, 486, April, 2010), and refinement was performed in PHENIX (Adams et al., *Acta crystall. D, Biol. Crystal.,* 66, 213, 2010). Final data collection and refinement statistics are presented in FIG. 12. Superimpositions of RSV F structures were performed using residues 225-455 which showed high levels of structural similarity. Antigenic site Ø rmsd calculations were based on residues 61-71 and 194-219 which were within 10 Å of the D25 antibody in the RSV F-D25 complex structure.

Correlation of Immunogenicity with different properties. The correlation between immunogenicity and the following properties were measured using Spearman correlation: elution volume, expression yield, antigenicity toward site-Ø antibodies (geometric mean of D25, AM22, and 5C4 $K_D$s), Motavizumab ($K_D$), quaternary antibodies (geometric mean of MPE8 and AM14 $K_D$s), and physical stability (average D25 reactivity retained after exposure to seven different physical extremes). The correlation is considered significant if the adjusted P-values based on Bonferroni correction is less than 0.05 (equivalent to $P<0.05/6=0.00833$).

Sera antigenic analysis. Mouse sera from a subset of immunization groups from the iterative optimization cycles were assessed for binding to prefusion RSV F in the presence of antigenic site Ø antibody D25 and quaternary preferring antibody AM14 using a fortébio Octet HTX instrument. Week 5 sera were diluted 1:300 in 1% BSA/PBS. Anti penta His, (HIS1K) sensor tips obtained from fortéBio were equilibrated in PBS prior to running an assay. RSV F DS-Cav1 trimeric protein at 20 ug/ml in 1% BSA/PBS was loaded onto HIS1K biosensors using the C-terminal His tag for 300s. The sensor tips were subsequently equilibrated in 1% BSA/PBS for 60s followed by capture of pre fusion specific antibodies D25 and AM14 at 50 ug/ml for 600s. HIS1K tips loaded with DS-Cav1/D25 or AM14 were equilibrated for 180s in 1% BSA/PBS followed by a serum association step for 300s and a subsequent dissociation step for an additional 300s. An identical assay was performed in the absence of antibodies D25 or AM14 to obtain serum response in the absence of competing antibodies. Data analysis was performed using Octet and GraphPad Prism 6 software.

TABLE A

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| None | RSV F | RSV F wild type | Foldon | N.A. | N.A. | N.A. | 513 |
| Design cycle 1 | sc1 | S155C, S290C, L373R | Foldon | 97-150 | 9 | GSGNVGLGG (SEQ ID NO: 117) | 513 |
| | sc1a | L373R | Foldon | 97-150 | 9 | SEQ ID NO: 117 | 513 |
| | sc2 | S155C, S290C, L373R | Foldon | 97-150 | 9 | GSGNWGLGG (SEQ ID NO: 118) | 513 |
| | sc3 | S155C, S290C, L373R | Foldon | 97-150 | 9 | GSGNIGLGG (SEQ ID NO: 119) | 513 |
| | sc3a | L373R | Foldon | 97-150 | 9 | SEQ ID NO: 119 | 513 |
| | sc3 DS-Cav1 | S155C, S190F, V207L, S290C, L373R | Foldon | 97-150 | 9 | SEQ ID NO: 119 | 513 |
| | sc3 DS-Cav1-F488W | S155C, S190F, V207L, S290C, L373R, F488W | Foldon | 97-150 | 9 | SEQ ID NO: 119 | 513 |
| | sc4 | S155C, S290C, L373R | Foldon | 97-150 | 11 | GSGGNGIGLGG (SEQ ID NO: 120) | 513 |
| | sc4a | L373R | Foldon | 97-150 | 11 | SEQ ID NO: 120 | 513 |
| | sc4 DS-Cav1 | S155C, S190F, V207L, S290C, L373R | Foldon | 97-150 | 11 | SEQ ID NO: 120 | 513 |
| | sc4 DS-Cav1-F488W | S155C, S190F, V207L, S290C, L373R, F488W | Foldon | 97-150 | 11 | SEQ ID NO: 120 | 513 |
| | sc5 | S155C, S290C, L373R | Foldon | 97-150 | 10 | GSGGSGGSGG (SEQ ID NO: 121) | 513 |
| | sc5a | L373R | Foldon | 97-150 | 10 | SEQ ID NO: 121 | 513 |
| | sc5a Cav1 | S190F, V207L, L373R | Foldon | 97-150 | 10 | SEQ ID NO: 121 | 513 |
| | sc5 DS- Cav1 | S155C, S190F, V207L, S290C, L373R | Foldon | 97-150 | 10 | SEQ ID NO: 121 | 513 |
| | sc6 | S155C, S290C, L373R | Foldon | 97-150 | 8 | GSGNVLGG (SEQ ID NO: 122) | 513 |
| | sc6a | L373R | Foldon | 97-150 | 8 | SEQ ID NO: 122 | 513 |
| | sc6 DS- Cav1 | S155C, S190F, V207L, S290C, L373R | Foldon | 97-150 | 8 | SEQ ID NO: 122 | 513 |
| | sc7 | S155C, S290C, L373R, D486C, E487P, F489C | None | 97-150 | 9 | SEQ ID NO: 117 | 491 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc7 DS-Cav1 | S155C, S290C, L373R, D486C, E487P, F489C | None | 97-150 | 9 | SEQ ID NO: 117 | 491 |
| | sc7a | L373R | None | 97-150 | 9 | SEQ ID NO: 117 | 491 |
| | sc7a Cav1 | S190F, V207L, L373R | None | 97-150 | 9 | SEQ ID NO: 117 | 491 |
| | sc8 | S155C, S290C, L373R, L512C, L513C | None | 97-150 | 9 | SEQ ID NO: 117 | 510 |
| | sc8 CAV1 | S155C, S190F, V207L, S290C, L373R, L512C, L513C | None | 97-150 | 9 | SEQ ID NO: 117 | 510 |
| | sc8 CAV1 F488W | S115C, S190F, V207L, S290C, L373R, F488W, L512C, L513C | None | 97-150 | 9 | SEQ ID NO: 117 | 510 |
| | sc8a | L373R | None | 97-150 | 9 | SEQ ID NO: 117 | 510 |
| | sc9 DS-Cav1 | S155C, S190F, V207L, S290C, L373R | Foldon | 105-145 | 2 | GS | 513 |
| | sc9a | L373R | Foldon | 105-145 | 2 | GS | 513 |
| | sc9 | S155C, S190F, L373R | Foldon | 105-145 | 2 | GS | 513 |
| | sc9a Cav1 | V207L, S290C, L373R | Foldon | 105-145 | 2 | GS | 513 |
| | sc10 DS | S155C, S290C, L373R, D486C, E487P, F489C | None | 105-145 | 2 | GS | 491 |
| | sc11 DS | S155C, S290C, L373R, L512C, L513C | None | 105-145 | 2 | GS | 513 |
| Design cycle 2 | sc9-1 DS-Cav1 | S155C, S190F, V207L, S290C, L373R | Foldon | 96-145 | 10 | MQSTPATNNG (SEQ ID NO: 123) | 513 |
| | sc9-2 DS-Cav1 | S155C, S190F, V207L, S290C, L373R | Foldon | 96-145 | 11 | MQSTPATNNGG (SEQ ID NO: 124 | 513 |
| | sc9-3 DS-Cav1 | S155C, S190F, V207L, S290C, L373R | Foldon | 96-145 | 12 | MOSTPATNNGQG (SEQ ID NO: 125) | 513 |
| | sc9-4 DS-Cav1 | S155C, S190F, V207L, S290C, L373R | Foldon | 96-145 | 13 | MQSTPATNNGGSG (SEQ ID NO: 126) | 513 |
| | sc9-5 DS-Cav1 | S155C, S190F, V207L, S290C, L373R | Foldon | 96-145 | 14 | MOSTPATNNGGSGS (SEQ ID NO: 127) | 513 |
| | sc9-6 DS-Cav1 | S155C, S190F, V207L, S290C, L373R | Foldon | 96-145 | 15 | MQSTPATNNGGSGGS (SEQ ID NO: 128) | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-7 DS-Cav1 | S155C, S190F, V207L, S290C, L373R | Foldon | 96-145 | 16 | MOSTPATNNGGSG GSG (SEQ ID NO: 129) | 513 |
| | sc9-8 DS-Cav1 | S155C, S190F, V207L, S290C, L373R | Foldon | 96-145 | 17 | MQSTPATNNGGGS GGSG (SEQ ID NO: 130) | 513 |
| | sc9-9 DS-Cav1 | S155C, S190F, V207L, S290C, L373R | Foldon | 96-145 | 7 | MQSTPAT (SEQ ID NO: 131) | 513 |
| | sc9-10 DS-Cav1 | S155C, S190F, V207L, S290C, L373R | Foldon | 96-145 | 9 | MOSTPATGS (SEQ ID NO: 132) | 513 |
| | sc9-11 DS-Cav1 | S155C, S190F, V207L, S290C, L373R | Foldon | 96-145 | 8 | MOSTPAGS (SEQ ID NO: 133) | 513 |
| | sc9-12 DS-Cav1 | S155C, S190F, V207L, S290C, L373R | Foldon | 96-145 | 7 | MQSTPGS (SEQ ID NO: 134) | 513 |
| | sc9-13 DS-Cav1 | S155C, S190F, V207L, S290C, L373R | Foldon | 96-145 | 6 | MOSTGS (SEQ ID NO: 135) | 513 |
| | sc9-14 DS-Cav1 | S155C, S190F, V207L, S290C, L373R | Foldon | 96-145 | 5 | MQSGS (SEQ ID NO: 136) | 513 |
| | sc9-15 DS-Cav1 | S155C, S190F, V207L, S290C, L373R | Foldon | 96-145 | 4 | MQGS ((SEQ ID NO: 137) | 513 |
| | sc9-16 DS-Cav1 | S155C, S190F, V207L, S290C, L373R | Foldon | 96-145 | 3 | MGS (SEQ ID NO: 138) | 513 |
| | sc9-17 DS-Cav1 | S155C, S190F, V207L, S290C, L373R | Foldon | 96-145 | 11 | MQSTPATGGSG (SEQ ID NO: 139) | 513 |
| | sc9-18 DS-Cav1 | S155C, S190F, V207L, S290C, L373R | Foldon | 96-145 | 12 | MQSTPATGGSGG (SEQ ID NO: 140) | 513 |
| | sc9-19 DS-Cav1 | S155C, S190F, V207L, S290C, L373R | Foldon | 96-145 | 13 | MQSTPATGGSGGSG (SEQ ID NO: 141) | 513 |
| | sc9-20 DS-Cav1 | S155C, S190F, V207L, S290C, L373R | Foldon | 96-145 | 11 | MQSTATGGSGN (SEQ ID NO: 142) | 513 |
| | sc9-21 DS-Cav1 | S155C, S190F, V207L, S290C, L373R | Foldon | 96-145 | 9 | MQSTPANGS (SEQ ID NO: 143) | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-22 DS-Cav1 | S155C, S190F, V207L, S290C, L373R | Foldon | 96-145 | 14 | ISSTSATGSGSAIA (SEQ ID NO: 144) | 513 |
| | sc9-23 DS-Cav1 | S155C, S190F, V207L, S290C, L373R | Foldon | 96-145 | 13 | VTSTSATGSGSAI (SEQ ID NO: 145) | 513 |
| | sc9-24 DS-Cav1 | S155C, S190F, V207L, S290C, L373R | Foldon | 96-145 | 14 | NSALSATGSGSAIA (SEQ ID NO: 146) | 513 |
| | sc9-25 DS-Cav1 | S155C, S190F, V207L, S290C, L373R | Foldon | 96-145 | 9 | ISSTTSTGS (SEQ ID NO: 147) | 513 |
| | sc9-26 DS-Cav1 | S155C, S190F, V207L, S290C, L373R | Foldon | 96-145 | 9 | VTSTTSTGS (SEQ ID NO: 148) | 513 |
| | sc9-27 DS-Cav1 | S155C, S190F, V207L, S290C, L373R | Foldon | 96-145 | 9 | NSALSSTGS (SEQ ID NO: 149) | 513 |
| | sc9-28 DS-Cav1 | S155C, S190F, V207L, S290C, L373R | Foldon | 96-145 | 11 | ISSTSATVGGS (SEQ ID NO: 150) | 513 |
| | sc9-29 DS-Cav1 | S155C, S190F, V207L, S290C, L373R | Foldon | 96-145 | 11 | VTSTSATTGGS (SEQ ID NO: 151) | 513 |
| | sc9-30 DS-Cav1 | S155C, S190F, V207L, S290C, L373R | Foldon | 96-145 | 10 | NSALSATGGS (SEQ ID NO: 152) | 513 |
| | sc9-31 DS-Cav1 | S155C, S190F, V207L, S290C, L373R | Foldon | 96-145 | 11 | ISSTTSTVGGS (SEQ ID NO: 153) | 513 |
| | sc9-32 DS-Cav1 | S155C, S190F, V207L, S290C, L373R | Foldon | 96-145 | 11 | VTSTTSTTGGS (SEQ ID NO: 154) | 513 |
| | sc9-33 DS-Cav1 | S155C, S190F, V207L, S290C, L373R | Foldon | 96-145 | 10 | NSALSSTGGS (SEQ ID NO: 155) | 513 |
| | sc9-34 DS-Cav1 | S155C, S190F, V207L, S290C, L373R | Foldon | 96-145 | 8 | MQSTPATG (SEQ ID NO: 156) | 513 |
| | sc9-35 DS-Cav1 | S155C, S190F, V207L, S290C, L373R | Foldon | 96-145 | 3 | MQN | 513 |
| | sc9-36 DS-Cav1 | S155C, S190F, V207L, S290C, L373R | Foldon | 96-145 | 2 | MG | 513 |
| | sc9-37 DS-Cav1 | S155C, S190F, V207L, S290C, L373R | Foldon | 96-145 | 2 | MN | 513 |
| | sc9-38 DS-Cav1 | S155C, S190F, V207L, S290C, L373R | Foldon | 96-145 | 1 | M | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-39 DS-Cav1 | S155C, S190F, V207L, S290C, L373R | Foldon | 96-145 | 8 | MQSTPATS (SEQ ID NO: 157) | 513 |
| | sc9-40 DS-Cav1 | S155C, S190F, V207L, S290C, L373R | Foldon | 96-145 | 9 | ARLLGSGSG (SEQ ID NO: 158) | 513 |
| | sc9-41 DS-Cav1 | S155C, S190F, V207L, S290C, L373R | Foldon | 96-145 | 8 | MQSTGGSG (SEQ ID NO: 159) | 513 |
| | sc9-42 DS-Cav1 | S155C, S190F, V207L, S290C, L373R | Foldon | 96-145 | 8 | AQSTGGSG (SEQ ID NO: 160) | 513 |
| | sc9-43 DS-Cav1 | S155C, S190F, V207L, S290C, L373R | Foldon | 96-145 | 8 | ARLLGGSG ((SEQ ID NO: 161) | 513 |
| | sc9-44 DS-Cav1 | S155C, S190F, V207L, S290C, L373R | Foldon | 96-145 | 8 | ARLLGGSG ((SEQ ID NO: 161) | 513 |
| | sc9-45 DS-Cav1 | S155C, S190F, V207L, S290C, L373R | Foldon | 96-145 | 7 | ARLLGSG (SEQ ID NO: 162) | 513 |
| Design cycle 3 | sc9-10 DS-Cav1 A149C Y458C | A149C, S155C, S190F, V207L, S290C, L373R, Y458C | Foldon | 103-145 | 2 | GS | 513 |
| | sc9-10 DS-Cav1 N183GC N428C | S155C, N183GC, S190F, V207L, S290C, L373R, N428C | Foldon | 103-145 | 2 | GS | 513 |
| | sc9-10 DS-Cav1 T100C Q361C | S155C, T100C, S190F, V207L, S290C, L373R, Q361C | Foldon | 103-145 | 2 | GS | 513 |
| | sc9-10 DS-Cav1 A74C E218C | S155C, S190F, V207L, S290C, L373R, A74C, E218C | Foldon | 103-145 | 2 | GS | 513 |
| | sc9-10 DS-Cav1 G143C S404C | S155C, S190F, V207L, S290C, L373R, G143C, S404C | Foldon | 103-145 | 2 | GS | 513 |
| | sc9-10 DS-Cav1 V144C V406C | S155C, S190F, V207L, S290C, L373R, V144C, V406C | Foldon | 103-145 | 2 | GS | 513 |
| | sc9-10 DS-Cav1 S146C S407C | S155C, S190F, V207L, S290C, L373R, S146C, S407C | Foldon | 103-145 | 2 | GS | 513 |
| | sc9-10 DS-Cav1 A153C K461C | S155C, S190F, V207L, S290C, L373R, A153C, K461C | Foldon | 103-145 | 2 | GS | 513 |
| | sc9-10 DS-Cav1 A346C N454C | S155C, S190F, V207L, S290C, L373R, A346C, N454C | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10 DS-Cav1 T369C T455C | S155C, S190F, V207L, S290C, L373R, T369C, T455C | Foldon | 103-145 | 2 | GS | 513 |
| | sc9-10 DS-Cav1 K399C Q494C | S155C, S190F, V207L, S290C, L373R, K399C, Q494C | Foldon | 103-145 | 2 | GS | 513 |
| | sc9-10 DS-Cav1 T400C D489C | S155C, S190F, V207L, S290C, L373R, T400C, D489C | Foldon | 103-145 | 2 | GS | 513 |
| | sc9-10 DS-Cav1 V402C L141C | S155C, S190F, V207L, S290C, L373R, V402C, L141C | Foldon | 103-145 | 2 | GS | 513 |
| | sc9-10 DS-Cav1 T374C N454C | S155C, S190F, V207L, S290C, L373R, T374C, N454C | Foldon | 103-145 | 2 | GS | 513 |
| | sc9-10 DS-Cav1 A146C N460C | S155C, S190F, V207L, S290C, L373R, A146C, N460C, Ala-Ala inserted between 146 and 147 | Foldon | 103-145 | 2 | GS | 513 |
| | sc9-10 DS-Cav1 N183C K427C | S155C, S190F, V207L, S290C, L373R, N183C, K427C, Gly inserted between 182 and 183 | Foldon | 103-145 | 2 | GS | 513 |
| | sc9-10 DS-Cav1 N183C K427C,Cys inserted between 427 and 428 | S155C, S190F, V207L, S290C, L373R, N183C, K427C, Cys inserted between 427 and 428 | Foldon | 103-145 | 2 | GS | 513 |
| | scRSVF9aC485C494xFd | L373R, S485C, Q494C | Foldon | 105-145 | 2 | GS | 513 |
| | scRSVF9aC419C420extxFd | L373R, K419C, T420C | Foldon | 105-145 | 2 | GS | 513 |
| | scRSVF9aC99C362xFd | L373R, L99C, SS362C | Foldon | 105-145 | 2 | GS | 513 |
| | scRSVF9aC99C361xFd | L373R, L99C, Q361C | Foldon | 105-145 | 2 | GS | 513 |
| | scRSVF9aC153C461xFd | L373R, A153C, K461C | Foldon | 105-145 | 2 | GS | 513 |
| | scRSVF9aC102C359xFd | L373R, A102C, K359C | Foldon | 105-145 | 2 | GS | 513 |
| | scRSVF9 DS-Cav1 C485C494xFd | S155C, S190F, V207L, S290C, L373R, S485C, Q494C | Foldon | 105-145 | 2 | GS | 513 |
| | scRSVF9 DS-Cav1 C419C420extxFd | S155C, S190F, V207L, S290C, L373R, K419C, T420C | Foldon | 105-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | scRSVF9 DS-Cav1 C99C362xFd | S155C, S190F, V207L, S290C, L373R, L99C, S362C | Foldon | 105-145 | 2 | GS | 513 |
| | scRSVF9 DS-Cav1 C99C361xFd | S155C, S190F, V207L, S290C, L373R, L99C, Q361C | Foldon | 105-145 | 2 | GS | 513 |
| | scRSVF9 DS-Cav1 C153C461xFd | S155C, S190F, V207L, S290C, L373R, A153C, K461C | Foldon | 105-145 | 2 | GS | 513 |
| | scRSVF9 DS-Cav1 C102C359xFd | S155C, S190F, V207L, S290C, L373R,A102C, K359C | Foldon | 105-145 | 2 | GS | 513 |
| | scRSV F 9axFd | L373R | Foldon | 105-145 | 2 | GS | 513 |
| | scRSV F 9aextxFd | L373R | Foldon | 105-145 | 2 | GS | 524 |
| | sc9a RSVF 74C218C xFd | L373R, A74C, E218C | Foldon | 105-145 | 2 | GS | 513 |
| | sc9a RSVF 146C460CxFd | L373R, S146C, N460C | Foldon | 105-145 | 2 | GS | 513 |
| | sc9a RSVF 149C458C xFd | L373R, A149C, Y458C | Foldon | 105-145 | 2 | GS | 513 |
| | sc9a RSVF 374C454C xFd | L373R, T374C, 454C | Foldon | 105-145 | 2 | GS | 513 |
| | scRSVF 74C218C xFd | S155C, S190F, V207L, S290C, L373R, A74C, E218C | Foldon | 105-145 | 2 | GS | 513 |
| | scRSVF 146C460C xFd | S155C, S190F, V207L, S290C, L373R, S146C, N460C | Foldon | 105-145 | 2 | GS | 513 |
| | scRSVF 149C458C xFd | S155C, S190F, V207L, S290C, L373R, A149C, Y458C | Foldon | 105-145 | 2 | GS | 513 |
| | scRSVF 374C454C xFd | S155C, S190F, V207L, S290C, L373R, T374C, 454C | Foldon | 105-145 | 2 | GS | 513 |
| | scRSVF9 C485C494xFd | S155C, S190F, V207L, S290C, L373R, S485C, Q494C | Foldon | 105-145 | 2 | GS | 513 |
| | scRSVF9 C519C520extxFd | S155C, S190F, V207L, S290C, L373R, 519C, 520C | Foldon | 105-145 | 2 | GS | 513 |
| | scRSVF9 C99C362xFd | S155C, S190F, V207L, S290C, L373R, L99C, S362C | Foldon | 105-145 | 2 | GS | 513 |
| | scRSVF9 C99C361xFd | S155C, S190F, V207L, S290C, L373R, L99C, Q361C | Foldon | 105-145 | 2 | GS | 513 |

TABLE A-continued

| Engineered RSV F glycoprotein variants. | | | | | | | |
|---|---|---|---|---|---|---|---|
| Design cycle | RSV F variant | Mutations | Additional trimerization domain | F1-F2 Linker residues | Linker residue length | Linker sequence | End residue |
| | scRSVF9 C153C461xFd | S155C, S190F, V207L, S290C, L373R, A153C, K461C | Foldon | 105-145 | 2 | GS | 513 |
| | scRSVF9 C102C359xFd | S155C, S190F, V207L, S290C, L373R, A102C, K359C | Foldon | 105-145 | 2 | GS | 513 |
| Design cycle 4 | sc9-10 DS-Cav1 A149C Y458C S46G-K465Q-S215P-E92D | A149C, S155C, S190F, V207L, S290C, L373R, Y458C, S46G, K465Q, S215P, E92D | Foldon | 103-145 | 2 | GS | 513 |
| | sc9-10 DS-Cav1 N183GC N428C S46G-S215P-E92D | S155C, N183GC, S190F, V207L, S290C, L373R, N428C, S46G, S215P, E92D | Foldon | 103-145 | 2 | GS | 513 |
| | sc9-10-A149C-E69L + E121I + Q279V + Q302V + Q279V + Q302V_CS | E121I, A149C, Y458C, Q279V, Q302V, S155C, S190F, V207L, S290C, L373R, E69L, Q279V, Q302V | Foldon | 103-145 | 2 | GS | 513 |
| | sc9-10-A149C-R282L + R336V_CS-Prolact | S155C, S190F, V207L, S290C, L373R, R282L, R336V | Foldon | 103-145 | 2 | GS | 513 |
| | sc9-10-A149C-E69L + E121L_CS-Prolact | S155C, S190F, V207L, S290C, A149C, L373R, E69L, E121L, Y458C | Foldon | 103-145 | 2 | GS | 513 |
| | sc9-10-A149C-Q279V + Q302V_CS-Prolact | S155C, S190F, V207L, S290C, L373R, Q279V, Q302V,A149C | Foldon | 103-145 | 2 | GS | 513 |
| | sc9-10-A149C-E69L + E121I + Q279V + Q302V + Q279V + Q302V_CS-Prolact | A149C, E69L, E1211, Q279V, Q302V, Q279V, S155C, S190F, V207L, S290C, L373R, Q302V, Y458C | Foldon | 103-145 | 2 | GS | 513 |
| | sc9-10-A149C-R282L + R336V_CS-Prolact-523 | S155C, S190F, V207L, S290C, L373R, A149C, R282L, R336V, Y458C | Foldon | 103-145 | 2 | GS | 513 |
| | sc9-10-A149C-E69L + E121L_CS-Prolact-523 | S155C, S190F, V207L, S290C, L373R, A149C, E69L, E121L,Y458C | Foldon | 103-145 | 2 | GS | 513 |
| | sc9-10-A149C-Q279V + Q302V_CS-Prolact-523 | S155C, S190F, V207L, S290C, L373R, A149C, Q279V, Q302V | Foldon | 103-145 | 2 | GS | 513523 |
| | sc9-10-A149C-E69L + E121I + Q279V + Q302V + Q279V + Q302V_CS-Prolact-523 | S155C, S190F, V207L, S290C, L373R, E69L, E121I, Q279V, Q302V, Q279V, Q302V, A149C, Y458C | Foldon | 103-145 | 2 | GS | 513523 |
| | sc9-10-N183GC-R282L + R336V_CS | S155C, S190F, V207L, S290C, L373R, R282L, R336V, N183GC, N428C | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10-N183GC-E69L + E121L_CS | S155C, S190F, V207L, S290C, L373R, E69L, E121L, N183GC, N428C | Foldon | 103-145 | 2 | GS | 513 |
| | sc9-10-N183GC-Q279V + Q302V_CS | S155C, S190F, V207L, S290C, L373R, Q279V, Q302V, N183GC, N428C | Foldon | 103-145 | 2 | GS | 513 |
| | sc9-10-N183GC- E69L + E121I + Q279V + Q302V + Q279V + Q302V_CS | E1211, Q279V, Q302V, Q279V, Q302V, S155C, S190F, V207L, S290C,L373R, E69L, N183GC, N428C | Foldon | 103-145 | 2 | GS | 513 |
| | sc9-10-N183GC-R282L + R336V_CS-Prolact | S155C, S190F, V207L, S290C, L373R, R282L, R336V, N183GC, N428C | Foldon | 103-145 | 2 | GS | 513 |
| | sc9-10-N183GC-E69L + E121L_CS-Prolact | S155C, S190F, V207L, S290C, L373R, E69L, E121L, N183GC, N428C | Foldon | 103-145 | 2 | GS | 513 |
| | sc9-10-N183GC-Q279V + Q302V_CS-Prolact | S155C, S190F, V207L, S290C, L373R, Q279V, Q302V, N183GC, N428C | Foldon | 103-145 | 2 | GS | 513 |
| | sc9-10 DS-Cav1 A149C Y458C S46G-K465Q-S215P-E92D | A149C, S155C, S190F, V207L, S290C, L373R, Y458C, S46G, K465Q, S215P, E92D | Foldon | 103-145 | 2 | GS | 513 |
| | sc9-10 DS-Cav1 N183GC N428C S46G-S215P-E92D | S155C, N183GC, S190F, V207L, S290C, L373R, N428C, S46G, S215P, E92D | Foldon | 103-145 | 2 | GS | 513 |
| | sc9-10-A149C-E69L + E121I + Q279V + Q302V + Q279V + Q302V | E121I, A149C, Y458C, Q279V, Q302V, S155C, S190F, V207L, S290C, L373R, E69L, Q279V, Q302V | Foldon | 103-145 | 2 | GS | 513 |
| | sc9-10-A149C-R282L + R336V-Prolact | S155C, S190F, V207L, S290C, L373R, R282L, R336V | Foldon | 103-145 | 2 | GS | 513 |
| | sc9-10-A149C-E69L + E121L-Prolact | S155C, S190F, V207L, S290C, A149C, L373R, E69L, E121L, Y458C | Foldon | 103-145 | 2 | GS | 513 |
| | sc9-10-A149C-Q279V + Q302V-Prolact | S155C, S190F, V207L, S290C, L373R, Q279V, Q302V,A149C | Foldon | 103-145 | 2 | GS | 513 |
| | sc9-10-A149C-E69L + E121I + Q279V + Q302V + Q279V + Q302V-Prolact | S155C, S190F, V207L, S290C, L373R, A149C, E69L, E1211, Q279V, Q302V, Q279V, Q302V, Y458C | Foldon | 103-145 | 2 | GS | 513 |
| | sc9-10-A149C-R282L + R336V-Prolact-523 | S155C, S190F, V207L, S290C, L373R, A149C, R282L, R336V, Y458C | Foldon | 103-145 | 2 | GS | 523 |
| | sc9-10-A149C-E69L + E121L -Prolact-523 | S155C, S190F, V207L, S290C, L373R, A149C, E69L, E121L, Y458C | Foldon | 103-145 | 2 | GS | 523 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10-A149C-Q279V + Q302V-Prolact-523 | S155C, S190F, V207L, S290C, L373R, A149C, Q279V, Q302V | Foldon | 103-145 | 2 | GS | 523 |
| | sc9-10-A149C-E69L + E121I + Q279V + Q302V + Q279V + Q302V-Prolact-523 | S155C, S190F, V207L, S290C, L373R, E69L, E1211, Q279V, Q302V, Q279V, Q302V, A149C, Y458C | Foldon | 103-145 | 2 | GS | 523 |
| | sc9-10-N183GC-R282L + R336V | S155C, S190F, V207L, S290C, L373R, R282L, R336V, N183GC, N428C | Foldon | 103-145 | 2 | GS | 513 |
| | sc9-10-N183GC-E69L + E121L | S155C, S190F, V207L, S290C, L373R, E69L, E121L, N183GC, N428C | Foldon | 103-145 | 2 | GS | 513 |
| | sc9-10-N183GC-Q279V + Q302V | S155C, S190F, V207L, S290C, L373R, Q279V, Q302V, N183GC, N428C | Foldon | 103-145 | 2 | GS | 513 |
| | sc9-10-N183GC-E69L + E121I + Q279V + Q302V + Q279V + Q302V | S155C, S190F, V207L, S290C, L373R, E69L, E121I, Q279V, Q302V, Q279V, Q302V, N183GC, N428C | Foldon | 103-145 | 2 | GS | 513 |
| | sc9-10-N183GC-R282L + R336V-Prolact | S155C, S190F, V207L, S290C, L373R, R282L, R336V, N183GC, N428C | Foldon | 103-145 | 2 | GS | 513 |
| | sc9-10-N183GC-E69L + E121L-Prolact | S155C, S190F, V207L, S290C, L373R, E69L, E121L, N183GC, N428C | Foldon | 103-145 | 2 | GS | 513 |
| | sc9-10-N183GC-Q279V + Q302V-Prolact | S155C, S190F, V207L, S290C, L373R, Q279V, Q302V, N183GC, N428C | Foldon | 103-145 | 2 | GS | 513 |
| | sc9-10-N183GC-E69L + E121I + Q279V + Q302V + Q279V + Q302V-Prolact | E1211, Q279V, Q302V, Q279V, Q302V, S155C, S190F, V207L, S290C, L373R, E69L, N183GC, N428C | Foldon | 103-145 | 2 | GS | 513 |
| | sc9-10-N183GC-R282L + R336V-Prolact-523 | S155C, S190F, V207L, S290C, L373R, R282L, R336V, N183GC, N428C | Foldon | 103-145 | 2 | GS | 523 |
| | sc9-10-N183GC-E69L + E121L-Prolact-523 | S155C, S190F, V207L, S290C, L373R, E69L, E121L, N183GC, N428C | Foldon | 103-145 | 2 | GS | 523 |
| | sc9-10-N183GC-Q279V + Q302V-Prolact-523 | S155C, S190F, V207L, S290C, L373R, Q279V, Q302V, N183GC, N428C | Foldon | 103-145 | 2 | GS | 523 |
| | sc9-10-N183GC-E69L + E121I + Q279V + Q302V + Q279V + Q302V-Prolact-523 | E1211, Q279V, Q302V, Q279V, Q302V, S155C, S190F, V207L, S290C, L373R, E69L, N183GC, N428C | Foldon | 103-145 | 2 | GS | 523 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10-N183GC, S155C, S190F, V207L, S290C, L373R, K65Q | S155C, S190F, V207L, S290C, L373R, N183GC, N428C, K65Q | Foldon | 103-145 | 2 | GS | 513 |
| | sc9-10-N183GC, S155C, S190F, V207L, S290C, L373R, K68Q | S155C, S190F, V207L, S290C, L373R, N183GC, N428C, K68Q | Foldon | 103-145 | 2 | GS | 513 |
| | sc9-10-N183GC, S155C, S190F, V207L, S290C, L373R, L95M | S155C, S190F, V207L, S290C, L373R, N183GC, N428C, L95M | Foldon | 103-145 | 2 | GS | 513 |
| | sc9-10-N183GC, S155C, S190F, V207L, S290C, L373R, I221M | S155C, S190F, V207L, S290C, L373R, N183GC, N428C, I221M | Foldon | 103-145 | 2 | GS | 513 |
| | sc9-10-N183GC, S155C, S190F, V207L, S290C, L373R, I221F | S155C, S190F, V207L, S290C, L373R, N183GC, N428C, 1221F | Foldon | 103-145 | 2 | GS | 513 |
| | sc9-10-N183GC, S155C, S190F, V207L, S290C, L373R, I221N | S155C, S190F, V207L, S290C, L373R, N183GC, N428C, I221N | Foldon | 103-145 | 2 | GS | 513 |
| | sc9-10-N183GC, S155C, S190F, V207L, S290C, L373R, T311A | S155C, S190F, V207L, S290C, L373R, N183GC, N428C, T311A | Foldon | 103-145 | 2 | GS | 513 |
| | sc9-10-N183GC, S155C, S190F, V207L, S290C, L373R, T311S | S155C, S190F, V207L, S290C, L373R, N183GC, N428C, T311S | Foldon | 103-145 | 2 | GS | 513 |
| | sc9-10-N183GC, S155C, S190F, V207L, S290C, L373R, T311G | S155C, S190F, V207L, S290C, L373R, N183GC, N428C, T311G | Foldon | 103-145 | 2 | GS | 513 |
| | sc9-10-A149C-Y458C-S46G-K465Q | S155C, S190F, V207L, S290C, L373R, A149C, Y458C-S46G-K465Q | Foldon | 103-145 | 2 | GS | 513 |
| | sc9-10-A149C-Y458C-S46G-K465Q-S215P | S155C, S190F, V207L, S290C, L373R, A149C, Y458C-S46G-K465Q-S215P | Foldon | 103-145 | 2 | GS | 513 |
| | sc9-10-A149C-Y458C-S46G-K465Q-S215P | S155C, S190F, V207L, S290C, L373R, A149C, Y458C-S46G-K465Q-S215P | Foldon | 103-145 | 2 | GS | 513 |
| | sc9-10-A149C-Y458C-S46G-K465Q-S215P-E92D-N67I | S155C, S190F, V207L, S290C, L373R, A149C, Y458C-S46G-K465Q-S215P-E92D-N67I | Foldon | 103-145 | 2 | GS | 513 |
| | sc9-10-A149C-Y458C-S46G-K465Q-S215P--N67I | S155C, S190F, V207L, S290C,L373R,A149C, Y458C | Foldon | 103-145 | 2 | GS | 513 |
| | sc9-10-N183GC-N428C-S46G | S155C, S190F, V207L, S290C, L373R, N183GC, N428C, S46G | Foldon | 103-145 | 2 | GS | 513 |

TABLE A-continued

| Design cycle | RSV F variant | Mutations | Additional trimerization domain | F1-F2 Linker residues | Linker residue length | Linker sequence | End residue |
|---|---|---|---|---|---|---|---|
| Engineered RSV F glycoprotein variants. | | | | | | | |
| | sc9-10-N183GC-N428C-S46G-K465Q | S155C, S190F, V207L, S290C, L373R, N183GC, N428C, S46G-K465Q | Foldon | 103-145 | 2 | GS | 513 |
| | sc9-10-N183GC-N428C-S46G-K465Q-S215P | S155C, S190F, V207L, S290C, L373R, N183GC, N428C, S46G-K465Q-S215P | Foldon | 103-145 | 2 | GS | 513 |
| | sc9-10-N183GC-N428C-S46G-K465Q-S215P-E92D | S155C, S190F, V207L, S290C, L373R, N183GC, N428C, S46G-K465Q-S215P-E92D | Foldon | 103-145 | 2 | GS | 513 |
| | sc9-10-N183GC-N428C-S46G-K465Q-S215P-E92D-N67I | S155C, S190F, V207L, S290C, L373R, N183GC, N428C, S46G-K465Q-S215P-E92D-N67I | Foldon | 103-145 | 2 | GS | 513 |
| | sc9-10-N183GC-N428C-S46G-K465Q-S215P-N67I | S155C, S190F, V207L, S290C, L373R, N183GC, N428C, S46G-K465Q-S215P-N67I | Foldon | 103-145 | 2 | GS | 513 |
| | sc9-10-N183GC-N428C-K470Q | S155C, S190F, V207L, S290C, L373R, N183GC, N428C, K470Q | Foldon | 103-145 | 2 | GS | 513 |
| | sc9-10-N183GC-R429Q | S155C, S190F, V207L, S290C, L373R, N183GC, N428C, R429Q | Foldon | 103-145 | 2 | GS | 513 |
| | sc9-10-N183GC-R429K | S155C, S190F, V207L, S290C, L373R, N183GC, N428C, R429K | Foldon | 103-145 | 2 | GS | 513 |
| | sc9-10-N183GC-K419Q | S155C, S190F, V207L, S290C, L373R, N183GC, N428C, K419Q | Foldon | 103-145 | 2 | GS | 513 |
| | sc9-10-N183GC-K327Q | S155C, S190F, V207L, S290C, L373R, N183GC, N428C, K327Q | Foldon | 103-145 | 2 | GS | 513 |
| | sc9-10N183GC-V384T/I431S/L467Q | S155C, S190F, V207L, S290C, L373R, N183GC, N428C, V384T/I431S/L467Q | Foldon | 103-145 | 2 | GS | 513 |
| | sc9-10-N183GC-F477K/L481Q/V482K/L503K/I506Q | S155C, S190F, V207L, S290C, L373R, N183GC, N428C, F477K/L481Q/V482K/L503K/I506Q | Foldon | 103-145 | 2 | GS | 513 |
| | sc9-10N183GC-S213P | S155C, S190F, V207L, S290C, L373R, N183GC, N428C, S213P | Foldon | 103-145 | 2 | GS | 513 |
| | sc9-10N183GC-I214P | S155C, S190F, V207L, S290C, L373R, N183GC, N428C, 1214P | Foldon | 103-145 | 2 | GS | 513 |
| | sc9-10N183GC-T72P | S155C, S190F, V207L, S290C, L373R, N183GC, N428C, T72P | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10N183GC-K327P | S155C, S190F, V207L, S290C, L373R, N183GC, N428C, K327P | Foldon | 103-145 | 2 | GS | 513 |
| | sc9-10N183GC-E328P | S155C, S190F, V207L, S290C, L373R, N183GC, N428C, E328P | Foldon | 103-145 | 2 | GS | 513 |
| | sc9-10N183GC-I431P | S155C, S190F, V207L, S290C, L373R, N183GC, N428C, 1431P | Foldon | 103-145 | 2 | GS | 513 |
| | sc9-10N183GC-L83F | S155C, S190F, V207L, S290C, L373R, N183GC, N428C, L83F | Foldon | 103-145 | 2 | GS | 513 |
| | sc9-10N183GC-S238Q | S155C, S190F, V207L, S290C, L373R, N183GC, N428C, S238Q | Foldon | 103-145 | 2 | GS | 513 |
| | sc9-10N183GC-T249I | S155C, S190F, V207L, S290C, L373R, N183GC, N428C, T249I | Foldon | 103-145 | 2 | GS | 513 |
| | sc9-10N183GC-N254L | S155C, S190F, V207L, S290C, L373R, N183GC, N428C, N254L | Foldon | 103-145 | 2 | GS | 513 |
| | BZGJ9-10-N183GC-N428C Prolact N216P | S155C, S190F, V207L, S290C, L373R, N183GC, N428C, N216P | Foldon | 103-145 | 2 | GS | 513 |
| | BZGJ9-10 V56C T189C | S155C, S190F, V207L, S290C, V56C T189C | Foldon | 103-145 | 2 | GS | 513 |
| | BZGJ9-10 V56C T189C S173P | S155C, S190F, V207L, S290C, V56C T189C S173P | Foldon | 103-145 | 2 | GS | 513 |
| | BZGJ9-10 V56C T189C T174P | S155C, S190F, V207L, S290C, V56C T189C T174P | Foldon | 103-145 | 2 | GS | 513 |
| | BZGJ9-10 V56C T189C N175P | S155C, S190F, V207L, S290C, V56C T189C N175P | Foldon | 103-145 | 2 | GS | 513 |
| | BZGJ9-10-A149C-V402A | S155C, S190F, V207L, S290C, L373R, A149C, Y458C, V402A | Foldon | 103-145 | 2 | GS | 513 |
| | BZGJ9-10-A149C-V402T | S155C, S190F, V207L, S290C, L373R, A149C, Y458C, V402T | Foldon | 103-145 | 2 | GS | 513 |
| | BZGJ9-10-A149C-V402T/T400V | S155C, S190F, V207L, S290C, L373R, A149C, Y458C, V402T/T400V | Foldon | 103-145 | 2 | GS | 513 |
| | BZGJ9-10-A149C-Q279N | S155C, S190F, V207L, S290C, L373R, A149C, Y458C, Q279N | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | BZGJ9-10-A149C-T249N | S155C, S190F, V207L, S290C, L373R, A149C, Y458C, T249N | Foldon | 103-145 | 2 | GS | 513 |
| | BZGJ9-10-A149C-K80Q | S155C, S190F, V207L, S290C, L373R, A149C, Y458C, K80Q | Foldon | 103-145 | 2 | GS | 513 |
| | BZGJ9-10-A149C-Q279N/K80Q | S155C, S190F, V207L, S290C, L373R, A149C, Y458C, Q279N/K80Q | Foldon | 103-145 | 2 | GS | 513 |
| | BZGJ9-10-A149C-V402A | S155C, S190F, V207L, S290C, L373R, A149C, Y458C, V402A | Foldon | 103-145 | 2 | GS | 513 |
| | BZGJ9-10-A149C-V402T | S155C, S190F, V207L, S290C, L373R, A149C, Y458C, V402T | Foldon | 103-145 | 2 | GS | 513 |
| | BZGJ9-10-A149C-V402T/T400V | S155C, S190F, V207L, S290C, L373R, A149C, Y458C, V402T/T400V | Foldon | 103-145 | 2 | GS | 513 |
| | BZGJ9-10-A149C-Q279N | S155C, S190F, V207L, S290C, L373R, A149C, Y458C, Q279N | Foldon | 103-145 | 2 | GS | 513 |
| | BZGJ9-10-A149C-T249N | S155C, S190F, V207L, S290C, L373R, A149C, Y458C, T249N | Foldon | 103-145 | 2 | GS | 513 |
| | BZGJ9-10-A149C-K80Q | S155C, S190F, V207L, S290C, L373R, A149C, Y458C, K80Q | Foldon | 103-145 | 2 | GS | 513 |
| | BZGJ9-10-A149C-Q279N/K80Q | S155C, S190F, V207L, S290C, L373R, A149C, Y458C, Q279N/K80Q | Foldon | 103-145 | 2 | GS | 513 |
| | BZGJ9-10-A149C-T249N/K80Q | S155C, S190F, V207L, S290C, L373R, A149C, Y458C, T249N/K80Q | Foldon | 103-145 | 2 | GS | 513 |
| | BZGJ9-10-A149C-V402T/T400V/Q279N/K80Q | S155C, S190F, V207L, S290C, L373R, A149C, Y458C | Foldon | 103-145 | 2 | GS | 513 |
| | BZGJ9-10-A149C-V402T/T400V/T249N/K80Q | S155C, S190F, V207L, S290C, L373R, A149C, Y458C, V402T/T400V/T249N/K80Q | Foldon | 103-145 | 2 | GS | 513 |
| | BZGJ9-10-A149C-V402A-Prolact | S155C, S190F, V207L, S290C, L373R, A149C, Y458C, V402A | Foldon | 103-145 | 2 | GS | 513 |
| | BZGJ9-10-A149C-V402T-Prolact | S155C, S190F, V207L, S290C, L373R, A149C, Y458C, V402T | Foldon | 103-145 | 2 | GS | 513 |
| | BZGJ9-10-A149C-V402T/T400V-Prolact | S155C, S190F, V207L, S290C, L373R, A149C, Y458C, V402T/T400V | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | BZGJ9-10-A149C-Q279N-Prolact | S155C, S190F, V207L, S290C, L373R, N183GC, N428C, Q279N | Foldon | 103-145 | 2 | GS | 513 |
| | BZGJ9-10-A149C-T249N-Prolact | S155C, S190F, V207L, S290C, L373R, N183GC, N428C, T249N | Foldon | 103-145 | 2 | GS | 513 |
| | BZGJ9-10-A149C-K80Q-Prolact | S155C, S190F, V207L, S290C, L373R, N183GC, N428C, K80Q | Foldon | 103-145 | 2 | GS | 513 |
| | BZGJ9-10-A149C-Q279N/K80Q-Prolact | S155C, S190F, V207L, S290C, L373R, N183GC, N428C, Q279N/K80Q | Foldon | 103-145 | 2 | GS | 513 |
| | BZGJ9-10-A149C-T249N/K80Q-Prolact | S155C, S190F, V207L, S290C, L373R, N183GC, N428C, T249N/K80Q | Foldon | 103-145 | 2 | GS | 513 |
| | BZGJ9-10-A149C-V402T/T400V/Q279N/K80Q-Prolact | S155C, S190F, V207L, S290C, L373R, N183GC, N428C, V402T/T400V/Q279N/K80Q | Foldon | 103-145 | 2 | GS | 513 |
| | BZGJ9-10-A149C-V402T/T400V/T249N/K80Q-Prolact | N183GC, N428C, V402T/T400V/T249N/K80Q S155C, S190F, V207L, S290C, L373R, | Foldon | 103-145 | 2 | GS | 513 |
| | sc9-10 N183GC-V402A | S155C, S190F, V207L, S290C, L373R, N183GC, N428C, V402A | Foldon | 103-145 | 2 | GS | 513 |
| | sc9-10 N183GC-V402T | S155C, S190F, V207L, S290C, L373R, N183GC, N428C, V402T | Foldon | 103-145 | 2 | GS | 513 |
| | sc9-10 N183GC-V402T/T400V | S155C, S190F, V207L, S290C, L373R, N183GC, N428C, V402T/T400V | Foldon | 103-145 | 2 | GS | 513 |
| | sc9-10 N183GC-Q279N | S155C, S190F, V207L, S290C, L373R, N183GC, N428C, Q279N | Foldon | 103-145 | 2 | GS | 513 |
| | sc9-10 N183GC-T249N | S155C, S190F, V207L, S290C, L373R, N183GC, N428C, T249N | Foldon | 103-145 | 2 | GS | 513 |
| | sc9-10 N183GC-K80Q | S155C, S190F, V207L, S290C, L373R, N183GC, N428C, K80Q | Foldon | 103-145 | 2 | GS | 513 |
| | sc9-10 N183GC-Q279N/K80Q | S155C, S190F, V207L, S290C, L373R, N183GC, N428C, Q279N/K80Q | Foldon | 103-145 | 2 | GS | 513 |
| | sc9-10 N183GC-T249N/K80Q | S155C, S190F, V207L, S290C, L373R, N183GC, N428C, T249N/K80Q | Foldon | 103-145 | 2 | GS | 513 |

TABLE A-continued

Engineered RSV F glycoprotein variants.

| Design cycle | RSV F variant | Mutations | Additional trimerization domain | F1-F2 Linker residues | Linker residue length | Linker sequence | End residue |
|---|---|---|---|---|---|---|---|
| | sc9-10 N183GC-V402T/T400V/Q279N/K80Q | S155C, S190F, V207L, S290C, L373R, N183GC, N428C, V402T/T400V/Q279N/K80Q | Foldon | 103-145 | 2 | GS | 513 |
| | sc9-10 N183GC-V402T/T400V/T249N/K80Q | S155C, S190F, V207L, S290C, L373R, N183GC, N428C, V402T/T400V/T249N/K80Q | Foldon | 103-145 | 2 | GS | 513 |
| | sc9-10 N183GC-V402A-Prolact | S155C, S190F, V207L, S290C, L373R, N183GC, N428C, v | Foldon | 103-145 | 2 | GS | 513 |
| | sc9-10 N183GC-V402T-Prolact | S155C, S190F, V207L, S290C, L373R, N183GC, N428C, V402T | Foldon | 103-145 | 2 | GS | 513 |
| | sc9-10 N183GC-V402T/T400V-Prolact | S155C, S190F, V207L, S290C, L373R, N183GC, N428C, V402T/T400V | Foldon | 103-145 | 2 | GS | 513 |
| | sc9-10 N183GC-Q279N-Prolact | S155C, S190F, V207L, S290C, L373R, N183GC, N428C, Q279N | Foldon | 103-145 | 2 | GS | 513 |
| | sc9-10 N183GC-T249N-Prolact | S155C, S190F, V207L, S290C, L373R, N183GC, N428C, T249N | Foldon | 103-145 | 2 | GS | 513 |
| | sc9-10 N183GC-K80Q-Prolact | S155C, S190F, V207L, S290C, L373R, N183GC, N428C, K80Q | Foldon | 103-145 | 2 | GS | 513 |
| | sc9-10 N183GC-Q279N/K80Q-Prolact | S155C, S190F, V207L, S290C, L373R, N183GC, N428C, Q279N/K80Q | Foldon | 103-145 | 2 | GS | 513 |
| | sc9-10 N183GC-T249N/K80Q-Prolact | S155C, S190F, V207L, S290C, L373R, N183GC, N428C, T249N/K80Q | Foldon | 103-145 | 2 | GS | 513 |
| | sc9-10 N183GC-V402T/T400V/Q279N/K80Q-Prolact | S155C, S190F, V207L, S290C, L373R, N183GC, N428C, V402T/T400V/Q279N/K80Q | Foldon | 103-145 | 2 | GS | 513 |
| | sc9-10 N183GC-V402T/T400V/T249N/K80Q-Prolact | N183GC, N428C, V402T/T400V/T249N/K80Q S155C, S190F, V207L, S290C, L373R, | Foldon | 103-145 | 2 | GS | 513 |

Prolactin leader sequence: MDSKGSSQKGSRLLLLLVVSNLLLPQGVVG (SEQ ID NO: 163)

Example 2

Immunization of Subjects

This example describes exemplary procedures for the immunization of a subject (such as a human or non-human primate) with the disclosed immunogens, and measurement of the corresponding immune response.

In some examples, a nucleic acid molecule encoding a disclosed recombinant RSV F ectodomain trimer (e.g., RSV A2 strain sc9-10, DS-Cav1, A149C-Y458C, SEQ ID NO: 1) can be cloned into expression vector CMV/R. The expression vectors are then transfected into 293F cells using 293Fectin (Invitrogen, Carlsbad, CA). Seven days after transfection, cell culture supernatant is harvested and passed over an antibody affinity column. After washing with PBS, bound proteins were eluted with 3M $MgCl_2$, 10 mM Tris pH 8.0. The eluate was concentrated to less than 5 ml with Centricon-70 and applied to a Superdex 200 column, equilibrated in 5 mM HEPES, pH 7.5, 150 mM NaCl, 0.02% azide. The peak corresponding to trimeric RSV F is identified, pooled, and concentrated or flash-frozen in liquid nitrogen and stored at −80° C. Some proteins are purified using HiTrap IMAC HP Column (GE, Piscataway, NJ), and subsequent gel-filtration using Superdex™ 200 (GE). In some examples the 6× His tag is cleaved off using 3C protease (Novagen, Madison, WI).

For vaccinations with the disclosed immunogens, the subject is immunized with polyIC-LC as the adjuvant. Five subjects in each group are vaccinated with 100 μg of protein and 500 μg polyIC-LC in 1 ml intramuscularly in the Quadriceps muscle for example at week 0, 4, 20. Sera are collected for example at week 2 (Post-1), 6 (Post-2), 24 (Post-3), and subsequently analyzed for their neutralization activities against a panel of RSV strains, and the profile of antibodies that mediate the neutralization.

Example 3

Stabilization of RSV F in a Prefusion Conformation in the Absence of S155C/S290C Substitutions This example provides antigenicity data for several embodiments of RSV F proteins that are stabilized in a prefusion conformation in the absence of the "DS" mutation (including S155C and S290C substitutions). Soluble RSV F ectodomain trimers were generated with subunits covalently fused with the sc9-10 mutation (linking residues 103-145 with a GS linker), pre-fusion conformation stabilized by the Cav1 substitution and an inter-protomer disulfide bond introduced by cysteine substitutions at one of: 98C-360C, 99C-360C, 100C-360C, 98C-361C, 99C-361C, 100C-361C, 98C-362C, 99C-362C, 100C-362C, 146C-458C, 369C-455C, 149C-458C, or 183GC-428C, and also included a C-terminal foldon trimerization domain. The proteins were expressed and purified as described above, and incubated at 4° C. for one week before assessment for binding to prefusion specific antibodies D25, AM14, and MPEG, as well as Motavizumab antibody. As shown in FIG. 14, of the tested constructs, the sc9-10, Cav1, 99-361 construct maintained the best antigenic profile.

Example 4

Induction of an Immune Response in Mammals

Bovine respiratory syncytial virus, a major cause of respiratory disease in calves, is closely related to human RSV. This example presents data showing successful induction of a neutralizing immune response in mice using an engineered version of bovine respiratory syncytial virus F with subunits covalently fused, fusion peptide removed, and pre-fusion conformation stabilized by cavity-filling mutations and intra- and inter-protomer disulfides. The engineered bovine RSV F proteins were recognized by prefusion-specific antibodies, AM14, D25, and MPE8, and elicited bovine respiratory syncytial virus-neutralizing titers >100-fold higher than those elicited by post-fusion F.

F protein from bovine stains of RSV was modified as discussed above with single chain mutations (sc9 or sc9-10) and various prefusion stabilizing mutations, including DS-Cav1, Q98C-Q361C, and A149C-Y458C. Many variants were designed, and their antigenicity and level of expression assessed in the 96-well microplate transient transfection format. The antigenic and physical properties of the new constructs were assessed (see the table below) and several were selected for immunization assays in mammals.

| | | | Antibody affinity $K_D$ (nM)[b] | | | | Physical stability (fractional antibody reactivity[c]) | | | | | | |
|---|---|---|---|---|---|---|---|---|---|---|---|---|---|
| | | | | QP[d] | | | Temperature | | | | Osmolarity | | Freeze- |
| Variant | | Yield | Site Ø | Site III | Site V | Site II | (° C.) | | pH | | (mM) | | thaw |
| number | bRSV F variant | (mg/l)[a] | D25 | MPE8 | AM14 | Mz[e] | 50 | 70 | 3.5 | 10.0 | 10 | 3000 | 10[f] |
| DS2-v1 | 391-2 sc9 DS-Cav1 Q98C Q361C | 2.80 | 24.3 | 0.4 | 8.6 | 0.8 | 0.9 | 0.8 | 1.2 | 1.0 | 1.0 | 0.9 | 1.0 |
| DS2-v33 | 391-2 sc9-10 DS-Cav1 Q98C Q361C | 2.44 | 57.5 | 0.8 | 12.8 | 1.2 | 1.0 | 1.0 | 0.9 | 0.9 | 0.8 | 0.8 | 1.0 |
| — | 391-2 DS-Cav1 | 3.66 | 0.4 | 0.2 | 1.8 | 0.8 | 0.7 | 0.1 | 0.9 | 1.2 | 0.9 | 0.6 | 1.0 |
| — | 391-2 post-F | 4.10 | >1000 | >1000 | >1000 | 0.6 | 1.0 | 1.0 | 0.8 | 1.1 | 0.9 | 0.6 | 1.0 |
| — | ATue51908 DS-Cav1 | 2.98 | 10.8 | 0.2 | 4.8 | 0.8 | 0.9 | 0.1 | 0.9 | 1.1 | 0.7 | 0.4 | 1.0 |
| DS2-v35 | ATue51908 sc9-10 DS-Cav1 A149C Y458C | 0.24 | 420 | 0.5 | 12.8 | 1.2 | 0.9 | 0.9 | 1.0 | 0.9 | 0.7 | 0.8 | 1.0 |

-continued

| | | | Antibody affinity $K_D$ (nM)[b] | | | | Physical stability (fractional antibody reactivity[c]) | | | | | | |
|---|---|---|---|---|---|---|---|---|---|---|---|---|---|
| | | | | QP[d] | | | Temperature | | | | Osmolarity | | Freeze- |
| Variant | | Yield | Site Ø | Site III | Site V | Site II | (° C.) | | pH | | (mM) | | thaw |
| number | bRSV F variant | (mg/l)[a] | D25 | MPE8 | AM14 | Mz[e] | 50 | 70 | 3.5 | 10.0 | 10 | 3000 | 10[f] |
| — | ATue51908 post-F | 3.80 | >1000 | >1000 | >1000 | 0.5 | 1.0 | 1.0 | 0.9 | 1.1 | 1.0 | 0.8 | 1.0 |
| — | RB94 DS-Cav1 | 0.76 | 24.3 | 0.2 | 4.9 | 0.9 | 0.6 | 0.1 | 1.2 | 1.3 | 0.8 | 0.5 | 1.0 |
| — | RB94 post-F | 4.78 | >1000 | >1000 | >1000 | 0.4 | 1.0 | 1.0 | 0.9 | 1.1 | 1.0 | 1.0 | 1.0 |

The properties of the trimer fraction purified by gel filtration are listed
[a]Yield reported is only for the trimer fraction
[b]When no binding was observed for 1 μM Fab, the $K_D$ is shown as >1000
[c]D25 was used for pre-F proteins and Mz was used for post-F proteins
[d]QP: quaternary-specific antibody sites
[e]Motavizumab (Mz)
[f]Ten cycles of freeze-thaw in the presence of 10% glycerol To evaluate immunogenicity, the DS2-v1, DS2-v33, and DS2-v35 constructs and several controls was used to immunize a group of 10 CB6F1/J mice. Each immunogen dose comprised 10 μg of protein adjuvanted with 50 μg of polyinosinic:polycytidylic acid (Poly I:C). Mice were primed and boosted intramuscularly at weeks 0 and 3, respectively. Analysis of week 5 sera revealed geometric mean reciprocal EC50 neutralization titers of 6880-11,453 for pre-F immunogen immunized mice, which were 33- to 55-fold higher (P<0.0001) than the titers (geometric mean 100-210) observed for the post-F immunogen-immunized mice (FIG. 15A). Neutralization titers elicited from pre-F-immunized mice were 82-110-fold greater than the calibrated protective titer of 100 (see McLellan, J. S. et al. Science 342, 592-598, 2013). To gauge the overall immunogenicity of each immunogen, the sera binding response to pre-F and post-F immunogens was assessed by ELISA (FIG. 15B). Similar to the neutralization results, the binding titers of pre-F elicited sera to the six pre-F immunogens were statistically comparable to each other with geometric mean end point-binding titers ranging from 4687 to 100,323.

It will be apparent that the precise details of the methods or compositions described may be varied or modified without departing from the spirit of the described embodiments. We claim all such modifications and variations that fall within the scope and spirit of the claims below.

We claim:

1. A recombinant respiratory syncytial virus (RSV) F ectodomain trimer, comprising:

three recombinant F2-F1 ectodomain protomers each comprising a deletion of RSV F positions 104-144 and a glycine-serine peptide linker between RSV F positions 103 and 145, wherein the recombinant F2-F1 ectodomain protomers comprise the following amino acid substitutions to stabilize the recombinant RSV F ectodomain trimer in a prefusion conformation:

a non-native disulfide bond between cysteines introduced by 155C and 290C substitutions;

190F and 207L substitutions; and (A) a non-native inter-protomer disulfide bond between cysteines introduced by 98C and 361C substitutions; or (B) a non-native inter-protomer disulfide bond between cysteines introduced by 183GC and 428C substitutions, and an amino acid sequence set forth as residues 26-475 of SEQ ID NO: 2, 6, 11, 30-35, 38-39, 42-43, 46-47, 50-51, or 54-55, or residues 31-480 of SEQ ID NO: 16 or 21; and wherein the amino acid substitutions are according to a reference RSV F sequence set forth as SEQ ID NO: 57.

2. The recombinant RSV F ectodomain trimer of claim 1, comprising (A) wherein the 155C and 290C substitutions are S155C and S290C substitutions, the 190F and 207L substitutions are S190F and V207L substitutions; and the 98C and 361C substitutions are Q98C and Q361C substitutions.

3. The recombinant RSV F ectodomain trimer of claim 1, wherein the recombinant $F_2$-$F_1$ ectodomain protomers each further comprise a L373R substitution.

4. The recombinant RSV F ectodomain trimer of claim 1, wherein the prefusion conformation comprises an antigenic site Ø.

5. The recombinant RSV F ectodomain trimer of claim 1, wherein the recombinant RSV F ectodomain trimer specifically binds to a RSV F prefusion specific antibody, particularly wherein the prefusion specific antibody is a D25 antibody, a AM22 antibody, a 5C4 antibody, or an MPE8 antibody.

6. The recombinant RSV F ectodomain trimer of claim 1, comprising (A) wherein the recombinant $F_2$-$F_1$ ectodomain protomers comprise RSV F positions 26-103 and RSV F position 145 to one of positions 510-525.

7. The recombinant RSV F ectodomain trimer of claim 6, wherein the recombinant $F_2$-$F_1$ ectodomain protomers comprise RSV F positions 26-103 and 145-513, or RSV F positions 26-103 and 145-523.

8. The recombinant RSV F ectodomain trimer of claim 1, comprising (A) wherein the recombinant RSV F ectodomain trimer comprises a bovine RSV F ectodomain trimer, a human subtype A RSV F ectodomain trimer, or a human subtype B RSV F ectodomain trimer.

9. The recombinant RSV F ectodomain trimer claim 1, comprising (A) wherein the recombinant F2-F1 ectodomain protomers each comprise, consist essentially of, or consist of, an amino acid sequence set forth as any one of:

residues 26-474 of any one of SEQ ID NOs: 36-37, 105-107, or 112-113;

residues 31-479 of any one of SEQ ID NOs: 108-109; or an amino acid sequence at least 90% identical thereto.

10. The recombinant RSV F ectodomain trimer of claim 1, wherein the recombinant $F_2$-$F_1$ ectodomain protomers are each linked to a C-terminal trimerization domain.

11. The recombinant RSV F ectodomain trimer of claim 10, wherein the C-terminal trimerization domain comprises a T4 Fibritin trimerization domain.

12. The recombinant RSV F ectodomain trimer of claim 11, wherein the T4 Fibritin trimerization domain comprises or consists of an amino acid sequence set forth as GYIPEAPRDGQAYVRKDGEWVLLSTF (SEQ ID NO: 66).

13. The recombinant RSV F ectodomain trimer of claim 10, wherein the trimerization domain is directly linked or linked by a peptide linker to RSV F position 511 or position 513 or position 523 of the recombinant $F_2$-$F_1$ ectodomain protomers in the RSV F ectodomain trimer.

14. The recombinant RSV F ectodomain trimer of claim 10, wherein the recombinant F2-F1 ectodomain protomers linked to the C-terminal T4 Fibritin trimerization domain each comprise, consist essentially of, or consist of, an amino acid sequence set forth as any one of:

residues 26-504 of any one of SEQ ID NOs: 36-37, 105-107, or 112-113;

residues 31-509 of any one of SEQ ID NOs: 108-109; or an amino acid sequence at least 90% identical thereto.

15. The recombinant RSV F ectodomain trimer of claim 1, wherein the recombinant RSV F ectodomain trimer is soluble.

16. The recombinant RSV F ectodomain trimer of claim 1, wherein the recombinant $F_2$-$F_1$ ectodomain protomers are each linked to a C-terminal transmembrane domain.

17. A virus-like particle comprising the recombinant RSV F ectodomain trimer of claim 1.

18. An isolated nucleic acid molecule encoding a recombinant $F_2$-$F_1$ ectodomain protomer of the recombinant RSV F ectodomain trimer of claim 1.

19. The nucleic acid molecule of claim 18, wherein:

the nucleic acid molecule encodes a precursor protein of the recombinant $F_2$-$F_1$ ectodomain protomer;

the precursor protein comprises, from N- to C-terminal, a signal peptide, a $F_2$ polypeptide, and a $F_1$ ectodomain;

the nucleic acid molecule comprises a sequence set forth as SEQ ID NO: 98 or SEQ ID NO: 99; and/or the nucleic acid molecule is an RNA molecule.

20. A vector comprising the nucleic acid molecule of claim 18, particularly wherein the vector is a viral vector.

21. An immunogenic composition comprising the recombinant RSV F ectodomain trimer of claim 1.

22. An isolated host cell comprising the vector of claim 20.

23. A method of producing a recombinant RSV F ectodomain trimer stabilized in a prefusion conformation, comprising:

expressing the nucleic acid molecule or vector of claim 18 in a host cell to produce the RSV F ectodomain trimer; and purifying the recombinant RSV F ectodomain trimer.

24. The recombinant RSV F ectodomain trimer produced by the method of claim 23.

25. A method of inducing an immune response to RSV F protein in a subject, comprising administering to the subject an effective amount of the recombinant RSV F ectodomain trimer of claim 1 to generate the immune response.

26. The method of claim 25, wherein the subject is a human or a bovine subject.

27. The recombinant RSV F ectodomain trimer of claim 10, wherein the recombinant F2-F1 ectodomain protomers linked to the C-terminal T4 Fibritin trimerization domain each comprise, consist essentially of, or consist of, an amino acid sequence set forth as any one of:

residues 26-505 of SEQ ID NO: 2, 6, 11, 30-35, 38-39, 42-43, 46-47, 50-51, or 54-55, or
residues 31-510 of SEQ ID NO: 16 or 21.

* * * * *

SEQUENCE LISTING

<160> NUMBER OF SEQ ID NOS: 163

<210> SEQ ID NO 1
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 1

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn

```
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 2
<211> LENGTH: 530

<212> TYPE: PRT
<213> ORGANISM: Artificial Sequence
<220> FEATURE:
<223> OTHER INFORMATION: Recombinant RSV F protein

<400> SEQUENCE: 2

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Gly Ser Gly Ser Ala Ile Ala Ser Gly
100 105 110

Val Ala Val Cys Lys Val Leu His Leu Glu Gly Glu Val Asn Lys Ile
115 120 125

Lys Ser Ala Leu Leu Ser Thr Asn Lys Ala Val Val Ser Leu Ser Gly
130 135 140

Cys Gly Val Ser Val Leu Thr Phe Lys Val Leu Asp Leu Lys Asn Tyr
145 150 155 160

Ile Asp Lys Gln Leu Leu Pro Ile Leu Asn Lys Gln Ser Cys Ser Ile
165 170 175

Ser Asn Ile Glu Thr Val Ile Glu Phe Gln Gln Lys Asn Asn Arg Leu
180 185 190

Leu Glu Ile Thr Arg Glu Phe Ser Val Asn Ala Gly Val Thr Thr Pro
195 200 205

Val Ser Thr Tyr Met Leu Thr Asn Ser Glu Leu Leu Ser Leu Ile Asn
210 215 220

Asp Met Pro Ile Thr Asn Asp Gln Lys Lys Leu Met Ser Asn Asn Val
225 230 235 240

Gln Ile Val Arg Gln Gln Ser Tyr Ser Ile Met Cys Ile Ile Lys Glu
245 250 255

Glu Val Leu Ala Tyr Val Val Gln Leu Pro Leu Tyr Gly Val Ile Asp
260 265 270

Thr Pro Cys Trp Lys Leu His Thr Ser Pro Leu Cys Thr Thr Asn Thr
275 280 285

Lys Glu Gly Ser Asn Ile Cys Leu Thr Arg Thr Asp Arg Gly Trp Tyr
290 295 300

Cys Asp Asn Ala Gly Ser Val Ser Phe Phe Pro Gln Ala Glu Thr Cys
305 310 315 320

Lys Val Gln Ser Asn Arg Val Phe Cys Asp Thr Met Asn Ser Arg Thr
325 330 335

Leu Pro Ser Glu Val Asn Leu Cys Asn Val Asp Ile Phe Asn Pro Lys
340 345 350

Tyr Asp Cys Lys Ile Met Thr Ser Lys Thr Asp Val Ser Ser Ser Val
355 360 365

Ile Thr Ser Leu Gly Ala Ile Val Ser Cys Tyr Gly Lys Thr Lys Cys
370 375 380

-continued

Thr Ala Ser Asn Lys Cys Arg Gly Ile Ile Lys Thr Phe Ser Asn Gly
385 390 395 400

Cys Asp Tyr Val Ser Asn Lys Gly Val Asp Thr Val Ser Val Gly Asn
405 410 415

Thr Leu Tyr Tyr Val Asn Lys Gln Glu Gly Lys Ser Leu Tyr Val Lys
420 425 430

Gly Glu Pro Ile Ile Asn Phe Tyr Asp Pro Leu Val Phe Pro Ser Asp
435 440 445

Glu Phe Asp Ala Ser Ile Ser Gln Val Asn Glu Lys Ile Asn Gln Ser
450 455 460

Leu Ala Phe Ile Arg Lys Ser Asp Glu Leu Leu Ser Ala Ile Gly Gly
465 470 475 480

Tyr Ile Pro Glu Ala Pro Arg Asp Gly Gln Ala Tyr Val Arg Lys Asp
485 490 495

Gly Glu Trp Val Leu Leu Ser Thr Phe Leu Gly Gly Leu Val Pro Arg
500 505 510

Gly Ser His His His His His His Ser Ala Trp Ser His Pro Gln Phe
515 520 525

Glu Lys
530

<210> SEQ ID NO 3
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 3

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Cys Pro Ala Thr Gly Ser Gly Ser Ala Ile Ala Ser Gly
100 105 110

Val Ala Val Cys Lys Val Leu His Leu Glu Gly Glu Val Asn Lys Ile
115 120 125

Lys Ser Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Gln Leu Leu Pro Ile Leu Asn Lys Gln Ser Cys Ser Ile Ser
165 170 175

Asn Ile Glu Thr Val Ile Glu Phe Gln Gln Lys Asn Asn Arg Leu Leu
180 185 190

Glu Ile Thr Arg Glu Phe Ser Val Asn Ala Gly Val Thr Thr Pro Val
195 200 205

-continued

```
Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Cys Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 4
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 4

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
```

-continued

```
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460
```

-continued

```
Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 5
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 5

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Gly Ser Gly Ser Ala Ile Cys Ser Gly
            100                 105                 110

Ile Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asn Asn Arg Leu Leu Pro Ile Leu Asn Gln Gln Ser Cys Arg Ile Ser
                165                 170                 175

Asn Ile Glu Thr Val Ile Glu Phe Gln Gln Met Asn Ser Arg Leu Leu
            180                 185                 190

Glu Ile Thr Arg Glu Phe Ser Val Asn Ala Gly Val Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asn Ile Lys
        275                 280                 285
```

-continued

```
Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Asp Thr Cys Lys
305                 310                 315                 320

Val Gln Ser Asn Arg Val Phe Cys Asp Thr Met Asn Ser Arg Thr Leu
                325                 330                 335

Pro Ser Glu Val Ser Leu Cys Asn Thr Asp Ile Phe Asn Ser Lys Tyr
            340                 345                 350

Asp Cys Lys Ile Met Thr Ser Lys Thr Asp Ile Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys Ser
    530


<210> SEQ ID NO 6
<211> LENGTH: 531
<212> TYPE: PRT
<213> ORGANISM: Artificial Sequence
<220> FEATURE:
<223> OTHER INFORMATION: Recombinant RSV F protein

<400> SEQUENCE: 6

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Gly Ser Gly Ser Ala Ile Ala Ser Gly
            100                 105                 110
```

-continued

```
Ile Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asn Asn Arg Leu Leu Pro Ile Leu Asn Gln Gln Ser Cys Arg Ile
                165                 170                 175

Ser Asn Ile Glu Thr Val Ile Glu Phe Gln Gln Met Asn Ser Arg Leu
            180                 185                 190

Leu Glu Ile Thr Arg Glu Phe Ser Val Asn Ala Gly Val Thr Thr Pro
        195                 200                 205

Leu Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Ser Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Ile Tyr Gly Val Ile Asp
            260                 265                 270

Thr Pro Cys Trp Lys Leu His Thr Ser Pro Leu Cys Thr Thr Asn Ile
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Asp Thr Cys
305                 310                 315                 320

Lys Val Gln Ser Asn Arg Val Phe Cys Asp Thr Met Asn Ser Arg Thr
                325                 330                 335

Leu Pro Ser Glu Val Ser Leu Cys Asn Thr Asp Ile Phe Asn Ser Lys
            340                 345                 350

Tyr Asp Cys Lys Ile Met Thr Ser Lys Thr Asp Ile Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Leu Glu Gly Lys Asn Leu Tyr Val Lys
            420                 425                 430

Gly Glu Pro Ile Ile Asn Tyr Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Arg Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys Ser
```

530

<210> SEQ ID NO 7
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 7

Met Glu Leu Leu Ile His Arg Ser Ser Ala Ile Phe Leu Thr Leu Ala
1 5 10 15

Val Asn Ala Leu Tyr Leu Thr Ser Ser Gln Asn Ile Thr Glu Glu Phe
20 25 30

Tyr Gln Ser Thr Cys Ser Ala Val Ser Arg Gly Tyr Phe Ser Ala Leu
35 40 45

Arg Thr Gly Trp Tyr Thr Ser Val Ile Thr Ile Glu Leu Ser Asn Ile
50 55 60

Lys Glu Thr Lys Cys Asn Gly Thr Asp Thr Lys Val Lys Leu Ile Lys
65 70 75 80

Gln Glu Leu Asp Lys Tyr Lys Asn Ala Val Thr Glu Leu Gln Leu Leu
85 90 95

Met Gln Asn Cys Pro Ala Ala Gly Ser Gly Ser Ala Ile Ala Ser Gly
100 105 110

Ile Ala Val Cys Lys Val Leu His Leu Glu Gly Glu Val Asn Lys Ile
115 120 125

Lys Asn Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asn Asn Arg Leu Leu Pro Ile Leu Asn Gln Gln Ser Cys Arg Ile Ser
165 170 175

Asn Ile Glu Thr Val Ile Glu Phe Gln Gln Met Asn Ser Arg Leu Leu
180 185 190

Glu Ile Thr Arg Glu Phe Ser Val Asn Ala Gly Val Thr Thr Pro Leu
195 200 205

Ser Thr Tyr Met Leu Thr Asn Ser Glu Leu Leu Ser Leu Ile Asn Asp
210 215 220

Met Pro Ile Thr Asn Asp Gln Lys Lys Leu Met Ser Ser Asn Val Gln
225 230 235 240

Ile Val Arg Gln Gln Ser Tyr Ser Ile Met Cys Ile Ile Lys Glu Glu
245 250 255

Val Leu Ala Tyr Val Val Gln Leu Pro Ile Tyr Gly Val Ile Asp Thr
260 265 270

Pro Cys Trp Lys Leu His Thr Ser Pro Leu Cys Thr Thr Asn Ile Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Asp Thr Cys Lys
305 310 315 320

Val Gln Cys Asn Arg Val Phe Cys Asp Thr Met Asn Ser Arg Thr Leu
325 330 335

Pro Ser Glu Val Ser Leu Cys Asn Thr Asp Ile Phe Asn Ser Lys Tyr
340 345 350

Asp Cys Lys Ile Met Thr Ser Lys Thr Asp Ile Ser Ser Ser Val Ile

```
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys Ser
    530


<210> SEQ ID NO 8
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 8

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Gly Ser Gly Ser Ala Ile Ala Ser Gly
            100                 105                 110

Ile Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asn Asn Arg Leu Leu Pro Ile Leu Asn Gln Gln Ser Cys Arg Ile Ser
                165                 170                 175

Asn Ile Glu Thr Val Ile Glu Phe Gln Gln Met Asn Ser Arg Leu Leu
```

-continued

```
            180                 185                 190

Glu Ile Thr Arg Glu Phe Ser Val Asn Ala Gly Val Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asn Ile Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Asp Thr Cys Lys
305                 310                 315                 320

Val Gln Ser Asn Arg Val Phe Cys Asp Cys Met Asn Ser Arg Thr Leu
                325                 330                 335

Pro Ser Glu Val Ser Leu Cys Asn Thr Asp Ile Phe Asn Ser Lys Tyr
            340                 345                 350

Asp Cys Lys Ile Met Thr Ser Lys Thr Asp Ile Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys Ser
    530
```

<210> SEQ ID NO 9
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 9

```
Met Ala Ala Thr Ala Met Arg Met Ile Ile Ser Ile Ile Phe Ile Ser
```

-continued

```
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Gly
            420                 425                 430
```

```
Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 10
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 10

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255
```

```
Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 11
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 11

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
```

```
                85                  90                  95

Met Gln Asn Glu Pro Ala Ser Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Glu Leu Leu Pro Lys Leu Asn Asn His Asp Cys Arg Ile
                165                 170                 175

Ser Asn Ile Glu Thr Val Ile Glu Phe Gln Gln Lys Asn Asn Arg Leu
            180                 185                 190

Leu Glu Ile Ala Arg Glu Phe Ser Val Asn Ala Gly Ile Thr Thr Pro
        195                 200                 205

Leu Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Ser Asn Val
225                 230                 235                 240

Gln Ile Val Arg Gln Gln Ser Tyr Ser Ile Met Cys Val Val Lys Glu
                245                 250                 255

Glu Val Ile Ala Tyr Val Val Gln Leu Pro Ile Tyr Gly Val Ile Asp
            260                 265                 270

Thr Pro Cys Trp Lys Leu His Thr Ser Pro Leu Cys Thr Thr Asp Asn
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Thr Asp Val Asn Leu Cys Asn Thr Asp Ile Phe Asn Thr Lys
            340                 345                 350

Tyr Asp Cys Lys Ile Met Thr Ser Lys Thr Asp Ile Ser Ser Ser Val
        355                 360                 365

Ile Thr Ser Ile Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Leu Glu Gly Lys Ala Leu Tyr Ile Lys
            420                 425                 430

Gly Glu Pro Ile Ile Asn Tyr Tyr Asp Pro Leu Val Phe Pro Ser Asp
        435                 440                 445

Glu Phe Asp Ala Ser Ile Ala Gln Val Asn Ala Lys Ile Asn Gln Ser
    450                 455                 460

Leu Ala Phe Ile Arg Arg Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510
```

```
Gly Ser His His His His His His Ser Ala Trp Ser His Pro Gln Phe
        515                 520                 525

Glu Lys
    530


<210> SEQ ID NO 12
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 12

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Cys Pro Ala Ser Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Cys Asn Arg Val Phe Cys Asp Thr Met Asn Ser Arg Thr Leu
                325                 330                 335
```

```
Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 13
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 13

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160
```

-continued

```
Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 14
<211> LENGTH: 534
<212> TYPE: PRT
<213> ORGANISM: Artificial Sequence
<220> FEATURE:
<223> OTHER INFORMATION: Recombinant RSV F protein -continued

<400> SEQUENCE: 14

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Val Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Thr Glu Thr Cys Lys Val Gln Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415
```

```
Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 15
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 15

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Val Cys Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240
```

```
Ser Ser Asn Val Gln Ile Val Arg Gln Gln Ser Tyr Ser Ile Met Cys
            245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Thr Glu Thr Cys Lys Val Gln Ser Asn Arg Val Phe Cys Asp Thr Met
            325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
            405                 410                 415

Ser Val Gly Asn Thr Leu Tyr Cys Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
            485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530
```

<210> SEQ ID NO 16
<211> LENGTH: 535
<212> TYPE: PRT
<213> ORGANISM: Artificial Sequence
<220> FEATURE:
<223> OTHER INFORMATION: Recombinant RSV F protein

<400> SEQUENCE: 16

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60
```

```
Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Val Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Gly Cys Gly Val Ser Val Leu Thr Phe Lys Val Leu
145                 150                 155                 160

Asp Leu Lys Asn Tyr Ile Asp Lys Glu Leu Leu Pro Gln Leu Asn Asn
                165                 170                 175

His Asp Cys Arg Ile Ser Asn Ile Glu Thr Val Ile Glu Phe Gln Gln
            180                 185                 190

Lys Asn Asn Arg Leu Leu Glu Ile Ala Arg Glu Phe Ser Val Asn Ala
        195                 200                 205

Gly Ile Thr Thr Pro Leu Ser Thr Tyr Met Leu Thr Asn Ser Glu Leu
    210                 215                 220

Leu Ser Leu Ile Asn Asp Met Pro Ile Thr Asn Asp Gln Lys Lys Leu
225                 230                 235                 240

Met Ser Ser Asn Val Gln Ile Val Arg Gln Gln Ser Tyr Ser Ile Met
                245                 250                 255

Cys Val Val Lys Glu Glu Val Ile Ala Tyr Val Val Gln Leu Pro Ile
            260                 265                 270

Tyr Gly Val Ile Asp Thr Pro Cys Trp Lys Leu His Thr Ser Pro Leu
        275                 280                 285

Cys Thr Thr Asp Asn Lys Glu Gly Ser Asn Ile Cys Leu Thr Arg Thr
    290                 295                 300

Asp Arg Gly Trp Tyr Cys Asp Asn Ala Gly Ser Val Ser Phe Phe Pro
305                 310                 315                 320

Gln Thr Glu Thr Cys Lys Val Gln Ser Asn Arg Val Phe Cys Asp Thr
                325                 330                 335

Met Asn Ser Arg Thr Leu Pro Thr Asp Val Asn Leu Cys Asn Thr Asp
            340                 345                 350

Ile Phe Asn Thr Lys Tyr Asp Cys Lys Ile Met Thr Ser Lys Thr Asp
        355                 360                 365

Ile Ser Ser Ser Val Ile Thr Ser Ile Gly Ala Ile Val Ser Cys Tyr
    370                 375                 380

Gly Lys Thr Lys Cys Thr Ala Ser Asn Lys Cys Arg Gly Ile Ile Lys
385                 390                 395                 400

Thr Phe Ser Asn Gly Cys Asp Tyr Val Ser Asn Lys Gly Val Asp Thr
                405                 410                 415

Val Ser Val Gly Asn Thr Leu Tyr Tyr Val Asn Lys Leu Glu Gly Lys
            420                 425                 430

Ala Leu Tyr Ile Lys Gly Glu Pro Ile Ile Asn Tyr Tyr Asp Pro Leu
        435                 440                 445

Val Phe Pro Ser Asp Glu Phe Asp Ala Ser Ile Ala Gln Val Asn Ala
    450                 455                 460

Lys Ile Asn Gln Ser Leu Ala Phe Ile Arg Arg Ser Asp Glu Leu Leu
465                 470                 475                 480
```

-continued

```
Ser Ala Ile Gly Gly Tyr Ile Pro Glu Ala Pro Arg Asp Gly Gln Ala
                485                 490                 495

Tyr Val Arg Lys Asp Gly Glu Trp Val Leu Leu Ser Thr Phe Leu Gly
            500                 505                 510

Gly Leu Val Pro Arg Gly Ser His His His His His His Ser Ala Trp
        515                 520                 525

Ser His Pro Gln Phe Glu Lys
    530                 535


<210> SEQ ID NO 17
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 17

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Cys Pro Ala Ser Gly Ser Gly Ser
            100                 105                 110

Ala Val Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300
```

-continued

```
Arg Gly Trp Tyr Cys Asp Asn Ala Gly Ser Val Ser Phe Phe Pro Gln
305                 310                 315                 320

Thr Glu Thr Cys Lys Val Gln Cys Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 18
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 18

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Val Ala Ser Gly Val Ala Val Cys Lys Val Leu His Leu Glu Gly
        115                 120                 125
```

```
Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Thr Glu Thr Cys Lys Val Gln Ser Asn Arg Val Phe Cys Asp Cys Met
                325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415

Ser Val Gly Asn Cys Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530
```

-continued

<210> SEQ ID NO 19
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 19

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Ile Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Met Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Gln Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
```

```
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 20
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 20

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Ile Cys Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
```

-continued

```
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Met Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Gln Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Thr Leu Tyr Cys Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 21
<211> LENGTH: 535
<212> TYPE: PRT
<213> ORGANISM: Artificial Sequence
<220> FEATURE:
<223> OTHER INFORMATION: Recombinant RSV F protein

<400> SEQUENCE: 21

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
```

-continued

```
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Glu Pro Ala Ser Gly Ser Gly Ser
            100                 105                 110

Ala Ile Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Gly Cys Gly Val Ser Val Leu Thr Phe Lys Val Leu
145                 150                 155                 160

Asp Leu Lys Asn Tyr Ile Asp Lys Glu Leu Leu Pro Lys Leu Asn Asn
                165                 170                 175

His Asp Cys Gln Ile Ser Asn Ile Ala Thr Val Ile Glu Phe Gln Gln
            180                 185                 190

Lys Asn Asn Arg Leu Leu Glu Ile Ala Arg Glu Phe Ser Val Asn Ala
        195                 200                 205

Gly Ile Thr Thr Pro Leu Ser Thr Tyr Met Leu Thr Asn Ser Glu Leu
    210                 215                 220

Leu Ser Leu Ile Asn Asp Met Pro Ile Thr Asn Asp Gln Lys Lys Leu
225                 230                 235                 240

Met Ser Ser Asn Val Gln Ile Val Arg Gln Gln Ser Tyr Ser Ile Met
                245                 250                 255

Cys Val Val Lys Glu Glu Val Met Ala Tyr Val Val Gln Leu Pro Ile
            260                 265                 270

Tyr Gly Val Ile Asp Thr Pro Cys Trp Lys Leu His Thr Ser Pro Leu
        275                 280                 285

Cys Thr Thr Asp Asn Lys Glu Gly Ser Asn Ile Cys Leu Thr Arg Thr
    290                 295                 300

Asp Arg Gly Trp Tyr Cys Asp Asn Ala Gly Ser Val Ser Phe Phe Pro
305                 310                 315                 320

Gln Ala Glu Thr Cys Lys Val Gln Ser Asn Arg Val Phe Cys Asp Thr
                325                 330                 335

Met Asn Ser Arg Thr Leu Pro Thr Asp Val Asn Leu Cys Asn Thr Asp
            340                 345                 350

Ile Phe Asn Ala Lys Tyr Asp Cys Lys Ile Met Thr Ser Lys Thr Asp
        355                 360                 365

Ile Ser Ser Ser Val Ile Thr Ser Ile Gly Ala Ile Val Ser Cys Tyr
    370                 375                 380

Gly Lys Thr Lys Cys Thr Ala Ser Asn Lys Cys Arg Gly Ile Ile Lys
385                 390                 395                 400

Thr Phe Ser Asn Gly Cys Asp Tyr Val Ser Asn Arg Gly Val Asp Thr
                405                 410                 415

Val Ser Val Gly Asn Thr Leu Tyr Tyr Val Asn Lys Leu Glu Gly Lys
            420                 425                 430

Ala Leu Tyr Ile Lys Gly Glu Pro Ile Ile Asn Tyr Tyr Asp Pro Leu
        435                 440                 445
```

```
Val Phe Pro Ser Asp Glu Phe Asp Ala Ser Ile Ala Gln Val Asn Ala
    450                 455                 460

Lys Ile Asn Gln Ser Leu Ala Phe Ile Arg Arg Ser Asp Glu Leu Leu
465                 470                 475                 480

Ser Ala Ile Gly Gly Tyr Ile Pro Glu Ala Pro Arg Asp Gly Gln Ala
                485                 490                 495

Tyr Val Arg Lys Asp Gly Glu Trp Val Leu Leu Ser Thr Phe Leu Gly
            500                 505                 510

Gly Leu Val Pro Arg Gly Ser His His His His His His Ser Ala Trp
        515                 520                 525

Ser His Pro Gln Phe Glu Lys
    530                 535


<210> SEQ ID NO 22
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 22

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Asn Cys Pro Ala Ser Gly Ser Gly Ser
            100                 105                 110

Ala Ile Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Met Ala Tyr Val Val Gln Leu Pro Ile Tyr
            260                 265                 270
```

```
Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Gln Cys Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 23
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 23

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95
```

```
Glu Leu Gln Ser Leu Met Gln Asn Glu Pro Ala Ser Gly Ser Gly Ser
            100                 105                 110

Ala Ile Ala Ser Gly Val Ala Val Cys Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Cys
                245                 250                 255

Val Val Lys Glu Glu Val Met Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Gln Ser Asn Arg Val Phe Cys Asp Cys Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Cys Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510
```

```
Leu Val Pro Arg Gly Ser His His His His His His Ser Ala Trp Ser
        515                 520                 525

His Pro Gln Phe Glu Lys
    530


<210> SEQ ID NO 24
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 24

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335
```

-continued

Pro Ser Glu Val Asn Leu Cys Asn Val Asp Ile Phe Asn Pro Lys Tyr
340 345 350

Asp Cys Lys Ile Met Thr Ser Lys Thr Asp Val Ser Ser Ser Val Ile
355 360 365

Thr Ser Leu Gly Ala Ile Val Ser Cys Tyr Gly Lys Thr Lys Cys Thr
370 375 380

Ala Ser Asn Lys Asn Arg Gly Ile Ile Lys Thr Phe Ser Asn Gly Cys
385 390 395 400

Asp Tyr Val Ser Asn Lys Gly Val Asp Thr Val Ser Val Gly Asn Thr
405 410 415

Leu Tyr Cys Val Asn Lys Gln Glu Gly Lys Ser Leu Tyr Val Lys Gly
420 425 430

Glu Pro Ile Ile Asn Phe Tyr Asp Pro Leu Val Phe Pro Ser Asp Glu
435 440 445

Phe Asp Ala Ser Ile Ser Gln Val Asn Glu Lys Ile Asn Gln Ser Leu
450 455 460

Ala Phe Ile Arg Lys Ser Asp Glu Leu Leu Ser Ala Ile Gly Gly Tyr
465 470 475 480

Ile Pro Glu Ala Pro Arg Asp Gly Gln Ala Tyr Val Arg Lys Asp Gly
485 490 495

Glu Trp Val Leu Leu Ser Thr Phe Leu Gly Gly Leu Val Pro Arg Gly
500 505 510

Ser His His His His His His Ser Ala Trp Ser His Pro Gln Phe Glu
515 520 525

Lys

<210> SEQ ID NO 25
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 25

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Gly Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Thr Gly Ser Gly Ser Ala Ile Cys Ser Gly
100 105 110

Val Ala Val Cys Lys Val Leu His Leu Glu Gly Glu Val Asn Lys Ile
115 120 125

Lys Ser Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Gln Leu Leu Pro Ile Leu Asn Lys Gln Ser Cys Ser Ile Ser

-continued

```
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 26
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 26

-continued

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415
```

```
Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 27
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 27

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
```

-continued

```
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 28
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 28

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80
```

```
Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495
```

```
Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 29
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 29

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
```

```
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 30
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 30

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160
```

```
Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530
```

<210> SEQ ID NO 31
<211> LENGTH: 530
<212> TYPE: PRT
<213> ORGANISM: Artificial Sequence
<220> FEATURE:

-continued

<223> OTHER INFORMATION: Recombinant RSV F protein

<400> SEQUENCE: 31

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

-continued

```
Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Gln Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 32
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220
```

```
Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Gln Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530
```

<210> SEQ ID NO 33
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 33

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45
```

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Gln Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
```

-continued

```
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 34
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 34

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
```

```
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Gln Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 35
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
```

-continued

```
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Gln Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530
```

<210> SEQ ID NO 36
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 36

Met Glu Leu Leu Ile His Arg Ser Ser Ala Ile Phe Leu Thr Leu Ala
1 5 10 15

Val Asn Ala Leu Tyr Leu Thr Ser Ser Gln Asn Ile Thr Glu Glu Phe
20 25 30

Tyr Gln Ser Thr Cys Ser Ala Val Ser Arg Gly Tyr Phe Ser Ala Leu
35 40 45

Arg Thr Gly Trp Tyr Thr Ser Val Ile Thr Ile Glu Leu Ser Asn Ile
50 55 60

Lys Glu Thr Lys Cys Asn Gly Thr Asp Thr Lys Val Lys Leu Ile Lys
65 70 75 80

Gln Glu Leu Asp Lys Tyr Lys Asn Ala Val Thr Glu Leu Gln Met Leu
85 90 95

Met Cys Asn Thr Pro Ala Ala Gly Ser Gly Ser Ala Ile Ala Ser Gly
100 105 110

Ile Ala Val Cys Lys Val Leu His Leu Glu Gly Glu Val Asn Lys Ile
115 120 125

Lys Asn Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asn Asn Arg Leu Leu Pro Ile Leu Asn Gln Gln Ser Cys Arg Ile Ser
165 170 175

Asn Pro Glu Thr Val Met Glu Phe Gln Gln Met Asn Ser Arg Leu Leu
180 185 190

Glu Ile Thr Arg Glu Phe Ser Val Asn Ala Gly Val Thr Thr Pro Leu
195 200 205

Ser Thr Tyr Met Leu Thr Asn Ser Glu Leu Leu Ser Leu Ile Asn Asp
210 215 220

Met Pro Ile Thr Asn Asp Gln Lys Lys Leu Met Ser Ser Asn Val Gln
225 230 235 240

Ile Val Arg Gln Gln Ser Tyr Ser Ile Met Cys Ile Ile Lys Glu Glu
245 250 255

Val Leu Ala Tyr Val Val Gln Leu Pro Ile Tyr Gly Val Ile Asp Thr
260 265 270

Pro Cys Trp Lys Leu His Thr Ser Pro Leu Cys Thr Thr Asn Ile Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Asp Thr Cys Lys
305 310 315 320

Val Cys Ser Asn Arg Val Phe Cys Asp Thr Met Asn Ser Arg Thr Leu
325 330 335

Pro Ser Glu Val Ser Leu Cys Asn Thr Asp Ile Phe Asn Ser Lys Tyr
340 345 350

Asp Cys Lys Ile Met Thr Ser Lys Thr Asp Ile Ser Ser Ser Val Ile
355 360 365

-continued

```
Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 37
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 37

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Asn
65                  70                  75                  80

Gln Glu Leu Asp Lys Tyr Lys Asn Ala Val Thr Glu Leu Gln Met Leu
                85                  90                  95

Met Cys Ser Thr Thr Ala Thr Gly Ser Gly Ser Ala Ile Ala Ser Gly
            100                 105                 110

Ile Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Phe Ser Lys Val Leu Asp Leu Lys Asn Tyr Ile
145                 150                 155                 160

Asp Lys Gln Leu Leu Pro Ile Leu Asn Lys Gln Ser Cys Arg Ile Ser
                165                 170                 175

Asn Ile Glu Thr Val Met Glu Phe Gln Gln Lys Asn Asn Arg Leu Leu
            180                 185                 190
```

```
Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Cys Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 38
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 38

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

-continued

```
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Cys Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445
```

```
Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 39
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 39

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270
```

```
Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Cys Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Cys Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 40
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 40

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95
```

```
Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510
```

```
Ser His His His His His His Ser Ala Trp Ser His Pro Gln Phe Glu
        515                 520                 525

Lys


<210> SEQ ID NO 41
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 41

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
```

```
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 42
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 42

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175
```

```
Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Cys Val Asn Lys Gln Glu Gly Gln Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530
```

<210> SEQ ID NO 43
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 43

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Cys Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415
```

```
Cys Leu Tyr Tyr Val Asn Lys Gln Glu Gly Gln Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 44
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 44

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Ile Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240
```

```
Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Cys Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 45
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 45

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
```

-continued

```
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Gln Glu Gly Gln Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495
```

```
Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 46
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 46

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320
```

```
Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Cys Val Asn Lys Gln Glu Gly Gln Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 47
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 47

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140
```

```
Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Pro Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Cys Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Cys Leu Tyr Tyr Val Asn Lys Gln Glu Gly Gln Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530
```

<210> SEQ ID NO 48
<211> LENGTH: 529
<212> TYPE: PRT

<213> ORGANISM: Artificial Sequence
<220> FEATURE:
<223> OTHER INFORMATION: Recombinant RSV F protein

<400> SEQUENCE: 48

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Gly Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Asp Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Pro
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
```

385 390 395 400

Asp Tyr Val Ser Asn Lys Gly Val Asp Thr Val Ser Val Gly Asn Cys
405 410 415

Leu Tyr Cys Val Asn Lys Gln Glu Gly Gln Ser Leu Tyr Val Lys Gly
420 425 430

Glu Pro Ile Ile Asn Phe Tyr Asp Pro Leu Val Phe Pro Ser Asp Glu
435 440 445

Phe Asp Ala Ser Ile Ser Gln Val Asn Glu Lys Ile Asn Gln Ser Leu
450 455 460

Ala Phe Ile Arg Lys Ser Asp Glu Leu Leu Ser Ala Ile Gly Gly Tyr
465 470 475 480

Ile Pro Glu Ala Pro Arg Asp Gly Gln Ala Tyr Val Arg Lys Asp Gly
485 490 495

Glu Trp Val Leu Leu Ser Thr Phe Leu Gly Gly Leu Val Pro Arg Gly
500 505 510

Ser His His His His His His Ser Ala Trp Ser His Pro Gln Phe Glu
515 520 525

Lys

<210> SEQ ID NO 49
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 49

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Met Leu
85 90 95

Met Gln Ser Thr Pro Ala Thr Gly Ser Gly Ser Ala Ile Ala Ser Gly
100 105 110

Val Ala Val Cys Lys Val Leu His Leu Glu Gly Glu Val Asn Lys Ile
115 120 125

Lys Ser Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Gln Leu Leu Pro Ile Leu Asn Lys Gln Ser Cys Ser Ile Ser
165 170 175

Asn Ile Glu Thr Val Met Glu Phe Gln Gln Lys Asn Asn Arg Leu Leu
180 185 190

Glu Ile Thr Arg Glu Phe Ser Val Asn Ala Gly Val Thr Thr Pro Val
195 200 205

Ser Thr Tyr Met Leu Thr Asn Ser Glu Leu Leu Ser Leu Ile Asn Asp
210 215 220

```
Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 50
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 50

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

-continued

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Met Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Lys Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Cys Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
```

```
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 51
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 51

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Met Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
```

```
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Cys Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Lys Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Cys Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 52
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 52

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
```

```
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Met Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 53
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 53

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Pro Glu Thr Val Met Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365
```

```
Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Tyr Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 54
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 54

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Pro Glu Thr Val Met Glu Phe Gln Gln Lys Asn Asn Arg Leu
            180                 185                 190

Leu Glu Ile Thr Arg Glu Phe Ser Val Asn Ala Gly Val Thr Thr Pro
```

```
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Lys Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Cys Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 55
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 55

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
```

-continued

```
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Pro Glu Thr Val Met Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Cys Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Lys Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Cys Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445
```

```
Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu Ser Ala Ile Gly Gly
465                 470                 475                 480

Tyr Ile Pro Glu Ala Pro Arg Asp Gly Gln Ala Tyr Val Arg Lys Asp
                485                 490                 495

Gly Glu Trp Val Leu Leu Ser Thr Phe Leu Gly Gly Leu Val Pro Arg
            500                 505                 510

Gly Ser His His His His His His Ser Ala Trp Ser His Pro Gln Phe
        515                 520                 525

Glu Lys
    530


<210> SEQ ID NO 56
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 56

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Met Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Pro Glu Thr Val Met Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Cys Ile Ile Lys Glu Glu
                245                 250                 255

Val Leu Ala Tyr Val Val Gln Leu Pro Leu Tyr Gly Val Ile Asp Thr
            260                 265                 270
```

```
Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Cys Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Lys Gly Ile Ile Lys Thr Phe Ser Asn Gly Cys
385                 390                 395                 400

Asp Tyr Val Ser Asn Lys Gly Val Asp Thr Val Ser Val Gly Asn Cys
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 57
<211> LENGTH: 574
<212> TYPE: PRT
<213> ORGANISM: Respiratory Syncytial Virus

<400> SEQUENCE: 57

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110
```

-continued

```
Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525
```

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 58
<211> LENGTH: 574
<212> TYPE: PRT
<213> ORGANISM: Respiratory Syncytial Virus

<400> SEQUENCE: 58

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 59
<211> LENGTH: 574
<212> TYPE: PRT
<213> ORGANISM: Respiratory Syncytial Virus

<400> SEQUENCE: 59

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
```

-continued

```
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Phe Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560
```

```
Lys Asp Gln Leu Ser Gly Ile Asn Asn Ile Ala Phe Ser Asn
                565                 570


<210> SEQ ID NO 60
<211> LENGTH: 574
<212> TYPE: PRT
<213> ORGANISM: Respiratory Syncytial Virus

<400> SEQUENCE: 60

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
```

```
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 61
<211> LENGTH: 574
<212> TYPE: PRT
<213> ORGANISM: Respiratory Syncytial Virus

<400> SEQUENCE: 61

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160
```

-continued

```
Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570
```

<210> SEQ ID NO 62
<211> LENGTH: 574
<212> TYPE: PRT
<213> ORGANISM: Respiratory Syncytial Virus

<400> SEQUENCE: 62

```
Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380
```

-continued

```
Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570


<210> SEQ ID NO 63
<211> LENGTH: 572
<212> TYPE: PRT
<213> ORGANISM: Respiratory Syncytial Virus

<400> SEQUENCE: 63

Met Ala Thr Thr Thr Met Arg Met Ile Ile Ser Ile Ile Leu Ile Ser
1               5                   10                  15

Thr Tyr Val Pro His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Gly Thr Asp Ser Lys Val Lys Leu Ile Lys
65                  70                  75                  80

Gln Glu Leu Glu Arg Tyr Asn Asn Ala Val Ala Glu Leu Gln Ser Leu
                85                  90                  95

Met Gln Asn Glu Pro Thr Ser Ser Ser Arg Ala Lys Arg Gly Ile Pro
            100                 105                 110

Glu Ser Ile His Tyr Thr Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190
```

```
Leu Asp Leu Lys Asn Tyr Ile Asp Lys Glu Leu Leu Pro Lys Val Asn
        195                 200                 205

Asn His Asp Cys Arg Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Ile Ile Asn Asp Met Pro Ile Thr Asn Asp Gln Lys Lys
            260                 265                 270

Leu Met Ser Val Cys Gln Ile Val Arg Gln Gln Ser Tyr Ser Ile Met
        275                 280                 285

Ser Val Leu Arg Glu Val Ile Ala Tyr Val Val Gln Leu Pro Leu Tyr
    290                 295                 300

Gly Val Ile Asp Thr Pro Cys Trp Lys Leu His Thr Ser Pro Leu Cys
305                 310                 315                 320

Thr Thr Asp Asn Lys Glu Gly Ser Asn Ile Cys Leu Thr Arg Thr Asp
                325                 330                 335

Arg Gly Trp Tyr Cys Asp Asn Ala Gly Ser Val Ser Phe Phe Pro Gln
            340                 345                 350

Ala Glu Thr Cys Lys Val Gln Ser Asn Arg Val Phe Cys Asp Thr Met
        355                 360                 365

Asn Ser Leu Thr Leu Pro Thr Asp Val Asn Leu Cys Asn Thr Asp Ile
    370                 375                 380

Phe Asn Ser Lys Tyr Asp Cys Lys Ile Met Thr Ser Lys Thr Asp Ile
385                 390                 395                 400

Ser Ser Ser Val Ile Thr Ser Ile Gly Ala Ile Val Ser Cys Tyr Gly
                405                 410                 415

Lys Thr Lys Cys Thr Ala Ser Asn Lys Asn Arg Gly Ile Ile Lys Thr
            420                 425                 430

Phe Ser Asn Gly Cys Asp Tyr Val Ser Asn Lys Gly Val Asp Thr Val
        435                 440                 445

Ser Val Gly Asn Thr Leu Tyr Tyr Val Asn Lys Leu Glu Gly Lys Ala
    450                 455                 460

Leu Tyr Ile Lys Gly Glu Pro Ile Ile Asn Tyr Tyr Asn Pro Leu Val
465                 470                 475                 480

Phe Pro Ser Asp Glu Phe Asp Ala Ser Ile Ala Gln Val Asn Ala Lys
                485                 490                 495

Ile Asn Gln Ser Leu Ala Phe Ile Arg Arg Ser Asp Glu Leu Leu His
            500                 505                 510

Ser Val Asp Val Gly Lys Ser Thr Thr Asn Val Val Ile Thr Thr Ile
        515                 520                 525

Ile Ile Val Ile Val Val Val Ile Leu Met Leu Ile Thr Val Gly Leu
    530                 535                 540

Leu Phe Tyr Cys Lys Thr Arg Ser Thr Pro Ile Met Leu Gly Lys Asp
545                 550                 555                 560

Gln Leu Ser Ser Ile Asn Asn Leu Ser Phe Ser Lys
                565                 570
```

```
<210> SEQ ID NO 64
<211> LENGTH: 574
<212> TYPE: PRT
<213> ORGANISM: Respiratory Syncytial Virus
```

<400> SEQUENCE: 64

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Arg Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

```
Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Val Ile Leu Met Leu Ile Ala Val
    530                 535                 540

Gly Leu Leu Phe Tyr Cys Lys Thr Arg Ser Thr Pro Ile Met Leu Gly
545                 550                 555                 560

Lys Asp Gln Leu Ser Gly Ile Asn Asn Leu Ser Phe Ser Lys
                565                 570


<210> SEQ ID NO 65
<211> LENGTH: 4
<212> TYPE: PRT
<213> ORGANISM: Artificial Sequence
<220> FEATURE:
<223> OTHER INFORMATION: Recombinant RSV F protein

<400> SEQUENCE: 65

Ser Ala Ile Gly
1


<210> SEQ ID NO 66
<211> LENGTH: 26
<212> TYPE: PRT
<213> ORGANISM: Artificial Sequence
<220> FEATURE:
<223> OTHER INFORMATION: Recombinant RSV F protein

<400> SEQUENCE: 66

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25


<210> SEQ ID NO 67
<211> LENGTH: 18
<212> TYPE: PRT
<213> ORGANISM: Artificial Sequence
<220> FEATURE:
<223> OTHER INFORMATION: Recombinant RSV F protein

<400> SEQUENCE: 67

Cys Cys His Asn Val Asn Ala Cys Cys Ser Thr Thr Asn Ile Cys Cys
1               5                   10                  15

Thr Thr


<210> SEQ ID NO 68
<211> LENGTH: 18
<212> TYPE: PRT
```

<213> ORGANISM: Artificial Sequence
<220> FEATURE:
<223> OTHER INFORMATION: Recombinant RSV F protein

<400> SEQUENCE: 68

Cys Cys His Asn Val Asn Thr Cys Cys Ser Thr Thr Asn Ile Cys Cys
1 5 10 15

Thr Thr

<210> SEQ ID NO 69
<211> LENGTH: 18
<212> TYPE: PRT
<213> ORGANISM: Artificial Sequence
<220> FEATURE:
<223> OTHER INFORMATION: Recombinant RSV F protein

<400> SEQUENCE: 69

Cys Cys His Ser Val Asp Val Cys Cys Ser Thr Thr Asn Val Cys Cys
1 5 10 15

Thr Thr

<210> SEQ ID NO 70
<211> LENGTH: 25
<212> TYPE: PRT
<213> ORGANISM: Artificial Sequence
<220> FEATURE:
<223> OTHER INFORMATION: Recombinant RSV F protein

<400> SEQUENCE: 70

Cys Cys His Asn Val Asn Ala Cys Cys Ser Thr Thr Asn Ile Cys Cys
1 5 10 15

Thr Thr Thr Asn Ile Cys Cys Thr Thr
20 25

<210> SEQ ID NO 71
<211> LENGTH: 25
<212> TYPE: PRT
<213> ORGANISM: Artificial Sequence
<220> FEATURE:
<223> OTHER INFORMATION: Recombinant RSV F protein

<400> SEQUENCE: 71

Cys Cys His Asn Val Asn Thr Cys Cys Ser Thr Thr Asn Ile Cys Cys
1 5 10 15

Thr Thr Thr Asn Ile Cys Cys Thr Thr
20 25

<210> SEQ ID NO 72
<211> LENGTH: 25
<212> TYPE: PRT
<213> ORGANISM: Artificial Sequence
<220> FEATURE:
<223> OTHER INFORMATION: Recombinant RSV F protein

<400> SEQUENCE: 72

Cys Cys His Ser Val Asp Val Cys Cys Ser Thr Thr Asn Val Cys Cys
1 5 10 15

Thr Thr Thr Asn Val Cys Cys Thr Thr
20 25

<210> SEQ ID NO 73
<211> LENGTH: 23
<212> TYPE: PRT
<213> ORGANISM: Artificial Sequence
<220> FEATURE:
<223> OTHER INFORMATION: Recombinant RSV F protein

<400> SEQUENCE: 73

Ile Leu Ala Ile Tyr Ser Thr Val Ala Ser Ser Leu Val Leu Leu Val
1 5 10 15

Ser Leu Gly Ala Ile Ser Phe
20

<210> SEQ ID NO 74
<211> LENGTH: 29
<212> TYPE: PRT
<213> ORGANISM: Artificial Sequence
<220> FEATURE:
<223> OTHER INFORMATION: Recombinant RSV F protein

<400> SEQUENCE: 74

Ile Ile Thr Ile Gly Ser Ile Cys Met Val Val Gly Ile Ile Ser Leu
1 5 10 15

Ile Leu Gln Ile Gly Asn Ile Ile Ser Ile Trp Val Ser
20 25

<210> SEQ ID NO 75
<211> LENGTH: 173
<212> TYPE: PRT
<213> ORGANISM: Artificial Sequence
<220> FEATURE:
<223> OTHER INFORMATION: Recombinant protein nanoparticle sequence

<400> SEQUENCE: 75

Glu Ser Gln Val Arg Gln Gln Phe Ser Lys Asp Ile Glu Lys Leu Leu
1 5 10 15

Asn Glu Gln Val Asn Lys Glu Met Gln Ser Ser Asn Leu Tyr Met Ser
20 25 30

Met Ser Ser Trp Cys Tyr Thr His Ser Leu Asp Gly Ala Gly Leu Phe
35 40 45

Leu Phe Asp His Ala Ala Glu Glu Tyr Glu His Ala Lys Lys Leu Ile
50 55 60

Ile Phe Leu Asn Glu Asn Asn Val Pro Val Gln Leu Thr Ser Ile Ser
65 70 75 80

Ala Pro Glu His Lys Phe Glu Gly Leu Thr Gln Ile Phe Gln Lys Ala
85 90 95

Tyr Glu His Glu Gln His Ile Ser Glu Ser Ile Asn Asn Ile Val Asp
100 105 110

His Ala Ile Lys Ser Lys Asp His Ala Thr Phe Asn Phe Leu Gln Trp
115 120 125

Tyr Val Ala Glu Gln His Glu Glu Glu Val Leu Phe Lys Asp Ile Leu
130 135 140

Asp Lys Ile Glu Leu Ile Gly Asn Glu Asn His Gly Leu Tyr Leu Ala
145 150 155 160

Asp Gln Tyr Val Lys Gly Ile Ala Lys Ser Arg Lys Ser
165 170

<210> SEQ ID NO 76
<211> LENGTH: 154
<212> TYPE: PRT
<213> ORGANISM: Artificial Sequence
<220> FEATURE:
<223> OTHER INFORMATION: Recombinant protein nanoparticle sequence

<400> SEQUENCE: 76

```
Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150
```

<210> SEQ ID NO 77
<211> LENGTH: 265
<212> TYPE: PRT
<213> ORGANISM: Artificial Sequence
<220> FEATURE:
<223> OTHER INFORMATION: Recombinant protein nanoparticle sequence

<400> SEQUENCE: 77

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205
```

-continued

```
Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265
```

<210> SEQ ID NO 78
<211> LENGTH: 265
<212> TYPE: PRT
<213> ORGANISM: Artificial Sequence
<220> FEATURE:
<223> OTHER INFORMATION: Recombinant protein nanoparticle sequence

<400> SEQUENCE: 78

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265
```

<210> SEQ ID NO 79
<211> LENGTH: 30
<212> TYPE: PRT
<213> ORGANISM: Artificial Sequence

```
<220> FEATURE:
<223> OTHER INFORMATION: Recombinant signal peptide sequence

<400> SEQUENCE: 79

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala
            20                  25                  30


<210> SEQ ID NO 80
<211> LENGTH: 24
<212> TYPE: PRT
<213> ORGANISM: Artificial Sequence
<220> FEATURE:
<223> OTHER INFORMATION: Recombinant signal peptide sequence

<400> SEQUENCE: 80

Met Pro Met Gly Ser Leu Gln Pro Leu Ala Thr Leu Tyr Leu Leu Gly
1               5                   10                  15

Met Leu Val Ala Ser Val Leu Ala
            20


<210> SEQ ID NO 81
<211> LENGTH: 539
<212> TYPE: PRT
<213> ORGANISM: Artificial Sequence
<220> FEATURE:
<223> OTHER INFORMATION: Recombinant RSV F protein

<400> SEQUENCE: 81

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220
```

Met Pro Ile Thr Asn Asp Gln Lys Lys Leu Met Ser Asn Asn Val Gln
225 230 235 240

Ile Val Arg Gln Gln Ser Tyr Ser Ile Met Cys Ile Ile Lys Glu Glu
245 250 255

Val Leu Ala Tyr Val Val Gln Leu Pro Leu Tyr Gly Val Ile Asp Thr
260 265 270

Pro Cys Trp Lys Leu His Thr Ser Pro Leu Cys Thr Thr Asn Thr Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Glu Thr Cys Lys
305 310 315 320

Val Gln Ser Asn Arg Val Phe Cys Asp Thr Met Asn Ser Arg Thr Leu
325 330 335

Pro Ser Glu Val Asn Leu Cys Asn Val Asp Ile Phe Asn Pro Lys Tyr
340 345 350

Asp Cys Lys Ile Met Thr Ser Lys Thr Asp Val Ser Ser Ser Val Ile
355 360 365

Thr Ser Leu Gly Ala Ile Val Ser Cys Tyr Gly Lys Thr Lys Cys Thr
370 375 380

Ala Ser Asn Lys Asn Arg Gly Ile Ile Lys Thr Phe Ser Asn Gly Cys
385 390 395 400

Asp Tyr Val Ser Asn Lys Gly Val Asp Thr Val Ser Val Gly Asn Thr
405 410 415

Leu Tyr Cys Val Asn Lys Gln Glu Gly Lys Ser Leu Tyr Val Lys Gly
420 425 430

Glu Pro Ile Ile Asn Phe Tyr Asp Pro Leu Val Phe Pro Ser Asp Glu
435 440 445

Phe Asp Ala Ser Ile Ser Gln Val Asn Glu Lys Ile Asn Gln Ser Leu
450 455 460

Ala Phe Ile Arg Lys Ser Asp Glu Leu Leu His Asn Val Asn Ala Gly
465 470 475 480

Lys Ser Thr Thr Ser Ala Ile Gly Gly Tyr Ile Pro Glu Ala Pro Arg
485 490 495

Asp Gly Gln Ala Tyr Val Arg Lys Asp Gly Glu Trp Val Leu Leu Ser
500 505 510

Thr Phe Leu Gly Gly Leu Val Pro Arg Gly Ser His His His His His
515 520 525

His Ser Ala Trp Ser His Pro Gln Phe Glu Lys
530 535

<210> SEQ ID NO 82
<211> LENGTH: 540
<212> TYPE: PRT
<213> ORGANISM: Artificial Sequence
<220> FEATURE:
<223> OTHER INFORMATION: Recombinant RSV F protein

<400> SEQUENCE: 82

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

```
Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Cys Lys Val Leu His Leu Glu Gly Glu Val Asn Lys Ile
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Cys Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu His Asn Val Asn Ala
```

```
465                 470                 475                 480

Gly Lys Ser Thr Thr Ser Ala Ile Gly Gly Tyr Ile Pro Glu Ala Pro
                485                 490                 495

Arg Asp Gly Gln Ala Tyr Val Arg Lys Asp Gly Glu Trp Val Leu Leu
            500                 505                 510

Ser Thr Phe Leu Gly Gly Leu Val Pro Arg Gly Ser His His His His
        515                 520                 525

His His Ser Ala Trp Ser His Pro Gln Phe Glu Lys
    530                 535                 540


<210> SEQ ID NO 83
<211> LENGTH: 539
<212> TYPE: PRT
<213> ORGANISM: Artificial Sequence
<220> FEATURE:
<223> OTHER INFORMATION: Recombinant RSV F protein

<400> SEQUENCE: 83

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Cys Ser Gly
            100                 105                 110

Val Ala Val Ser Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Ser Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
```

```
    290                 295                 300

Asp Asn Ala Gly Ser Val Ser Phe Phe Pro Gln Ala Glu Thr Cys Lys
305                 310                 315                 320

Val Gln Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu His Asn Val Asn Ala Gly
465                 470                 475                 480

Lys Ser Thr Thr Ser Ala Ile Gly Gly Tyr Ile Pro Glu Ala Pro Arg
                485                 490                 495

Asp Gly Gln Ala Tyr Val Arg Lys Asp Gly Glu Trp Val Leu Leu Ser
            500                 505                 510

Thr Phe Leu Gly Gly Leu Val Pro Arg Gly Ser His His His His His
        515                 520                 525

His Ser Ala Trp Ser His Pro Gln Phe Glu Lys
    530                 535


<210> SEQ ID NO 84
<211> LENGTH: 540
<212> TYPE: PRT
<213> ORGANISM: Artificial Sequence
<220> FEATURE:
<223> OTHER INFORMATION: Recombinant RSV F protein

<400> SEQUENCE: 84

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Gly Ser Gly Ser Ala Ile Ala Ser Gly
            100                 105                 110

Val Ala Val Ser Lys Val Leu His Leu Glu Gly Glu Val Asn Lys Ile
```

-continued

```
        115                 120                 125

Lys Ser Ala Leu Leu Ser Thr Asn Lys Ala Val Val Ser Leu Ser Gly
    130                 135                 140

Cys Gly Val Ser Val Leu Thr Phe Lys Val Leu Asp Leu Lys Asn Tyr
145                 150                 155                 160

Ile Asp Lys Gln Leu Leu Pro Ile Leu Asn Lys Gln Ser Cys Ser Ile
                165                 170                 175

Ser Asn Ile Glu Thr Val Ile Glu Phe Gln Gln Lys Asn Asn Arg Leu
            180                 185                 190

Leu Glu Ile Thr Arg Glu Phe Ser Val Asn Ala Gly Val Thr Thr Pro
        195                 200                 205

Val Ser Thr Tyr Met Leu Thr Asn Ser Glu Leu Leu Ser Leu Ile Asn
    210                 215                 220

Asp Met Pro Ile Thr Asn Asp Gln Lys Lys Leu Met Ser Asn Asn Val
225                 230                 235                 240

Gln Ile Val Arg Gln Gln Ser Tyr Ser Ile Met Ser Ile Ile Lys Glu
                245                 250                 255

Glu Val Leu Ala Tyr Val Val Gln Leu Pro Leu Tyr Gly Val Ile Asp
            260                 265                 270

Thr Pro Cys Trp Lys Leu His Thr Ser Pro Leu Cys Thr Thr Asn Thr
        275                 280                 285

Lys Glu Gly Ser Asn Ile Cys Leu Thr Arg Thr Asp Arg Gly Trp Tyr
    290                 295                 300

Cys Asp Asn Ala Gly Ser Val Ser Phe Phe Pro Gln Ala Glu Thr Cys
305                 310                 315                 320

Lys Val Gln Ser Asn Arg Val Phe Cys Asp Thr Met Asn Ser Arg Thr
                325                 330                 335

Leu Pro Ser Glu Val Asn Leu Cys Asn Val Asp Ile Phe Asn Pro Lys
            340                 345                 350

Tyr Asp Cys Lys Ile Met Thr Ser Lys Thr Asp Val Ser Ser Ser Val
        355                 360                 365

Ile Thr Ser Leu Gly Ala Ile Val Ser Cys Tyr Gly Lys Thr Lys Cys
    370                 375                 380

Thr Ala Ser Asn Lys Cys Arg Gly Ile Ile Lys Thr Phe Ser Asn Gly
385                 390                 395                 400

Cys Asp Tyr Val Ser Asn Lys Gly Val Asp Thr Val Ser Val Gly Asn
                405                 410                 415

Thr Leu Tyr Tyr Val Asn Lys Gln Glu Gly Lys Ser Leu Tyr Val Lys
            420                 425                 430

Gly Glu Pro Ile Ile Asn Phe Tyr Asp Pro Leu Val Phe Pro Ser Asp
        435                 440                 445

Glu Phe Asp Ala Ser Ile Ser Gln Val Asn Glu Lys Ile Asn Gln Ser
    450                 455                 460

Leu Ala Phe Ile Arg Lys Ser Asp Glu Leu Leu His Asn Val Asn Ala
465                 470                 475                 480

Gly Lys Ser Thr Thr Ser Ala Ile Gly Gly Tyr Ile Pro Glu Ala Pro
                485                 490                 495

Arg Asp Gly Gln Ala Tyr Val Arg Lys Asp Gly Glu Trp Val Leu Leu
            500                 505                 510

Ser Thr Phe Leu Gly Gly Leu Val Pro Arg Gly Ser His His His His
        515                 520                 525

His His Ser Ala Trp Ser His Pro Gln Phe Glu Lys
    530                 535                 540
```

-continued

<210> SEQ ID NO 85
<211> LENGTH: 12
<212> TYPE: PRT
<213> ORGANISM: Artificial Sequence
<220> FEATURE:
<223> OTHER INFORMATION: Peptide Linker

<400> SEQUENCE: 85

Met Gly Ser Gly Gly Asn Gly Ile Gly Leu Gly Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Peptide Linker

<400> SEQUENCE: 86

Met Gly Ser Gly Asn Val Gly Leu Gly Gly
1               5                   10

<210> SEQ ID NO 87
<211> LENGTH: 18
<212> TYPE: PRT
<213> ORGANISM: Artificial Sequence
<220> FEATURE:
<223> OTHER INFORMATION: Peptide Linker

<400> SEQUENCE: 87

Met Gln Ser Thr Pro Ala Thr Asn Asn Gly Ser Gly Ser Ala Ile Ala
1               5                   10                  15

Ser Gly

<210> SEQ ID NO 88
<211> LENGTH: 10
<212> TYPE: PRT
<213> ORGANISM: Artificial Sequence
<220> FEATURE:
<223> OTHER INFORMATION: Peptide Linker

<400> SEQUENCE: 88

Asn Ser Ala Leu Ser Ala Thr Gly Ser Gly
1               5                   10

<210> SEQ ID NO 89
<211> LENGTH: 4
<212> TYPE: PRT
<213> ORGANISM: Artificial Sequence
<220> FEATURE:
<223> OTHER INFORMATION: Peptide Linker

<400> SEQUENCE: 89

Thr Gly Ser Gly
1

<210> SEQ ID NO 90
<211> LENGTH: 8
<212> TYPE: PRT
<213> ORGANISM: Artificial Sequence
<220> FEATURE:
<223> OTHER INFORMATION: Peptide Linker

<400> SEQUENCE: 90

Met Gln Ser Thr Pro Ala Thr Gly 1 5

<210> SEQ ID NO 91
<211> LENGTH: 10
<212> TYPE: PRT
<213> ORGANISM: Artificial Sequence
<220> FEATURE:
<223> OTHER INFORMATION: Peptide Linker

<400> SEQUENCE: 91

Met Gln Ser Thr Pro Ala Thr Gly Ser Gly
1 5 10

<210> SEQ ID NO 92
<211> LENGTH: 15
<212> TYPE: PRT
<213> ORGANISM: Artificial Sequence
<220> FEATURE:
<223> OTHER INFORMATION: Peptide Linker

<400> SEQUENCE: 92

Met Gln Ser Thr Pro Ala Thr Gly Gly Ser Gly Gly Ser Gly Gly
1 5 10 15

<210> SEQ ID NO 93
<211> LENGTH: 6
<212> TYPE: PRT
<213> ORGANISM: Artificial Sequence
<220> FEATURE:
<223> OTHER INFORMATION: Peptide Linker

<400> SEQUENCE: 93

Met Gln Ser Thr Gly Gly
1 5

<210> SEQ ID NO 94
<211> LENGTH: 6
<212> TYPE: PRT
<213> ORGANISM: Artificial Sequence
<220> FEATURE:
<223> OTHER INFORMATION: Peptide Linker

<400> SEQUENCE: 94

Ala Gln Ser Thr Gly Gly
1 5

<210> SEQ ID NO 95
<211> LENGTH: 12
<212> TYPE: PRT
<213> ORGANISM: Artificial Sequence
<220> FEATURE:
<223> OTHER INFORMATION: Peptide Linker

<400> SEQUENCE: 95

Met Gln Ser Thr Pro Ala Thr Asn Gln Gly Ser Gly
1 5 10

<210> SEQ ID NO 96
<211> LENGTH: 1593
<212> TYPE: DNA
<213> ORGANISM: Artificial Sequence
<220> FEATURE:
<223> OTHER INFORMATION: Recombinant RSV F sequence

<400> SEQUENCE: 96
atggaactgc tgatcctgaa ggctaacgcc attaccacta tcctgactgc tgtgactttt 60

```
tgctttgcat ccggccagaa cattaccgag gaattctacc agtccacatg ctctgccgtg    120

agtaaaggat acctgagcgc tctgcggacc ggctggtata catccgtgat cactattgag    180

ctgtctaaca ttaaggaaaa caaatgtaac ggcaccgacg ctaaggtgaa actgatcaag    240

caggagctgg ataagtataa aaatgcagtg acagaactgc agctgctgat gcagtccacc    300

cctgccacag ggagtggatc agccatctgt tctggagtgg cagtctgcaa agtcctgcac    360

ctggagggcg aagtgaacaa gatcaaatcc gctctgctgt ctactaacaa ggcagtggtc    420

agcctgtcca atggcgtgtc cgtcctgacc tttaaggtgc tggacctgaa aaattacatc    480

gataagcagc tgctgccaat tctgaacaaa cagtcttgta gtatctcaaa catcgagaca    540

gtgattgaat tccagcagaa gaacaatagg ctgctggaga tcactcgcga gttcagcgtg    600

aacgccgggg tcaccacacc agtgtccacc tacatgctga caaatagtga gctgctgtca    660

ctgatcaacg acatgcccat taccaatgat cagaagaaac tgatgtccaa caatgtgcag    720

attgtcaggc agcagagcta ttccatcatg tgcatcatta aggaggaagt cctggcttac    780

gtggtccagc tgcctctgta tggcgtgatc gacaccccat gctggaaact gcatacatct    840

cccctgtgta ctaccaacac aaaggaagga agtaatatct gcctgacacg gactgacaga    900

ggctggtact gtgataacgc agggtctgtg agtttctttc cccaggccga gacctgcaag    960

gtccagtcta acagagtgtt ctgtgacact atgaatagca ggaccctgcc ttccgaagtc   1020

aacctgtgca atgtggacat cttcaaccca aagtacgatt gtaagatcat gactagcaag   1080

accgatgtca gctcctctgt gatcacttca ctgggagcca ttgtgagctg ctacggcaag   1140

acaaaatgta ctgctagcaa caaaaatcgg gggatcatta agaccttcag taacggatgt   1200

gactatgtct caaacaaggg ggtggataca gtgagtgtcg gaaacactct gtactgtgtc   1260

aataagcagg agggcaaaag cctgtacgtg aagggggaac ctatcattaa cttctatgac   1320

ccactggtgt tcccctccga cgagtttgat gcctcaatca gccaggtgaa cgaaaagatc   1380

aaccagtctc tggcttttat ccgcaagtct gatgagctgc tgagtgcaat cggcgggtac   1440

attcccgaag cacctcgaga cggccaggcc tatgtccgga aagatgggga gtgggtgctg   1500

ctgtcaacct tcctgggagg actggtgcca cgaggaagcc accatcacca tcaccattca   1560

gcctggagcc accctcagtt tgagaagtga tga                                1593
```

<210> SEQ ID NO 97
<211> LENGTH: 1596
<212> TYPE: DNA
<213> ORGANISM: Artificial Sequence
<220> FEATURE:
<223> OTHER INFORMATION: Recombinant RSV F sequence

<400> SEQUENCE: 97

```
atggaactgc tgatcctgaa ggctaacgcc attaccacta tcctgactgc tgtgactttt     60

tgctttgcat ccggccagaa cattaccgag gaattctacc agtccacatg ctctgccgtg    120

agtaaaggat acctgagcgc tctgcggacc ggctggtata catccgtgat cactattgag    180

ctgtctaaca ttaaggaaaa caaatgtaac ggcaccgacg ctaaggtgaa actgatcaag    240

caggagctgg ataagtataa aaatgcagtg acagaactgc agctgctgat gcagtccacc    300

cctgccacag ggagtggatc agccatcgct tctggagtgg cagtctgcaa agtcctgcac    360

ctggagggcg aagtgaacaa gatcaaatcc gctctgctgt ctactaacaa ggcagtggtc    420

agcctgtccg gctgtggcgt gtccgtcctg acctttaagg tgctggacct gaaaaattac    480

atcgataagc agctgctgcc aattctgaac aaacagtctt gtagtatctc aaacatcgag    540
```

acagtgattg aattccagca gaagaacaat aggctgctgg agatcactcg cgagttcagc 600
gtgaacgccg gggtcaccac accagtgtcc acctacatgc tgacaaatag tgagctgctg 660
tcactgatca acgacatgcc cattaccaat gatcagaaga aactgatgtc caacaatgtg 720
cagattgtca ggcagcagag ctattccatc atgtgcatca ttaaggagga agtcctggct 780
tacgtggtcc agctgcctct gtatggcgtg atcgacaccc catgctggaa actgcataca 840
tctcccctgt gtactaccaa cacaaaggaa ggaagtaata tctgcctgac acggactgac 900
agaggctggt actgtgataa cgcagggtct gtgagtttct ttccccaggc cgagacctgc 960
aaggtccagt ctaacagagt gttctgtgac actatgaata gcaggaccct gccttccgaa 1020
gtcaacctgt gcaatgtgga catcttcaac cccaaagtacg attgtaagat catgactagc 1080
aagaccgatg tcagctcctc tgtgatcact tcactgggag ccattgtgag ctgctacggc 1140
aagacaaaat gtactgctag caacaaatgt cgggggatca ttaagacctt cagtaacgga 1200
tgtgactatg tctcaaacaa gggggtggat acagtgagtg tcggaaacac tctgtactat 1260
gtcaataagc aggagggcaa aagcctgtac gtgaaggggg aacctatcat taacttctat 1320
gacccactgg tgttcccctc cgacgagttt gatgcctcaa tcagccaggt gaacgaaaag 1380
atcaaccagt ctctggcttt tatccgcaag tctgatgagc tgctgagtgc aatcggcggg 1440
tacattcccg aagcacctcg agacggccag gcctatgtcc ggaaagatgg ggagtgggtg 1500
ctgctgtcaa ccttcctggg aggactggtg ccacgaggaa gccaccatca ccatcaccat 1560
tcagcctgga gccaccctca gtttgagaag tgatga 1596

<210> SEQ ID NO 98
<211> LENGTH: 1610
<212> TYPE: DNA
<213> ORGANISM: Artificial Sequence
<220> FEATURE:
<223> OTHER INFORMATION: Recombinant RSV F sequence

<400> SEQUENCE: 98
tctagaccac catggagctg ctgatccaca ggagctccgc catcttcctg acactggccg 60
tgaatgccct gtacctgaca tctagccaga acatcaccga ggagttctat cagtccacct 120
gctctgccgt gagcaggggc tacttttccg ccctgcgcac cggctggtat acatccgtga 180
tcaccatcga gctgtctaat atcaaggaga ccaagtgtaa cggcaccgac acaaaggtga 240
agctgatcaa gcaggagctg gataagtaca agaatgccgt gacagagctg cagatgctga 300
tgtgcaacac cccagcagca ggcagcggct ccgccatcgc cagcggcatc gccgtgtgca 360
aggtgctgca cctggagggc gaggtgaaca agatcaagaa tgccctgctg tccacaaata 420
aggccgtggt gtctctgagc aacggcgtgt ctgtgctgac ctttaaggtg ctggacctga 480
agaactatat caacaatcgg ctgctgccta tcctgaatca gcagtcttgc agaatcagca 540
acccagagac agtgatggag ttccagcaga tgaattcccg gctgctggag atcaccagag 600
agttttctgt gaacgccggc gtgaccacac cactgagcac atacatgctg accaattccg 660
agctgctgtc tctgatcaac gacatgccca tcaccaatga tcagaagaag ctgatgtcct 720
ctaacgtgca gatcgtgcgc cagcagtcct attctatcat gtgcatcatc aaggaggagg 780
tgctggccta cgtggtgcag ctgcctatct atggcgtgat cgacacacca tgctggaagc 840
tgcacaccag ccccctgtgc accacaaaca tcaaggaggg ctccaatatc tgcctgacca 900
ggacagaccg cggctggtac tgtgataatg ccggcagcgt gtccttcttt cctcaggccg 960
acacatgcaa ggtgtgctcc aatagggtgt tctgcgatac aatgaactct cgcaccctgc 1020
catccgaggt gtctctgtgc aacacagaca tctttaattc taagtacgat tgtaagatca 1080
tgaccagcaa gacagatatc agctcctctg tgatcacctc tctgggcgcc atcgtgagct 1140
gctacggcaa gaccaagtgt acagcctcca acaagaataa gggcatcatc aagaccttca 1200
gcaatggctg tgactacgtg agcaacaagg gcgtggatac agtgagcgtg ggcaacaccc 1260
tgtactatgt gaataagctg gagggcaaga acctgtacgt gaagggcgag cctatcatca 1320
actactatga cccactggtg ttcccctccg acgagtttga tgcctctatc agccaggtga 1380
acgagaagat caatcagagc ctggccttta tccggagaag cgatgagctg ctgtccgcca 1440
tcggcggcta catcccagag gcacctaggg acggacaggc atatgtgaga aaggatggcg 1500
agtgggtgct gctgtctacc ttcctgggag gactggtgcc aaggggcagc caccaccacc 1560
accaccacag cgcctggtcc caccctcagt ttgagaagtg atgaggatcc 1610

<210> SEQ ID NO 99
<211> LENGTH: 1610
<212> TYPE: DNA
<213> ORGANISM: Artificial Sequence
<220> FEATURE:
<223> OTHER INFORMATION: Recombinant RSV F sequence

<400> SEQUENCE: 99
tctagaccac catggagctg cccatcctga aggccaacgc catcaccaca atcctggccg 60
ccgtgacatt ctgctttgcc agctcccaga atatcacaga ggagttctac cagagcacct 120
gttccgccgt gtctaaggga tacctgagcg ccctgaggac cggatggtat acatccgtga 180
tcaccatcga gctgtctaac atcaaggaga acaagtgcaa tggcaccgac gccaaggtga 240
agctgatcaa ccaggagctg gataagtata agaatgccgt gacagagctg cagatgctga 300
tgtgctctac cacagcaacc ggctctggca gcgccatcgc aagcggcatc gccgtgtgca 360
aggtgctgca cctggagggc gaggtgaaca agatcaagtc tgccctgctg agcaccaaca 420
aggccgtggt gtccctgtct aatggcgtgt ccgtgctgtt ttctaaggtg ctggacctga 480
agaattacat cgataagcag ctgctgccta tcctgaacaa gcagagctgc aggatctcca 540
atatcgagac agtgatggag ttccagcaga agaacaatag gctgctggag atcacccgcg 600
agttttctgt gaacgccggc gtgaccacac ctgtgagcac atacatgctg accaattctg 660
agctgctgag cctgatcaac gacatgccaa tcaccaatga tcagaagaag ctgatgagca 720
acaatgtgca gatcgtgcgc cagcagagct attccatcat gtgcatcatc aaggaggagg 780
tgctggccta cgtggtgcag ctgcctctgt atggcgtgat cgacacacca tgctggaagc 840
tgcacacctc cccccctgtgc accacaaaca caaaggaggg ctctaatatc tgcctgaccc 900
ggacagacag aggctggtac tgtgataacg ccggctctgt gagcttcttt ccccaggccg 960
agacctgcaa ggtgtgctcc aacagggtgt tctgcgacac aatgaattcc cgcaccctgc 1020
cctctgaggt gaacctgtgc aatgtggaca tctttaatcc taagtacgat tgtaagatca 1080
tgaccagcaa gacagacgtg agcagctccg tgatcacatc tctgggcgcc atcgtgagct 1140
gctacggcaa gaccaagtgt acagcctcca acaagaataa gggcatcatc aagaccttca 1200
gcaacggctg tgactacgtg agcaataagg gcgtggatac agtgtccgtg ggcaacaccc 1260
tgtactatgt gaataagcag gagggcaagt ctctgtacgt gaagggcgag cctatcatca 1320
acttctatga cccactggtg ttccccagcg acgagtttga tgcctccatc tctcaggtga 1380
acgagaagat caatcagtcc ctggccttta tccggaagag cgatgagctg ctgtccgcca 1440
tcggcggcta catcccagag gcacctaggg acggacaggc atatgtgaga aaggatggcg 1500
agtgggtgct gctgagcacc ttcctgggag gactggtgcc aagaggctcc caccaccacc 1560
accaccacag cgcctggtcc cacccccagt ttgagaagtg atgaggatcc 1610

<210> SEQ ID NO 100
<211> LENGTH: 529
<212> TYPE: PRT
<213> ORGANISM: Artificial Sequence
<220> FEATURE:
<223> OTHER INFORMATION: Recombinant RSV F sequence

<400> SEQUENCE: 100

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Cys Thr Pro Ala Thr Gly Ser Gly Ser Ala Ile Cys Ser Gly
100 105 110

Val Ala Val Ser Lys Val Leu His Leu Glu Gly Glu Val Asn Lys Ile
115 120 125

Lys Ser Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Gln Leu Leu Pro Ile Leu Asn Lys Gln Ser Cys Ser Ile Ser
165 170 175

Asn Ile Glu Thr Val Ile Glu Phe Gln Gln Lys Asn Asn Arg Leu Leu
180 185 190

Glu Ile Thr Arg Glu Phe Ser Val Asn Ala Gly Val Thr Thr Pro Val
195 200 205

Ser Thr Tyr Met Leu Thr Asn Ser Glu Leu Leu Ser Leu Ile Asn Asp
210 215 220

Met Pro Ile Thr Asn Asp Gln Lys Lys Leu Met Ser Asn Asn Val Gln
225 230 235 240

Ile Val Arg Gln Gln Ser Tyr Ser Ile Met Ser Ile Ile Lys Glu Glu
245 250 255

Val Leu Ala Tyr Val Val Gln Leu Pro Leu Tyr Gly Val Ile Asp Thr
260 265 270

Pro Cys Trp Lys Leu His Thr Ser Pro Leu Cys Thr Thr Asn Thr Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Glu Thr Cys Lys
305 310 315 320

Val Cys Ser Asn Arg Val Phe Cys Asp Thr Met Asn Ser Arg Thr Leu
325 330 335

```
Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 101
<211> LENGTH: 530
<212> TYPE: PRT
<213> ORGANISM: Artificial Sequence
<220> FEATURE:
<223> OTHER INFORMATION: Recombinant RSV F sequence

<400> SEQUENCE: 101

```
Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Cys Thr Pro Ala Ala Gly Ser Gly Ser Ala Ile Cys Ser Gly
            100                 105                 110

Ile Ala Val Ser Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160
```

-continued

```
Asn Asn Arg Leu Leu Pro Ile Leu Asn Gln Gln Ser Cys Arg Ile Ser
                165                 170                 175

Asn Ile Glu Thr Val Ile Glu Phe Gln Gln Met Asn Ser Arg Leu Leu
            180                 185                 190

Glu Ile Thr Arg Glu Phe Ser Val Asn Ala Gly Val Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Ser Ile Ile Lys Glu Glu
                245                 250                 255

Val Leu Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asn Ile Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Asp Thr Cys Lys
305                 310                 315                 320

Val Cys Ser Asn Arg Val Phe Cys Asp Thr Met Asn Ser Arg Thr Leu
                325                 330                 335

Pro Ser Glu Val Ser Leu Cys Asn Thr Asp Ile Phe Asn Ser Lys Tyr
            340                 345                 350

Asp Cys Lys Ile Met Thr Ser Lys Thr Asp Ile Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys Ser
    530
```

<210> SEQ ID NO 102
<211> LENGTH: 529
<212> TYPE: PRT
<213> ORGANISM: Artificial Sequence
<220> FEATURE:
<223> OTHER INFORMATION: Recombinant RSV F sequence

<400> SEQUENCE: 102

Met Ala Ala Thr Ala Met Arg Met Ile Ile Ser Ile Ile Phe Ile Ser
1 5 10 15

Thr Tyr Met Thr His Ile Thr Leu Cys Gln Asn Ile Thr Glu Glu Phe
20 25 30

Tyr Gln Ser Thr Cys Ser Ala Val Ser Arg Gly Tyr Leu Ser Ala Leu
35 40 45

Arg Thr Gly Trp Tyr Thr Ser Val Val Thr Ile Glu Leu Ser Lys Ile
50 55 60

Gln Lys Asn Val Cys Lys Ser Thr Asp Ser Lys Val Lys Leu Ile Lys
65 70 75 80

Gln Glu Leu Glu Arg Tyr Asn Asn Ala Val Ile Glu Leu Gln Ser Leu
85 90 95

Met Gln Cys Glu Pro Ala Ser Gly Ser Gly Ser Ala Ile Ala Ser Gly
100 105 110

Val Ala Val Ser Lys Val Leu His Leu Glu Gly Glu Val Asn Lys Ile
115 120 125

Lys Asn Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Glu Leu Leu Pro Lys Leu Asn Asn His Asp Cys Arg Ile Ser
165 170 175

Asn Ile Glu Thr Val Ile Glu Phe Gln Gln Lys Asn Asn Arg Leu Leu
180 185 190

Glu Ile Ala Arg Glu Phe Ser Val Asn Ala Gly Ile Thr Thr Pro Leu
195 200 205

Ser Thr Tyr Met Leu Thr Asn Ser Glu Leu Leu Ser Leu Ile Asn Asp
210 215 220

Met Pro Ile Thr Asn Asp Gln Lys Lys Leu Met Ser Ser Asn Val Gln
225 230 235 240

Ile Val Arg Gln Gln Ser Tyr Ser Ile Met Ser Val Val Lys Glu Glu
245 250 255

Val Ile Ala Tyr Val Val Gln Leu Pro Ile Tyr Gly Val Ile Asp Thr
260 265 270

Pro Cys Trp Lys Leu His Thr Ser Pro Leu Cys Thr Thr Asp Asn Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Glu Thr Cys Lys
305 310 315 320

Val Cys Ser Asn Arg Val Phe Cys Asp Thr Met Asn Ser Arg Thr Leu
325 330 335

Pro Thr Asp Val Asn Leu Cys Asn Thr Asp Ile Phe Asn Thr Lys Tyr
340 345 350

Asp Cys Lys Ile Met Thr Ser Lys Thr Asp Ile Ser Ser Ser Val Ile
355 360 365

Thr Ser Ile Gly Ala Ile Val Ser Cys Tyr Gly Lys Thr Lys Cys Thr
370 375 380

Ala Ser Asn Lys Asn Arg Gly Ile Ile Lys Thr Phe Ser Asn Gly Cys
385 390 395 400

Asp Tyr Val Ser Asn Lys Gly Val Asp Thr Val Ser Val Gly Asn Thr

```
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 103
<211> LENGTH: 534
<212> TYPE: PRT
<213> ORGANISM: Artificial Sequence
<220> FEATURE:
<223> OTHER INFORMATION: Recombinant RSV F sequence

<400> SEQUENCE: 103

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Gln Cys Glu Pro Ala Ser Gly Ser Gly Ser
            100                 105                 110

Ala Val Ala Ser Gly Val Ala Val Ser Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240
```

```
Ser Ser Asn Val Gln Ile Val Arg Gln Gln Ser Tyr Ser Ile Met Ser
                245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Thr Glu Thr Cys Lys Val Cys Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 104
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 104

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60
```

```
Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Gln Cys Glu Pro Ala Ser Gly Ser Gly Ser
            100                 105                 110

Ala Ile Ala Ser Gly Val Ala Val Ser Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Ser
                245                 250                 255

Val Val Lys Glu Glu Val Met Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Cys Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480
```

```
Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 105
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 105

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Cys Ser Thr Pro Ala Thr Gly Ser Gly Ser Ala Ile Cys Ser Gly
            100                 105                 110

Val Ala Val Ser Lys Val Leu His Leu Glu Gly Glu Val Asn Lys Ile
        115                 120                 125

Lys Ser Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Gln Leu Leu Pro Ile Leu Asn Lys Gln Ser Cys Ser Ile Ser
                165                 170                 175

Asn Ile Glu Thr Val Ile Glu Phe Gln Gln Lys Asn Asn Arg Leu Leu
            180                 185                 190

Glu Ile Thr Arg Glu Phe Ser Val Asn Ala Gly Val Thr Thr Pro Val
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Asn Asn Val Gln
225                 230                 235                 240

Ile Val Arg Gln Gln Ser Tyr Ser Ile Met Ser Ile Ile Lys Glu Glu
                245                 250                 255

Val Leu Ala Tyr Val Val Gln Leu Pro Leu Tyr Gly Val Ile Asp Thr
            260                 265                 270

Pro Cys Trp Lys Leu His Thr Ser Pro Leu Cys Thr Thr Asn Thr Lys
        275                 280                 285

Glu Gly Ser Asn Ile Cys Leu Thr Arg Thr Asp Arg Gly Trp Tyr Cys
    290                 295                 300
```

-continued

```
Asp Asn Ala Gly Ser Val Ser Phe Phe Pro Gln Ala Glu Thr Cys Lys
305                 310                 315                 320

Val Cys Ser Asn Arg Val Phe Cys Asp Thr Met Asn Ser Arg Thr Leu
                325                 330                 335

Pro Ser Glu Val Asn Leu Cys Asn Val Asp Ile Phe Asn Pro Lys Tyr
            340                 345                 350

Asp Cys Lys Ile Met Thr Ser Lys Thr Asp Val Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Gln Glu Gly Lys Ser Leu Tyr Val Lys Gly
            420                 425                 430

Glu Pro Ile Ile Asn Phe Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Lys Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 106
<211> LENGTH: 530
<212> TYPE: PRT
<213> ORGANISM: Artificial Sequence
<220> FEATURE:
<223> OTHER INFORMATION: Recombinant RSV F protein

<400> SEQUENCE: 106

Met Glu Leu Leu Ile His Arg Ser Ser Ala Ile Phe Leu Thr Leu Ala
1               5                   10                  15

Val Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Cys Asn Thr Pro Ala Ala Gly Ser Gly Ser Ala Ile Cys Ser Gly
            100                 105                 110

Ile Ala Val Ser Lys Val Leu His Leu Glu Gly Glu Val Asn Lys Ile
        115                 120                 125

Lys Asn Ala Leu Leu Ser Thr Asn Lys Ala Val Val Ser Leu Ser Asn
```

```
    130                 135                 140

Gly Val Ser Val Leu Thr Phe Lys Val Leu Asp Leu Lys Asn Tyr Ile
145                 150                 155                 160

Asn Asn Arg Leu Leu Pro Ile Leu Asn Gln Gln Ser Cys Arg Ile Ser
                165                 170                 175

Asn Ile Glu Thr Val Ile Glu Phe Gln Gln Met Asn Ser Arg Leu Leu
            180                 185                 190

Glu Ile Thr Arg Glu Phe Ser Val Asn Ala Gly Val Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Ser Ile Ile Lys Glu Glu
                245                 250                 255

Val Leu Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asn Ile Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Asp Thr Cys Lys
305                 310                 315                 320

Val Cys Ser Asn Arg Val Phe Cys Asp Thr Met Asn Ser Arg Thr Leu
                325                 330                 335

Pro Ser Glu Val Ser Leu Cys Asn Thr Asp Ile Phe Asn Ser Lys Tyr
            340                 345                 350

Asp Cys Lys Ile Met Thr Ser Lys Thr Asp Ile Ser Ser Ser Val Ile
        355                 360                 365

Thr Ser Leu Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Cys Val Asn Lys Leu Glu Gly Lys Asn Leu Tyr Val Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ser Gln Val Asn Glu Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys Ser
    530

<210> SEQ ID NO 107
```

<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 107

Met Ala Ala Thr Ala Met Arg Met Ile Ile Ser Ile Ile Phe Ile Ser
1 5 10 15

Thr Tyr Met Thr His Ile Thr Leu Cys Gln Asn Ile Thr Glu Glu Phe
20 25 30

Tyr Gln Ser Thr Cys Ser Ala Val Ser Arg Gly Tyr Leu Ser Ala Leu
35 40 45

Arg Thr Gly Trp Tyr Thr Ser Val Val Thr Ile Glu Leu Ser Lys Ile
50 55 60

Gln Lys Asn Val Cys Lys Ser Thr Asp Ser Lys Val Lys Leu Ile Lys
65 70 75 80

Gln Glu Leu Glu Arg Tyr Asn Asn Ala Val Ile Glu Leu Gln Ser Leu
85 90 95

Met Cys Asn Glu Pro Ala Ser Gly Ser Gly Ser Ala Ile Ala Ser Gly
100 105 110

Val Ala Val Ser Lys Val Leu His Leu Glu Gly Glu Val Asn Lys Ile
115 120 125

Lys Asn Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Glu Leu Leu Pro Lys Leu Asn Asn His Asp Cys Arg Ile Ser
165 170 175

Asn Ile Glu Thr Val Ile Glu Phe Gln Gln Lys Asn Asn Arg Leu Leu
180 185 190

Glu Ile Ala Arg Glu Phe Ser Val Asn Ala Gly Ile Thr Thr Pro Leu
195 200 205

Ser Thr Tyr Met Leu Thr Asn Ser Glu Leu Leu Ser Leu Ile Asn Asp
210 215 220

Met Pro Ile Thr Asn Asp Gln Lys Lys Leu Met Ser Ser Asn Val Gln
225 230 235 240

Ile Val Arg Gln Gln Ser Tyr Ser Ile Met Ser Val Val Lys Glu Glu
245 250 255

Val Ile Ala Tyr Val Val Gln Leu Pro Ile Tyr Gly Val Ile Asp Thr
260 265 270

Pro Cys Trp Lys Leu His Thr Ser Pro Leu Cys Thr Thr Asp Asn Lys
275 280 285

Glu Gly Ser Asn Ile Cys Leu Thr Arg Thr Asp Arg Gly Trp Tyr Cys
290 295 300

Asp Asn Ala Gly Ser Val Ser Phe Phe Pro Gln Ala Glu Thr Cys Lys
305 310 315 320

Val Cys Ser Asn Arg Val Phe Cys Asp Thr Met Asn Ser Arg Thr Leu
325 330 335

Pro Thr Asp Val Asn Leu Cys Asn Thr Asp Ile Phe Asn Thr Lys Tyr
340 345 350

Asp Cys Lys Ile Met Thr Ser Lys Thr Asp Ile Ser Ser Ser Val Ile
355 360 365

Thr Ser Ile Gly Ala Ile Val Ser Cys Tyr Gly Lys Thr Lys Cys Thr
370 375 380

```
Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys
```

<210> SEQ ID NO 108
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 108

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30

Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Lys Ser Thr Asp Ser Lys
65                  70                  75                  80

Val Lys Leu Ile Lys Gln Glu Leu Glu Arg Tyr Asn Asn Ala Val Val
                85                  90                  95

Glu Leu Gln Ser Leu Met Cys Asn Glu Pro Ala Ser Gly Ser Gly Ser
            100                 105                 110

Ala Val Ala Ser Gly Val Ala Val Ser Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Gln Leu Asn Asn His
                165                 170                 175

Asp Cys Arg Ile Ser Asn Ile Glu Thr Val Ile Glu Phe Gln Gln Lys
            180                 185                 190

Asn Asn Arg Leu Leu Glu Ile Ala Arg Glu Phe Ser Val Asn Ala Gly
        195                 200                 205
```

```
Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Ser
                245                 250                 255

Val Val Lys Glu Glu Val Ile Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Thr Glu Thr Cys Lys Val Cys Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Thr Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Lys Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 109
<211> LENGTH: 534
<212> TYPE: PRT
<213> ORGANISM: Artificial Sequence
<220> FEATURE:
<223> OTHER INFORMATION: Recombinant RSV F protein

<400> SEQUENCE: 109

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Val Gly Gln Asn
            20                  25                  30
```

```
Ile Thr Glu Glu Phe Tyr Gln Ser Thr Cys Ser Ala Val Ser Arg Gly
        35                  40                  45

Tyr Leu Ser Ala Leu Arg Thr Gly Trp Tyr Thr Ser Val Val Thr Ile
    50                  55                  60

Glu Leu Ser Lys Ile Gln Lys Asn Val Cys Asn Ser Thr Asp Ser Asn
65                  70                  75                  80

Val Lys Leu Ile Lys Gln Glu Leu Glu Arg Tyr Asn Asn Ala Val Val
                85                  90                  95

Glu Leu Gln Ser Leu Met Cys Asn Glu Pro Ala Ser Gly Ser Gly Ser
            100                 105                 110

Ala Ile Ala Ser Gly Val Ala Val Ser Lys Val Leu His Leu Glu Gly
        115                 120                 125

Glu Val Asn Lys Ile Lys Asn Ala Leu Leu Ser Thr Asn Lys Ala Val
    130                 135                 140

Val Ser Leu Ser Asn Gly Val Ser Val Leu Thr Phe Lys Val Leu Asp
145                 150                 155                 160

Leu Lys Asn Tyr Ile Asp Lys Glu Leu Leu Pro Lys Leu Asn Asn His
                165                 170                 175

Asp Cys Gln Ile Ser Asn Ile Ala Thr Val Ile Glu Phe Gln Gln Lys
            180                 185                 190

Asn Asn Arg Leu Leu Glu Ile Ala Arg Glu Phe Ser Val Asn Ala Gly
        195                 200                 205

Ile Thr Thr Pro Leu Ser Thr Tyr Met Leu Thr Asn Ser Glu Leu Leu
    210                 215                 220

Ser Leu Ile Asn Asp Met Pro Ile Thr Asn Asp Gln Lys Lys Leu Met
225                 230                 235                 240

Ser Ser Asn Val Gln Ile Val Arg Gln Gln Ser Tyr Ser Ile Met Ser
                245                 250                 255

Val Val Lys Glu Glu Val Met Ala Tyr Val Val Gln Leu Pro Ile Tyr
            260                 265                 270

Gly Val Ile Asp Thr Pro Cys Trp Lys Leu His Thr Ser Pro Leu Cys
        275                 280                 285

Thr Thr Asp Asn Lys Glu Gly Ser Asn Ile Cys Leu Thr Arg Thr Asp
    290                 295                 300

Arg Gly Trp Tyr Cys Asp Asn Ala Gly Ser Val Ser Phe Phe Pro Gln
305                 310                 315                 320

Ala Glu Thr Cys Lys Val Cys Ser Asn Arg Val Phe Cys Asp Thr Met
                325                 330                 335

Asn Ser Arg Thr Leu Pro Thr Asp Val Asn Leu Cys Asn Thr Asp Ile
            340                 345                 350

Phe Asn Ala Lys Tyr Asp Cys Lys Ile Met Thr Ser Lys Thr Asp Ile
        355                 360                 365

Ser Ser Ser Val Ile Thr Ser Ile Gly Ala Ile Val Ser Cys Tyr Gly
    370                 375                 380

Lys Thr Lys Cys Thr Ala Ser Asn Lys Asn Arg Gly Ile Ile Lys Thr
385                 390                 395                 400

Phe Ser Asn Gly Cys Asp Tyr Val Ser Asn Arg Gly Val Asp Thr Val
                405                 410                 415

Ser Val Gly Asn Thr Leu Tyr Tyr Val Asn Lys Leu Glu Gly Lys Ala
            420                 425                 430

Leu Tyr Ile Lys Gly Glu Pro Ile Ile Asn Tyr Tyr Asp Pro Leu Val
        435                 440                 445

Phe Pro Ser Asp Glu Phe Asp Ala Ser Ile Ala Gln Val Asn Ala Lys
```

```
    450                 455                 460

Ile Asn Gln Ser Leu Ala Phe Ile Arg Arg Ser Asp Glu Leu Leu Ser
465                 470                 475                 480

Ala Ile Gly Gly Tyr Ile Pro Glu Ala Pro Arg Asp Gly Gln Ala Tyr
                485                 490                 495

Val Arg Lys Asp Gly Glu Trp Val Leu Leu Ser Thr Phe Leu Gly Gly
            500                 505                 510

Leu Val Pro Arg Gly Ser His His His His His His Ser Ala Trp Ser
        515                 520                 525

His Pro Gln Phe Glu Lys
    530


<210> SEQ ID NO 110
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 110

Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Cys Glu Pro Ala Ser Gly Ser Gly Ser Ala Val Ala Ser Gly
            100                 105                 110

Val Ala Val Ser Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Gln Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Ser Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
```

```
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Thr Glu Thr Cys Lys
305                 310                 315                 320

Val Cys Ser Asn Arg Val Phe Cys Asp Thr Met Asn Ser Leu Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Gly
            420                 425                 430

Glu Pro Ile Ile Asn Tyr Tyr Asp Pro Leu Val Phe Pro Ser Asp Glu
        435                 440                 445

Phe Asp Ala Ser Ile Ala Gln Val Asn Ala Lys Ile Asn Gln Ser Leu
    450                 455                 460

Ala Phe Ile Arg Arg Ser Asp Glu Leu Leu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 111
<211> LENGTH: 528
<212> TYPE: PRT
<213> ORGANISM: Artificial Sequence
<220> FEATURE:
<223> OTHER INFORMATION: Recombinant RSV F protein

<400> SEQUENCE: 111

Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Ile Glu Leu Gln Ser Leu
                85                  90                  95

Met Gln Cys Glu Pro Ala Ser Gly Ser Gly Ser Ala Ile Ala Ser Gly
            100                 105                 110
```

-continued

```
Val Ala Val Ser Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Lys Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Ser Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Cys Ser Asn Arg Val Phe Cys Asp Thr Met Asn Ser Leu Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Glu
            420                 425                 430

Pro Ile Ile Asn Tyr Tyr Asp Pro Leu Val Phe Pro Ser Asp Glu Phe
        435                 440                 445

Asp Ala Ser Ile Ala Gln Val Asn Ala Lys Ile Asn Gln Ser Leu Ala
    450                 455                 460

Phe Ile Arg Arg Ser Asp Glu Leu Leu Ser Ala Ile Gly Gly Tyr Ile
465                 470                 475                 480

Pro Glu Ala Pro Arg Asp Gly Gln Ala Tyr Val Arg Lys Asp Gly Glu
                485                 490                 495

Trp Val Leu Leu Ser Thr Phe Leu Gly Gly Leu Val Pro Arg Gly Ser
            500                 505                 510

His His His His His His Ser Ala Trp Ser His Pro Gln Phe Glu Lys
        515                 520                 525
```

<210> SEQ ID NO 112
<211> LENGTH: 529
<212> TYPE: PRT
<213> ORGANISM: Artificial Sequence
<220> FEATURE:
<223> OTHER INFORMATION: Recombinant RSV F protein

<400> SEQUENCE: 112

```
Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Cys Asn Glu Pro Ala Ser Gly Ser Gly Ser Ala Val Ala Ser Gly
            100                 105                 110

Val Ala Val Cys Lys Val Leu His Leu Glu Gly Glu Val Asn Lys Ile
        115                 120                 125

Lys Asn Ala Leu Leu Ser Thr Asn Lys Ala Val Val Ser Leu Ser Asn
    130                 135                 140

Gly Val Ser Val Leu Thr Phe Lys Val Leu Asp Leu Lys Asn Tyr Ile
145                 150                 155                 160

Asp Lys Glu Leu Leu Pro Gln Leu Asn Asn His Asp Cys Arg Ile Ser
                165                 170                 175

Asn Ile Glu Thr Val Ile Glu Phe Gln Gln Lys Asn Asn Arg Leu Leu
            180                 185                 190

Glu Ile Ala Arg Glu Phe Ser Val Asn Ala Gly Ile Thr Thr Pro Leu
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Thr Glu Thr Cys Lys
305                 310                 315                 320

Val Cys Ser Asn Arg Val Phe Cys Asp Thr Met Asn Ser Leu Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365
```

Thr Ser Ile Gly Ala Ile Val Ser Cys Tyr Gly Lys Thr Lys Cys Thr
370 375 380

Ala Ser Asn Lys Asn Arg Gly Ile Ile Lys Thr Phe Ser Asn Gly Cys
385 390 395 400

Asp Tyr Val Ser Asn Lys Gly Val Asp Thr Val Ser Val Gly Asn Thr
405 410 415

Leu Tyr Tyr Val Asn Lys Leu Glu Gly Lys Ala Leu Tyr Ile Lys Gly
420 425 430

Glu Pro Ile Ile Asn Tyr Tyr Asp Pro Leu Val Phe Pro Ser Asp Glu
435 440 445

Phe Asp Ala Ser Ile Ala Gln Val Asn Ala Lys Ile Asn Gln Ser Leu
450 455 460

Ala Phe Ile Arg Arg Ser Asp Glu Leu Leu Ser Ala Ile Gly Gly Tyr
465 470 475 480

Ile Pro Glu Ala Pro Arg Asp Gly Gln Ala Tyr Val Arg Lys Asp Gly
485 490 495

Glu Trp Val Leu Leu Ser Thr Phe Leu Gly Gly Leu Val Pro Arg Gly
500 505 510

Ser His His His His His His Ser Ala Trp Ser His Pro Gln Phe Glu
515 520 525

Lys

<210> SEQ ID NO 113
<211> LENGTH: 528
<212> TYPE: PRT
<213> ORGANISM: Artificial Sequence
<220> FEATURE:
<223> OTHER INFORMATION: Recombinant RSV F protein

<400> SEQUENCE: 113

Met Ala Ala Thr Ala Met Arg Met Ile Ile Ser Ile Ile Phe Ile Ser
1 5 10 15

Thr Tyr Met Thr His Ile Thr Leu Cys Gln Asn Ile Thr Glu Glu Phe
20 25 30

Tyr Gln Ser Thr Cys Ser Ala Val Ser Arg Gly Tyr Leu Ser Ala Leu
35 40 45

Arg Thr Gly Trp Tyr Thr Ser Val Val Thr Ile Glu Leu Ser Lys Ile
50 55 60

Gln Lys Asn Val Cys Lys Ser Thr Asp Ser Lys Val Lys Leu Ile Lys
65 70 75 80

Gln Glu Leu Glu Arg Tyr Asn Asn Ala Val Ile Glu Leu Gln Ser Leu
85 90 95

Met Cys Asn Glu Pro Ala Ser Gly Ser Gly Ser Ala Ile Ala Ser Gly
100 105 110

Val Ala Val Cys Lys Val Leu His Leu Glu Gly Glu Val Asn Lys Ile
115 120 125

Lys Asn Ala Leu Leu Ser Thr Asn Lys Ala Val Val Ser Leu Ser Asn
130 135 140

Gly Val Ser Val Leu Thr Phe Lys Val Leu Asp Leu Lys Asn Tyr Ile
145 150 155 160

Asp Lys Glu Leu Leu Pro Lys Leu Asn Asn His Asp Cys Arg Ile Ser
165 170 175

Asn Ile Glu Thr Val Ile Glu Phe Gln Gln Lys Asn Asn Arg Leu Leu
180 185 190

Glu Ile Ala Arg Glu Phe Ser Val Asn Ala Gly Ile Thr Thr Pro Leu

```
        195                 200                 205

Ser Thr Tyr Met Leu Thr Asn Ser Glu Leu Leu Ser Leu Ile Asn Asp
    210                 215                 220

Met Pro Ile Thr Asn Asp Gln Lys Lys Leu Met Ser Ser Asn Val Gln
225                 230                 235                 240

Ile Val Arg Gln Gln Ser Tyr Ser Ile Met Cys Val Val Lys Glu Glu
                245                 250                 255

Val Ile Ala Tyr Val Val Gln Leu Pro Ile Tyr Gly Val Ile Asp Thr
            260                 265                 270

Pro Cys Trp Lys Leu His Thr Ser Pro Leu Cys Thr Thr Asp Asn Lys
        275                 280                 285

Glu Gly Ser Asn Ile Cys Leu Thr Arg Thr Asp Arg Gly Trp Tyr Cys
    290                 295                 300

Asp Asn Ala Gly Ser Val Ser Phe Phe Pro Gln Ala Glu Thr Cys Lys
305                 310                 315                 320

Val Cys Ser Asn Arg Val Phe Cys Asp Thr Met Asn Ser Leu Thr Leu
                325                 330                 335

Pro Thr Asp Val Asn Leu Cys Asn Thr Asp Ile Phe Asn Thr Lys Tyr
            340                 345                 350

Asp Cys Lys Ile Met Thr Ser Lys Thr Asp Ile Ser Ser Ser Val Ile
        355                 360                 365

Thr Ser Ile Gly Ala Ile Val Ser Cys Tyr Gly Lys Thr Lys Cys Thr
    370                 375                 380

Ala Ser Asn Lys Asn Arg Gly Ile Ile Lys Thr Phe Ser Asn Gly Cys
385                 390                 395                 400

Asp Tyr Val Ser Asn Lys Gly Val Asp Thr Val Ser Val Gly Asn Thr
                405                 410                 415

Leu Tyr Tyr Val Asn Lys Leu Glu Gly Lys Ala Leu Tyr Ile Lys Glu
            420                 425                 430

Pro Ile Ile Asn Tyr Tyr Asp Pro Leu Val Phe Pro Ser Asp Glu Phe
        435                 440                 445

Asp Ala Ser Ile Ala Gln Val Asn Ala Lys Ile Asn Gln Ser Leu Ala
    450                 455                 460

Phe Ile Arg Arg Ser Asp Glu Leu Leu Ser Ala Ile Gly Gly Tyr Ile
465                 470                 475                 480

Pro Glu Ala Pro Arg Asp Gly Gln Ala Tyr Val Arg Lys Asp Gly Glu
                485                 490                 495

Trp Val Leu Leu Ser Thr Phe Leu Gly Gly Leu Val Pro Arg Gly Ser
            500                 505                 510

His His His His His His Ser Ala Trp Ser His Pro Gln Phe Glu Lys
        515                 520                 525
```

<210> SEQ ID NO 114
<211> LENGTH: 574
<212> TYPE: PRT
<213> ORGANISM: Respiratory Syncytial Virus

<400> SEQUENCE: 114

```
Met Ala Thr Thr Ala Met Arg Met Ile Ile Ser Ile Ile Phe Ile Ser
1               5                   10                  15

Thr Tyr Val Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45
```

```
Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Val Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Gln Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Thr Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
```

```
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Val Ile Leu Met Leu Ile Ala Val
    530                 535                 540

Gly Leu Leu Phe Tyr Cys Lys Thr Lys Ser Thr Pro Ile Met Leu Gly
545                 550                 555                 560

Lys Asp Gln Leu Ser Gly Ile Asn Asn Leu Ser Phe Ser Lys
                565                 570


<210> SEQ ID NO 115
<211> LENGTH: 574
<212> TYPE: PRT
<213> ORGANISM: Respiratory Syncytial Virus

<400> SEQUENCE: 115

Met Ala Thr Thr Thr Met Arg Met Ile Ile Ser Ile Ile Ile Ile Phe
1               5                   10                  15

Ile Tyr Val Gln His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Asn Ser Thr Asp Ser Asn Val Lys Leu Ile Lys
65                  70                  75                  80

Gln Glu Leu Glu Arg Tyr Asn Asn Ala Val Val Glu Leu Gln Ser Leu
                85                  90                  95

Met Gln Asn Glu Pro Ala Ser Ser Ser Arg Ala Lys Arg Gly Ile Pro
            100                 105                 110

Glu Leu Ile His Tyr Lys Arg Asn Ser Thr Lys Lys Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Gln Ile Ser Asn Ile Ala Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270
```

-continued

```
Leu Met Ser Ser Asn Val Gln Ile Val Arg Gln Gln Ser Tyr Ser Ile
        275                 280                 285

Met Ser Val Val Lys Glu Glu Val Met Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Ala Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Arg Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Gly Glu Pro Ile Ile Asn Tyr Tyr Asp Pro
465                 470                 475                 480

Leu Val Phe Pro Ser Asp Glu Phe Asp Ala Ser Ile Ala Gln Val Asn
                485                 490                 495

Ala Lys Ile Asn Gln Ser Leu Ala Phe Ile Arg Arg Ser Asp Glu Leu
            500                 505                 510

Leu His Ser Val Asp Val Gly Lys Ser Thr Thr Asn Val Val Ile Thr
        515                 520                 525

Thr Ile Ile Ile Val Ile Val Val Val Ile Leu Met Leu Ile Ala Val
    530                 535                 540

Gly Leu Leu Phe Tyr Ser Lys Thr Arg Ser Thr Pro Ile Met Leu Gly
545                 550                 555                 560

Lys Asp Gln Leu Ser Gly Ile Asn Asn Leu Ser Phe Ser Lys
                565                 570
```

<210> SEQ ID NO 116
<211> LENGTH: 573
<212> TYPE: PRT
<213> ORGANISM: Respiratory Syncytial Virus

<400> SEQUENCE: 116

```
Met Ala Ala Thr Ala Met Arg Met Ile Ile Ser Ile Ile Phe Ile Ser
1               5                   10                  15

Thr Tyr Met Thr His Ile Thr Leu Cys Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Val Thr Ile Glu Leu Ser Lys Ile
    50                  55                  60

Gln Lys Asn Val Cys Lys Ser Thr Asp Ser Lys Val Lys Leu Ile Lys
65                  70                  75                  80
```

-continued

```
Gln Glu Leu Glu Arg Tyr Asn Asn Ala Val Ile Glu Leu Gln Ser Leu
                85                  90                  95

Met Gln Asn Glu Pro Ala Ser Phe Ser Arg Ala Lys Arg Gly Ile Pro
            100                 105                 110

Glu Leu Ile His Tyr Thr Arg Asn Ser Thr Lys Arg Phe Tyr Gly Leu
        115                 120                 125

Met Gly Lys Lys Arg Lys Arg Arg Phe Leu Gly Phe Leu Leu Gly Ile
    130                 135                 140

Gly Ser Ala Ile Ala Ser Gly Val Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Glu Leu Leu Pro Lys Val Asn
        195                 200                 205

Asn His Asp Cys Arg Ile Ser Asn Ile Glu Thr Val Ile Glu Phe Gln
    210                 215                 220

Gln Lys Asn Asn Arg Leu Leu Glu Ile Ala Arg Glu Phe Ser Val Asn
225                 230                 235                 240

Ala Gly Ile Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Val Val Lys Glu Glu Val Ile Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asp Asn Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Thr Asp Val Asn Leu Cys Asn Thr
    370                 375                 380

Asp Ile Phe Asn Thr Lys Tyr Asp Cys Lys Ile Met Thr Ser Lys Thr
385                 390                 395                 400

Asp Ile Ser Ser Ser Val Ile Thr Ser Ile Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Ala Leu Tyr Ile Lys Glu Pro Ile Ile Asn Tyr Tyr Asp Pro Leu
465                 470                 475                 480

Val Phe Pro Ser Asp Glu Phe Asp Ala Ser Ile Ala Gln Val Asn Ala
                485                 490                 495
```

-continued

```
Lys Ile Asn Gln Ser Leu Ala Phe Ile Arg Arg Ser Asp Glu Leu Leu
            500                 505                 510

His Ser Val Asp Val Gly Lys Ser Thr Thr Asn Val Val Ile Thr Thr
        515                 520                 525

Ile Ile Ile Val Ile Val Val Val Ile Leu Met Leu Ile Ala Val Gly
    530                 535                 540

Leu Leu Phe Tyr Cys Lys Thr Arg Ser Thr Pro Ile Met Leu Gly Lys
545                 550                 555                 560

Asp Gln Leu Ser Gly Ile Asn Asn Leu Ser Phe Ser Lys
                565                 570


<210> SEQ ID NO 117
<211> LENGTH: 9
<212> TYPE: PRT
<213> ORGANISM: Artificial Sequence
<220> FEATURE:
<223> OTHER INFORMATION: Peptide Linker

<400> SEQUENCE: 117

Gly Ser Gly Asn Val Gly Leu Gly Gly
1               5


<210> SEQ ID NO 118
<211> LENGTH: 9
<212> TYPE: PRT
<213> ORGANISM: Artificial Sequence
<220> FEATURE:
<223> OTHER INFORMATION: Peptide Linker

<400> SEQUENCE: 118

Gly Ser Gly Asn Trp Gly Leu Gly Gly
1               5


<210> SEQ ID NO 119
<211> LENGTH: 9
<212> TYPE: PRT
<213> ORGANISM: Artificial Sequence
<220> FEATURE:
<223> OTHER INFORMATION: Peptide Linker

<400> SEQUENCE: 119

Gly Ser Gly Asn Ile Gly Leu Gly Gly
1               5


<210> SEQ ID NO 120
<211> LENGTH: 11
<212> TYPE: PRT
<213> ORGANISM: Artificial Sequence
<220> FEATURE:
<223> OTHER INFORMATION: Peptide Linker

<400> SEQUENCE: 120

Gly Ser Gly Gly Asn Gly Ile Gly Leu Gly Gly
1               5                   10


<210> SEQ ID NO 121
<211> LENGTH: 10
<212> TYPE: PRT
<213> ORGANISM: Artificial Sequence
<220> FEATURE:
<223> OTHER INFORMATION: Peptide Linker

<400> SEQUENCE: 121

Gly Ser Gly Gly Ser Gly Gly Ser Gly Gly
1               5                   10
```

<210> SEQ ID NO 122
<211> LENGTH: 8
<212> TYPE: PRT
<213> ORGANISM: Artificial Sequence
<220> FEATURE:
<223> OTHER INFORMATION: Peptide Linker

<400> SEQUENCE: 122

Gly Ser Gly Asn Val Leu Gly Gly
1               5

<210> SEQ ID NO 123
<211> LENGTH: 10
<212> TYPE: PRT
<213> ORGANISM: Artificial Sequence
<220> FEATURE:
<223> OTHER INFORMATION: Peptide Linker

<400> SEQUENCE: 123

Met Gln Ser Thr Pro Ala Thr Asn Asn Gly
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Peptide Linker

<400> SEQUENCE: 124

Met Gln Ser Thr Pro Ala Thr Asn Asn Gly Gly
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Peptide Linker

<400> SEQUENCE: 125

Met Gln Ser Thr Pro Ala Thr Asn Asn Gly Gln Gly
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Peptide Linker

<400> SEQUENCE: 126

Met Gln Ser Thr Pro Ala Thr Asn Asn Gly Gly Ser Gly
1               5                   10

<210> SEQ ID NO 127
<211> LENGTH: 14
<212> TYPE: PRT
<213> ORGANISM: Artificial Sequence
<220> FEATURE:
<223> OTHER INFORMATION: Peptide Linker

<400> SEQUENCE: 127

Met Gln Ser Thr Pro Ala Thr Asn Asn Gly Gly Ser Gly Ser
1               5                   10

<210> SEQ ID NO 128
<211> LENGTH: 15
<212> TYPE: PRT
<213> ORGANISM: Artificial Sequence
<220> FEATURE:
<223> OTHER INFORMATION: Peptide Linker

<400> SEQUENCE: 128

Met Gln Ser Thr Pro Ala Thr Asn Asn Gly Gly Ser Gly Gly Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Peptide Linker

<400> SEQUENCE: 129

Met Gln Ser Thr Pro Ala Thr Asn Asn Gly Gly Ser Gly Gly Ser Gly
1               5                   10                  15

<210> SEQ ID NO 130
<211> LENGTH: 17
<212> TYPE: PRT
<213> ORGANISM: Artificial Sequence
<220> FEATURE:
<223> OTHER INFORMATION: Peptide Linker

<400> SEQUENCE: 130

Met Gln Ser Thr Pro Ala Thr Asn Asn Gly Gly Gly Ser Gly Gly Ser
1               5                   10                  15

Gly

<210> SEQ ID NO 131
<211> LENGTH: 7
<212> TYPE: PRT
<213> ORGANISM: Artificial Sequence
<220> FEATURE:
<223> OTHER INFORMATION: Peptide Linker

<400> SEQUENCE: 131

Met Gln Ser Thr Pro Ala Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Peptide Linker

<400> SEQUENCE: 132

Met Gln Ser Thr Pro Ala Thr Gly Ser
1               5

<210> SEQ ID NO 133
<211> LENGTH: 8
<212> TYPE: PRT
<213> ORGANISM: Artificial Sequence
<220> FEATURE:
<223> OTHER INFORMATION: Peptide Linker

<400> SEQUENCE: 133

Met Gln Ser Thr Pro Ala Gly Ser
1               5

<210> SEQ ID NO 134
<211> LENGTH: 7
<212> TYPE: PRT
<213> ORGANISM: Artificial Sequence
<220> FEATURE:
<223> OTHER INFORMATION: Peptide Linker

<400> SEQUENCE: 134

Met Gln Ser Thr Pro Gly Ser
1               5

<210> SEQ ID NO 135
<211> LENGTH: 6
<212> TYPE: PRT
<213> ORGANISM: Artificial Sequence
<220> FEATURE:
<223> OTHER INFORMATION: Peptide Linker

<400> SEQUENCE: 135

Met Gln Ser Thr Gly Ser
1               5

<210> SEQ ID NO 136
<211> LENGTH: 5
<212> TYPE: PRT
<213> ORGANISM: Artificial Sequence
<220> FEATURE:
<223> OTHER INFORMATION: Peptide Linker

<400> SEQUENCE: 136

Met Gln Ser Gly Ser
1               5

<210> SEQ ID NO 137
<211> LENGTH: 4
<212> TYPE: PRT
<213> ORGANISM: Artificial Sequence
<220> FEATURE:
<223> OTHER INFORMATION: Peptide Linker

<400> SEQUENCE: 137

Met Gln Gly Ser
1

<210> SEQ ID NO 138
<211> LENGTH: 4
<212> TYPE: PRT
<213> ORGANISM: Artificial Sequence
<220> FEATURE:
<223> OTHER INFORMATION: Peptide Linker

<400> SEQUENCE: 138

Met Gly Ser Gly
1

<210> SEQ ID NO 139
<211> LENGTH: 11
<212> TYPE: PRT
<213> ORGANISM: Artificial Sequence
<220> FEATURE:
<223> OTHER INFORMATION: Peptide Linker

<400> SEQUENCE: 139

Met Gln Ser Thr Pro Ala Thr Gly Gly Ser Gly
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Peptide Linker

<400> SEQUENCE: 140

Met Gln Ser Thr Pro Ala Thr Gly Gly Ser Gly Gly
1 5 10

<210> SEQ ID NO 141
<211> LENGTH: 14
<212> TYPE: PRT
<213> ORGANISM: Artificial Sequence
<220> FEATURE:
<223> OTHER INFORMATION: Peptide Linker

<400> SEQUENCE: 141

Met Gln Ser Thr Pro Ala Thr Gly Gly Ser Gly Gly Ser Gly
1 5 10

<210> SEQ ID NO 142
<211> LENGTH: 11
<212> TYPE: PRT
<213> ORGANISM: Artificial Sequence
<220> FEATURE:
<223> OTHER INFORMATION: Peptide Linker

<400> SEQUENCE: 142

Met Gln Ser Thr Ala Thr Gly Gly Ser Gly Asn
1 5 10

<210> SEQ ID NO 143
<211> LENGTH: 9
<212> TYPE: PRT
<213> ORGANISM: Artificial Sequence
<220> FEATURE:
<223> OTHER INFORMATION: Peptide Linker

<400> SEQUENCE: 143

Met Gln Ser Thr Pro Ala Asn Gly Ser
1 5

<210> SEQ ID NO 144
<211> LENGTH: 14
<212> TYPE: PRT
<213> ORGANISM: Artificial Sequence
<220> FEATURE:
<223> OTHER INFORMATION: Peptide Linker

<400> SEQUENCE: 144

Ile Ser Ser Thr Ser Ala Thr Gly Ser Gly Ser Ala Ile Ala
1 5 10

<210> SEQ ID NO 145
<211> LENGTH: 13
<212> TYPE: PRT
<213> ORGANISM: Artificial Sequence
<220> FEATURE:
<223> OTHER INFORMATION: Peptide Linker

<400> SEQUENCE: 145

Val Thr Ser Thr Ser Ala Thr Gly Ser Gly Ser Ala Ile
1 5 10

<210> SEQ ID NO 146
<211> LENGTH: 14
<212> TYPE: PRT
<213> ORGANISM: Artificial Sequence
<220> FEATURE:
<223> OTHER INFORMATION: Peptide Linker

<400> SEQUENCE: 146

Asn Ser Ala Leu Ser Ala Thr Gly Ser Gly Ser Ala Ile Ala
1 5 10

<210> SEQ ID NO 147
<211> LENGTH: 9
<212> TYPE: PRT
<213> ORGANISM: Artificial Sequence
<220> FEATURE:
<223> OTHER INFORMATION: Peptide Linker

<400> SEQUENCE: 147

Ile Ser Ser Thr Thr Ser Thr Gly Ser
1 5

<210> SEQ ID NO 148
<211> LENGTH: 9
<212> TYPE: PRT
<213> ORGANISM: Artificial Sequence
<220> FEATURE:
<223> OTHER INFORMATION: Peptide Linker

<400> SEQUENCE: 148

Val Thr Ser Thr Thr Ser Thr Gly Ser
1 5

<210> SEQ ID NO 149
<211> LENGTH: 9
<212> TYPE: PRT
<213> ORGANISM: Artificial Sequence
<220> FEATURE:
<223> OTHER INFORMATION: Peptide Linker

<400> SEQUENCE: 149

Asn Ser Ala Leu Ser Ser Thr Gly Ser
1 5

<210> SEQ ID NO 150
<211> LENGTH: 11
<212> TYPE: PRT
<213> ORGANISM: Artificial Sequence
<220> FEATURE:
<223> OTHER INFORMATION: Peptide Linker

<400> SEQUENCE: 150

Ile Ser Ser Thr Ser Ala Thr Val Gly Gly Ser
1 5 10

<210> SEQ ID NO 151
<211> LENGTH: 11
<212> TYPE: PRT
<213> ORGANISM: Artificial Sequence
<220> FEATURE:
<223> OTHER INFORMATION: Peptide Linker

<400> SEQUENCE: 151

Val Thr Ser Thr Ser Ala Thr Thr Gly Gly Ser
1 5 10

<210> SEQ ID NO 152

<211> LENGTH: 10
<212> TYPE: PRT
<213> ORGANISM: Artificial Sequence
<220> FEATURE:
<223> OTHER INFORMATION: Peptide Linker

<400> SEQUENCE: 152

Asn Ser Ala Leu Ser Ala Thr Gly Gly Ser
1 5 10

<210> SEQ ID NO 153
<211> LENGTH: 11
<212> TYPE: PRT
<213> ORGANISM: Artificial Sequence
<220> FEATURE:
<223> OTHER INFORMATION: Peptide Linker

<400> SEQUENCE: 153

Ile Ser Ser Thr Thr Ser Thr Val Gly Gly Ser
1 5 10

<210> SEQ ID NO 154
<211> LENGTH: 11
<212> TYPE: PRT
<213> ORGANISM: Artificial Sequence
<220> FEATURE:
<223> OTHER INFORMATION: Peptide Linker

<400> SEQUENCE: 154

Val Thr Ser Thr Thr Ser Thr Thr Gly Gly Ser
1 5 10

<210> SEQ ID NO 155
<211> LENGTH: 10
<212> TYPE: PRT
<213> ORGANISM: Artificial Sequence
<220> FEATURE:
<223> OTHER INFORMATION: Peptide Linker

<400> SEQUENCE: 155

Asn Ser Ala Leu Ser Ser Thr Gly Gly Ser
1 5 10

<210> SEQ ID NO 156
<211> LENGTH: 8
<212> TYPE: PRT
<213> ORGANISM: Artificial Sequence
<220> FEATURE:
<223> OTHER INFORMATION: Peptide Linker

<400> SEQUENCE: 156

Met Gln Ser Thr Pro Ala Thr Gly
1 5

<210> SEQ ID NO 157
<211> LENGTH: 8
<212> TYPE: PRT
<213> ORGANISM: Artificial Sequence
<220> FEATURE:
<223> OTHER INFORMATION: Peptide Linker

<400> SEQUENCE: 157

Met Gln Ser Thr Pro Ala Thr Ser
1 5

<210> SEQ ID NO 158
<211> LENGTH: 9

<212> TYPE: PRT
<213> ORGANISM: Artificial Sequence
<220> FEATURE:
<223> OTHER INFORMATION: Peptide Linker

<400> SEQUENCE: 158

Ala Arg Leu Leu Gly Ser Gly Ser Gly
1 5

<210> SEQ ID NO 159
<211> LENGTH: 8
<212> TYPE: PRT
<213> ORGANISM: Artificial Sequence
<220> FEATURE:
<223> OTHER INFORMATION: Peptide Linker

<400> SEQUENCE: 159

Met Gln Ser Thr Gly Gly Ser Gly
1 5

<210> SEQ ID NO 160
<211> LENGTH: 8
<212> TYPE: PRT
<213> ORGANISM: Artificial Sequence
<220> FEATURE:
<223> OTHER INFORMATION: Peptide Linker

<400> SEQUENCE: 160

Ala Gln Ser Thr Gly Gly Ser Gly
1 5

<210> SEQ ID NO 161
<211> LENGTH: 8
<212> TYPE: PRT
<213> ORGANISM: Artificial Sequence
<220> FEATURE:
<223> OTHER INFORMATION: Peptide Linker

<400> SEQUENCE: 161

Ala Arg Leu Leu Gly Gly Ser Gly
1 5

<210> SEQ ID NO 162
<211> LENGTH: 7
<212> TYPE: PRT
<213> ORGANISM: Artificial Sequence
<220> FEATURE:
<223> OTHER INFORMATION: Peptide Linker

<400> SEQUENCE: 162

Ala Arg Leu Leu Gly Ser Gly
1 5

<210> SEQ ID NO 163
<211> LENGTH: 30
<212> TYPE: PRT
<213> ORGANISM: Artificial Sequence
<220> FEATURE:
<223> OTHER INFORMATION: Recombinant signal peptide

<400> SEQUENCE: 163

Met Asp Ser Lys Gly Ser Ser Gln Lys Gly Ser Arg Leu Leu Leu Leu
1 5 10 15

Leu Val Val Ser Asn Leu Leu Leu Pro Gln Gly Val Val Gly
20 25 30